(12) United States Patent
Choe et al.

(10) Patent No.: US 8,952,130 B2
(45) Date of Patent: Feb. 10, 2015

(54) DESIGNER LIGANDS OF TGF-β SUPERFAMILY

(75) Inventors: Senyon Choe, Solana Beach, CA (US); George Allendorph, San Diego, CA (US); Michael J. Isaacs, Redwood City, CA (US)

(73) Assignees: The Salk Institute for Biological Studies, La Jolla, CA (US); joint Center for Biosciences, Incheon (KR)

( * ) Notice: Subject to any disclaimer, the term of this patent is extended or adjusted under 35 U.S.C. 154(b) by 623 days.

(21) Appl. No.: 12/712,069

(22) Filed: Feb. 24, 2010

(65) Prior Publication Data

US 2010/0221777 A1 Sep. 2, 2010

Related U.S. Application Data

(60) Provisional application No. 61/155,066, filed on Feb. 24, 2009.

(51) Int. Cl.
| | | |
|---|---|---|
| *C07K 14/51* | (2006.01) | |
| *C07H 21/04* | (2006.01) | |
| *C07K 14/495* | (2006.01) | |
| *A61K 38/00* | (2006.01) | |

(52) U.S. Cl.
CPC .............. *C07K 14/495* (2013.01); *A61K 38/00* (2013.01)
USPC ........................................ 530/350; 536/23.1

(58) Field of Classification Search
None
See application file for complete search history.

(56) References Cited

U.S. PATENT DOCUMENTS

| | | | |
|---|---|---|---|
| 4,877,864 A | 10/1989 | Wang et al. | |
| 5,013,649 A | 5/1991 | Wang et al. | |
| 5,106,748 A | 4/1992 | Wozney et al. | |
| 5,108,922 A | 4/1992 | Wang et al. | |
| 5,116,738 A | 5/1992 | Wang et al. | |
| 5,141,905 A | 8/1992 | Rosen et al. | |
| 5,155,058 A | 10/1992 | Fujiwara et al. | |
| 5,283,317 A | 2/1994 | Saifer et al. | |
| 5,677,196 A | 10/1997 | Herron et al. | |
| 6,333,168 B1 * | 12/2001 | Jessell et al. | 435/69.1 |
| 6,521,750 B2 | 2/2003 | Hair et al. | |
| 6,846,906 B1 * | 1/2005 | Oppermann et al. | 530/350 |

FOREIGN PATENT DOCUMENTS

| | | |
|---|---|---|
| WO | WO 87/05330 | 9/1987 |
| WO | WO/91/05802 | 5/1991 |
| WO | WO/92/07004 | 4/1992 |
| WO | WO 96/26432 | 8/1996 |
| WO | 0020591 A2 | 4/2000 |
| WO | WO 00/20607 | 4/2000 |
| WO | 2005113585 A2 | 12/2005 |
| WO | 2006047728 A2 | 5/2006 |

OTHER PUBLICATIONS

Muenster et al. Antagonism of Activin by activin chimeras. Vitam Horm. 2011;85:105-28.*
Allendorph et al. Designer TGFβ superfamily ligands with diversified functionality. PLoS One. 2011;6(11):e26402. Epub Nov. 4, 2011.*
Sun PD, Davies DR. The cystine-knot growth-factor superfamily. Annu Rev Biophys Biomol Struct. 1995;24:269-91.*
Chaudhury A, Howe PH. The tale of transforming growth factor-beta (TGFbeta) signaling: a soigné enigma. IUBMB Life. Oct. 2009;61(10):929-39.*
Cho, Jeong Han, International Search Report and Written Opinion for PCT/US2010/025260, Korean Intellectual Property Office, Date of Mailing Nov. 10, 2010.
Korupolu et al., "Activin A/Bone Morphogenetic Protein (BMP) Chimeras Exhibit BMP-like Activity and Antagonize Activin and Myostatin," J. Biological Chemistry 283(7): 3782-3790 (2008).
Database Geneseq, "Human bone morphogenetic protein-2 SEQ ID:1," XP002676912, retrieved from EBI accession No. GSP: AWF74151, Database accession No. AWF74151 (Apr. 16, 2009).
Database Geneseq, "16.5 kD subunit of ovine inhibin," XP002676913, retrieved from EBI accession No. GSP: AAR12088, Database accession No. AAR12088 (Aug. 1, 1991).
Database Geneseq, "Human osteogenic protein-1 (OP1)," XP002676914, retrieved from EBI accession No. GSP: AEK67267, Database accession No. AEK67267 (Nov. 30, 2006).
Database Geneseq, "Human BMP-9 polypeptie," XP002676915, retrieved from EBI accession No. GSP: AAR86903, Database accession No. AAR86903 (May 10, 1996).
Database Geneseq, "Bone morphogenetic protein-12," XP002676916, retrieved from EBI accession No. GSP: AAW54067, Database accession No. AAW54067 (Aug. 10, 1998).
Database UniProt, XP002676917, retrieved from EBI accession No. UNIPROT: Q6DTL9, Database accession No. Q6DTL9 (Aug. 16, 2004).
Muenster, "An activin-A/C Chimera exhibits activin and myostatin antagonistic properties," Journal of Biological Chemistry, vol. 280, No. 44, pp. 36626-26632 (2005).
Extended European Research Report dated Jun. 14, 2012 issued in European Application No. 10746779.7, filed Feb. 24, 2010.
Massagué, et al. "TGFβ Signaling in Growth Control, Cancer, and Heritable Disorders", Cell, vol. 103, 295-309, Oct. 13, 2000.
Massagué, et al. "The logic of TGFβ signaling" FEBS Letters 580 (2006) 2811-2820.
Massagué, "TGFβ in Cancer", Cell 134, Jul. 25, 2008, 215-231.
Mehta, et al. "The TGFβ superfamily in cardiovascular biology", Cardiovascular Research 74 (2007) 181-183.

* cited by examiner

*Primary Examiner* — David Romeo
(74) *Attorney, Agent, or Firm* — Knobbe, Martens, Olson & Bear LLP

(57) ABSTRACT

The present disclosure relates to chimeric polypeptide having TGF-beta activity, nucleic acids encoding the polypeptides, and host cells for producing the polypeptides.

16 Claims, 21 Drawing Sheets

FIG. 7B  BMP-2

FIG. 7C  activin

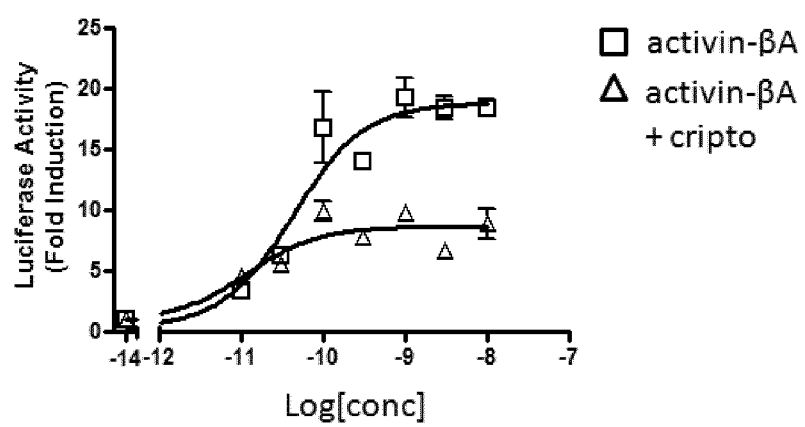
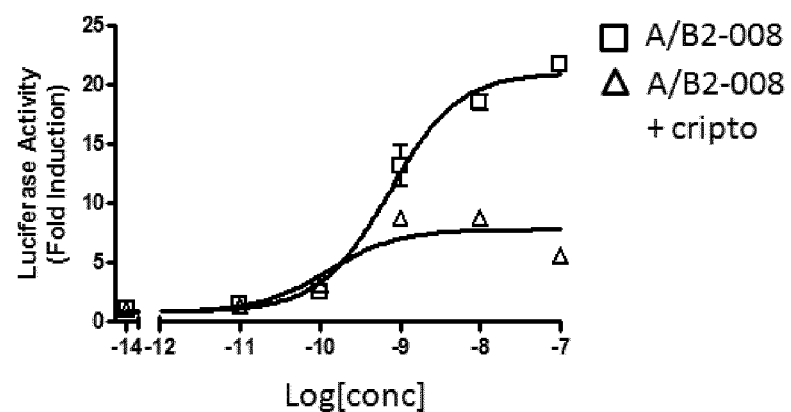
FIGURE 14

FIG. 18

```
                              1                                                    J1                          2                            J2
BMP-2  (SEQ ID NO:2)   ---------------QAKHKQRKRLKS----------------SCKRHPLYVDF-SDVGWNDWIVAPPGYHAFYCHGECP
BMP-3  (SEQ ID NO:43)  ---------------------------------QWIEPRNCARRYLKVDF-ADIGWSEWIISPKSFDAYYCSGACQ
BMP-4  (SEQ ID NO:45)  ---------------SPKHHSQRARKKNK----------------NCRRHSLYVDF-SDVGWNDWIVAPPGYQAFYCHGDCP
BMP-5  (SEQ ID NO:47)  ----------NQNRNKSSSHQDSSRMSSVGDYNTSEQ-KQACKKHELYVSF-RDLGWQDWIIAPEGYAAFYCDGECS
BMP-6  (SEQ ID NO:49)  ----------QQSRNRSTQSQDVARVSSASDYNSSEL-KTACRKHELYVSF-QDLGWQDWIIAPKGYAANYCDGECS
BMP-7  (SEQ ID NO:51)  STGSKQRSQNRSKTPKNQEALRMANVAENSSSDQ-RQACKKHELYVSF-RDLGWQDWIIAPEGYAAYYCEGECA
BMP-8  (SEQ ID NO:53)  -AVRPLRRRQPKKSNELPQANRLPGIFDDVHGSHGRQVCRRHELYVSF-QDLGWLDWVIAPQGYSAYYCEGECS
BMP-9  (SEQ ID NO:55)  -------------------SAGAG------SHCQKTSLRVNF-EDIGWDSWIIAPKEYEAYECKGGCF
BMP-10 (SEQ ID NO:57)  --------------------NAKG------NYCKRTPLYIDF-KEIGWDSWIIAPPGYEAYECRGVCN
BMP-15 (SEQ ID NO:59)  -------------QADGISAEVTASSSKHSG----PENNQCSLHPFQISF-RQLGWDHWIIAPPFYTPNYCKGTCL
GDF-1  (SEQ ID NO:61)  ----------------DAEPVLGGPGGACRARRLYVSF-REVGWHRWVIAPRGFLANYCQGQCA
GDF-3  (SEQ ID NO:63)  -----------------AAIPVPKLSCKNLCHRHQLFINF-RDLGWHKWIIAPKGFMANYCHGECP
GDF-5  (SEQ ID NO:65)  ---------APLATRQ-----GKRPSKNLKARCSRKALHVNF-KDMGWDDWIIAPLEYEAFHCEGLCE
GDF-6  (SEQ ID NO:67)  ----------TAFASRH-----GKRHGKKSRLRCSKKPLHVNF-KELGWDDWIIAPLEYEAYHCEGVCD
GDF-7  (SEQ ID NO:69)  ----------TALAGTRTSQGSGGAGRGHGRGRSRCSRKPLHVDF-KELGWDDWIIAPLDYEAYHCEGLCD
GDF-8  (SEQ ID NO:71)  ---------------DFGLDCDEHSTESRCCRYPLTVDF-EAFGWDWIIAPKRYKANYCSGECEF
GDF-9  (SEQ ID NO:73)  -GQETVSSELKKPLGPASFNLSEYFRQFLLPQNECELHDFRLSF-SQLKWDNWIVAPHRYNPRYCKGDCP
GDF-10 (SEQ ID NO:75)  -------------KTMQKARRKQWDEPRVCSRRYLKVDF-ADIGWNEWIISPKSFDAYYCAGACE
GDF-11 (SEQ ID NO:77)  -------------NLGLDCDEHSSESRCCRYPLTVDF-EAFGWDWIIAPKRYKANYCSGQCEY
GDF-15 (SEQ ID NO:79)  --------------ARNGDDCPLGPGRCCRLHTVRASL-EDLGWADWVLSPREVQVTMCIGACP
NODAL  (SEQ ID NO:81)  -----------------HHLPDRSQLCRKVKFQVDF-NLIGWGSWIIYPKQYNAYRCEGECP
ACTIVIN-A (SEQ ID NO:83) -----------------GLECDGKV--NICCKKQFFVSF-KDIGWNDWIIAPSGYHANYCEGECP
ACTIVIN-B (SEQ ID NO:85) -----------------GLECDGRT--NLCCRQQFFIDF-RLIGWNDWIIAPTGYYGNYCEGSCP
ACTIVIN-C (SEQ ID NO:87) -----------------GIDCQGGS--RMCCRQEFFVDF-REIGWHDWIIQPEGYAMNFCIGQCP
ACTIVIN-E (SEQ ID NO:89) -----------------TPTCEPAT--PLCCRRDHYVDF-QELGWIDWLQPEGYQLNYCSGQCP
INHIBIN-A (SEQ ID NO:91) STPLMSWPWSPSALRLLQRPPEEPAAHANCHRVALNISF-QELGWERWIVYPPSFIFHYCHGGCG
TGF-beta1 (SEQ ID NO:93) -----------------RALDTNYCFSSTEKNCCVRQLYIDFRKDLGW-KWIHEPKGYHANFCLGPCP
TGF-beta2 (SEQ ID NO:95) -----------------ALDAAYCFRNVQDNCCLRPLYIDFKRDLGW-KWIHEPKGYNANFCAGACP
TGF-beta3 (SEQ ID NO:97) -----------------ALDTNYCFRNLEENCCVRPLYIDFRQDLGW-KWVHEPKGYYANFCSGPCP
```

FIG. 18 (Cont'd)

|  | 3 | J3 | 4 | J4 | 5 | J5 |
|---|---|---|---|---|---|---|
| BMP-2 (SEQ ID NO:2) | FPLADHLNST | ----NHAIVQTLVNSVN-SK-IPKACCV | ----PTELSAISMLYLD |
| BMP-3 (SEQ ID NO:43) | FPMPKSLKPS | ----NHATIQSIVRAVGVVPGIPEPCCV | ----PEKMSSLSILFFD |
| BMP-4 (SEQ ID NO:45) | FPLADHLNST | ----NHAIVQTLVNSVN-SS-IPKACCV | ----PTELSAISMLYLD |
| BMP-5 (SEQ ID NO:47) | FPLNAHMNAT | ----NHAIVQTLVHLMFPDH-VPKPCCA | ----PTKLNAISVLYFD |
| BMP-6 (SEQ ID NO:49) | FPLNAHMNAT | ----NHAIVQTLVHLMNPEY-VPKPCCA | ----PTKLNAISVLYFD |
| BMP-7 (SEQ ID NO:51) | FPLNSYMNAT | ----NHAIVQTLVHFINPET-VPKPCCA | ----PTQLNAISVLYFD |
| BMP-8 (SEQ ID NO:53) | FPLDSCMNAT | ----NHAILQSLVHLMKPNA-VPKACCA | ----PTKLSATSVLYYD |
| BMP-9 (SEQ ID NO:55) | FPLADDVTPT | ----KHAIVQTLVHLKFPTK-VGKACCV | ----PTKLSPISVLYKD |
| BMP-10 (SEQ ID NO:57) | YPLAEHLTPT | ----KHAIIQALVHLKNSQK-ASKACCV | ----PTKLEPISILYLD |
| BMP-15 (SEQ ID NO:59) | RVLRDGLNSP | ----NHAIIQNLINQLVDQS-VPRPSCV | ----PYKYVPISVLMIE |
| GDF-1 (SEQ ID NO:61) | LPVALSGSGGPPALNHAVLRALMHAAAPGA-ADLPCCV | ----PARLSPISVLFFD |
| GDF-3 (SEQ ID NO:63) | FSITISLNSS | ----NYAFMQALMHAVDP-E-IPQAVCI | ----PTKLSPISMLYQD |
| GDF-5 (SEQ ID NO:65) | FPLRSHLEPT | ----NHAVIQTLMNSMDPES-TPPTCCV | ----PTRLSPISILFID |
| GDF-6 (SEQ ID NO:67) | FPLRSHLEPT | ----NHAIIQTLMNSMDPGS-TPPSCCV | ----PTKLTPISILYID |
| GDF-7 (SEQ ID NO:69) | FPLRSHLEPT | ----NHAIIQTLLNSMAPDA-APASCCV | ----PARLSPISILYID |
| GDF-8 (SEQ ID NO:71) | VFL------- | ---QKYPHT---HLVHQ--ANPRGSAGPCCT | ----PTKMSPINMLYFN |
| GDF-9 (SEQ ID NO:73) | RAVGHRYGSP | ----VHTMVQNIIYEKLDSS-VPRPSCV | ----PAKYSPLSVLTIE |
| GDF-10 (SEQ ID NO:75) | FPMPKIVRPS | ----NHATIQSIVRAVGIIPGIPEPCCV | ----PDKMNSLGVLFLD |
| GDF-11 (SEQ ID NO:77) | MFM------- | ---QKYPHT---HLVQQ--ANPRGSAGPCCT | ----PTKMSPINMLYFN |
| GDF-15 (SEQ ID NO:79) | SQFRAAN--- | ----MHAQIKTSLHRLKPDT-EPAPCCV | ----PASYNPMVLIQKT |
| NODAL (SEQ ID NO:81) | NPVGEEFHPT | ----NHAYIQSLLKRYQPHR-VPSTCCA | ----PVKTKPLSMLYVD |
| ACTIVIN-A (SEQ ID NO:83) | SHIAG-TSGSSLSFHSTVINHYRMRGHSPFANLKSCCV | ----PTKLRPMSMLYYD |
| ACTIVIN-B (SEQ ID NO:85) | AYLAG-VPGSASSFHTAVVNQYRMRGLNP-GTVNSCCI | ----PTKLSTMSMLYFD |
| ACTIVIN-C (SEQ ID NO:87) | LHIAG-MPGIAASFHTAVLNLLKANTAAGTTGGGSCCV | ----PTARRPLSLLYYD |
| ACTIVIN-E (SEQ ID NO:89) | PHLAG-SPGIAASFHSAVFSLLKANNPWPAS--TSCCV | ----PTARRPLSLLYLD |
| INHIBIN-A (SEQ ID NO:91) | LHIPPNLSLP | ----VPGAPPTPAQPYSLLP-GAQPCCAALPGTMRPLHVRTTS |
| TGF-beta1 (SEQ ID NO:93) | YIWS------ | ----LDTQYSKVLALYNQ--HNPGASAAPCCV | ----PQALEPLPIVYYV |
| TGF-beta2 (SEQ ID NO:95) | YLWS------ | ----SDTQHSRVLSLYNT--INPEASASPCCV | ----SQDLEPLTILYYI |
| TGF-beta3 (SEQ ID NO:97) | YLRS------ | ----ADTTHSTVLGLYNT--LNPEASASPCCV | ----PQDLEPLTILYYV |

FIG. 18 (Cont'd)

| | |
|---|---|
| BMP-2 (SEQ ID NO:2) | ENEKVVLK-NYQDMVVEGCGCR 114 |
| BMP-3 (SEQ ID NO:43) | ENKNVVLK-VYPNMTVESCACR 110 |
| BMP-4 (SEQ ID NO:45) | EYDKVVLK-NYQEMVVEGCGCR 116 |
| BMP-5 (SEQ ID NO:47) | DSSNVILK-KYRNMVVRSCGCH 132 |
| BMP-6 (SEQ ID NO:49) | DNSNVILK-KYRNMVVRACGCH 132 |
| BMP-7 (SEQ ID NO:51) | DSSNVILK-KYRNMVVRACGCH 139 |
| BMP-8 (SEQ ID NO:53) | SSNNVILR-KHRNMVVKACGCH 139 |
| BMP-9 (SEQ ID NO:55) | DMGVPTLKYHYEGMSVAECGCR 110 |
| BMP-10 (SEQ ID NO:57) | -KGVVTYKFKYEGMAVSECGCR 108 |
| BMP-15 (SEQ ID NO:59) | ANGSILYK-EYEGMIAESCTCR 125 |
| GDF-1 (SEQ ID NO:61) | NSDNVVLR-QYEDMVVDECGCR 119 |
| GDF-3 (SEQ ID NO:63) | NNDNVILR-HYEDMVVDECGCG 114 |
| GDF-5 (SEQ ID NO:65) | SANNVVYK-QYEDMVVESCGCR 120 |
| GDF-6 (SEQ ID NO:67) | AGNNVVYK-QYEDMVVESCGCR 120 |
| GDF-7 (SEQ ID NO:69) | AANNVVYK-QYEDMVVEACGCR 129 |
| GDF-8 (SEQ ID NO:71) | GKEQIIYG-KIPAMVVDRCGCS 109 |
| GDF-9 (SEQ ID NO:73) | PDGSIAYK-EYEDMIATKCTCR 135 |
| GDF-10 (SEQ ID NO:75) | ENRNVVLK-VYPNMSVDTCACR 119 |
| GDF-11 (SEQ ID NO:77) | DKQQIIYG-KIPGMVVDRCGGS 109 |
| GDF-15 (SEQ ID NO:79) | DTGVSLQT--YDDLLAKDCHCI 112 |
| NODAL (SEQ ID NO:81) | NGR-VLLD-HHKDMIVEECGCL 110 |
| ACTIVIN-A (SEQ ID NO:83) | DGQNIIKK-DIQNMIVEECGCS 116 |
| ACTIVIN-B (SEQ ID NO:85) | DEYNIVKR-DVPNMIVEECGCA 115 |
| ACTIVIN-C (SEQ ID NO:87) | RDSNIVKT-DIPDMVVEACGCS 116 |
| ACTIVIN-E (SEQ ID NO:89) | HNGNVVKT-DVPDMVVEACGCS 114 |
| INHIBIN-A (SEQ ID NO:91) | DGGYSFKYETVPNLLTQHCACI 134 |
| TGF-beta1 (SEQ ID NO:93) | GRKPKVE--QLSNMIVRSCKCS 113 |
| TGF-beta2 (SEQ ID NO:95) | GKTPKIE--QLSNMIVKSCKCS 112 |
| TGF-beta3 (SEQ ID NO:97) | GRTPKVE--QLSNMVVKSCKCS 112 |

DESIGNER LIGANDS OF TGF-β SUPERFAMILY

CROSS REFERENCE TO RELATED APPLICATIONS

The application claims priority under 35 U.S.C. §119 to U.S. Provisional Application Ser. No. 61/155,066, filed, Feb. 24, 2009, the disclosure of which is incorporated herein by reference.

STATEMENT REGARDING FEDERALLY SPONSORED RESEARCH

The invention was funded, in part, by a grant from the National Institutes of Health grant number HD013527. The government has certain right in this invention.

TECHNICAL FIELD

The present disclosure relates to biomolecular engineering and design, and engineered proteins and nucleic acids.

BACKGROUND

Activins and Bone Morphogenetic Proteins (BMPs) are members of the much larger Transforming Growth Factor-beta (TGF-β) superfamily. Due to their pervasiveness in numerous developmental and cellular processes, TGF-β ligands have been the focus of great interest. For TGF-β ligands to be successfully used as therapeutic tools, several hurdles need to be overcome. The ability to specifically modify and alter the properties of TGF-β ligands, as well as generate those ligands in significant quantities is required.

SUMMARY

The disclosure provides non-naturally occurring chimeric polypeptides having an activity provided by a TGF-beta family of proteins. The chimeric polypeptides of the disclosure comprises two or more segments or fragments from parental TGF-beta proteins operably linked such that the resulting polypeptide is capable of modulating a pathway associated with a TGF-beta family of proteins. In one embodiment, the pathway is a SMAD or DAXX pathway.

In one embodiment, the disclosure provides designer TGF-beta ligands that can be synthesized by selecting and conjoining different sequence segments of TGF-beta superfamily ligands to construct new ligands (designer ligands). These novel ligands possess entirely new protein sequence library that differs from naturally existing TGF-beta superfamily ligands. This approach originates primarily from the recognition of the structural commonality among natural TGF-beta superfamily ligands. All ~40 TGF-beta superfamily ligands share the same overall architecture with generic characteristics for each region of the protein. The framework of TGF-beta ligands can be divided into (generally) six subdomains (also called sequence segments; marked in six different colors in FIG. 19) that all superfamily members share.

In one embodiment, the disclosure also provides a recombinant polypeptide comprising: at least two peptide segments, a first segment of the polypeptide comprising a sequence having at least 80% identity to a first TGF-beta family protein and a second segment comprising a sequence having at least 80% identity to a second TGF-beta family protein, wherein the segments are operably linked and have activity of at least one of the first or second parental TGF-beta family protein. In one embodiment, the polypeptide comprises an N-terminal segment from BMP-2. In another embodiment, the at least two peptide segments comprise 6 peptide segments operably linked N-terminus to C-terminus. In yet another embodiment, each of the first and second TGF-beta family proteins have structural similarity and each segment corresponds to a structural motif. In yet a further embodiment, the first TGF-beta family protein is BMP-2 and the second TGF-beta family protein is activin. In one embodiment, the segments of the BMP-2 protein comprise segment 1: amino acid residue from about 1 to about $x_1$ of SEQ ID NO:2 ("1b"); segment 2 is from about amino acid residue $x_1$ to about $x_2$ of SEQ ID NO:2 ("2b"); segment 3 is from about amino acid residue $x_2$ to about $x_3$ of SEQ ID NO:2 ("3b"); segment 4 is from about amino acid residue $x_3$ to about $x_4$ of SEQ ID NO:2 ("4b"); segment 5 is from about amino acid residue $x_4$ to about $x_5$ of SEQ ID NO:2 ("5b"); and segment 6 is from about amino acid residue $x_5$ to about $x_6$ of SEQ ID NO:2 ("6b"); and wherein: $x_1$ is residue 25, 26, 27, 28, 29, 30, 31, 32, 33, 34, or 35 of SEQ ID NO:2; $x_2$ is residue 45, 46, 47, or 48 of SEQ ID NO:2; $x_3$ is residue 65, 66, 67, or 68 of SEQ ID NO:2; $x_4$ is residue 76, 77, 78, 79, 80, 81 or 82 of SEQ ID NO:2; $x_5$ is residue 88, 89, 90, 91, 92, 93, or 94 of SEQ ID NO:2; and $x_6$ is residue 112, 113, or 114 or SEQ ID NO:2, corresponding to the C-terminus of BMP-2; and the segments of the activin protein comprise segment 1, amino acid residue from about 1 to about $x_1$ of SEQ ID NO:5 ("1a"); segment 2 is from about amino acid residue $x_1$ to about $x_2$ of SEQ ID NO:5 ("2a"); segment 3 is from about amino acid residue $x_2$ to about $x_3$ of SEQ ID NO:5 ("3a"); segment 4 is from about amino acid residue $x_3$ to about $x_4$ of SEQ ID NO:5 ("4a"); segment 5 is from about amino acid residue $x_4$ to about $x_5$ of SEQ ID NO:5 ("5a"); and segment 6 is from about amino acid residue $x_5$ to about $x_6$ of SEQ ID NO:5 ("6a"); and wherein: $x_1$ is residue 22, 23, 24, 25, 26, 27, 28, 29, 30, 31 or 32 of SEQ ID NO:5; $x_2$ is residue 42, 43, 44, or 45 of SEQ ID NO:5; $x_3$ is residue 61, 62, 63, or 64 of SEQ ID NO:5; $x_4$ is residue 78, 79, 80, 81, 82, 83 or 84 of SEQ ID NO:5; $x_5$ is residue 90, 91, 92, 93, 94, 95 or 96 of SEQ ID NO:5; and $x_6$ is residue 114, 115, or 116 or SEQ ID NO:5; and wherein the polypeptide has an order of segment 1-segment 2-segment 3-segment 4-segment 5-segment 6. In a further embodiment, the polypeptide comprises a sequence of segments selected from the group consisting of 1b2b3b4b5b6a; 1b2b3b4b5a6a; 1b2b3b4b5a6b; 1b2b3a4a5a6a; 1b2b3a4a5b6a; 1b2a3a4a5a6a; 1b2a3a4a5a6a L66V/V67I; 1b(1a_II)2a3a4a5a6a; 1b2a3a4a5a6b; 1b2a3a4a5b6b; 1b2a3a4a5b6a; 1b2a3b4b5b6a; 1b2a3b4b5a6a; and 1b2a3b4b5a6b.

The disclosure also provides a recombinant polypeptide comprising at least 80%, 90%, 95%, 98% or 99% identity to a sequence as set forth in SEQ ID NO:7, 9, 11, 13, 15, 17, 19, 1, 23, 25, 2, 29, 31, 33, 35, 37, 39 or 41 and wherein the polypeptide modulates the SMAD or DAXX pathway.

The disclosure also provides a chimeric TGF-beta family polypeptide comprising a segment of a first TGF-beta family protein operably linked to a segment of a second different TGF-beta family protein to provide a chimeric polypeptide having SMAD or DAXX modulating activity.

The disclosure also provides a polynucleotide encoding a polypeptide of the disclosure. In one embodiment, the polynucleotide has at least 80%, 90%, 95%, 98%, 99% or more identity to a sequence selected from the group consisting of SEQ ID NO: 6, 8, 10, 12, 14, 16, 18, 20, 22, 24, 26, 28, 30, 32, 24, 26, 28, and 40. Vectors comprising such polynucleotides are also provided along with recombinant cells.

In an alternate embodiment, the disclosure provides novel ligands for members of the TGF-beta superfamily, wherein the ligand is a chimeric protein with at least one of six subdomians from a foreign or different member of the TGF-beta superfamily.

The disclosure comprises a chimeric polypeptide comprising a first domain from a first TGF-beta family member, a crossover point at J1 (see, e.g., FIG. 18), a second domain from the same or second TGF-beta family member, a crossover point at J2 (see, e.g., FIG. 18), a third domain from the same or third TGF-beta family member, a crossover point at J3 (see, e.g., FIG. 18), a fourth domain from the same or fourth TGF-beta family member, a crossover point at J4 (see e.g., FIG. 18), a fifth domain from the same or fifth TGF-beta family member, a crossover point at J5 (see, e.g., FIG. 18), and a second domain from the same or sixth TGF-beta family member. In one embodiment, the chimera is derived from 2, 3, 4, 5, or 6 different TGF-beta family members. In yet another embodiment a crossover at J3 is optional.

BRIEF DESCRIPTION OF THE FIGURES

FIG. 7 depicts a structure/sequence alignment for chimera design strategy. FIG. 7B shows the monomer structure of BMP-2 and FIG. 7C shows the monomer structure of Activin-βA.

FIG. 9A shows differentiated H9 cells after 3 passages (1 ng/mL, AB2-008; no FGF2). FIG. 9B shows differentiated H9 cells after 3 passages (10 ng/mL, AB2-008; no FGF2). FIG. 9C shows differentiated H9 cells after 11 passages (100 ng/mL, AB2-008; no FGF2). FIG. 9D shows differentiated H9 cells after 12 passages (1 ng/mL, AB2-008; 100 ng/mL, FGF2). FIG. 9E shows H9 cells after 13 passages (10 ng/mL, AB2-008; 100 ng/mL, FGF2). And FIG. 9F shows differentiated H9 cells after 9 passages (100 ng/mL, AB2-008; 100 ng/mL, FGF2). In the figures, differentiated cells are denoted by arrows.

FIG. 14 shows co-receptor binding by Activin-βA and AB2-008. Smad-2-Luciferase activity in HEK cells in the presence of and absence Cripto with (A) activin-βA, and with (B) AB2-008.

FIG. 18 provides an alignment of the sequences of several members of the TGF-beta superfamily, with the relative segments defined for each member.

DETAILED DESCRIPTION

Figure 1:
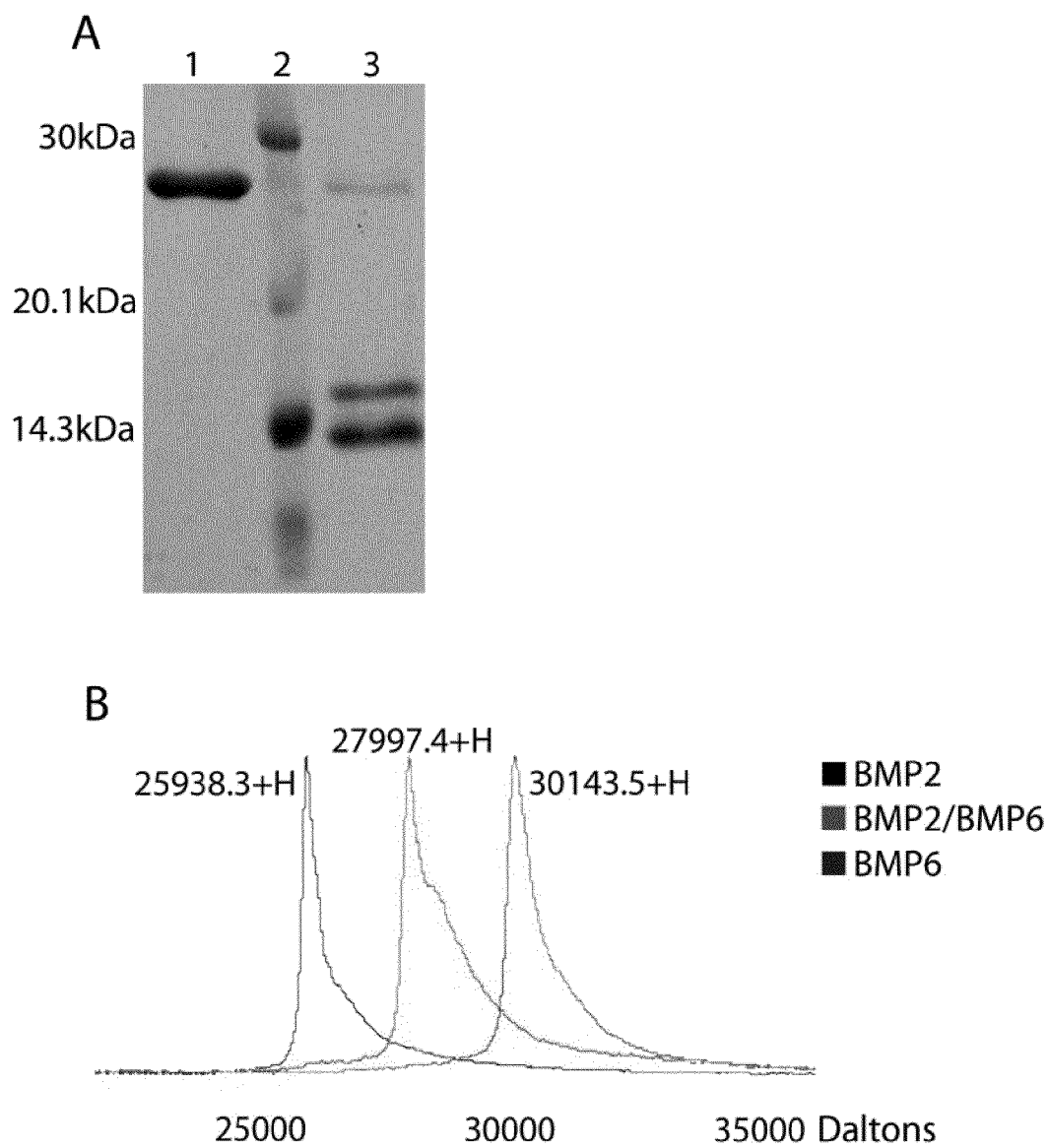
FIG. 1A-B shows BMP2/BMP6 sample characterization. Panel A: BMP2/BMP6 sample on SDS-PAGE. The BMP2/BMP6 sample non-reduced in lane one, molecular weight marker in lane two, and the BMP2/BMP6 sample reduced in lane three. Panel B: SELDI-TOF-MS overlaid results from separate samples of BMP2, BMP6, and BMP2/BMP6 ligands.

As used herein and in the appended claims, the singular forms "a," "and," and "the" include plural referents unless the context clearly dictates otherwise. Thus, for example, reference to "a domain" includes a plurality of such domains and reference to "the protein" includes reference to one or more proteins, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Although methods and materials similar or equivalent to those described herein can be used in the practice of the disclosed methods and compositions, the exemplary methods and materials are described herein.

Unless defined otherwise, all technical and scientific terms used herein have the same meaning as commonly understood to one of ordinary skill in the art to which this disclosure belongs. Thus, as used throughout the instant application, the following terms shall have the following meanings.

"Amino acid" is a molecule having the structure wherein a central carbon atom (the alpha-carbon atom) is linked to a hydrogen atom, a carboxylic acid group (the carbon atom of which is referred to herein as a "carboxyl carbon atom"), an amino group (the nitrogen atom of which is referred to herein as an "amino nitrogen atom"), and a side chain group, R. When incorporated into a peptide, polypeptide, or protein, an amino acid loses one or more atoms of its amino acid carboxylic groups in the dehydration reaction that links one amino acid to another. As a result, when incorporated into a protein, an amino acid is referred to as an "amino acid residue."

"Protein" or "polypeptide" refers to any polymer of two or more individual amino acids (whether or not naturally occurring) linked via a peptide bond, and occurs when the carboxyl carbon atom of the carboxylic acid group bonded to the alpha-carbon of one amino acid (or amino acid residue) becomes covalently bound to the amino nitrogen atom of amino group bonded to the -carbon of an adjacent amino acid. The term "protein" is understood to include the terms "polypeptide" and "peptide" (which, at times may be used interchangeably herein) within its meaning. In addition, proteins comprising multiple polypeptide subunits (e.g., DNA polymerase III, RNA polymerase II) or other components (for example, an RNA molecule, as occurs in telomerase) will also be understood to be included within the meaning of "protein" as used herein. Similarly, fragments of proteins and polypeptides are also within the scope of the disclosure and may be referred to herein as "proteins." In one aspect of the disclosure, a polypeptide comprises a chimera of two or more parental peptide segments.

As used herein, TGF-beta superfamily member refers to a TGF-beta superfamily (including bone morphogenic factors) gene or protein of any species, particularly a mammalian species, including but not limited to bovine, ovine, porcine, murine, equine, and human. "TGF-beta superfamily polypeptide" refers to the amino acid sequences of purified TGF-beta superfamily protein obtained from any species, particularly a mammalian species, including bovine, ovine, porcine, murine, equine, and human and from any source, whether natural, synthetic, semi-synthetic, or recombinant.

"Peptide segment" refers to a portion or fragment of a larger polypeptide or protein. A peptide segment need not on its own have functional activity, although in some instances, a peptide segment may correspond to a domain of a polypeptide wherein the domain has its own biological activity. A stability-associated peptide segment is a peptide segment found in a polypeptide that promotes stability, function, or folding compared to a related polypeptide lacking the peptide segment.

A particular amino acid sequence of a given protein (i.e., the polypeptide's "primary structure," when written from the amino-terminus to carboxy-terminus) is determined by the nucleotide sequence of the coding portion of a mRNA, which is in turn specified by genetic information, typically genomic DNA (including organelle DNA, e.g., mitochondrial or chloroplast DNA). Thus, determining the sequence of a gene assists in predicting the primary sequence of a corresponding polypeptide and more particular the role or activity of the polypeptide or proteins encoded by that gene or polynucleotide sequence.

"Fused," "operably linked," and "operably associated" are used interchangeably herein to broadly refer to a chemical or physical coupling of two otherwise distinct domains, wherein each domain has independent biological function. As such, the present disclosure provides TGF-beta (e.g., BMP or activins) domains that are fused to one another such that they function as a polypeptide having a TGF-beta family activity or an improvement or change in ligand specificity of a TGF-beta family of polypeptides. In one embodiment, a chimeric polypeptide comprising a plurality of domains from two parental TGF-beta family polypeptides are linked such that they are part of the same coding sequence, each domain encoded by a polynucleotide from a parental TGF-beta family polypeptide, wherein the polynucleotides are in frame such that the polynucleotide when transcribed encodes a single mRNA that when translated comprises a plurality of domains as a single polypeptide. Typically, the coding domains will be linked "in-frame" either directly of separated by a peptide linker and encoded by a single polynucleotide. Various coding sequences for peptide linkers and peptide are known in the art.

"Polynucleotide" or "nucleic acid" refers to a polymeric form of nucleotides. In some instances a polynucleotide comprises a sequence that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the disclosure can be ribonucleotides, deoxyribonucleotides, or modified forms of either nucleotide. A polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The term polynucleotide encompasses genomic DNA or RNA (depending upon the organism, i.e., RNA genome of viruses), as well as mRNA encoded by the genomic DNA, and cDNA.

"Nucleic acid segment," "oligonucleotide segment" or "polynucleotide segment" refers to a portion of a larger polynucleotide molecule. The polynucleotide segment need not correspond to an encoded functional domain of a protein; however, in some instances the segment will encode a functional domain of a protein. A polynucleotide segment can be about 6 nucleotides or more in length (e.g., 6-20, 20-50, 50-100, 100-200, 200-300, 300-400 or more nucleotides in length).

"Chimera" or "chimeric protein" or "chimeric polypeptide" refers to a combination of at least two segments of at least two different parent proteins. As appreciated by one of skill in the art, the segments need not actually come from each of the parents, as it is the particular sequence that is relevant, and not the physical nucleic acids themselves. For example, a chimeric BMP will have at least two segments from two different parent BMPs; or BMP and other member of the TGF-beta superfamily, or alternatively, an unrelated protein. A chimeric protein may also be an "interspecies," "intergenic," etc. fusion of protein structures (the same or different member protein) expressed by different kinds of organisms. In a one embodiment, two segments are connected so as to result in a new chimeric protein. In other words, a protein will not be a chimera if it has the identical sequence of either one of the full-length parents. A chimeric protein can comprise more than two segments from two different parent proteins.

Figure 19:
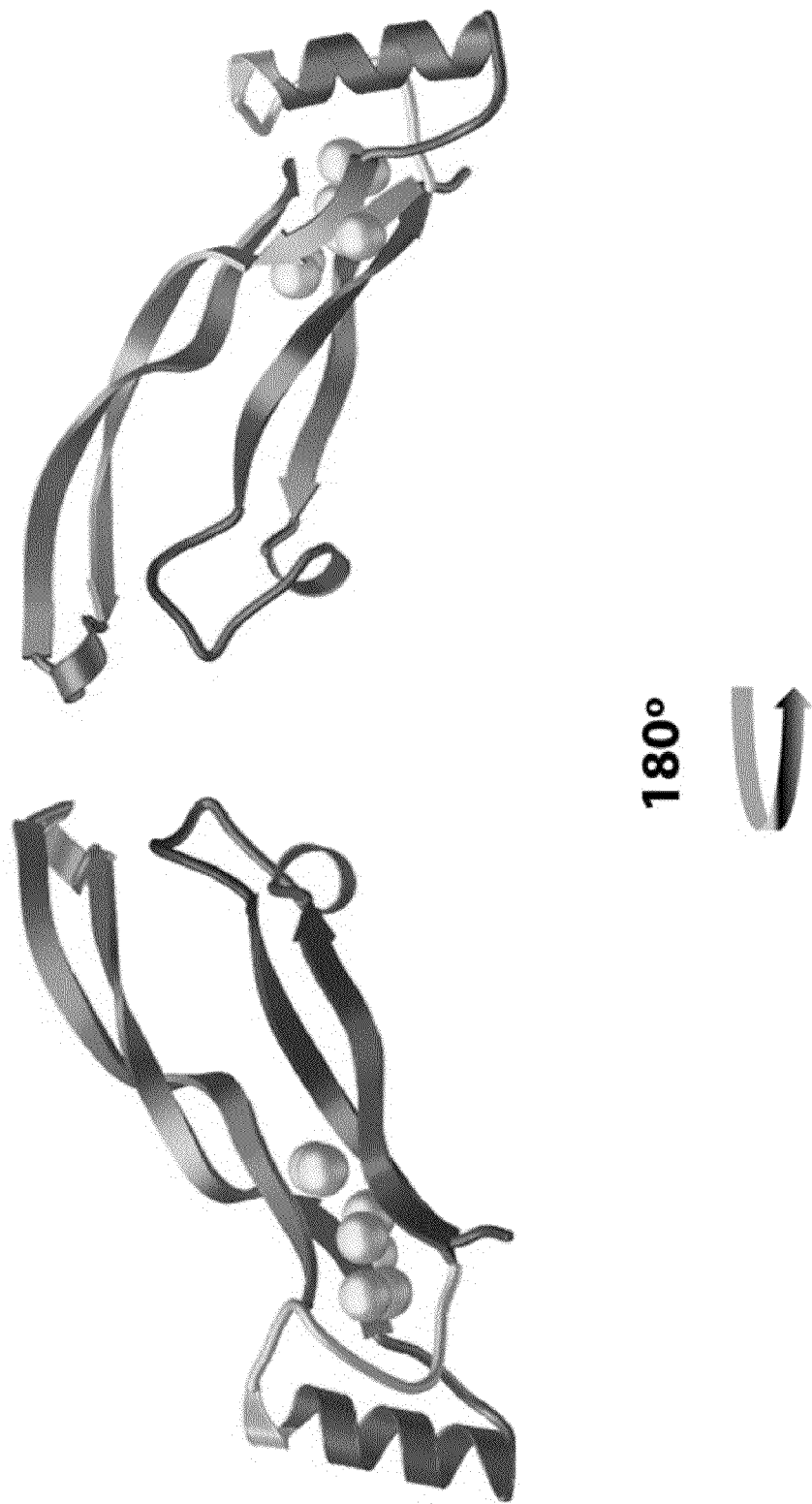
FIG. 19 shows the six subdomains (fragments) on a single subunit of the TGF-beta superfamily ligand's scaffold.

For example, there may be 2, 3, 4, 5, 6 or 10-20, or more parents from which the domains may be derived in generating a final chimera or library of chimeras. The segment of each parent protein can be very short or very long, the segments can range in length of contiguous amino acids from 1 to about the full length of the protein. In one embodiment, the minimum length is 5 amino acids. Generally, the segment or subdomain, is one of six subdomains, alternatively five subdomains (see FIGS. 18 and 19). The six segments of a TGF-beta superfamily member are identified based on the structural architecture of the member protein and/or the primary amino acid sequence as aligned against other homologous member proteins. As identified, the member protein is generally divided into 6 distinct sections (although, alternatively, 5 distinct sections) based on segments derived to minimize alterations, or alternatively viewed, maximize alterations, to the aligned native TGF-beta member sequence during chimera engineering. Generally, FIG. 18 shows the relative positions of the distinct segments overlapping the aligned sequences of each of several TGF-beta superfamily members. The vertical line denotes a general position for cross-over between domains in generating the chimera. The amino acids that can overlap the two domains can be defined as being plus or minus about 5 amino acids (or alternatively, 8, 7, 6, 5, 4, 3, 2 or 1 amino acids) in either direction of the vertical line. Also in FIG. 18 is shown a boxed set of amino acids that identify additional junctions that can be used to generate chimera. The J1-J5 junctions are positions general conservation across the TGF-beta family proteins that can be used to generate cross-over points.

Although relatively distinct, the segments may comprise a particular amino acid sequence or an original amino acid sequence that is amenable to substitution(s), insertion(s), additional amino acid(s) at either or both termini of the original sequence, or other modifications. By "amenable", it is meant that the structural integrity of each segment is maintained as compared to the domain of the original sequence. For example, a segment described herein of a TGF-beta superfamily member may shift by 10, 5, 3, 2, or 1, or preferably no more than 1 amino acid on either or both termini of segment as identified.

In one embodiment, the disclosure provides a chimeric protein comprising a fusion of at least one segment from a TGF-beta member with a second segment from a second TGF-beta member, wherein the first segment is foreign to the second TGF-beta member. Utilizing the five-six subdomains (segments) on a single subunit of the TGF-beta superfamily ligand as a scaffold framework, new (designer) sequences can be recombinantly linked by mixing segments from different TGF-beta ligands in the same order as they appear in nature. This assembly produces new sequences that are partly similar to one of several different target sequences, but distinctly different from any naturally occurring sequences.

In one embodiment, a single crossover point is defined for two parents. The crossover location defines where one parent's amino acid segment will stop and where the next parent's amino acid segment will start. Thus, a simple chimera would only have one crossover location where the segment before that crossover location would belong to one parent and the segment after that crossover location would belong to the second parent. In one embodiment, the chimera has more than one crossover location. For example, 2, 3, 4, 5, 6, 7, 8, 9, 10, 11-30, or more crossover locations. In a particular embodiment, the parental strands are defined as having 4 or 5 crossover locations. How these crossover locations are named and defined are both discussed below. In an embodiment where there are two crossover locations and two parents, there will be a first contiguous segment from a first parent, followed by a second contiguous segment from a second parent, followed by a third contiguous segment from the first parent. Contiguous is meant to denote that there is nothing of significance interrupting the segments. These contiguous segments are connected to form a contiguous amino acid sequence. For example, a BMP-2/activin chimera derived from a BMP-2 wild-type parental strand and an activin wild-type parental strand with two crossovers would comprise a first segment from either BMP-2 or activin, a second segment from the opposite parental strand compared to the first segment operably linked to the first strand and comprising a structural motif downstream of the first strand and a third segment strand from the opposite parental strand compared to the second segment and from the same parental strand as the first segment operably linked to the second strand and comprising a structural motif downstream of the second strand all connected in one contiguous amino acid chain.

As appreciated by one of skill in the art, variants of chimeras exist as well as the exact sequences. In otherwords conservative amino acid substitutions may be incorporated into the chimera (e.g., from about 1-10 conservative amino acid substitutions). Thus, not 100% of each segment need be present in the final chimera if it is a variant chimera. The amount that may be altered, either through additional residues or removal or alteration of residues will be defined as the term variant is defined. Of course, as understood by one of skill in the art, the above discussion applies not only to amino acids but also nucleic acids which encode for the amino acids.

"Conservative amino acid substitution" refers to the interchangeability of residues having similar side chains, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, isoleucine, and methionine; an amino acid with hydroxyl side chain is substituted with another amino acid with a hydroxyl side chain, e.g., serine and threonine; an amino acids having aromatic side chains is substituted with another amino acid having an aromatic side chain, e.g., phenylalanine, tyrosine, tryptophan, and histidine; an amino acid with a basic side chain is substituted with another amino acid with a basis side chain, e.g., lysine, arginine, and histidine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively.

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Reference sequence" refers to a defined sequence used as a basis for a sequence comparison. A reference sequence may be a subset of a larger sequence, for example, a segment of a full-length gene or polypeptide sequence. Generally, a reference sequence can be at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptides are typically performed by comparing sequences of the two polynucleotides or polypeptides over a "comparison window" to identify and compare local regions of sequence similarity.

"Sequence identity" means that two amino acid sequences are substantially identical (i.e., on an amino acid-by-amino acid basis) over a window of comparison. The term "sequence similarity" refers to similar amino acids that share the same biophysical characteristics. The term "percentage of sequence identity" or "percentage of sequence similarity" is calculated by comparing two optimally aligned sequences over the window of comparison, determining the number of positions at which the identical residues (or similar residues) occur in both polypeptide sequences to yield the number of matched positions, dividing the number of matched positions by the total number of positions in the window of comparison (i.e., the window size), and multiplying the result by 100 to yield the percentage of sequence identity (or percentage of sequence similarity). With regard to polynucleotide sequences, the terms sequence identity and sequence similarity have comparable meaning as described for protein sequences, with the term "percentage of sequence identity" indicating that two polynucleotide sequences are identical (on a nucleotide-by-nucleotide basis) over a window of comparison. As such, a percentage of polynucleotide sequence identity (or percentage of polynucleotide sequence similarity, e.g., for silent substitutions or other substitutions, based upon the analysis algorithm) also can be calculated. Maximum correspondence can be determined by using one of the sequence algorithms described herein (or other algorithms available to those of ordinary skill in the art) or by visual inspection.

As applied to polypeptides, the term substantial identity or substantial similarity means that two peptide sequences, when optimally aligned, such as by the programs BLAST, GAP or BESTFIT using default gap weights or by visual inspection, share sequence identity or sequence similarity. Similarly, as applied in the context of two nucleic acids, the term substantial identity or substantial similarity means that the two nucleic acid sequences, when optimally aligned, such as by the programs BLAST, GAP or BESTFIT using default gap weights (described in detail below) or by visual inspection, share sequence identity or sequence similarity.

One example of an algorithm that is suitable for determining percent sequence identity or sequence similarity is the FASTA algorithm, which is described in Pearson, W. R. & Lipman, D. J., (1988) Proc. Natl. Acad. Sci. USA 85:2444. See also, W. R. Pearson, (1996) Methods Enzymology 266: 227-258. Preferred parameters used in a FASTA alignment of DNA sequences to calculate percent identity or percent similarity are optimized, BL50 Matrix 15: −5, k-tuple=2; joining penalty=40, optimization=28; gap penalty −12, gap length penalty=−2; and width=16.

Another example of a useful algorithm is PILEUP. PILEUP creates a multiple sequence alignment from a group of related sequences using progressive, pairwise alignments to show relationship and percent sequence identity or percent sequence similarity. It also plots a tree or dendogram showing the clustering relationships used to create the alignment. PILEUP uses a simplification of the progressive alignment method of Feng & Doolittle, (1987) J. Mol. Evol. 35:351-360. The method used is similar to the method described by Higgins & Sharp, CABIOS 5:151-153, 1989. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity (or percent sequence similarity) relationship using the following parameters: default gap weight (3.00), default gap length weight (0.10), and weighted end gaps. PILEUP can be obtained from the GCG sequence analysis software package, e.g., version 7.0 (Devereaux et al., (1984) Nuc. Acids Res. 12:387-395).

Another example of an algorithm that is suitable for multiple DNA and amino acid sequence alignments is the CLUSTALW program (Thompson, J. D. et al., (1994) Nuc. Acids Res. 22:4673-4680). CLUSTALW performs multiple pairwise comparisons between groups of sequences and assembles them into a multiple alignment based on sequence identity. Gap open and Gap extension penalties were 10 and 0.05 respectively. For amino acid alignments, the BLOSUM algorithm can be used as a protein weight matrix (Henikoff and Henikoff, (1992) Proc. Natl. Acad. Sci. USA 89:10915-10919).

FIG. 18, for example, shows an alignment of a number of TGF-beta family members. One of skill in the art can readily determine from the alignment those amino acids that are conserved across the family as well as those that are not conserved.

"Functional" refers to a polypeptide which possesses either the native biological activity of the naturally-produced proteins of its type, or any specific desired activity, for example as judged by its ability to bind to ligand or cognate molecules or induce a particular biological function (e.g., stimulate muscle growth, bone growth and the like).

The Transforming Growth Factor-beta (TGF-β) superfamily of proteins is comprised of extracellular cytokines found in the vast majority of human cells. The TGF-β superfamily ligands, of which there are ~40, can be subdivided into smaller families including TGF-β, Bone Morphogenetic Proteins (BMPs), activin and inhibin, Growth and Differentiation Factors (GDFs), Nodal, Müllerian Inhibiting Substance (MIS), and Glial cell line-Derived Neurotrophic Factors (GDNFs). TGF-β superfamily members are found in a diverse range of cell types and play roles in many fundamental cellular events including dorsal/ventral patterning and left/right axis determination to bone formation and tissue repair. More recently, several TGF-β ligands have been shown to be involved in the maintenance or direct the differentiation of stem cells. Due to their pervasiveness, regulation of TGF-β ligand signaling holds promise for the treatment of a wide range of different diseases from skeletal and muscle abnormalities to numerous neoplastic events. Exemplary sequences are provided herein for various members of this family or proteins, however, one of skill in the art can easily identify homologs and variants using publicly available databases by word search or sequence BLAST searches.

There are generally recognized several subfamilies within the superfamily of TGF-beta (TGF-β1-β5) as well as the differentiation factors (e.g., Vg-1), the hormones activin and inhibin, the Mullerian inhibiting substance (MIS), osteogenic and morphogenic proteins (e.g., OP-1, OP-2, OP-3, other BMPs), the developmentally regulated protein Vgr-1, the growth/differentiation factors (e.g., GDF-1, GDF-3, GDF-9 and dorsalin-1), etc. See, e.g., Spam and Roberts (1990) in Peptide Growth Factors and Their Receptors, Spom and Roberts, eds., Springer-Verlag: Berlin pp. 419-472; Weeks and Melton (1987) Cell 51: 861-867; Padgett et al. (1987) Nature 325: 81-84; Mason et al. (1985) Nature 318: 659-663; Mason et al. (1987) Growth Factors 1: 77-88; Cate et al. (1986) Cell 45: 685-698; PCT/US90/05903; PCT/US91/07654; PCT/WO94/10202; U.S. Pat. Nos. 4,877,864; 5,141,905; 5,013,649; 5,116,738; 5,108,922; 5,106,748; and U.S. Pat. No. 5,155,058; Lyons et al. (1989) Proc. Natl. Acad. Sci. USA 86: 4554-58; McPherron et al. (1993) J. Biol. Chem. 268: 3444-3449; Basler et al. (1993) Cell 73: 687-702.

Morphogenic proteins of the TGF-beta superfamily include the mammalian osteogenic protein-1 (OP-1, also known as BMP-7), osteogenic protein-2 (OP-2, also known as BMP-8), osteogenic protein-3 (053), BMP-2 (also known as BMP-2A or CBMP-2A, and the *Drosophila* homolog DPP), BMP-3, BMP-4 (also known as BMP-2B or CBMP-2B), BMP-5, BMP-6 and its murine homolog Vgr-1, BMP-9, BMP-10, BMP-11, BMP-12, GDF3 (also known as Vgr2), GDF-8, GDF-9, GDF-10, GDF-11, GDF-12, BMP-13, BMP-14, BMP-15, GDF-5 (also known as CDMP-1 or MP52), GDF-6 (also known as CDMP-2 or BMP13), GDF-7 (also known as CDMP-3 or BMP-12), the *Xenopus* homolog Vgl and NODAL, UNIVIN, SCREW, ADMP, NEURAL, etc.

One major roadblock for research involving many of the TGF-β superfamily ligands has been the inability to generate significant quantities of the proteins. While, BMP-2 is known to refold efficiently in vitro, other TGF-β ligands (activin, Nodal, and BMP-7 for instance) have not shown the same refolding properties. Other expression systems are available to obtain functional TGF-β ligands. Activin, for example, is expressed using stably transfected cell lines, such as CHO or transiently transfected cell lines, such as HEK293 cells.

The largest sub-family of the TGF-β superfamily is the BMP/GDF family, which comprises nearly half of all known ligands. Many of the ligands in BMP/GDF family share both BMP and GDF designations, such as GDF-7 which also referred to as BMP-12. In conjunction with being largest family, the BMP/GDF family is also the most extensively studied family. For example, x-ray crystal structures have been solved for BMP-2 alone, bound to its type I receptor, or as a ternary complex bound to both its receptor types. Additionally, BMP-2, along with BMP-7, has been utilized as an effective treatment for certain bone injuries. One of the reasons for the large amount of structural and therapeutic work involving the BMP/GDF family has been the ability to chemically refold these ligands. Indeed, BMP-2 is one of the most successful TGF-β ligands at refolding, with optimized conditions reported to yield up to 63% active dimer from starting material. However, if specific amino acids of BMP-2 could be incorporated into other TGF-β ligands, it may allow for these otherwise non-refoldable ligands to be refolded opening up the remainder of the TGF-β superfamily to be better studied.

TGF-β ligands are synthesized as inactive precursor molecules composed of an N-terminal pro-domain and a C-terminal mature domain linked by a protease cleavage site. To be become active, the mature domain must be cleaved from the pro-domain, commonly by a convertase, such as furin. Members of the TGF-β superfamily are classified together due to the conserved structural architecture found in their mature domains. In general, each mature ligand monomer contains 7 cysteines, 6 of which form three intra-disulfide bonds arranged in a 'cystine knot' motif. Stretching outward from the 'cystine knot' are 4 beta strands, creating 2 curved fingers. The last remaining cysteine forms an inter-disulfide bond with a second ligand monomer, generating a covalently linked dimer. The dimer has the overall appearance of a butterfly with the 'cystine knot' as the body and the fingers spreading out like wings. The functional subunit for the TGF-β superfamily is the dimer and they been shown to exist both as homo- and heterodimers in vivo. Some family members, such as GDF-9 and BMP-15, lack the cysteine required to form the inter-disulfide bond yet they are still able to form stable dimers.

To initiate the signaling process, TGF-β dimers must recruit two sets of receptors, termed type I and type II. These receptors are serine/threonine kinases possessing an extracellular domain (ECD) ordered into a three-finger toxin fold, a single transmembrane domain, and a large intracellular kinase domain. TGF-β ligands have been shown to display preferences in their affinity for the different receptor types. Activin and Nodal exhibit high affinity for type II receptors, while BMP-2 and GDF-5 possess higher affinity for type I receptors. Following the binding of two high affinity receptors to a TGF-β ligand, two lower affinity receptors are then able to bind and join the complex. Upon binding of all four receptors to the TGF-β ligand, forming a 6-member ternary complex, the downstream signaling cascade is initiated. The constitutively active type II receptors phosphorylate the type I receptors which, in turn, bind and phosphorylate intracellular signaling molecules called Smads. The Smad molecules then are able to translocate to the nucleus and interact directly with transcriptional regulators. Multiple mechanisms are employed to closely regulate TGF-β signaling at different stages of the cascade: Extracellular antagonists, including Noggin, follistatin, and Inhibin; pseudo-receptors lacking the intracellular kinase domain, similar to BAMBI; or through intracellular molecules, such as inhibitory Smads.

TGF-β superfamily shows a high degree of promiscuity by receptors for the ligands. While there are over 40 TGF-β ligands, there are only 12 receptors (7 type I and 5 type II). Therefore, receptors must be able to interact with a multitude of different ligands. For instance, ActRII is known to bind activin and BMP-7 with high affinity, but binds BMP-2 with much lower affinity. In GDF-5, a single amino acid has been found which determines its type I receptor preference, while in BMP-3 a single point mutation was discovered which alters type II receptor affinity as well as imparting function to the ligand. The disclosure provides methods to create modified TGF-β ligands with novel receptor binding properties thereby diversifying TGF-β ligand function as well as compositions having such activity.

The disclosure demonstrates a TGF-beta signaling complex by utilizing novel ligand constructs. Using synthesized chimeric homo- or heterodimeric ligands the ligands the disclosure provides compositions for use in dissecting the signaling of TGF-beta family proteins. Furthermore, utilizing such ligands allows a method for distinguishing contributions of two type I receptor interfaces from each other, and two type II receptor interfaced each other. The methods and compositions of the disclosure demonstrate a correlation between ligand-receptor affinity, signaling activity, and biological activity. The methods and compositions of the disclosure shed light on the mechanism and requirements of the TGF-beta superfamily signaling complex assembly. In addition the chimeric ligands provide novel polypeptide for use in treating diseases and disorders associated with TGF-β family of proteins.

The disclosure provides methods of making and novel chimeric TGF-β ligands which possess the ability to be expressed and refolded using, for example, an *E. coli* or mammalian expression system. These chimeras either mimic a specific TGF-β ligand's signaling characteristics or display unique signaling properties not seen in nature. In one embodiment, the disclosure uses activin-βA and BMP-2 as a template to generate an activin/BMP-2 chimera with the refolding efficiency of BMP-2 and the signaling properties of activin-βA; however it should be recognized that any number of TGF-beta protein family members can be used. The chimera design scheme of the disclosure yielded additional TGF-beta member chimera (e.g., activin/BMP-2) ligands with unnatural signaling characteristics and biological activity. Such chimeric TGF-beta family polypeptides expand the library of TGF-β ligands available for structural studies as well as facilitate the development of novel TGF-β ligands as therapeutic agents.

In one embodiment the disclosure provides a series of activin/BMP-2 chimeric ligands which possess unique signaling properties. For example, an activin/BMP-2 ligand of the disclosure exhibited the refolding characteristics of wild type BMP-2 while retaining activin-like signaling attributes in both in vitro and in vivo studies. Further, 'super' ligands were generated which are more potent than wild type BMP-2 and were not inhibited by the BMP antagonist Noggin. The disclosure also provides chimeric TGF-beta polypeptides comprising an N-terminus of wild type BMP-2mq operably linked to a different TGF-β ligand polypeptide segment. The disclosure demonstrates that the N-terminal portion of wild type BMP-2mq is enough to switch a previously non-refolding ligand into a refoldable ligand. These findings highlight a method for obtaining activin and the other TGF-β ligand mimics and indicate how this strategy can be utilized to expand the library of TGF-β ligands by diversifying their functionality and promote the development of unnatural ligands for therapeutic purposes.

The nucleic acid sequences and polypeptide sequences of BMP-2 and naturally occurring variants are known. A wild-type BMP-2 nucleic acid sequence (SEQ ID NO:1) and polypeptide (SEQ ID NO:2) from *Rattus* sp. are provided. Met at the position N-terminal to the residue 1 (Q) results from translation of the bacterial initiation codon (ATG). Furthermore activins are also known in the art (see, e.g., SEQ ID NO:5). The disclosure provides a number of chimeric TGF-beta family polypeptides having at least one N-terminal domain from a BMP-2 and at lease one second domain form another TGF-beta family members wherein the chimeric polypeptide display activities different than wild-type parental proteins.

In one embodiment, two factors were considered when looking to design the segments of the chimeras. First was a structural consideration. The overall TGF-β monomer fold is divided into 6 sections naturally: Beta strand 1 and 2, the pre-helix loop, alpha helix 1, and beta strand 3 and 4. The identification and characterization of these subdomains are further described in Example 4. The disclosure utilized a chimeric structures to mimic these natural regions in the design. Thus, each segment can be indicated by 1, 2, 3, 4, 5, and 6. The second consideration was to minimize alterations to the aligned native TGF-beta member sequence during chimera engineering. Therefore, those regions with sequence identity between the 2 protein sequences were identified as putative cross-over points. These regions are suitable for the overlaps in DNA sequence for PCR strategy and will minimize any changes to the natural sequences. FIG. 7 illustrates the sequence and structure of these considerations. The regions are boxed and numbered according to their section and are mapped onto the ligand monomer. The areas which can be used for the cross-over points as segmental boundaries are shaded as a sequence range in orange. Residue numbering in one embodiment is based on BMP-2 (SEQ ID NO:2). Thus, cross-over points in generating a chimeric polypeptide of the disclosure can be identified by identifying similar structural motifs in combination with at least 60%, 70%, 80%, 90%, 95%, 98%, 99% or 100% identity in a segment of the sequence between changes in the structural motif. Cross-overs at these regions (which may be between 3 to 20 amino acids) minimize disruption of the resulting chimeric polypeptide providing a stabilized chimera.

For example, a chimeric polypeptide comprising the algorithm 1b2b3b4b5b6a indicates 6 segments, the letter indicating the parental strand of each segment. Thus, in the example "1b2b3b4b5b6a", segment 1 is from parental strand "b" for BMP-2mq, segment 2 is from parental strand "b" for BMP-2mq, segment 3 is from parental strand "b" for BMP-2mq, segment 4 is from parental strand "b" for BMP-2mq, segment 5 is from parental strand "b" for BMP-2mq, and segment 6 is from parental strand "a" for Activin.

In one embodiment, crossover between segments of BMP-2mq and a second TGF-beta family protein can occur where structural similarity and sequence similarly overlap. FIG. 7 depicts such an overlap between BMP-2mq and activin, wherein crossovers can be generated between about residue D25-P35, G45-P48; T65-N68; K76-T82; and S88-E94 (residue numbering is based on BMP-2 (SEQ ID NO:2)). Sequence alignment of BMP-2 and activin-βA highlight the boundaries of segments 1 through 6. Activin has the extra disulfide bond formed between two Cys. Red (or first shaded boxes on lower sequences) box notes two amino acids of AB2-009 swapped into AB2-008. Blue (second shaded box L/Y on lower lines) box notes one amino acid changed in Segment 5 of BMP2 for all chimera. For clarity, BMP-2's Segment 5 contains YYD instead of YLD. Green (KKQ-FFVSFKDI) box denotes a segment introduced into AB2-008 to make AB2-010, marked as (1a_II) of AB2-010.

FIG. 18 further depicts such crossover regions with reference to additional members of the TGF-β family or proteins. For example, with reference to FIG. 18, one of skill in the art can see that BMP-3 (SEQ ID NO:43) comprises 110 amino acids. The first vertical line demonstrates a general region of cross over and can comprise from 1-5 amino acids on either side of the vertical line. Accordingly, a first domain from BMP-3 can comprise amino acid 1 to about $x_1$, wherein $x_1$ is an amino acid corresponding to residue 20-29 (e.g., x1 is 20, 21, 22, 23, 24, 25, 26, 27, 28, or 29). As further shown in FIG. 18, "J1" corresponds to residues 20-23 of SEQ ID NO:43). J1 refers to a junction region having conservation across the various species in the TGF-β family of proteins. Accordingly, a first domain of BMP-3 comprises amino acids 1 to about $x_1$, wherein $x_1$ will be either V or G and the following chimeric domain from a second TGF-β family member will begin with either G or W. Using FIG. 18 as a template one of skill in the art can readily identify the cross-over regions (or junctions points) for the various members of the TGF-β family. It is important to note that not every chimera is required to have 6 distinct domains. For example, a cross over at junction 3 (J3) may not be necessary such that only 5 or fewer domains from distinct family member are present in the final chimera.

Other methods for identifying crossover locations may be employed in the generation of chimeric TGF-beta family polypeptides. For example, SCHEMA is a computational based method for predicting which fragments of homologous proteins can be recombined without affecting the structural integrity of the protein (see, e.g., Meyer et al., (2003) Protein Sci., 12:1686-1693). Chimeras with higher stability are identifiable by determining the additive contribution of each segment to the overall stability, either by use of linear regression of sequence-stability data, or by reliance on consensus analysis of the MSAs of folded versus unfolded proteins. SCHEMA recombination ensures that the chimeras retain biological function and exhibit high sequence diversity by conserving important functional residues while exchanging tolerant ones.

As presented in this disclosure, it has been found that when these recombined, functional chimeric TGF-beta family polypeptides are generated their ligand specificity can be improved or biological activity can be altered or improved compared to a unrecombined parental polypeptide. Because of differences in activity/ligand profiles, these engineered chimeric TGF-beta family polypeptides provide a unique basis to screen for activities for ligand specific activation and inhibition, provide novel therapeutic polypeptides and research reagents.

For example, in the chimeras of the disclosure, domain 1, 2, 3, 4, 5, and 6 can be selected from the following sequences (Table A) wherein the polypeptide comprises a structure (domain 1-domain 2-domain 3-domain 4-domain 5-domain 6):

TABLE A

| Amino acids (domain #) | SEQ ID NO: | Variable definition |
|---|---|---|
| 1-$x_1$ (1) | 2 | $x_1$ is 25, 26, 27, 28, 29, 30, 31, 32, 33, 34, or 35 |
| 1-$x_1$ (1) | 5 | $x_1$ is 22, 23, 24, 25, 26, 27, 28, 29, 30, 31 or 32 |
| 1-$x_1$ (1) | 43 | $x_1$ is 20, 21, 22, 23, 24, 25, 26, 27, 28, or 29 |
| 1-$x_1$ (1) | 45 | $x_1$ is 27, 28, 29, 30, 31, 32, 33, 34, 35, or 36 |
| 1-$x_1$ (1) | 47 | $x_1$ is 43, 44, 44, 46 47, 48, 49, 50, 51, or 52 |
| 1-$x_1$ (1) | 49 | $x_1$ is 43, 44, 44, 46 47, 48, 49, 50, 51, or 52 |
| 1-$x_1$ (1) | 51 | $x_1$ is 50, 51, 52, 53, 54, 55, 56, 57, 58, 59, or 60 |
| 1-$x_1$ (1) | 53 | $x_1$ is 50, 51, 52, 53, 54, 55, 56, 57, 58, 59, or 60 |
| 1-$x_1$ (1) | 55 | $x_1$ is 19, 20, 21, 22, 23, 24, 25, 26 27, or 28 |
| 1-$x_1$ (1) | 57 | $x_1$ is 18, 19, 20, 21, 22, 23, 24, 25, 26 or 27 |
| 1-$x_1$ (1) | 59 | $x_1$ is 36, 37, 38, 29, 40, 41, 42, 43, 44, or 45 |
| 1-$x_1$ (1) | 61 | $x_1$ is 25, 26, 27, 28, 29, 30, 31, 32, 33 or 34 |
| 1-$x_1$ (1) | 63 | $x_1$ is 25, 26, 27, 28, 29, 30, 31, 32, 33 or 34 |
| 1-$x_1$ (1) | 65 | $x_1$ is 30, 31, 32, 33, 34, 35, 36, 37, 38, 39 or 40 |
| 1-$x_1$ (1) | 67 | $x_1$ is 30, 31, 32, 33, 34, 35, 36, 37, 38, 39 or 40 |
| 1-$x_1$ (1) | 69 | $x_1$ is 40, 41, 42, 43, 44, 45, 46, 47, 48 or 49 |
| 1-$x_1$ (1) | 71 | $x_1$ is 25, 26, 27, 28, 29, 30, 31, 32, 33 or 34 |
| 1-$x_1$ (1) | 73 | $x_1$ is 45, 46, 47, 48, 49, 50, 51, 52, 53, 54, or 55 |
| 1-$x_1$ (1) | 75 | $x_1$ is 28, 29, 30, 31, 32, 33, 34, 35, 36, or 37 |
| 1-$x_1$ (1) | 77 | $x_1$ is 25, 26, 27, 28, 29, 30, 31, 32, 33 or 34 |

TABLE A-continued

| Amino acids (domain #) | SEQ ID NO: | Variable definition |
|---|---|---|
| 1-$x_1$ (1) | 79 | $x_1$ is 24, 25, 26, 27, 28, 29, 30, 31, 32, or 33 |
| 1-$x_1$ (1) | 81 | $x_1$ is 21, 22, 23, 24, 25, 26, 27, 28, 29 or 30 |
| 1-$x_1$ (1) | 83 | $x_1$ is 22, 23, 24, 25, 26, 27, 28, 29, 30 or 31 |
| 1-$x_1$ (1) | 85 | $x_1$ is 22, 23, 24, 25, 26, 27, 28, 29, 30 or 31 |
| 1-$x_1$ (1) | 87 | $x_1$ is 22, 23, 24, 25, 26, 27, 28, 29, 30 or 31 |
| 1-$x_1$ (1) | 89 | $x_1$ is 22, 23, 24, 25, 26, 27, 28, 29, 30 or 31 |
| 1-$x_1$ (1) | 91 | $x_1$ is 42, 43, 44, 45, 46, 47, 48, 49, 50 or 51 |
| 1-$x_1$ (1) | 93 | $x_1$ is 28, 29, 30, 31, 32, 33, 34, 35, 36 or 37 |
| 1-$x_1$ (1) | 95 | $x_1$ is 24, 25, 26, 27, 28, 29, 30, 31, 32 or 33 |
| 1-$x_1$ (1) | 97 | $x_1$ is 24, 25, 26, 27, 28, 29, 30, 31, 32 or 33 |
| $x_1$-$x_2$ (2) | 2 | $x_1$ is 25, 26, 27, 28, 29, 30, 31, 32, 33, 34 or 35<br>$x_2$ is 43, 44, 45, 46, 47, 48, 49, 50, 51, or 52 |
| $x_1$-$x_2$ (2) | 5 | $x_1$ is 22, 23, 24, 25, 26, 27, 28, 29, 30, 31 or 32<br>$x_2$ is 41, 42, 43, 44, 45, 46, 47, 48, 49, 50 or 51 |
| $x_1$-$x_2$ (2) | 43 | $x_1$ is 20, 21, 22, 23, 24, 25, 26, 27, 28 or 29<br>$x_2$ is 38, 39, 40, 41, 42, 43, 44, 45, 46 or 47 |
| $x_1$-$x_2$ (2) | 45 | $x_1$ is 27, 28, 29, 30, 31, 32, 33, 34, 35 or 36<br>$x_2$ is 46, 47, 48, 49, 50, 51, 52, 53, 54 or 55 |
| $x_1$-$x_2$ (2) | 47 | $x_1$ is 43, 44, 44, 46 47, 48, 49, 50, 51 or 52<br>$x_2$ is 61, 62, 63, 64, 65, 66, 67, 68, 69 or 70 |
| $x_1$-$x_2$ (2) | 49 | $x_1$ is 43, 44, 44, 46 47, 48, 49, 50, 51 or 52<br>$x_2$ is 61, 62, 63, 64, 65, 66, 67, 68, 69 or 70 |
| $x_1$-$x_2$ (2) | 51 | $x_1$ is 50, 51, 52, 53, 54, 55, 56, 57, 58, 59 or 60<br>$x_2$ is 68, 69, 70, 71, 72, 73, 74, 75, 76, 77 or 78 |
| $x_1$-$x_2$ (2) | 53 | $x_1$ is 50, 51, 52, 53, 54, 55, 56, 57, 58, 59 or 60<br>$x_2$ is 68, 69, 70, 71, 72, 73, 74, 75, 76, 77 or 78 |
| $x_1$-$x_2$ (2) | 55 | $x_1$ is 19, 20, 21, 22, 23, 24, 25, 26 27, or 28<br>$x_2$ is 38, 39, 40, 41, 42, 43, 44, 45, 46 or 47 |
| $x_1$-$x_2$ (2) | 57 | $x_1$ is 18, 19, 20, 21, 22, 23, 24, 25, 26 or 27<br>$x_2$ is 37, 38, 39, 40, 41, 42, 43, 44, 45 or 49 |
| $x_1$-$x_2$ (2) | 59 | $x_1$ is 36, 37, 38, 29, 40, 41, 42, 43, 44 or 45<br>$x_2$ is 53, 54, 55, 56, 57, 58, 59, 60, 61 or 62 |
| $x_1$-$x_2$ (2) | 61 | $x_1$ is 25, 26, 27, 28, 29, 30, 31, 32, 33 or 34<br>$x_2$ is 43, 44, 45, 46, 47, 48, 49, 50, 51, 52 or 53 |
| $x_1$-$x_2$ (2) | 63 | $x_1$ is 25, 26, 27, 28, 29, 30, 31, 32, 33 or 34<br>$x_2$ is 43, 44, 45, 46, 47, 48, 49, 50, 51, 52 or 53 |
| $x_1$-$x_2$ (2) | 65 | $x_1$ is 30, 31, 32, 33, 34, 35, 36, 37, 38, 39 or 40<br>$x_2$ is 48, 49, 50, 51, 52, 53, 54, 55, 56, 57 or 58 |
| $x_1$-$x_2$ (2) | 67 | $x_1$ is 30, 31, 32, 33, 34, 35, 36, 37, 38, 39 or 40<br>$x_2$ is 48, 49, 50, 51, 52, 53, 54, 55, 56, 57 or 58 |
| $x_1$-$x_2$ (2) | 69 | $x_1$ is 40, 41, 42, 43, 44, 45, 46, 47, 48 or 49<br>$x_2$ is 57, 58, 59, 60, 61, 62, 63, 64, 65 or 66 |
| $x_1$-$x_2$ (2) | 71 | $x_1$ is 25, 26, 27, 28, 29, 30, 31, 32, 33 or 34<br>$x_2$ is 43, 44, 45, 46, 47, 48, 49, 50, 51, or 52 |
| $x_1$-$x_2$ (2) | 73 | $x_1$ is 45, 46, 47, 48, 49, 50, 51, 52, 53, 54, or 55<br>$x_2$ is 63, 64, 65, 66, 67, 68, 69, 70, 71, 72 or 73 |
| $x_1$-$x_2$ (2) | 75 | $x_1$ is 28, 29, 30, 31, 32, 33, 34, 35, 36, or 37<br>$x_2$ is 46, 47, 48, 49, 50, 51, 52, 53, 54 or 55 |
| $x_1$-$x_2$ (2) | 77 | $x_1$ is 25, 26, 27, 28, 29, 30, 31, 32, 33 or 34<br>$x_2$ is 43, 44, 45, 46, 47, 48, 49, 50, 51, 52 or 53 |
| $x_1$-$x_2$ (2) | 79 | $x_1$ is 24, 25, 26, 27, 28, 29, 30, 31, 32 or 33<br>$x_2$ is 44, 45, 46, 47, 48, 49, 50, 51, 52 or 53 |
| $x_1$-$x_2$ (2) | 81 | $x_1$ is 21, 22, 23, 24, 25, 26, 27, 28, 29 or 30<br>$x_2$ is 39, 40, 41, 42, 43, 44, 45, 46, 47 or 48 |
| $x_1$-$x_2$ (2) | 83 | $x_1$ is 22, 23, 24, 25, 26, 27, 28, 29, 30 or 31<br>$x_2$ is 41, 42, 43, 44, 45, 46, 47, 48, 49, 50 or 51 |
| $x_1$-$x_2$ (2) | 85 | $x_1$ is 22, 23, 24, 25, 26, 27, 28, 29, 30 or 31<br>$x_2$ is 41, 42, 43, 44, 45, 46, 47, 48, 49, 50 or 51 |
| $x_1$-$x_2$ (2) | 87 | $x_1$ is 22, 23, 24, 25, 26, 27, 28, 29, 30 or 31<br>$x_2$ is 41, 42, 43, 44, 45, 46, 47, 48, 49, 50 or 51 |
| $x_1$-$x_2$ (2) | 89 | $x_1$ is 22, 23, 24, 25, 26, 27, 28, 29, 30 or 31<br>$x_2$ is 41, 42, 43, 44, 45, 46, 47, 48, 49, 50 or 51 |
| $x_1$-$x_2$ (2) | 91 | $x_1$ is 42, 43, 44, 45, 46, 47, 48, 49, 50 or 51<br>$x_2$ is 59, 60, 61, 62, 63, 65, 65, 66, 67 or 68 |
| $x_1$-$x_2$ | 93 | $x_1$ is 28, 29, 30, 31, 32, 33, 34, 35, 36 or 37 |

TABLE A-continued

| Amino acids (domain #) | SEQ ID NO: | Variable definition |
|---|---|---|
| (2) | | $x_2$ is 46, 47, 48, 49, 50, 51, 52, 53, 54 or 55 |
| $x_1$-$x_2$ (2) | 95 | $x_1$ is 24, 25, 26, 27, 28, 29, 30, 31, 32 or 33<br>$x_2$ is 44, 45, 46, 47, 48, 49, 50, 51, 52 or 53 |
| $x_1$-$x_2$ (2) | 97 | $x_1$ is 24, 25, 26, 27, 28, 29, 30, 31, 32 or 33<br>$x_2$ is 44, 45, 46, 47, 48, 49, 50, 51, 52 or 53 |
| $x_2$-$x_3$ (3) | 2 | $x_2$ is 43, 44, 45, 46, 47, 48, 49, 50, 51, or 52<br>$x_3$ is 58, 59, 60, 61, 62, 63, 64, 65, 66, 67, 68, 69 or 70 |
| $x_2$-$x_3$ (3) | 5 | $x_2$ is 41, 42, 43, 44, 45, 46, 47, 48, 49, 50 or 51<br>$x_3$ is 55, 56, 57, 58, 59, 60, 61, 62, 63, 6, 4 65, 66, 67, 68, 69, 70, 71, 72, 73, or 74 |
| $x_2$-$x_3$ (3) | 43 | $x_2$ is 38, 39, 40, 41, 42, 43, 44, 45, 46 or 47<br>$x_3$ is 52, 53, 54, 55, 56, 57, 58, 59, 60, 61, 62, 63, 64 or 65 |
| $x_2$-$x_3$ (3) | 45 | $x_2$ is 46, 47, 48, 49, 50, 51, 52, 53, 54 or 55<br>$x_3$ is 61, 62, 63, 64, 65, 66, 67, 68, 69, 70, 71, 72, 73 or 74 |
| $x_2$-$x_3$ (3) | 47 | $x_2$ is 61, 62, 63, 64, 65, 66, 67, 68, 69 or 70<br>$x_3$ is 75, 76, 77, 78, 79, 80, 81, 82, 83, 84, 85, 86, 87 or 88 |
| $x_2$-$x_3$ (3) | 49 | $x_2$ is 61, 62, 63, 64, 65, 66, 67, 68, 69 or 70<br>$x_3$ is 75, 76, 77, 78, 79, 80, 81, 82, 83, 84, 85, 86, 87 or 88 |
| $x_2$-$x_3$ (3) | 51 | $x_2$ is 68, 69, 70, 71, 72, 73, 74, 75, 76, 77 or 78<br>$x_3$ is 82, 83, 84, 85, 86, 87, 88, 89, 90, 91, 92, 93, 94 or 95 |
| $x_2$-$x_3$ (3) | 53 | $x_2$ is 68, 69, 70, 71, 72, 73, 74, 75, 76, 77 or 78<br>$x_3$ is 82, 83, 84, 85, 86, 87, 88, 89, 90, 91, 92, 93, 94 or 95 |
| $x_2$-$x_3$ (3) | 55 | $x_2$ is 38, 39, 40, 41, 42, 43, 44, 45, 46 or 47<br>$x_3$ is 52, 53, 54, 55, 56, 57, 58, 59, 60, 61, 62, 63, 64 or 65 |
| $x_2$-$x_3$ (3) | 57 | $x_2$ is 37, 38, 39, 40, 41, 42, 43, 44, 45 or 49<br>$x_3$ is 51, 52, 53, 54, 55, 56, 57, 58, 59, 60, 61, 62, 63, or 64 |
| $x_2$-$x_3$ (3) | 59 | $x_2$ is 53, 54, 55, 56, 57, 58, 59, 60, 61 or 62<br>$x_3$ is 68, 69, 70, 71, 72, 73, 74, 75, 76, 77, 78, 79, 80 or 81 |
| $x_2$-$x_3$ (3) | 61 | $x_2$ is 43, 44, 45, 46, 47, 48, 49, 50, 51, 52 or 53<br>$x_3$ is 57, 58, 59, 60, 61, 62, 63, 64, 65, 66, 67, 68, 69, 70, 71, 72, 73, 74, 75 or 76 |
| $x_2$-$x_3$ (3) | 63 | $x_2$ is 43, 44, 45, 46, 47, 48, 49, 50, 51, 52 or 53<br>$x_3$ is 58, 59, 60, 61, 62, 63, 64, 65, 66, 67, 68, 69 or 70 |
| $x_2$-$x_3$ (3) | 65 | $x_2$ is 48, 49, 50, 51, 52, 53, 54, 55, 56, 57 or 58<br>$x_3$ is 63, 64, 65, 66, 67, 68, 69, 70, 71, 72, 73, 74 or 75 |
| $x_2$-$x_3$ (3) | 67 | $x_2$ is 48, 49, 50, 51, 52, 53, 54, 55, 56, 57 or 58<br>$x_3$ is 63, 64, 65, 66, 67, 68, 69, 70, 71, 72, 73, 74 or 75 |
| $x_2$-$x_3$ (3) | 69 | $x_2$ is 57, 58, 59, 60, 61, 62, 63, 64, 65 or 66<br>$x_3$ is 72, 73, 74, 75, 76, 77, 78, 79, 80, 81, 82, 83 or 84 |
| $x_2$-$x_3$ (3) | 71 | $x_2$ is 43, 44, 45, 46, 47, 48, 49, 50, 51, or 52<br>$x_3$ is 53, 54, 55, 56, 57, 58, 59, 60, 61, 62, 63, 64 or 65 |
| $x_2$-$x_3$ (3) | 73 | $x_2$ is 63, 64, 65, 66, 67, 68, 69, 70, 71, 72 or 73<br>$x_3$ is 78, 79, 80, 81, 82, 83, 84, 85, 86, 87, 88, 89 or 90 |
| $x_2$-$x_3$ (3) | 75 | $x_2$ is 46, 47, 48, 49, 50, 51, 52, 53, 54 or 55<br>$x_3$ is 61, 62, 63, 64, 65, 66, 67, 68, 69, 70, 71, 72 or 73 |
| $x_2$-$x_3$ (3) | 77 | $x_2$ is 43, 44, 45, 46, 47, 48, 49, 50, 51, 52 or 53<br>$x_3$ is 54, 55, 56, 57, 58, 59, 60, 61, 62, 63, 64 or 65 |
| $x_2$-$x_3$ (3) | 79 | $x_2$ is 44, 45, 46, 47, 48, 49, 50, 51, 52 or 53<br>$x_3$ is 56, 57, 58, 59, 60, 61, 62, 63, 64, 65, 66, 67 or 68 |
| $x_2$-$x_3$ (3) | 81 | $x_2$ is 39, 40, 41, 42, 43, 44, 45, 46, 47 or 48<br>$x_3$ is 54, 55, 56, 57, 58, 59, 60, 61, 62, 63, 64, 65 or 66 |
| $x_2$-$x_3$ (3) | 83 | $x_2$ is 41, 42, 43, 44, 45, 46, 47, 48, 49, 50 or 51<br>$x_3$ is 55, 56, 5, 58, 59, 60, 61, 62, 63, 64, 65, 66, 67, 68, 69, 70, 71, 72, 73, or 74 |
| $x_2$-$x_3$ (3) | 85 | $x_2$ is 41, 42, 43, 44, 45, 46, 47, 48, 49, 50 or 51<br>$x_3$ is 55, 56, 5, 58, 59, 60, 61, 62, 63, 64, 65, 66, 67, 68, 69, 70, 71, 72, 73, or 74 |
| $x_2$-$x_3$ (3) | 87 | $x_2$ is 41, 42, 43, 44, 45, 46, 47, 48, 49, 50 or 51<br>$x_3$ is 55, 56, 5, 58, 59, 60, 61, 62, 63, 64, 65, 66, 67, 68, 69, 70, 71, 72, 73, or 74 |
| $x_2$-$x_3$ (3) | 89 | $x_2$ is 41, 42, 43, 44, 45, 46, 47, 48, 49, 50 or 51<br>$x_3$ is 55, 56, 5, 58, 59, 60, 61, 62, 63, 64, 65, 66, 67, 68, 69, 70, 71, 72, 73, or 74 |
| $x_2$-$x_3$ (3) | 91 | $x_2$ is 59, 60, 61, 62, 63, 65, 65, 66, 67 or 68<br>$x_3$ is 74, 75, 76, 77, 78, 79, 80, 81, 82, 83, 84, 85, 86 or 87 |
| $x_2$-$x_3$ (3) | 93 | $x_2$ is 46, 47, 48, 49, 50, 51, 52, 53, 54 or 55<br>$x_3$ is 58, 59, 60, 61, 62, 63, 64, 65, 66, 67, 68, 69 or 70 |
| $x_2$-$x_3$ (3) | 95 | $x_2$ is 44, 45, 46, 47, 48, 49, 50, 51, 52 or 53<br>$x_3$ is 54, 55, 56, 57, 58, 59, 60, 61, 62, 63, 64 or 65 |
| $x_2$-$x_3$ (3) | 97 | $x_2$ is 44, 45, 46, 47, 48, 49, 50, 51, 52 or 53<br>$x_3$ is 54, 55, 56, 57, 58, 59, 60, 61, 62, 63, 64 or 65 |
| $x_3$-$x_4$ (4) | 2 | $x_3$ is 58, 59, 60, 61, 62, 63, 64, 65, 66, 67, 68, 69 or 70<br>$x_4$ is 78, 79, 80, 81, 82, 83, 84 or 85 |
| $x_3$-$x_4$ (4) | 5 | $x_3$ is 55, 56, 57, 58, 59, 60, 61, 62, 63, 6, 4 65, 66, 67, 68, 69, 70, 71, 72, 73, or 74<br>$x_4$ is 79, 80, 81, 82, 83, 84, 85 or 86 |
| $x_3$-$x_4$ (4) | 43 | $x_3$ is 52, 53, 54, 55, 56, 57, 58, 59, 60, 61, 62, 63, 64 or 65<br>$x_4$ is 73, 74, 75, 76, 77, 78, 79 or 80 |
| $x_3$-$x_4$ (4) | 45 | $x_3$ is 61, 62, 63, 64, 65, 66, 67, 68, 69, 70, 71, 72, 73 or 74<br>$x_4$ is 79, 80, 81, 82, 83, 84, 85 or 86 |
| $x_3$-$x_4$ (4) | 47 | $x_3$ is 75, 76, 77, 78, 79, 80, 81, 82, 83, 84, 85, 86, 87 or 88<br>$x_4$ is 95, 96, 97, 98, 99, 100, 101, 102 or 103 |
| $x_3$-$x_4$ (4) | 49 | $x_3$ is 75, 76, 77, 78, 79, 80, 81, 82, 83, 84, 85, 86, 87 or 88<br>$x_4$ is 95, 96, 97, 98, 99, 100, 101, 102 or 103 |
| $x_3$-$x_4$ (4) | 51 | $x_3$ is 82, 83, 84, 85, 86, 87, 88, 89, 90, 91, 92, 93, 94 or 95<br>$x_4$ is 102, 103, 104, 105, 106, 107, 108, 109 or 110 |
| $x_3$-$x_4$ (4) | 53 | $x_3$ is 82, 83, 84, 85, 86, 87, 88, 89, 90, 91, 92, 93, 94 or 95<br>$x_4$ is 102, 103, 104, 105, 106, 107, 108, 109 or 110 |
| $x_3$-$x_4$ (4) | 55 | $x_3$ is 52, 53, 54, 55, 56, 57, 58, 59, 60, 61, 62, 63, 64 or 65<br>$x_4$ is 72, 73, 74, 75, 76, 77, 78, 79 or 80 |
| $x_3$-$x_4$ (4) | 57 | $x_3$ is 51, 52, 53, 54, 55, 56, 57, 58, 59, 60, 61, 62, 63, or 64<br>$x_4$ is 71, 72, 73, 74, 75, 76, 77, 78 or 79 |
| $x_3$-$x_4$ (4) | 59 | $x_3$ is 68, 69, 70, 71, 72, 73, 74, 75, 76, 77, 78, 79, 80 or 81<br>$x_4$ is 78, 79, 80, 81, 82, 83, 84, 85 or 86 |
| $x_3$-$x_4$ (4) | 61 | $x_3$ is 57, 58, 59, 60, 61, 62, 63, 64, 65, 66, 67, 68, 69, 70, 71, 72, 73, 74, 75 or 76<br>$x_4$ is 82, 83, 84, 85, 86, 87, 88, 89 or 90 |
| $x_3$-$x_4$ (4) | 63 | $x_3$ is 58, 59, 60, 61, 62, 63, 64, 65, 66, 67, 68, 69 or 70<br>$x_4$ is 77, 78, 79, 80, 81, 82, 83, 84 or 85 |
| $x_3$-$x_4$ (4) | 65 | $x_3$ is 63, 64, 65, 66, 67, 68, 69, 70, 71, 72, 73, 74 or 75<br>$x_4$ is 83, 84, 85, 86, 87, 88, 89, 90 or 91 |
| $x_3$-$x_4$ (4) | 67 | $x_3$ is 63, 64, 65, 66, 67, 68, 69, 70, 71, 72, 73, 74 or 75<br>$x_4$ is 83, 84, 85, 86, 87, 88, 89, 90 or 91 |
| $x_3$-$x_4$ (4) | 69 | $x_3$ is 72, 73, 74, 75, 76, 77, 78, 79, 80, 81, 82, 83 or 84<br>$x_4$ is 92, 93, 94, 95, 96, 97, 98, 99 or 100 |
| $x_3$-$x_4$ (4) | 71 | $x_3$ is 53, 54, 55, 56, 57, 58, 59, 60, 61, 62, 63, 64 or 65<br>$x_4$ is 72, 73, 74, 75, 76, 77, 78, 79 or 80 |
| $x_3$-$x_4$ (4) | 73 | $x_3$ is 78, 79, 80, 81, 82, 83, 84, 85, 86, 87, 88, 89 or 90<br>$x_4$ is 98, 99, 100, 101, 102, 103, 104, 105 or 106 |
| $x_3$-$x_4$ (4) | 75 | $x_3$ is 61, 62, 63, 64, 65, 66, 67, 68, 69, 70, 71, 72 or 73<br>$x_4$ is 82, 83, 84, 85, 86, 87, 88, 89, or 90 |
| $x_3$-$x_4$ (4) | 77 | $x_3$ is 54, 55, 56, 57, 58, 59, 60, 61, 62, 63, 64 or 65<br>$x_4$ is 72, 73, 74, 75, 76, 77, 78, 79 or 80 |
| $x_3$-$x_4$ (4) | 79 | $x_3$ is 56, 57, 58, 59, 60, 61, 62, 63, 64, 65, 66, 67 or 68<br>$x_4$ is 76, 77, 78, 79, 80, 81, 82, 83 or 84 |
| $x_3$-$x_4$ (4) | 81 | $x_3$ is 54, 55, 56, 57, 58, 59, 60, 61, 62, 63, 64, 65 or 66<br>$x_4$ is 74, 75, 76, 77, 78, 79, 80, 81 or 82 |
| $x_3$-$x_4$ (4) | 83 | $x_3$ is 55, 56, 5, 58, 59, 60, 61, 62, 63, 64, 65, 66, 67, 68, 69, 70, 71, 72, 73, or 74<br>$x_4$ is 79, 80, 81, 82, 83, 84, 85, 86 or 87 |
| $x_3$-$x_4$ (4) | 85 | $x_3$ is 55, 56, 5, 58, 59, 60, 61, 62, 63, 64, 65, 66, 67, 68, 69, 70, 71, 72, 73, or 74<br>$x_4$ is 78, 79, 80, 81, 82, 83, 84, 85 or 86 |
| $x_3$-$x_4$ (4) | 87 | $x_3$ is 55, 56, 5, 58, 59, 60, 61, 62, 63, 64, 65, 66, 67, 68, 69, 70, 71, 72, 73, or 74<br>$x_4$ is 79, 80, 81, 82, 83, 84, 85, 86 or 87 |
| $x_3$-$x_4$ (4) | 89 | $x_3$ is 55, 56, 5, 58, 59, 60, 61, 62, 63, 64, 65, 66, 67, 68, 69, 70, 71, 72, 73, or 74<br>$x_4$ is 77, 78, 79, 80, 81, 82, 83, 84 or 85 |
| $x_3$-$x_4$ (4) | 91 | $x_3$ is 74, 75, 76, 77, 78, 79, 80, 81, 82, 83, 84, 85, 86 or 87<br>$x_4$ is 96, 97, 98, 99, 100, 101, 102, 103 or 104 |
| $x_3$-$x_4$ (4) | 93 | $x_3$ is 58, 59, 60, 61, 62, 63, 64, 65, 66, 67, 68, 69 or 70<br>$x_4$ is 77, 78, 79, 80, 81, 82, 83, 84, or 85 |
| $x_3$-$x_4$ (4) | 95 | $x_3$ is 54, 55, 56, 57, 58, 59, 60, 61, 62, 63, 64 or 65<br>$x_4$ is 76, 77, 78, 79, 80, 81, 82, 83 or 84 |
| $x_3$-$x_4$ (4) | 97 | $x_3$ is 54, 55, 56, 57, 58, 59, 60, 61, 62, 63, 64 or 65<br>$x_4$ is 76, 77, 78, 79, 80, 81, 82, 83 or 84 |
| $x_4$-$x_5$ (5) | 2 | $x_4$ is 78, 79, 80, 81, 82, 83, 84 or 85<br>$x_5$ is 89, 90, 91, 92, 93, 94, 95, 96, 97 or 98 |
| $x_4$-$x_5$ (5) | 5 | $x_4$ is 79, 80, 81, 82, 83, 84, 85 or 86<br>$x_5$ is 91, 92, 93, 94, 95, 96, 97, 98, 99 or 100 |
| $x_4$-$x_5$ (5) | 43 | $x_4$ is 73, 74, 75, 76, 77, 78, 79 or 80<br>$x_5$ is 85, 86, 87, 88, 89, 90 91, 92 or 93 |
| $x_4$-$x_5$ (5) | 45 | $x_4$ is 79, 80, 81, 82, 83, 84, 85 or 86<br>$x_5$ is 91, 92, 93, 94, 95, 96, 97, 98, 99 or 100 |
| $x_4$-$x_5$ (5) | 47 | $x_4$ is 95, 96, 97, 98, 99, 100, 101, 102 or 103<br>$x_5$ 107, 108, 109, 110, 111, 112, 113, 114 or 115 |
| $x_4$-$x_5$ | 49 | $x_4$ is 95, 96, 97, 98, 99, 100, 101, 102 or 103 |

TABLE A-continued

| Amino acids (domain #) | SEQ ID NO: | Variable definition |
|---|---|---|
| (5) | | $x_5$ is 107, 108, 109, 110, 111, 112, 113, 114 or 115 |
| $x_4$-$x_5$ (5) | 51 | $x_4$ is 102, 103, 104, 105, 106, 107, 108, 109 or 110<br>$x_5$ is 114, 115, 116, 117, 118, 119, 120, 121, or 122 |
| $x_4$-$x_5$ (5) | 53 | $x_4$ is 102, 103, 104, 105, 106, 107, 108, 109 or 110<br>$x_5$ is 114, 115, 116, 117, 118, 119, 120, 121, or 122 |
| $x_4$-$x_5$ (5) | 55 | $x_4$ is 72, 73, 74, 75, 76, 77, 78, 79 or 80<br>$x_5$ is 84, 85, 86, 87, 88, 89, 90, 91, 92 or 93 |
| $x_4$-$x_5$ (5) | 57 | $x_4$ is 71, 72, 73, 74, 75, 76, 77, 78 or 79<br>$x_5$ is 83, 84, 85, 86, 87, 88, 89, 90, 91, or 92 |
| $x_4$-$x_5$ (5) | 59 | $x_4$ is 78, 79, 80, 81, 82, 83, 84, 85 or 86<br>$x_5$ is 100, 101, 102, 103, 104, 106, 106, 107 or 108 |
| $x_4$-$x_5$ (5) | 61 | $x_4$ is 82, 83, 84, 85, 86, 87, 88, 89 or 90<br>$x_5$ is 94, 95, 96, 97, 98, 99, 100, 101 or 102 |
| $x_4$-$x_5$ (5) | 63 | $x_4$ is 77, 78, 79, 80, 81, 82, 83, 84 or 85<br>$x_5$ is 89, 90, 91, 92, 93, 94, 95, 96, 97 or 98 |
| $x_4$-$x_5$ (5) | 65 | $x_4$ is 83, 84, 85, 86, 87, 88, 89, 90 or 91<br>$x_5$ is 95, 96, 97, 98, 99, 100, 101, 102 or 103 |
| $x_4$-$x_5$ (5) | 67 | $x_4$ is 83, 84, 85, 86, 87, 88, 89, 90 or 91<br>$x_5$ is 95, 96, 97, 98, 99, 100, 101, 102 or 103 |
| $x_4$-$x_5$ (5) | 69 | $x_4$ is 92, 93, 94, 95, 96, 97, 98, 99 or 100<br>$x_5$ is 104, 105, 106, 107, 108, 109, 110, 111 or 112 |
| $x_4$-$x_5$ (5) | 71 | $x_4$ is 72, 73, 74, 75, 76, 77, 78, 79 or 80<br>$x_5$ is 84, 85, 86, 87, 88, 89, 90, 91, 92 or 93 |
| $x_4$-$x_5$ (5) | 73 | $x_4$ is 98, 99, 100, 101, 102, 103, 104, 105 or 106<br>$x_5$ is 110, 111, 112, 113, 114, 115, 116, 117 or 118 |
| $x_4$-$x_5$ (5) | 75 | $x_4$ is 82, 83, 84, 85, 86, 87, 88, 89, or 90<br>$x_5$ is 94, 95, 96, 97, 98, 99, 100, 101 or 102 |
| $x_4$-$x_5$ (5) | 77 | $x_4$ is 72, 73, 74, 75, 76, 77, 78, 79 or 80<br>$x_5$ is 84, 85, 86, 87, 88, 89, 90, 91, 92 or 93 |
| $x_4$-$x_5$ (5) | 79 | $x_4$ is 76, 77, 78, 79, 80, 81, 82, 83 or 84<br>$x_5$ is 88, 89, 90, 91, 92, 93, 94, 95 or 96 |
| $x_4$-$x_5$ (5) | 81 | $x_4$ is 74, 75, 76, 77, 78, 79, 80, 81 or 82<br>$x_5$ is 86, 87, 88, 89, 90, 91, 92, 93 or 94 |
| $x_4$-$x_5$ (5) | 83 | $x_4$ is 79, 80, 81, 82, 83, 84, 85, 86 or 87<br>$x_5$ is 91, 92, 93, 94, 95, 96, 97, 98, 99 or 100 |
| $x_4$-$x_5$ (5) | 85 | $x_4$ is 78, 79, 80, 81, 82, 83, 84, 85 or 86<br>$x_5$ is 90, 91, 92, 93, 94, 95, 96, 97, 98 or 99 |
| $x_4$-$x_5$ (5) | 87 | $x_4$ is 79, 80, 81, 82, 83, 84, 85, 86 or 87<br>$x_5$ is 91, 92, 93, 94, 95, 96, 97, 98, 99 or 100 |
| $x_4$-$x_5$ (5) | 89 | $x_4$ is 77, 78, 79, 80, 81, 82, 83, 84 or 85<br>$x_5$ is 89, 90, 91, 92, 93, 94, 95, 96, 97 or 98 |
| $x_4$-$x_5$ (5) | 91 | $x_4$ is 96, 97, 98, 99, 100, 101, 102, 103 or 104<br>$x_5$ is 108, 109, 110, 111, 112, 113, 114, 115 or 116 |
| $x_4$-$x_5$ (5) | 93 | $x_4$ is 77, 78, 79, 80, 81, 82, 83, 84, or 85<br>$x_5$ is 89, 90, 91, 92, 93, 94, 95, 96, 97 or 98 |
| $x_4$-$x_5$ (5) | 95 | $x_4$ is 76, 77, 78, 79, 80, 81, 82, 83 or 84<br>$x_5$ is 88, 89, 90, 91, 92, 93, 94, 95 or 96 |
| $x_4$-$x_5$ (5) | 97 | $x_4$ is 76, 77, 78, 79, 80, 81, 82, 83 or 84<br>$x_5$ is 88, 89, 90, 91, 92, 93, 94, 95 or 96 |
| $x_5$-114 (6) | 2 | $x_5$ is 89, 90, 91, 92, 93, 94, 95, 96, 97 or 98 |
| $x_5$-116 (6) | 5 | $x_5$ is 91, 92, 93, 94, 95, 96, 97, 98, 99 or 100 |
| $x_5$-110 (6) | 43 | $x_5$ is 85, 86, 87, 88, 89, 90 91, 92 or 93 |
| $x_5$-116 (6) | 45 | $x_5$ is 91, 92, 93, 94, 95, 96, 97, 98, 99 or 100 |
| $x_5$-132 (6) | 47 | $x_5$ is 107, 108, 109, 110, 111, 112, 113, 114 or 115 |
| $x_5$-132 (6) | 49 | $x_5$ is 107, 108, 109, 110, 111, 112, 113, 114 or 115 |
| $x_5$-139 (6) | 51 | $x_5$ is 114, 115, 116, 117, 118, 119, 120, 121, or 122 |
| $x_5$-139 (6) | 53 | $x_5$ is 114, 115, 116, 117, 118, 119, 120, 121, or 122 |
| $X_5$-110 (6) | 55 | $x_5$ is 84, 85, 86, 87, 88, 89, 90, 91, 92 or 93 |
| $x_5$-108 (6) | 57 | $x_5$ is 83, 84, 85, 86, 87, 88, 89, 90, 91, or 92 |
| $x_5$-125 (6) | 59 | $x_5$ is 100, 101, 102, 103, 104, 106, 106, 107 or 108 |
| $x_5$-119 (6) | 61 | $x_5$ is 94, 95, 96, 97, 98, 99, 100, 101 or 102 |
| $x_5$-114 (6) | 63 | $x_5$ is 89, 90, 91, 92, 93, 94, 95, 96, 97 or 98 |
| $x_5$-120 (6) | 65 | $x_5$ is 95, 96, 97, 98, 99, 100, 101, 102 or 103 |
| $x_5$-120 (6) | 67 | $x_5$ is 95, 96, 97, 98, 99, 100, 101, 102 or 103 |
| $x_5$-129 (6) | 69 | $x_5$ is 104, 105, 106, 107, 108, 109, 110, 111 or 112 |
| $x_5$-109 (6) | 71 | $x_5$ is 84, 85, 86, 87, 88, 89, 90, 91, 92 or 93 |
| $x_5$-135 (6) | 73 | $x_5$ is 110, 111, 112, 113, 114, 115, 116, 117 or 118 |
| $x_5$-119 (6) | 75 | $x_5$ is 94, 95, 96, 97, 98, 99, 100, 101 or 102 |
| $x_5$-109 (6) | 77 | $x_5$ is 84, 85, 86, 87, 88, 89, 90, 91, 92 or 93 |
| $x_5$-113 (6) | 79 | $x_5$ is 88, 89, 90, 91, 92, 93, 94, 95 or 96 |
| $x_5$-110 (6) | 81 | $x_5$ is 86, 87, 88, 89, 90, 91, 92, 93 or 94 |
| $x_5$-116 (6) | 83 | $x_5$ is 91, 92, 93, 94, 95, 96, 97, 98, 99 or 100 |
| $x_5$-115 (6) | 85 | $x_5$ is 90, 91, 92, 93, 94, 95, 96, 97, 98 or 99 |
| $x_5$-116 (6) | 87 | $x_5$ is 91, 92, 93, 94, 95, 96, 97, 98, 99 or 100 |
| $x_5$-114 (6) | 89 | $x_5$ is 89, 90, 91, 92, 93, 94, 95, 96, 97 or 98 |
| $x_5$-134 (6) | 91 | $x_5$ is 108, 109, 110, 111, 112, 113, 114, 115 or 116 |
| $x_5$-113 (6) | 93 | $x_5$ is 89, 90, 91, 92, 93, 94, 95, 96, 97 or 98 |
| $x_5$-112 (6) | 95 | $x_5$ is 88, 89, 90, 91, 92, 93, 94, 95 or 96 |
| $x_5$-112 (6) | 97 | $x_5$ is 88, 89, 90, 91, 92, 93, 94, 95 or 96 |

In some embodiments, domain 3 may be derived from the same parent as either domain 2, domain 4 or both domain 3 and 4.

In some embodiment, J1 (Junction 1) between domain 1 and domain 2 comprises the consensus sequence $Z_1Z_2W$, wherein $Z_1$ is selected from the group L, V, F, and M, and $Z_2$ is G or K, wherein 2 of the 3 amino acids are found at the C-terminus of the first domain or the N-terminus of the second domain. In some embodiment, J2 (Junction 2) between domain 2 and domain 3 comprises the consensus sequence $CZ_1G$, wherein $Z_1$ is selected from the group H, S, A, L, I, E, K, Q and D, wherein 2 of the 3 amino acids are found at the C-terminus of the second domain or the N-terminus of the third domain. In some embodiment, J3 (Junction 3) between domain 3 and domain 4 comprises the consensus sequence $Z_1Z_2Z_3$, wherein $Z_1$ is selected from the group T, S, P, G and I, $Z_2$ is selected from the group consisting of N, K, V, M, H and Y, and $Z_3$ is selected from the group consisting of H, Y, S, T and P, wherein 2 of the 3 amino acids are found at the C-terminus of the third domain or the N-terminus of the fourth domain. In some embodiment, J4 (Junction 4) between domain 4 and domain 5 comprises the consensus sequence $Z_1CZ_2$, wherein $Z_1$ is selected from the group C, S and V, and $Z_2$ is selected from the group consisting of V, A, I and T, wherein 2 of the 3 amino acids are found at the C-terminus of the fourth domain or the N-terminus of the Fifth domain. In some embodiment, J5 (Junction 1) between the domain 5 and domain 6 comprises the consensus sequence $Z_1Z_2Z_3$, wherein $Z_1$ is selected from the group L, R and V, $Z_2$ is selected from the group consisting of T, Q, Y, F and M, and $Z_3$ is selected from the group consisting of L, F, Y, K, I, Q, V and T, wherein 2 of the 3 amino acids are found at the C-terminus of the fifth domain or the N-terminus of the sixth domain.

In one embodiment, the disclosure provides the following domains (Table B) for reach of the TGF-beta family members that may be recombined to form a chimera of the disclosure having increased or improved biological activity (e.g., resistance to inactivation and the like).

TABLE B

| | Domain 1 | Domain 2 | Domain 3 | Domain 4 | Domain 5 | Domain 6 |
|---|---|---|---|---|---|---|
| BMP-2 | 1-30 | 31-48 | 49-68 | 69-81 | 82-93 | 94-114 |
| BMP-3 | 1-24 | 25-42 | 43-62 | 63-77 | 78-89 | 90-110 |
| BMP-4 | 1-32 | 33-50 | 51-70 | 71-83 | 84-95 | 96-116 |
| BMP-5 | 1-47 | 48-65 | 66-85 | 86-99 | 100-111 | 112-132 |
| BMP-6 | 1-47 | 48-65 | 66-85 | 86-99 | 100-111 | 112-132 |
| BMP-7 | 1-54 | 55-72 | 73-92 | 93-106 | 107-118 | 119-139 |
| BMP-8 | 1-54 | 55-72 | 73-92 | 93-106 | 107-118 | 119-139 |
| BMP-9 | 1-24 | 25-42 | 43-62 | 63-76 | 77-88 | 89-110 |
| BMP-10 | 1-23 | 24-41 | 42-61 | 62-75 | 76-87 | 88-108 |
| BMP-15 | 1-40 | 41-58 | 59-78 | 79-92 | 93-104 | 105-125 |
| GDF-1 | 1-30 | 31-48 | 49-72 | 73-86 | 87-98 | 99-119 |
| GDF-3 | 1-30 | 31-48 | 49-68 | 69-81 | 82-93 | 94-114 |
| GDF-5 | 1-35 | 36-53 | 54-73 | 74-87 | 88-99 | 100-120 |
| GDF-6 | 1-35 | 36-53 | 54-73 | 74-87 | 88-99 | 100-120 |
| GDF-7 | 1-44 | 45-62 | 63-82 | 83-96 | 97-108 | 109-129 |
| GDF-8 | 1-30 | 31-48 | 49-63 | 64-76 | 77-88 | 89-109 |
| GDF-9 | 1-50 | 51-68 | 69-88 | 89-102 | 103-114 | 115-135 |
| GDF-10 | 1-33 | 34-51 | 52-71 | 72-86 | 87-98 | 99-119 |
| GDF-11 | 1-30 | 31-48 | 49-63 | 64-76 | 77-88 | 89-109 |
| GDF-15 | 1-31 | 32-49 | 50-66 | 67-80 | 81-92 | 93-112 |
| NODAL | 1-26 | 27-44 | 45-64 | 65-78 | 79-90 | 91-110 |
| ACTIVIN-A | 1-27 | 28-45 | 46-68 | 69-83 | 84-95 | 96-116 |
| Activin-B | 1-27 | 28-45 | 46-68 | 69-82 | 83-94 | 95-115 |
| Activin-C | 1-27 | 28-45 | 46-68 | 69-83 | 84-95 | 96-116 |
| Activin-E | 1-27 | 28-45 | 46-68 | 69-81 | 82-93 | 94-114 |
| INHIBIN-A | 1-46 | 47-64 | 65-84 | 85-100 | 101-112 | 113-134 |
| TGF-beta1 | 1-32 | 33-50 | 51-68 | 69-81 | 82-93 | 94-113 |
| TGF-beta2 | 1-31 | 32-49 | 50-67 | 68-80 | 81-92 | 93-112 |
| TGF-beta3 | 1-31 | 32-49 | 50-67 | 68-80 | 81-92 | 93-112 |

Thus, as illustrated by various embodiments herein, the disclosure provides chimeric TGF-beta family polypeptides, wherein a first TGF-beta family protein (i.e., a first parental protein) is recombined with a second different TGF-beta family protein to provide a chimeric polypeptide. Table 2, below, provides exemplary chimeric polypeptides of the disclosure. In some embodiments, the polypeptide comprises one or more domains of a BMP-2 protein, wherein the segments of the BMP-2 protein comprise segment 1: amino acid residue from about 1 to about $x_1$ of SEQ ID NO:2 ("1b"); segment 2 is from about amino acid residue $x_1$ to about $x_2$ of SEQ ID NO:2 ("2b"); segment 3 is from about amino acid residue $x_2$ to about $x_3$ of SEQ ID NO:2 ("3b"); segment 4 is from about amino acid residue $x_3$ to about $x_4$ of SEQ ID NO:2 ("4b"); segment 5 is from about amino acid residue $x_4$ to about $x_5$ of SEQ ID NO:2 ("5b"); and segment 6 is from about amino acid residue $x_5$ to about $x_6$ of SEQ ID NO:2 ("6b"); and wherein: $x_1$ is residue 25, 26, 27, 28, 29, 30, 31, 32, 33, 34, or 35 of SEQ ID NO:2; $x_2$ is residue 45, 46, 47, or 48 of SEQ ID NO:2; $x_3$ is residue 65, 66, 67, or 68 of SEQ ID NO:2; $x_4$ is residue 76, 77, 78, 79, 80, 81 or 82 of SEQ ID NO:2; $x_5$ is residue 88, 89, 90, 91, 92, 93, or 94 of SEQ ID NO:2; and $x_6$ is residue 112, 113, or 114 or SEQ ID NO:2, corresponding to the C-terminus of BMP-2, such that a contiguous polypeptide comprising segments 1b2b3b4b5b6b comprises a wild-type BMP-2 following the translation initiation codon (ATG). Homologs and proteins having at least about 80%, 90%, 95%, 98%, and 99% identity to the foregoing sequences are also included by the disclosure.

In other embodiments, the polypeptide comprises one or more domains of an activin protein, wherein the segments of the activin protein comprise segment 1: amino acid residue from about 1 to about $x_1$ of SEQ ID NO:5 ("1a"); segment 2 is from about amino acid residue $x_1$ to about $x_2$ of SEQ ID NO:5 ("2a"); segment 3 is from about amino acid residue $x_2$ to about $x_3$ of SEQ ID NO:5 ("3a"); segment 4 is from about amino acid residue $x_3$ to about $x_4$ of SEQ ID NO:5 ("4a"); segment 5 is from about amino acid residue $x_4$ to about $x_5$ of SEQ ID NO:5 ("5a"); and segment 6 is from about amino acid residue $x_5$ to about $x_6$ of SEQ ID NO:5 ("6a"); and wherein: $x_1$ is residue 22, 23, 24, 25, 26, 27, 28, 29, 30, 31 or 32 of SEQ ID NO:5; $x_2$ is residue 42, 43, 44, or 45 of SEQ ID NO:5; $x_3$ is residue 61, 62, 63, or 64 of SEQ ID NO:5; $x_4$ is residue 78, 79, 80, 81, 82, 83 or 84 of SEQ ID NO:5; $x_5$ is residue 90, 91, 92, 93, 94, 95 or 96 of SEQ ID NO:5; and $x_6$ is residue 114, 115, or 116 or SEQ ID NO:5, corresponding to the C-terminus of activin, such that a continguous polypeptide comprising segments 1a2a3a4a5a6a comprises a wild-type mature activin protein. Homologs and proteins having at least about 80%, 90%, 95%, 98%, and 99% identity to the foregoing sequences are also included by the disclosure.

In some embodiments, chimeric TGF-beta family polypeptide has a chimeric segmental structure selected from the group consisting of: 1b2b3b4b5b6b; 1b2b3b4b5b6a; 1b2b3b4b5a6a; 1b2b3b4b5a6b; 1b2b3a4a5a6a; 1b2b3a4a5b6a; 1b2a3a4a5a6a; 1b2a3a4a5a6a L66V/V67I; 1b(1a_II)2a3a4a5a6a; 1b2a3a4a5a6b; 1b2a3a4a5b6b; 1b2a3a4a5b6a; 1b2a3b4b5b6a; 1b2a3b4b5a6a; and 1b2a3b4b5a6b.

In other embodiment, the chimeric polypeptide may be fused to an additional heterologous polypeptide to generate a chimeric fusion polypeptide. The heterologous polypeptide may be, for example, a peptide useful for purification or that permits oligomerization of multiple chimeric polypeptides of the disclosure. The heterologous may be chemically conjugated to the chimeric polypeptide or may be operably linked in-frame with a coding sequence for the chimeric polypeptide.

In more particular embodiments, the polypeptide comprises a sequence that is (a) at least 80%, 90%, 95%, 98%, or 99% identical to sequence selected from the group consisting of SEQ ID NO: 7, 9, 11, 13, 15, 17, 19, 21, 23, 25, 27, 29, 31, and 33 and has BMP-2 activity; (b) comprises a sequence as set forth in SEQ ID NO: 7, 9, 11, 13, 15, 17, 19, 21, 23, 25, 27, 29, 31, and 33; (c) is encoded by a polynucleotide comprising a sequence selected from the group consisting of SEQ ID NO:6, 8, 10, 12, 14, 16, 18, 20, 22, 24, 26, 28, 30, and 32; or (d) comprises a sequence described by an algorithm selected from the group consisting of 1b2b3b4b5b6b; 1b2b3b4b5b6a; 1b2b3b4b56a; 1b2b3b4b5a6b; 1b2b3b4a5a6a; 1b2b3b4a5b6b; 1b2b3b4a5a6b; 1b2b3b4a5a6a; 1b2b3a4a5a6a; 1b2b3a4a5a6b; 1b2b3a4a5b6b; 1b2b3a4a5a6a; 1b2b3a4b5b6a; 1b2b3a4b5a6a; 1b2b3a4a5b6a; 1b2b3a4b5a6a; 1b2a3a4a5a6a; 1b2a3a4a5a6b; 1b2a3a4a5b6b; 1b2a3a4a5a6a; 1b2a3a4b5b6b; 1b2a3a4b5b6a; 1b2a3a4b5a6b; 1b2a3a4b5a6a; 1b2a3b4b5b6b; 1b2a3b4b5b6a; 1b2a3b4a5a6a; 1b2a3b4a5b6a; 1b2a3b4a5b6b; 1b2a3b4a5a6b; 1b2a3a4a5a6a L66V/V67I; and 1b(1a_II)2a3a4a5a6a. In yet another embodiment, the disclosure provides a chimeric TGF-beta polypeptide comprising a segment from BMP-2 and segments from BMP-7 (e.g., a 1b-BMP7 polypeptide; see, e.g., SEQ ID NO:35). In yet another embodiment, the disclosure provides a chimeric TGF-beta polypeptide comprising a segment from BMP-2 and segments from BMP-9

(e.g., a 1b-BMP9; see, e.g., SEQ ID NO:37). In yet another embodiment, the disclosure provides a chimeric TGF-beta polypeptide comprising a segment from BMP-2 and segments from GDF-7 (e.g., a 1b-GDF7; see, e.g., SEQ ID NO:39). In yet another embodiment, the disclosure provides a chimeric TGF-beta polypeptide comprising a segment from BMP-2 and segments from GDF-8 (e.g., a 1b-GDF8; see, e.g., SEQ ID NO:41). The chimeric polypeptides of the disclosure retain a TGF-beta protein family member activity. Such activity can be measured in any number of ways as described below. In some embodiments, the chimeric polypeptide has BMP-2 activity, but is not inhibited by Noggin.

In some embodiments, segment of a chimeric polypeptide is 100% identical to the parental strand from which the segment was derived. In other embodiments the segment can comprise an amino acid sequence that has at least 60%, 70%, 80%, 90%, 95%, 96%, 97%, 98%, or 99% or more identity to a corresponding segment in a parental strand. For example, the segment may have one or more conservative amino acid substitutions (e.g., 1-5 conservative amino acid substitutions).

In some embodiments, the chimeric TGF-beta family polypeptide may have improved activity compared to one or more of the parental strands from which the chimeric polypeptide is generated. Biological activity of a chimeric polypeptide of the disclosure can be measured using any number of recognized assays in the art for TGF-beta activity. Such assays include, but are not limited to, BIAcore (Surface Plasmon Resonance); $C_2C_{12}$ luciferase assay: Smad 1/5 reporter system; HEK293 luciferase assay: Smad 2/3 reporter system; FSH (Follicle Stimulating Hormone) release assay: in rat pituitary cells; BRE (BMP Response Element) luciferase assay: Smad 1/5 reporter HEK 293 cells; Cripto binding assay: Luciferase response measured in presence/absence of Crptio; Human Stem Cell assay: Maintenance or Differentiation of H9 cells; NMR binding Studies; Micro mass culture: Bone formation measured in Chick embryos; X-ray Crystallography: Determine Structure of ligand:receptor complexes; Native Gel: Visualization of ligand:receptor complexes; Size Exclusion Chromatography (SEC): Visualization of ligand:receptor complexes; Velocity Scan Ultracentrifugation: Visualize ligand:receptor complex formation; and Seldi mass Spectrometry: Accurately determine size of ligands.

The chimeric TGF-beta family polypeptides described herein may be prepared in various forms, such as lysates, crude extracts, or isolated preparations.

In some embodiments, the isolated chimeric polypeptide is a substantially pure polypeptide composition. A "substantially pure polypeptide" refers to a composition in which the polypeptide species is the predominant species present (i.e., on a molar or weight basis it is more, abundant than any other individual macromolecular species in the composition), and is generally a substantially purified composition when the object species comprises at least about 50 percent of the macromolecular species present by mole or % weight. Generally, a substantially pure polypeptide composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species.

In certain embodiments, the disclosure contemplates making functional variants by modifying the structure of chimeras. Such modifications may be made, for example, for such purposes as enhancing therapeutic efficacy, or stability (e.g., ex vivo shelf life and resistance to proteolytic degradation in vivo, improve stability, solubility, bioavailability, or biodistribution of the chimeric protein, etc.). For example, but not by way of limitation, the derivatives include chimeras that have been modified, e.g., by acetylation, carboxylation, acylation glycosylation, pegylation, phosphorylation, farnesylation, biotinylation, lipidation, amidation, derivatization by known protecting/blocking groups, proteolytic cleavage, linkage to a cellular ligand or other protein such as an organic deriatizing agent, etc. Any of numerous chemical modifications may be carried out by known techniques, including, but not limited to specific chemical cleavage, acetylation, formylation, metabolic synthesis, etc. Additionally, the derivative may contain one or more non-natural amino acids, such as those with ketone-containing side chain, polyethylene glycols, lipids, poly- or mono-saccharide, and phosphates. Effects of such non-natural amino acid elements on the functionality of a chimeric TGF-beta superfamily protein may be tested as described herein for other TGF-beta superfamily protein variants. When a chimeric TGF-beta superfamily protein is produced in cells by cleaving a nascent form of the precursor protein, post-translational processing may also be important for correct folding and/or function of the protein. Different cells (such as CHO, HeLa, MDCK, 293, W138, NIH-3T3 or HEK293) have specific cellular machinery and characteristic mechanisms for such post-translational activities and may be chosen to ensure the correct post-translational modification and processing of the precursor protein into a chimeric TGF-beta superfamily protein. In vitro cell-free expression system in combination with its associated engineered tRNA synthase and tRNA can be utilized to ensure the correct modification in a specific amino acid position genetically tagged to introduce non-natural amino acids.

Modified chimeras can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains.

In certain embodiments, the disclosure contemplates making mutations in a proteolytic cleavage site of the chimera sequence to make the site less susceptible to proteolytic cleavage. Computer analysis (using a commercially available software, e.g., MacVector, Omega, PCGene, Molecular Simulation, Inc.) can be used to identify proteolytic cleavage sites. As will be recognized by one of skill in the art, most of the described mutations, variants or modifications may be made at the nucleic acid level or, in some cases, by post translational modification or chemical synthesis. Such techniques are well known in the art.

In certain embodiments, the disclosure contemplates specific mutations of a chimera sequences so as to alter the glycosylation of the chimera. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (where "X" is any amino acid) which are specifically recognized by appropriate cellular glycosylation enzymes. The alteration may also be made by the addition of, or substitution by, one or more serine or threonine residues to the sequence of the wild-type polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties is by chemical or enzymatic coupling of glycosides to the polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on a chimera may be accomplished chemically and/or enzymatically. Chemical deglycosylation may involve, for example, exposure to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on polypeptides can be achieved by the use of a variety of endo- and exo-glycosidases as described by Thotakura et al. (1987) Meth. Enzymol. 138:350. The nucleic acid and/or amino acid sequence of a propeptide may be adjusted, as appropriate, depending on the type of expression system used, as mammalian, yeast, insect and plant cells may all introduce differing glycosylation patterns that can be affected by the amino acid sequence of the peptide.

In some embodiments, the chimeric polypeptide can be in the form of arrays. The polypeptide may be in a soluble form, for example as solutions in the wells of mircotitre plates, or immobilized onto a substrate. The substrate can be a solid substrate or a porous substrate (e.g, membrane), which can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments.

The disclosure also provides polynucleotides encoding the chimeric TGF-beta family polypeptides disclosed herein. The polynucleotides may be operably linked to one or more heterologous regulatory or control sequences that control gene expression to create a recombinant polynucleotide capable of expressing the polypeptide. Expression constructs containing a polynucleotide encoding the chimeric polypeptide can be introduced into appropriate host cells to express the polypeptide. Polynucleotide sequences encoding various domains or full chimera of the disclosure can be determined without undue efforts based upon the various codons that are associated with an amino acid of in a polypeptide. Furthermore, the disclosure provides exemplary sequences of the TGF-β family member. Deriving the sequences of a domain or chimera from the sequences provided herein is readily performed by one of skill in the art. Given the knowledge of specific sequences of the TGF-beta family of proteins, and the specific descriptions of the chimeric polypeptides herein (e.g., the segment structure of the chimeric domains), the nucleic acid sequence of the engineered chimera will be apparent to the skilled artisan. The knowledge of the codons corresponding to various amino acids coupled with the knowledge of the amino acid sequence of the polypeptides allows those skilled in the art to make different polynucleotides encoding the polypeptides of the disclosure. Thus, the present disclosure contemplates each and every possible variation of the polynucleotides that could be made by selecting combinations based on possible codon choices, and all such variations are to be considered specifically disclosed for any of the polypeptides described herein.

In some embodiments, the polynucleotides comprise polynucleotides that encode the polypeptides described herein but have about 80% or more sequence identity, about 85% or more sequence identity, about 90% or more sequence identity, about 91% or more sequence identity, about 92% or more sequence identity, about 93% or more sequence identity, about 94% or more sequence identity, about 95% or more sequence identity, about 96% or more sequence identity, about 97% or more sequence identity, about 98% or more sequence identity, or about 99% or more sequence identity at the nucleotide level to a reference polynucleotide encoding a chimera or parental TGF-beta family polypeptide.

In some embodiments, the isolated polynucleotides encoding the polypeptides may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, 3rd Ed., Cold Spring Harbor Laboratory Press; and Current Protocols in Molecular Biology, Ausubel. F. ed., Greene Pub. Associates, 1998, updates to 2007.

In some embodiments, the polynucleotides are operatively linked to control sequences for the expression of the polynucleotides and/or polypeptides. In some embodiments, the control sequence may be an appropriate promoter sequence, which can be obtained from genes encoding extracellular or intracellular polypeptides, either homologous or heterologous to the host cell.

In some embodiments, the control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used.

In some embodiments, the control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used.

In some embodiments, the control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide-coding region may be required where the coding sequence does not naturally contain a signal peptide coding region.

The disclosure is further directed to a recombinant expression vector comprising a polynucleotide encoding the chimeric TGF-beta polypeptides described herein, and one or more expression regulating regions such as a promoter and a terminator, a replication origin, etc., depending on the type of hosts into which they are to be introduced. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell or in vitro cell-free reaction mixture into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon, may be used.

In some embodiments, the expression vector of the disclosure contains one or more selectable markers, which permit easy selection of transformed cells. A selectable marker is a gene the product of which provides for biocide or viral resistance, resistance to heavy metals, prototrophy to auxotrophs, and the like.

In another embodiments, the disclosure provides a host cell comprising a polynucleotide encoding the chimeric TGF-beta polypeptide, the polynucleotide being operatively linked to one or more control sequences for expression of the fusion polypeptide in the host cell. Host cells for use in expressing the fusion polypeptides encoded by the expression vectors of the present disclosure are well known in the art. Appropriate culture mediums and growth conditions for the above-described host cells are well known in the art.

Expression vectors can be designed for expression of chimeras in prokaryotic or eukaryotic cells. For example, chimeras of the disclosure can be expressed in bacterial or prokaryote cells such as E. Coli, insect cells (e.g., the baculovirus expression system), yeast cells, microalgae, plant cells or mammalian cells as well as in vitro cell-free expression system. Some suitable host cells are discussed further in Goeddel, Gene Expression Technology: Methods in Enzymology 185, Academic Press, San Diego, Calif. (1990).

While one example of an expression system discussed is an E. coli expression system, to those skilled in the art, these proteins can be easily be cloned into and expressed from a large number of other expression systems. The advantages include, but are not limited to, achieving post-translational modifications as would be seen in the organism the protein was derived from (in this case H. sapiens), expression of the ligands without the start methionine required for bacterial expression, and easy incorporation of non-natural amino acids or additional chemical modifications. Suitable prokaryotes include but are not limited to eubacteria, such as Gram-negative or Gram-positive organisms, for example, Enterobacteriaceae such as E. coli. Various E. coli strains are publicly available, such as E. coli K12 strain MM294 (ATCC 31,446); E. coli X1776 (ATCC 31,537); E. coli strain W3110 (ATCC 27,325) and K5 772 (ATCC 53,635). In addition to prokaryotes, eukaryotic microbes such as filamentous fungi or yeast are suitable cloning or expression hosts for VEGF-E-encoding vectors. Saccharomyces cerevisiae is a commonly used lower eukaryotic host microorganism.

Suitable host cells for the expression of chimeras are derived from unicellular and multicellular organisms. Examples of invertebrate cells include insect cells such as Drosophila S2 and Spodoptera Sf9, as well as plant cells. Plant expression systems have also been used successfully to express modified proteins. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); Chinese hamster ovary cells/–DHFR(CHO, Urlaub and Chasin, Proc. Natl. Acad. Sci. USA, 77:4216 (1980)); mouse sertoli cells (TM4, Mather, Biol. Reprod., 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

Alternate protein expression systems include human embryonic kidney (HEK) 293 cells, insect cell line (S. frugiperda) utilizing the baculovirus expression system, yeast expression systems not limited to P. pastoris and S. cerevisiae, and numerous Microalgae strains. Transgenic animals can be used to express correctly modified protein. In essence, the animals become living 'bioreactors' capable of expressing large amounts of the desired protein in an easily harvested fluid or tissue, such as the milk from a cow. Cell-free in vitro expression systems using either the bacterial or wheat germ cell lysate can be employed. Cell-free expression system will permit inserting a wide range of non-natural amino acids or epitope tags with higher efficiency and greater specificity.

Examples of bacterial vectors include pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, and pRIT5 (Pharmacia). Examples of vectors for expression in the yeast S. cerevisiae include pYepSec1 (Baldari et al., EMBO J. 6:229 (1987)), pMFa (Kurjan and Herskowitz, Cell 30:933 (1982)), pJRY88 (Schultz et al., Gene 54:113 (1987)), and pYES2 (Invitrogen Corporation, San Diego, Calif.). Baculovirus vectors available for expression of nucleic acids to produce proteins in cultured insect cells (e.g., Sf9 cells) include the pAc series (Smith et al., Mol. Cell. Biol. 3:2156 (1983)) and the pVL series (Lucklow and Summers Virology 170:31 (1989)).

Examples of mammalian expression vectors include pWL-NEO, pSV2CAT, pOG44, pXT1, pSG (Stratagene) pSVK3, PBPV, pMSG, PSVL (Pharmacia), pCDM8 (Seed, Nature 329:840 (1987)) and pMT2PC (Kaufman et al., EMBO J. 6:187 (1987)). When used in mammalian cells, the expression vector's control functions are often provided by viral regulatory elements. For example, commonly used promoters are derived from polyoma, adenovirus 2, cytomegalovirus and Simian Virus 40.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, adenovirus, geminivirus, and caulimovirus vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

The chimera of the disclosure can be made by using methods well known in the art. Polynucleotides can be synthesized by recombinant techniques, such as that provided in Sambrook et al., 2001, Molecular Cloning: A Laboratory Manual, 3rd Ed., Cold Spring Harbor Laboratory Press; and Current Protocols in Molecular Biology, Ausubel. F. ed., Greene Pub. Associates, 1998, updates to 2007. Polynucleotides encoding the enzymes, or the primers for amplification can also be prepared by standard solid-phase methods, according to known synthetic methods, for example using phosphoramidite method described by Beaucage et al., (1981) Tet Lett 22:1859-69, or the method described by Matthes et al., (1984) EMBO J. 3:801-05, e.g., as it is typically practiced in automated synthetic methods. In addition, automated peptide synthesizers are commercially available (e.g., Advanced ChemTech Model 396; Milligen/Biosearch 9600).

Figure 17:
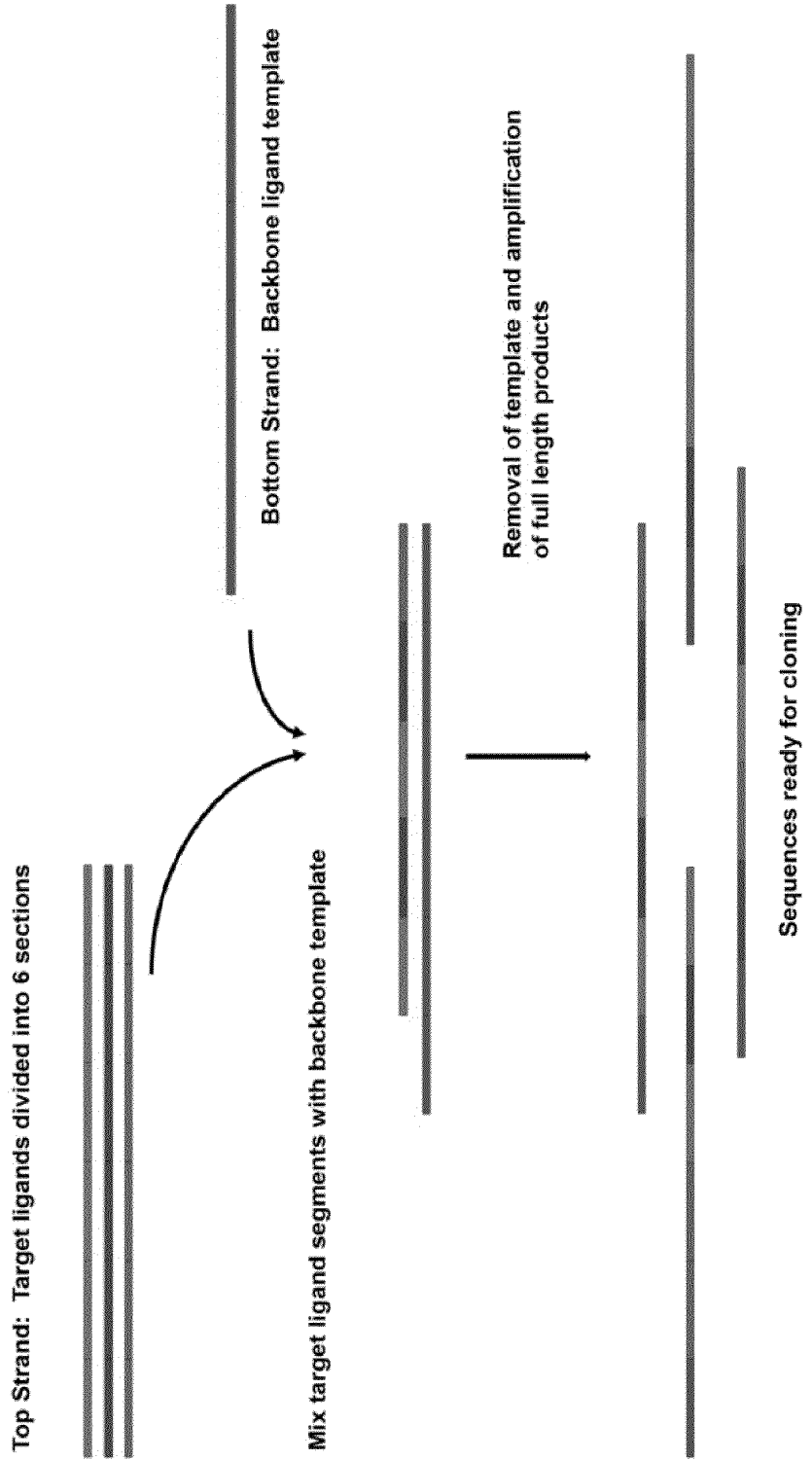
FIG. 17 is a schematic description of the RASCH method.

In a one embodiment, the disclosure is directed to a method to accelerate construction of large chimera libraries. Accordingly, the disclosure provides a recombinant strategy termed RASCH (RAndom Segmental CHimera) See FIG. 17. It uses a template sequence (first strand from one TGF-beta superfamily member) and a few target sequences (second (third, fourth, fifth, sixth) strand from one or more alternate TGF-beta superfamily members), whose subdomains are to be linked. The template DNA sequence is used to promote efficient coupling of the target sequences and is degraded once subdomains are linked. Following the gene construction to create the chimeric sequences, the new ligands are chemically refolded into functional dimer. This dimerization process permits additional diversification of the final sequence by mixing and dimerizing two different sequences of both natural and designer origins. Therefore, the RASCH method can be used to diversify the approximate 40 natural protein sequences of TGF-beta superfamily ligands into ten of thousands or more variant sequences, each distinct from any naturally-occurring TGF-beta superfamily ligand sequences.

Engineered polypeptide expressed in a host cell can be recovered from the cells and or the culture medium using any one or more of the well known techniques for protein purification, including, among others, lysozyme treatment, sonication, filtration, salting-out, ultra-centrifugation, chromatography, and affinity separation (e.g., substrate bound antibodies).

Chromatographic techniques for isolation of the polypeptides include, among others, reversed phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

Assays to determine activity are well known in the art. The present disclosure relates to assays to test for biological activity of chimeric proteins, more preferably, to assays to test for clinical activity. Such activity can include enhanced agonistic or antagonistic TGF-beta activity, combined or novel biological activity, and the like.

In certain embodiments, a chimeric protein of the disclosure comprising an agonist of a TGF-beta superfamily protein comprises an antagonist of a different TGF-beta superfamily protein.

Irrespective of which protein expression, harvesting, and, folding methodologies are used, certain of the subject chimeric proteins can bind, preferentially to a pre-selected receptor and can now be identified using standard methodologies, e.g., ligand/receptor binding assays, well known, and thoroughly documented in the art. See, e.g., Legerski gl al. (1992) Bio h~_Biophys. Res. Comm. 183: 672679; Frakar et al. (1978) Biochem. Bio12-hys. Res. Comm 80:849-857; Chio et el. (1990) Nature 343: 266-269; Dahlman et al. (1988) Biochem 27: 1813-1817; Strader et el. (1989) J. Biol. Chem. 264: 13572-13578; and DDowd et al. (1988) J. Biol. Chem. 263: 15985-15992.

Typically, in a ligand/receptor binding assay, the native or parent TGF-beta superfamily member of interest having a known, quantifiable affinity for a pre-selected receptor is labeled with a detectable moiety, for example, a radiolabel, a chromogenic label, or a fluorogenic label. Aliquots of purified receptor, receptor binding domain fragments, or cells expressing the receptor of interest on their surface are incubated with the labeled TGF-beta superfamily member in the presence of various concentrations of the unlabeled chimeric protein. The relative binding affinity of a candidate chimeric protein may be measured by quantitating the ability of the chimeric protein to inhibit the binding of the labeled TGF-beta superfamily member with the receptor. In performing the assay, fixed concentrations of the receptor and the TGF-beta superfamily member are incubated in the presence and absence of unlabeled chimeric protein. Sensitivity may be increased by preincubating the receptor with the chimeric protein before adding the labeled template TGF-beta superfamily member. After the labeled competitor has been added, sufficient time is allowed for adequate competitor binding, and then free and bound labeled TGF-beta superfamily members are separated from one another, and one or the other measured. Labels useful in the practice of the screening procedures include radioactive labels, chromogenic labels, spectroscopic labels such as those disclosed in Haughland (1994) "Handbook of Fluorescent and Research Chemicals," 5 ed. by Molecular Probes, Inc., Eugene, Oreg., or conjugated enzymes having high turnover rates, i.e., horseradish peroxidase, alkaline phosphatase, or agalactosidase, used in combination with chemiluminescent or fluorogenic substrates. The biological activity, namely the agonist or antagonist properties of the resulting chimeric protein constructs can subsequently be characterized using conventional in vivo and in vitro assays that have been developed to measure the biological activity of any TGF-beta superfamily member. It is appreciated, however, the type of assay used preferably depends on the TGF-a superfamily member upon which the chimeric protein is based. For example, chimeric constructs based upon naturally occurring BMP-2 protein may be assayed using any of the biological assays that have been developed to date for measuring BMP-2 activity, described in more detail below.

The presence of multimers among the subject chimeric proteins can be detected visually either by standard SDS-PAGE in the absence of a reducing agent such as DTT or by HPLC (e.g., C18 reverse phase HPLC). Multimeric proteins of the present disclosure can have an apparent molecular weight proportionally greater than the monomeric subunit, e.g., in the range about 28-36 kDa for a dimer, as compared to monomeric subunits, which may have an apparent molecular weight of about 14-18 kDa. The multimeric protein can readily be visualized on an electrophoresis gel by comparison to commercially available molecular weight standards. The dimeric protein also elutes from a C18 RP HPLC (45-50% acetonitrile:0.1% TFA) at a time point different from that for its monomeric counterpart.

A second assay evaluates the presence of dimer (e.g., OP-1 dimers) by its ability to bind to hydroxyapatite. Optimally-folded dimer binds a hydroxyapatite column well in pH7, 10 mM phosphate, 6M urea, and 0.142M NaCl (dimer elutes at 0.25 M NaCl) as compared to monomer, which does not bind substantially at those concentrations (monomer elutes at 0.1M NaCl). A third assay evaluates the presence of dimer by the protein's resistant to trypsin or pepsin digestion. The folded dimeric species is substantially resistant to both enzymes, particularly trypsin, which cleaves only a small portion of the N-terminus of the mature protein, leaving a biologically active dimeric species only slightly smaller in size than the untreated dimer (each monomer in amino acids smaller after trypsin cleavage). By contrast, the monomers and misfolded dimers are substantially degraded. In the assay, the protein is subjected to an enzyme digest using standard conditions, e.g., digestion in a standard buffer such as 50 mM Tris buffer, pH 8, containing 4 M urea, 100 mM NaCl, 0.3% Tween-80 and 20 mM methylamine. Digestion is allowed to occur at 37° C. for on the order of 16 hours, and the product visualized by any suitable means, preferably SDS PAGE.

The biological activity of the subject chimeric proteins, for example, the chimeric proteins having one or more segments from BMPs, can be assessed by any of a number of means as described in WO00/20607. For example, the protein's ability to induce endochondral bone formation can be evaluated using the well characterized rat subcutaneous bone assay. In the assay bone formation is measured by histology, as well as by alkaline phosphatase and/or osteoclacin production. In addition, osteogenic proteins having high specific bone forming activity, such as OP-1, BMP-2, BMR4, BMP-5 and BMP-6, also induce alkaline phosphatase activity in an in vitro rat osteoblast or osteosarcoma cell-based assay. Such assays are well described in the art. See, for example, Sabokdar of al. (1994) Bone and Mineral 27:57-67.; Knutsen et al. (1993) Biochem Biophvs Res. Commun 194:1352-1358; and Maliakal et al. (1994) Growth Factors 1:227-234).

By contrast, osteogenic proteins having low specific bone forming activity, such as CDMP-1 and CDMP-2, for example, do not induce alkaline phosphatase activity in the cell based osteoblast assay. The assay thus provides a ready method for evaluating biological activity of B1b9 mutants. For example, CDMP-1, CDMP-2 and CMDP-3 all are competent to induce bone formation, although with a lower specific activity than BMP-2, BW-4, BV-5, BMP-6 or OP-1. Conversely, BMP-2, BMP-4, BMP-5, BPylP-6 and OP-1 all can induce articular cartilage formation, albeit with a lower specific activity than CDMP-1, CDMP-2 or CDMP-3. Accordingly, a chimeric protein having one or more segment from CDMP, designed and described herein to be a chimeric protein competent to induce alkaline phosphatase activity in the cell-based assay, is expected to demonstrate a higher specific bone forming activity in the rat animal bioassay.

The chimeric protein's biological activity can also be readily evaluated by the protein's ability to inhibit epithelial cell growth. A useful, well characterized in vitro assay utilizes mink lung cells or melanoma cells. See WO00/20607. Other assays for other members of the TGF-beta superfamily are well described in the literature and can be performed without undue experimentation.

In certain embodiment, the disclosure provides methods and agents for control and maintain skeletal muscle mass in a host, preferably a human. Therefore, any chimeric protein of the disclosure that is expected to affect muscle-related function of a TGF-beta superfamily protein such as for example GDF-8 can be tested in whole cells or tissues, in vitro or in vivo, to confirm their ability to modulate skeletal muscle mass. GDF-8 (also known as myostatin) is a negative regulator of skeletal muscle growth. GDF-8 knockout mice have approximately twice the skeletal muscle mass of normal mice. The effects of increased muscle mass on bone modeling may be investigated, e.g., by examining bone mineral content (BMC) and bone mineral density (BMD) in the femora of female GDF-8 knockout mice. Dual-energy X-ray absorptiometry (DEXA) densitometry can be used to measure whole-femur BMC and BMD, and PQCT densitometry can be used to calculate BMC and BMD from cross-sections of tissues. Hamrick, Anat Rec. 2003 May; 272A(1):388-91. As is known in the art, a chimeric protein of the disclosure may be introduced into the GDF-8 knockout mice, and similar assays can be used to determine the effect of the chimeric protein on skeletal muscle mass and bone density.

The dystrophic phenotype in the mdx mouse model of Duchenne muscular dystrophy (DMD) may also be employed to test the biological activity of a chimeric protein of the disclosure. It was reported that blockade of endogenous myostatin by using intraperitoneal injections of blocking antibodies for three months resulted in an increase in body weight, muscle mass, muscle size and absolute muscle strength in mdx mouse muscle along with a significant decrease in muscle degeneration and concentrations of serum creatine kinase. Bogdanovich et al., Nature. 2002 Nov. 28; 420(6914): 418-21. Similar study may be employed to determine whether a chimeric protein of the disclosure potentiates or inhibits the endogenous GDF-8 activity.

In certain embodiments, the disclosure provides methods and agents for modulating neurogenesis. For example, GDF-11 is known to inhibit olfactory epithelium neurogenesis in vitro by inducing p27(Kip1) and reversible cell cycle arrest in progenitors. Wu et al. Neuron. 2003 Jan. 23; 37(2):197-207. The effect of a chimeric protein of the disclosure on neurogenesis can be similarly tested. Further, the effect of a chimeric protein of the disclosure on GDF-11's effect on neurogenesis can also be tested using similar assays as described in Wu et al. Id.

In certain embodiment, the disclosure provides methods and agents for stimulating bone formation and increasing bone mass. Therefore, any chimeric protein of the disclosure that is expected to affect bone-related function of a TGF-beta superfamily protein such as for example BMP-2, BMP-3, GDF-10, BMP-4, BMP-7, or BMP-8, can be tested in whole cells or tissues, in vitro or in vivo, to confirm their ability to modulate bone or cartilage growth. Various methods known in the art can be utilized for this purpose.

For example, BMP-3 inhibits BMP2-mediated induction of Msx2 and blocks BMP2-mediated differentiation of osteoprogenitor cells into osteoblasts. Thus, the effect of a subject chimer protein, preferably one comprising a segment from a BMP-2 or BMP-3, on bone or cartilage growth can be determined by their effect on the osteogenic activity of BMP-2, for example, by measuring induction of Msx2 or differentiation of osteoprogenitor cells into osteoblasts in cell based assays (see, e.g., Daluiski et al., Nat. Genet. 2001, 27(1):84-8; Hino et al., Front Biosci. 2004, 9:1520-9). Similarly, a subject chimeric protein, preferably one comprising a segment from a BMP-2 or BMP-3, may be tested for its osteogenic or anti-osteogenic activity or its agonistic or antagonistic effect on BMP-2-mediated osteogenesis.

Another example of cell-based assays includes analyzing the osteogenic or anti-osteogenic activity of a subject chimeric and test compounds in mesenchymal progenitor and osteoblastic cells. To illustrate, recombinant adenoviruses expressing a subject chimeric protein were constructed to infect pluripotent mesenchyimal progenitor C3H10T1/2 cells, preosteoblastic C2C12 cells, and osteoblastic TE-85 cells. Osteogenic activity is then determined by measuring the induction of alkaline phosphatase, osteocalcin, and matrix mineralization (see, e.g., Cheng et al., J bone Joint Surg Am. 2003, 85-A(8):1544-52).

Further, the disclosure contemplates in vivo assays to measure bone or cartilage growth. For example, Namkung-Matthai et al., Bone, 28:80-86 (2001) discloses a rat osteoporotic model in which bone repair during the early period after fracture is studied. Kubo et al., Steroid Biochemistry & Molecular Biology, 68:197-202 (1999) also discloses a rat osteoporotic model in which bone repair during the late period after fracture is studied. These references are incorporated by reference herein in their entirety for their disclosure of rat model for study on osteoporotic bone fracture. In certain aspects, the present disclosure makes use of fracture healing assays that are known in the art. These assays include fracture technique, histological analysis, and biomechanical analysis, which are described in, for example, U.S. Pat. No. 6,521,750, which is incorporated by reference in its entirety for its disclosure of experimental protocols for causing as well as measuring the extent of fractures, and the repair process.

It is understood that the screening assays of the disclosure apply to not only the subject chimeric proteins and variants thereof, but also any test compounds including agonists and antagonist of the chimeric proteins or their variants themselves. Further, these screening assays are useful for drug target verification and quality control purposes.

In other embodiment, the disclosure relates to the use of the subject chimeric TGF-beta superfamily proteins to identify compounds which can modulate activities of the chimeric proteins. Compounds identified through this screening can be tested in tissues (e.g., bone and/or cartilage) or cells (e.g., muscle cells) to assess their ability to modulate the test tissues or cells (e.g., bone/cartilage growth or muscle cell growth) in vitro. Optionally, these compounds can further be tested in animal models to assess their ability to modulate, e.g., bone/cartilage growth or muscle control and maintenance in vivo.

A variety of assay formats will suffice and, in light of the disclosure, those not expressly described herein will nevertheless be comprehended by one of ordinary skill in the art. As described herein, the test compounds (agents) of the disclosure may be created by any combinatorial chemical method. Alternatively, the subject compounds may be naturally occurring biomolecules synthesized in vivo or in vitro. Compounds (agents) to be tested for their ability to act as modulators of bone or cartilage growth can be produced, for example, by bacteria, yeast, plants or other organisms (e.g., natural products), produced chemically (e.g., small molecules, including peptidomimetics), or produced recombinantly. Test compounds contemplated by the present disclosure include non-peptidyl organic molecules, peptides, polypeptides, peptidomimetics, sugars, hormones, and nucleic acid molecules. In a specific embodiment, the test agent is a small organic molecule having a molecular weight of less than about 2,000 daltons.

The test compounds of the disclosure can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase, photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between a chimeric TGF-beta superfamily protein and its binding protein (e.g., the chimeric protein itself or a TGF-beta receptor protein or fragments thereof).

Merely to illustrate, in an exemplary screening assay of the present disclosure, the compound of interest is contacted with an isolated and purified chimeric protein which is ordinarily capable of binding to a TGF-beta receptor protein or fragments thereof, as appropriate for the intention of the assay. To the mixture comprising a subject chimeric protein and a TGF-beta receptor protein is then added a composition containing a test compound. Detection and quantification of the chimeric protein receptor complexes provides a means for determining the compound's efficacy at inhibiting (or potentiating) complex formation between the chimeric TGF-beta superfamily protein and its binding protein, e.g., the TGF-beta receptor or fragments thereof. The efficacy of the compound can be assessed by generating dose response curves from data obtained using various concentrations of the test compound. Moreover, a control assay can also be performed to provide a baseline for comparison. For example, in a control assay, an isolated and purified chimeric TGF-beta superfamily protein is added to a composition (cell-free or cell-based) containing a TGF-beta receptor protein or fragment thereof, and the formation of the chimeric protein-receptor complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system. Alternatively, cells expressing a TGF-beta receptor protein or fragments thereof on their surfaces can be used in certain assays.

Complex formation between a subject chimeric TGF-beta superfamily protein and its binding protein may be detected by a variety of techniques. For instance, modulation of the formation of complexes can be quantitated using, for example, detectably labeled proteins such as radiolabelled (e.g., 32P, 35S, 14C or 3H), fluorescently labeled (e.g., FITC), or enzymatically labeled chimeric protein or its binding protein, by immunoassay, or by chromatographic detection.

In certain embodiments, the present disclosure contemplates the use of fluorescence polarization assays and fluorescence resonance energy transfer (FRET) assays in measuring, either directly or indirectly, the degree of interaction between a chimeric TGF-beta superfamily protein and its binding protein (e.g., a TGF-beta receptor protein or fragments thereof). Further, other modes of detection such as those based on optical waveguides (PCT Publication WO 96/26432 and U.S. Pat. No. 5,677,196), surface plasmon resonance (SPR), surface charge sensors, and surface force sensors are compatible with many embodiments of the disclosure.

Moreover, the present disclosure contemplates the use of an interaction trap assay, also known as the "two hybrid assay," for identifying agents that disrupt or potentiate interaction between a chimeric TGF-beta superfamily protein and its binding protein (e.g., a TGF-beta receptor protein or fragments thereof). See for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696).

Chimera polynucleotides, polypeptides, antibodies, cells and other reagents of the disclosure have a wide variety of uses, both in vitro and in vivo. For example, in representative embodiments, these reagents may be used in vitro or in vivo (e.g., in an animal model) to study the processes of mineralization, bone formation, and bone loss. Further, "knock in" and "knock out" animals can be used as animal models of disease or as screening tools (discussed more below) for compounds that interact with the chimera polynucleotides or polypeptides. It will be apparent to those skilled in the art that any suitable vector can be used to deliver the polynucleotide to a cell or subject. The choice of delivery vector can be made based on a number of factors known in the art, including age and species of the target host, in vitro versus in vivo delivery, level and persistence of expression desired, intended purpose (e.g., for therapy or screening), the target cell or organ, route of delivery, size of the isolated polynucleotide, safety concerns, and the like.

Chimeric polypeptide of the disclosure may be formulated for use in various biological systems including in vivo. Any of a variety of art-known methods can be used to administer a chimera either alone or in combination with other active agents. For example, administration can be parenterally by injection or by gradual infusion over time. The agent (s) can be administered by such means as oral, rectal, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, intracavity, and inhalation administration, administration to the liver by intraportal delivery, as well as direct organ injection (e.g., into the liver, into the brain for delivery to the central nervous system, into the pancreas). The most suitable route in any given case will depend on the nature and severity of the condition being treated and on the nature of the particular compound which is being used.

The disclosure also provides a pharmaceutical preparation comprising a subject chimeric protein and a pharmaceutically acceptable carrier. A pharmaceutical preparation may be employed to promote growth of a tissue or diminishing or prevent loss of a tissue in a subject, preferably a human. The targeted tissue can be, for example, bone, cartilage, skeletal muscle, cardiac muscle and/or neuronal tissue.

In another aspect, a chimeric TGF-beta polypeptide can be formulated either alone or in combination with other agents for administration (e.g., as a lotion, cream, spray, gel, or ointment). It may be formulated into liposomes to reduce toxicity or increase bioavailability. Other methods for delivery include oral methods that entail encapsulation of the in microspheres or proteinoids, aerosol delivery (e.g., to the lungs), or transdermal delivery (e.g., by iontophoresis or transdermal electroporation). Other methods of administration will be known to those skilled in the art.

Preparations for parenteral administration of a composition comprising a chimeric TGF-beta polypeptide include sterile aqueous or non-aqueous solutions, suspensions, and emulsions. Examples of non-aqueous solvents are propylene glycol, polyethylene glycol, vegetable oils (e.g., olive oil), and injectable organic esters such as ethyl oleate. Examples of aqueous carriers include water, saline, and buffered media, alcoholic/aqueous solutions, and emulsions or suspensions. Examples of parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives such as, other antimicrobial, antioxidants, cheating agents, inert gases and the like also can be included.

The disclosure provides various disease and disorders that may be modulated by a TGF-beta protein family member comprising contacting or administering a therapeutically effective amount of a chimeric TGF-beta polypeptide either alone or in combination with other agents to a subject who has, or is at risk of having, such a disorder.

A therapeutically effective amount can be measured as the amount sufficient to decrease a subject's symptoms associated with the diseases or disorder. Typically, the subject is treated with an amount of a therapeutic composition sufficient to reduce a symptom of a disease or disorder by at least 50%, 90% or 100%. Generally, the optimal dosage will depend upon the disorder and factors such as the weight of the subject, the age, the weight, sex, and degree of symptoms. For example, with respect to bone morphogenesis, optionally, the dosage may vary with the type of matrix used in the reconstitution and the types of compounds in the composition. The addition of other known growth factors to the final composition, may also affect the dosage. Progress can be monitored by periodic assessment of bone growth and/or repair, for example, X-rays, histomorphometric determinations, and tetracycline labeling. Nonetheless, suitable dosages can readily be determined by one skilled in the art. Typically, a suitable dosage is 0.5 to 40 mg/kg body weight, e.g., 1 to 8 mg/kg body weight.

As mentioned previously, the compositions and methods of the disclosure can include the use of additional (e.g., in addition to a chimeric TGF-beta polypeptide) therapeutic agents (e.g., an inhibitor of TNF, an antibiotic, and the like). The chimeric TGF-beta polypeptide, other therapeutic agent(s), and/or antibiotic(s) can be administered, simultaneously, but may also be administered sequentially.

A pharmaceutical composition comprising a chimera according to the disclosure can be in a form suitable for administration to a subject using carriers, excipients, and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, anti-oxidants, chelating agents, and inert gases. Other pharmaceutically acceptable carriers include aqueous solutions, non-toxic excipients, including salts, preservatives, buffers and the like, as described, for instance, in Remington's Pharmaceutical Sciences, 15th ed., Easton: Mack Publishing Co., 1405-1412, 1461-1487 (1975), and The National Formulary XIV., 14th ed., Washington: American Pharmaceutical Association (1975), the contents of which are hereby incorporated by reference. The pH and exact concentration of the various components of the pharmaceutical composition are adjusted according to routine skills in the art. See Goodman and Gilman's, The Pharmacological Basis for Therapeutics (7th ed.).

The pharmaceutical compositions according to the disclosure may be administered locally or systemically. A "therapeutically effective dose" is the quantity of an agent according to the disclosure necessary to prevent, to cure, or at least partially arrest a symptoms associated with a disease or disorder or to promote cell growth, proliferation or differentiation. Amounts effective for this use will, of course, depend on the severity of the disease, disorder, or desired effect and will depend on weight and general state of the subject. Typically, dosages used in vitro may provide useful guidance in the amounts useful for in situ administration of the pharmaceutical composition, and animal models may be used to determine effective dosages for treatment of infections. Various considerations are described, e.g., in Langer, Science, 249: 1527, (1990); Gilman et al. (eds.) (1990), each of which is herein incorporated by reference. Dosages of pharmaceutically active compounds can be determined by methods known in the art, see, e.g., Remington's Pharmaceutical Sciences (Maack Publishing Co., Easton, Pa.); Remington, The Science & Practice of Pharmacy, (Lippincott Williams & Wilkins; Twenty first Edition). The therapeutically effective dosage of any specific compound will vary somewhat from compound to compound, and patient to patient, and will depend upon the condition of the patient and the route of delivery. As a general proposition, a dosage from about 0.1 to about 100 mg/kg will have therapeutic efficacy, with all weights being calculated based upon the weight of the compound, including the cases where a salt is employed. Toxicity concerns at the higher level can restrict intravenous dosages to a lower level such as up to about 10 to about 20 mg/kg, with all weights being calculated based upon the weight of the compound, including the cases where a salt is employed. A dosage from about 10 mg/kg to about 50 mg/kg can be employed for oral administration. Typically, a dosage from about 0.5 mg/kg to 15 mg/kg can be employed for intramuscular injection. Particular dosages are about 1 µmol/kg to 50 µmol/kg, and more particularly to about 22 µmol/kg and to 33 µmol/kg of the compound for intravenous or oral administration, respectively.

In particular embodiments of the disclosure, more than one administration (e.g., two, three, four, or more administrations) can be employed over a variety of time intervals (e.g., hourly, daily, weekly, monthly, etc.) to achieve therapeutic effects.

The compositions and chimera of the disclosure find use in veterinary and medical applications. Suitable subjects include both avians and mammals, with mammals being preferred. The term "avian" as used herein includes, but is not limited to, chickens, ducks, geese, quail, turkeys, and pheasants. The term "mammal" as used herein includes, but is not limited to, humans, bovines, ovines, caprines, equines, felines, canines, lagomorphs, etc. Human subjects include neonates, infants, juveniles, and adults. In other embodiments, the subject is an animal model of bone disease.

As used herein, "administering a therapeutically effective amount" is intended to include methods of giving or applying a pharmaceutical composition of the disclosure to a subject that allow the composition to perform its intended therapeutic function.

The pharmaceutical composition can be administered in a convenient manner, such as by injection (subcutaneous, intravenous, etc.), oral administration, inhalation, transdermal application, or rectal administration. Depending on the route of administration, the pharmaceutical composition can be coated with a material to protect the pharmaceutical composition from the action of enzymes, acids, and other natural conditions that may inactivate the pharmaceutical composition. The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. In all cases, the composition should be sterile and should be fluid to the extent that easy syringability exists. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be typical to include isotonic agents, for example, sugars, polyalcohols, such as mannitol, sorbitol, or sodium chloride in the composition. Prolonged absorption of the injectable compositions can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle that contains a basic dispersion medium and the required other ingredients from those enumerated above.

The pharmaceutical composition can be orally administered, for example, with an inert diluent or an assimilable edible carrier. The pharmaceutical composition and other ingredients can also be enclosed in a hard or soft-shell gelatin capsule, compressed into tablets, or incorporated directly into the individual's diet. For oral therapeutic administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5% to about 80% of the weight of the unit.

The tablets, troches, pills, capsules, and the like can also contain the following: a binder, such as gum gragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Of course, any material used in preparing any dosage unit form should be pharmaceutically pure and substantially non-toxic/biocompatible in the amounts employed. In addition, the pharmaceutical composition can be incorporated into sustained-release preparations and formulations.

Thus, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the pharmaceutical composition, use thereof in the therapeutic compositions and methods of treatment is contemplated. Supplementary active compounds can also be incorporated into the compositions.

In certain embodiments, the therapeutic method of the disclosure includes administering the composition topically, systemically, or locally as an implant or device. When administered, the therapeutic composition described by the disclosure are generally in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than the chimeras of the disclosure may also optionally be included in the composition as described above, may alternatively or additionally, be administered simultaneously or sequentially with the chimeras in the methods of the described herein. For example, preferably for bone and/or cartilage formation, the composition would include a matrix capable of delivering BMP chimeras or other therapeutic compounds to the site of bone and/or cartilage damage, providing a structure for the developing bone and cartilage and optimally capable of being resorbed into the body. For example, the matrix may provide slow release of the BMP chimeras. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the aforementioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

Certain compositions disclosed herein may be administered topically, either to skin or to mucosal membranes. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

It is especially advantageous to formulate parenteral compositions in dosage unit form for ease of administration and uniformity of dosage. "Dosage unit form" as used herein, refers to physically discrete units suited as unitary dosages for the individual to be treated; each unit containing a predetermined quantity of pharmaceutical composition is calculated to produce the desired therapeutic effect in association with the required pharmaceutical carrier. The specification for the dosage unit forms of the disclosure are related to the characteristics of the pharmaceutical composition and the particular therapeutic effect to be achieve.

The principal pharmaceutical composition is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

One of the challenges to using chimeras as therapeutics is the ability to deliver the proteins effectively. The chimeras of the disclosure can be delivered by several different methods. In the blood stream, the half-life of most TGF-β ligands is on the order of minutes. To compensate for the ligands being degraded so quickly, current therapies involving TGF-β ligands use very high doses of the proteins. Alternatively, several means to directly modify the ligands or delivery systems are available to help improve the stability or sustained release properties of the ligands.

(1) Direct modification of the protein includes PEGylation as one common form of modification. In this method, polyethylene glycol (PEG) is covalently attached to the protein in hopes of improving stability by increasing solubility, resistance to proteolysis, and decreased immunogenicity.

(2) Rational modification of residues on the protein surface. By improving any electrostatic instability, without changing overall protein function, the overall stability of molecule can be improved. Using continuum electrostatic models, residues contributing to instability can be located and then analyzed to see if it can be mutated to a more favorable residue.

(3) Fusing the ligand to another protein or portion of a protein is another technique to increase protein stability and solubility. The antibody constant fragment (Fc) is common fusion partner used to improve the stability and solubility.

(4) The use of liposomes can be used as a protein delivery vehicle. Liposomes are composed of any number of different phospholipids, which self assemble to form spheres. The protein of interest is encapsulated inside the bilayer, protecting it from the outside environment. The phospholipid composition influences the exact properties of the liposome and can be tailored to release the protein under any number of desired conditions. Polymer/liposome composite systems are also available to be used as delivery systems. Ideally, this type of system combines the advantages of each system to improve protein delivery.

(5) Similar to liposomes, polymers can be used as protein drug delivery systems. The polymers are used to make a matrix, commonly what is termed a hydrogel due to the high water content of the material. The advantage of using the gel is it allows for long term, sustained release as well as protecting the protein from proteolysis. As with the liposomes, the polymers used to make the gel influence its properties. There are two general classifications for the materials used to make the hydorgels: natural and unnatural polymers. Common materials used to create hydrogels using natural polymers include collagen, gelatin, fibrin, Hyaluronic acid, alginate, chitosan, and dextran. Synthetic polymers used to make hydrogels include Poly(ethylene oxide), Poly(acrylic acid), Poly(N-isopropylacrylamide), Poly(vinyl alcohol), and Polyphosphazene.

Figure 8:
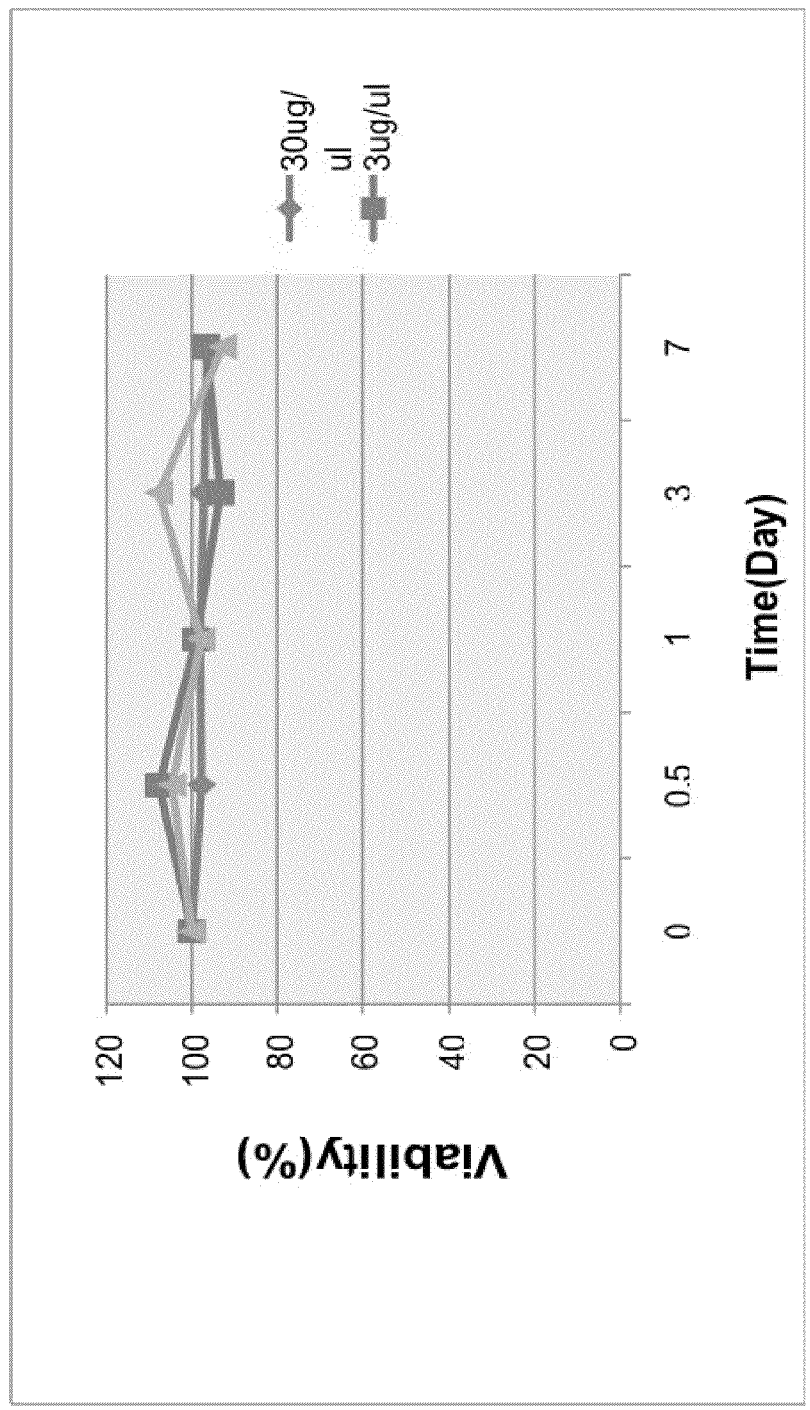
FIG. 8 provides a graph showing cell viability in the presence of xerogel material (lowest concentration, green, 0.3 ug/ul; medium concentration, red, 3 ug/ul; high concentration, blue, 30 ug/ul).

(6) A different kind of hydrogel can be created without the use of polymers, either natural or unnatural. Considered to be a bioactive glass, or Xerogel, this material is created from silica and calcium phosphate layer capable of absorbing the protein of interest. See, e.g., FIG. 8. The Xerogel increases the sustained release time of the protein up to weeks. FIG. 1 shows results from cell viability assay using osteoblast cell line MC3T3 by MTT assay, which shows that the xerogel material is nontoxic up to the highest concentration of 30 mg/ml in the culture media we tested.

Chimera of the disclosure alone or in combination with a pharmaceutically acceptable carrier can be used to treat any number of disease and disorder or modulate cellular or tissue activity.

The chimeric polypeptides of the disclosure can be used to treat any number of disease or disorders where modulating of TGF-beta activity provides a therapeutic benefit. For example, the chimera of the disclosure can be used in subjects suffering from osteoporosis, cartilage disease or periodontal diseases. The chimera can be used to promote bone and/or cartilage formation, inhibiting bone loss/density or demineralization, promoting bone deposition and the like. Alternatively, the chimera can be used to inhibit excessive bone density and growth. In other embodiment, the chimera can be used in the treatment of endocrine diseases and disorders, hyperparathyroidism, Cushing's disease, malabsorption, renal tubular acidosis, or thyrotoxicosis.

The chimera of the disclosure can also be used in the treatment or modulating of sexual development, pituitary hormone production, and creation of bone and cartilage. The chimera can also be used for the treatment of cell proliferative diseases and disorders, cell growth and differentiation associated with inflammation, allergy, autoimmune diseases, infectious diseases, and tumors.

Ina further aspect, the chimera of the disclosure can be used in the treatment of neuromuscular disorders, such as muscular dystrophy and muscle atrophy, congestive obstructive pulmonary disease, muscle wasting syndrome, obesity or other metabolic diseases including, for example, type 2 diabetes.

The chimera of the disclosure can be used in degenerative muscle diseases characterized by abnormal amount, development or metabolic activity of muscle tissue, including gradual weakening and deterioration of skeletal muscles. Examples of muscle disease and disorders include, but are not limited to, a muscle wasting disorder, cachexia, anorexia, AIDS wasting syndrome, muscular dystrophies, Duchenne Muscular Dystrophy (DMD), Becker Muscular Dystrophy (BMD), Myotonic Dystrophy (MMD) (also known as Steinert's Disease), Oculopharyngeal Muscular Dystrophy (OPMD), Emery-Dreifuss Muscular Dystrophy (EDMD), Limb-Girdle Muscular Dystrophy (LGMD), Facioscapulohumeral Muscular Dystrophy (FSH or FSHD) (also known as Landouzy-Dejerine), Congenital Muscular Dystrophy (CMD), and Distal Muscular Dystrophy (DD).

The chimera of the disclosure can be used in methods and compositions to prevent, treat, or alleviate symptoms of a neurodegenerative disease or disorder including, but not limited to, Alzheimer's Disease (AD), Parkinson's Disease (PD), Amyotrophic Lateral Sclerosis (ALS), and Huntington's disease (HD), and other neuromuscular diseases, motor neuron diseases, diseases of the neuromuscular junction, and/or inflammatory myopathies.

A subject may have a disorder associated with abnormal cell growth and differentiation which may cause inflammation, allergy, autoimmune diseases, infectious diseases, and/or tumors. A subject may have a heart disorder, such as a disorder associated with excessive cardiomyocyte proliferation or growth, or a disorder in which it would be desirable to stimulate cardiomyocyte growth or proliferation. Subject chimeric TGF-beta superfamily proteins may be designed for the treatment of essentially any disorder that is amenable to treatment by agonists or antagonists of a member of the TGF-beta superfamily.

The following examples are meant to further explain, but not limited the foregoing disclosure or the appended claims.

EXAMPLES

Example 1

Generation of TGF-β Chimeras

To generate these novel TGF-β ligands, a modified directed evolution approach was utilized. Typically, this technique involves making a large number of random protein sequences, greater than $10^3$, either by mixing the sequences of homologous genes or inserting random mutations and then screening for the desired ligand properties. In one set of experiments, sequences that were known to refold efficiently, termed the backbone ligand, were combined with a second ligand sequence containing signaling properties desire to mimic the target ligand. Using a structure guided approach, several TGF-β ligand crystal structures were analyzed and divided into 6 distinct sections. These sections roughly encompass the following regions of the ligand: section 1, N-terminus and beta strand 1; section 2, beta strand 2; section 3, pre-helix loop; section 4, alpha helix; section 5, beta strand 3; and section 6, beta stand 4 and C-terminus. Using this protocol, 64 different ligand combinations are possible for each set of TGF-β ligands chosen to be recombined. When two or more parental chains are from different subfamilies (e.g. BMP/GDF v.s. TGFbeta), the difference between their signaling mechanisms may not be captured if sections 3 and 4 are separated. To be broadly applicable as the design principle, it is also part of the design to keep two structural segments, sections 3 and 4, can be treated as one section of either of the parental gene (referred to as section 3*4).

The strategy was implemented by making activin/BMP-2 chimeras using activin-βA as a target ligand and BMP-2 as the backbone ligand. Activin-βA was picked as the target ligand as it is biologically very interesting. BMP-2 was chosen as the backbone ligand because it has been shown to refold with excellent efficiency, >10% dimer yield from starting denatured inclusion bodies, and these dimers have been shown to be active in both in vitro and in vivo experiments. To design the various sections, a sequence alignment of BMP-2 and activin-βA was performed to locate regions of sequence identity between the ligands (FIG. 7). These regions were used as the boundaries for the different sections. By using these parts of the sequence as the overlap regions for the oligonucleotides during PCR changes will not be introduced into either the BMP-2 or activin-βA sequences. The sequence alignment was then used in conjunction with data from previously solved BMP-2 and activin-βA structures to ultimately determine the 6 sections (FIG. 7*a*-*c*). Due to limitations with regions of identity between the sequences, the sections had to be shifted slightly from ideal. Particularly, the pre-helix loop and the majority of the α-helix were combined into one section, while the remainder of the α-helix to the beginning of beta strand 3 was placed into a different section (FIG. 7*b* and *c*). Additionally, 3-point mutations were inserted to allow for the cloning strategy to be successful. At the end of section 3, the BMP-2 sequence is TLVN, while the activin-βA sequence is TVIN (FIG. 7*a*). Since these residue differences are conservative, the leucine and valine from the BMP-2 were introduced into the corresponding activin-βA sequence. The third mutation is found at the end of section 5. Here, the BMP-2 sequence is LYLD, while the equivalent activin-βA sequence is LYYD (FIG. 7*a*). Since this residue difference is less conserved than the previous two, the tyrosine from activin-pA was inserted into the corresponding BMP-2 sequence.

The N-terminus of activin-βA contains 2 additional cysteines (FIG. 7*a*) which form a $4^{th}$ intra-disulfide bond. To eliminate the potential of this extra disulfide bond complicating the refolding process, the section which contained these residues was eliminated from section 1 of activin-βA chimera design.

For the activin/BMP-2 chimeras, the mature domains of human BMP-2 and human activin-βA were initially divided into 6 sections each and primers were designed for each section. For BMP-2, the primers coded for the following protein sequences: Section 1, QAKHKQRKRLKSSCKRHPLYVDFSDVGWND (SEQ ID NO: 98); Section 2, WIVAPPGYHAFYCHGECP (SEQ ID NO: 99); Section 3, FPLADHLNSTNHAIVQTLVN (SEQ ID NO: 100); Section 4, SVNSKIPKACCVP (SEQ ID NO: 101); Section 5, TELSAISMLYYD (SEQ ID NO: 102); Section 6, ENEKVVLKNYQDMVVEGCGCR (SEQ ID NO: 103). For activin-βA, the primers coded for the following protein sequences: Section 1, RGLECDGKVNICCKKQFFVSFKDIGWNDW (SEQ ID NO: 104); Section 2, WIIAPSGYHANYCEGECP (SEQ ID NO: 105); Section 3, SHIAGTSGSSLSFHSTLVN (SEQ ID NO: 106); Section 4, HYRMRGHSPFANLKSCCVP (SEQ ID NO: 107); Section 5, TKLRPMSMLYYD (SEQ ID NO: 108); Section 6, DGQNIIKKDIQNMIVEECGCS (SEQ ID NO: 109). An overlapping PCR strategy was used to mix the various sections together to generate full length chimeras. To generate the 1b chimeras, two oligos were used to insert the BMP-2 sequence QAKHKQRKRLKSSCKRHPLYVDFSDVGWNDII (SEQ ID NO: 110) into the target gene. Outer primers for all constructs were constructed to incorporate a 5' NdeI site and a 3' XhoI site for cloning into pET21a expression vector. The desired protein sequences were confirmed by DNA sequencing.

The chimeras were labeled according to the sections they contained. For example, 1b2b3b4a5a6b, in which the b's represent that the section was taken from BMP-2 and the a's represent that the section was derived from activin-βA. The chimeras were also given shorthand numeric designations, such as A/B2-020, so that any functional assays could be undertaken in a blind manner. Table 1 sets forth some of the various chimeras:

TABLE 1

| BMP-2/activin constructs | Sample Designation | DNA Sequence | Protein Sequence | Exemplary Characteristics |
|---|---|---|---|---|
| 1b2b3a4a5a6a | AB2-001 | ATGCAAGCCAAACACAAACAGCGGAAACGCCTTAA GTCCAGCTGTAAGAGACACACCCTTTGTACGTGACTTC AGTGACTGGGGTGGAATGACTGGATTGTGGCTCCC CCGGGGTATCACGCCCTTTACTGCCACGGAGAATGC CCTTCTCTATAGCAGGCACGTCCGGTCCTCCACTGT CCTTCCACTCAACG TABLE 1-continued

| BMP-2/activin constructs | Sample Designation | DNA Sequence | Protein Sequence | Exemplary Characteristics |
|---|---|---|---|---|
| 1b2b3b4b5b6b (BMP-2$_{mq}$) | AB2-005 | ATGCAAGCCAAACACAAACAGCGGAAACGCCTTAA GTCCAGCTGTAAGAGACACCCTTTGTACGTGACTTC AGTGACTGGGGTGGAATGACTGGATTGTGCCTCCC CCGGGGTATCACGCCTTTACTGCCACGGAGAATGC CCTTTTCCTCTGGCTGATCATCTGAACTCCACTAATC ATGCCATTGTTCAGACGTTGGTCAACTCTGTTAACTC TAAGATTCCTAAGGCATGCTGTGTCCCGACAGAACT CAGTGCTATCTTCGATGCTGTACCTTGACGAGAATGA AAAGGTTGTATTAAAGAACTATCAGGACATGGTGTGT GGAGGGTTGTGGGTGTCGC (SEQ ID NO: 1) | M Q A K H Q R K R L K S S C K R H P L Y V D F S D V G W N D W I V A P P G Y H A F Y C H G E C P F P L A D H L N S T N H A I V Q T L V N S K I P K A C C V P T E L S A I S M L Y L D E N E K V V L K N Y Q D M V V E G C G C R (SEQ ID NO: 14) | AB2-005 (BMP-2$_{mq}$) contains one amino acid (Met) added at the N-terminus of mature BMP-2. Met originates from the translation initiation codon (ATG). Unless it is truncated during the folding process, it can remain as the N-terminus of AB2-005. |
| 1b2b3a4a5b6b | AB2-006 | ATGCAAGCCAAACACAAACAGCGGAAACGCCTTAA GTCCAGCTGTAAGAGACACCCTTTGTACGTGACTTC AGTGACTGGGGTGGAATGACTGGATCATTGCTCCC TCTGGCTATCATGCCAACTACTGCGAGGAGAATGC CCTTCTCCATATAGCAGGCACGTCCGGTCCTCACTGT CCTTCCACTCAACGTTGGTCAACCACTACGGCATGCG GGGCCATAGCCCCCTTTGCCAACCTCAAATCGTGCTGT GTCCCGACAACTCAGTGCTATCTCGATGTTGTACC TTGACGAGAATGGTTGTATTAAAGAACTATC AGGACATGGTTGTGAGGGTTGTGGGTGTCGC (SEQ ID NO: 24) | M Q A K H Q R K R L K S S C K R H P L Y V D F S D V G W N D W I I A P S G Y H A N Y C E G E C P S H I T G S G S F H S T L V N H Y R M R G H S P F A N L K S C C V P T E L S A I S M L Y L D E N E K V V L K N Y Q D M V V E G C G C R (SEQ ID NO: 25) | Activity in stem cell differentiation assays unlike BMP-2. |
| 1b2a3a4a5a6b | AB2-007 | ATGCAAGCCAAACACAAACAGCGGAAACGCCTTAA GTCCAGCTGTAAGAGACACCCTTTGTACGTGACTTC AGTGACTGGGGTGGAATGACTGGATCATTGCTCCC TCTGGCTATCATGCCAACTACTGCGAGGGAGAATGC CCTTCTCCATATAGCAGGCACGTCCGGTCCTCACTGT CCTTCCACTCAACGTTGGTCAACCACTACGGCATGCG GGGCCATAGCCCCCTTTGCCAACCTCAAATCGTGCTGT GTCCCGACAACTCAGTGCTATCTCGATGTTGTAC CTTGACGAGAATGGTTGTATTAAAGAACTATC AGGACATGGTTGTGAGGGTTGTGGGTGTCGC (SEQ ID NO: 22) | M Q A K H Q R K R L K S S C K R H P L Y V D F S D V G W N D W I I A P S G Y H A N Y C E G E C P S H I A G T S G S F H S T L V N H Y R M R G H S P F A N L K S C C V P T K L R P M S M L Y L D E N E K V V L K N Y Q D M V V E G C G C R (SEQ ID NO: 23) | Activity in stem cell differentiation assays unlike BMP-2. |
| 1b2a3a4a5a6a | AB2-008 | ATGCAAGCCAAACACAAACAGCGGAAACGCCTTAA GTCCAGCTGTAAGAGACACCCTTTGTACGTGACTTC AGTGACTGGGGTGGAATGACTGGATCATTGCTCCC TCTGGCTATCATGCCAACTACTGCGAGGGAGAATGC CCTTCCCATATAGCAGGCACGTCCGGGTCCTCACTGT CCTTCCATTCAACGTTGGTCAACCTCAAATCGTGCTGT GGGCCATAGCCCCCTTTGCCAACCTCAAATCGTGCTGT GTCCCGACCAAGCTGAGAACCATGTCCATGTTGTACT ATGATGTGCTCAAAACATCATCAAAAGGACATTC AGAACATGATCTGAGGAGTGTGGGTGCTCA (SEQ ID NO: 16) | M Q A K H Q R K R L K S S C K R H P L Y V D F S D V G W N D W I I A P S G Y H A N Y C E G E C P S H I A G T S G S F H S T L R P M S M L Y Y D D G Q N I I K K D I Q N M I V E E C G C S (SEQ ID NO: 17) | Functions like activin-βA in cell signaling and in vivo experiments, ~4-fold lower potency; replaces TGF-beta 1 in chemically-defined stem cell media containing FGF2. |
| 1b2a3a4a5a6a L66V/V67I | AB2-009 | ATGCAAGCCAAACACAAACAGCGGAAACGCCTTAA GTCCAGCTGTAAGAGACACCCTTTGTACGTGACTTC | M Q A K H Q R K R L K S S C K R H P L Y V D F S D V G W N D W I I A P S G Y H A N Y C E G E C P S H I | Functions like activin-βA in cell signaling |

TABLE 1-continued

| BMP-2/activin constructs | Sample Designation | DNA Sequence | Protein Sequence | Exemplary Characteristics |
|---|---|---|---|---|
| | | AGTGACGTGGGGTGGAATGACTGGATCATTGCTCCC<br>TCTGGCTATCATGCCAACTACTGCGAGGGAGAATGC<br>CCTTCCCATATAGCAGGCACGTCCGGGTCCTCACTGT<br>CCTTCCATTCAACGGTGATCAACCACTACCGCATGCG<br>GGGCCATAGCCCCTTTGCCAACCTCAAATCGTGCTGT<br>GTCCCGACCAAGCTGAGACCCATGTCCATGTTGTACT<br>ATGATGATGGTCAAAACATCATCAAAAAGGACATTC<br>AGAACATGATCGTGGAGGAGTGTGGGTGCTCA<br>(SEQ ID NO: 18) | A G T S G S S L S F H S T V I N H Y R M R G H S P F<br>A N L K S C C V P T K L R P M S M L Y Y D D G Q N I<br>I K K D I Q N M I V E E C G C S<br>(SEQ ID NO: 19) | and in vivo experiments, ~10-fold lower potency in activin-βA signaling activity. |
| 1b(1a_II)2a3a4a5a6a | AB2-010 | ATGCAAGCCAAACACAAACAGCGGAAACGCCTTAA<br>GTCCAGCTGTAAGAAACAGTTCTTTGTCAGTTTCAAG<br>GACATCGGGTGGAATGACTGGATCATTGCTCCCTCT<br>GGCTATCATGCCAACTACTGCGAGGGAGAATGCCCT<br>TCCCATATAGCAGGCACGTCCGGGTCCTCACTGTCCT<br>TCCATTCAACGTTGGTCAACCACTACCGCATGCGGG<br>GCCATAGCCCCTTTGCCAACCTCAAATCGTGCTGTGT<br>CCCGACCAAGCTGAGACCCATGTCCATGTTGTACTAT<br>GATGATGGTCAAAACATCATCAAAAAGGACATTCAG<br>AACATGATCGTGGAGGAGTGTGGGTGCTCA<br>(SEQ ID NO: 20) | M Q A K H K Q R K R L K S S C K K Q F F V S F K D I<br>G W N D W I I A P S G Y H A N Y C E G E C P S H I A<br>G T S G S S L S F H S T L V N H Y R M R G H S P F A<br>N L K S C C V P T K L R P M S M L Y Y D D G Q N I I<br>K K D I Q N M I V E E C G C S<br>(SEQ ID NO: 21) | Functions like activin-βA in cell signaling and in vivo experiments, ~20-fold lower potency in activin-βA signaling. |
| 1b2b3b4b5a6a | AB2-011 | ATGCAAGCCAAACACCAACAGCGGAAACGCCTTAAG<br>TCCAGCTGTAAGAGACACCCTTTGTACGTGGACTTCA<br>GTGACGTGGGGTGGAATGACTGGATTGTGGCTCCCC<br>CGGGGTATCACGCCTTTTACTGCCACGGAGAATGCC<br>CTTTTCCTCTGGCTGATCATCTGAACTCCACTAATCA<br>TGCCATTGTTCAGACGTTGGTCAACTCTGTTAACTCT<br>AAGATTCCTAAGGCATGCTGTGTCCCGACCAAGCTG<br>AGACCCTCCATGTTGTACTATGATGATGGTCAAAAC<br>ATCATCAAAAAGGACATTCAGAACATGATCGTGGAG<br>GAGTGTGGGTGCTCA<br>(SEQ ID NO: 8) | M Q A K H Q Q R K R L K S S C K R H P L Y V D F S D<br>V G W N D W I V A P P G Y H A F Y C H G E C P F P L<br>A D H L N S T N H A I V Q T L V N S V N S K I P K A<br>C C V P T K L R P S M L Y Y D D G Q N I I K K D I Q<br>N M I V E E C G C S<br>(SEQ ID NO: 9) | ‘Super” BMP-2 activity, unable to be inhibited by Noggin |
| 1b2b3b4b5b6a | AB2-012 | ATGCAAGCCAAACACAAACAGCGGAAACGCCTTAA<br>GTCCAGCTGTAAGAGACACCCTTTGTACGTGGACTTC<br>AGTGACGTGGGGTGGAATGACTGGATTGTGGCTCCC<br>CCGGGGTATCACGCCTTTTACTGCCACGGAGAATGC<br>CCTTTTCCTCTGGCTGATCATCTGAACTCCACTAATC<br>ATGCCATTGTTCAGACGTTGGTCAACTCTGTTAACTC<br>TAAGATTCCTAAGGCATGCTGTGTCCCGACAGAACT<br>CAGTGCTATCTCGATGTTGTACTATGATGATGGTCGA<br>AACATCATCAAAAAGGACATTCAGAACATGATCGTG<br>GAGGAGTGTGGGTGCTCA<br>(SEQ ID NO: 6) | M Q A K H K Q R K R L K S S C K R H P L Y V D F S D<br>V G W N D W I V A P P G Y H A F Y C H G E C P F P L<br>A D H L N S T N H A I V Q T L V N S V N S K I P K A<br>C C V P T E L S A I S M L Y Y D D G R N I I K K D I<br>Q N M I V E E C G C S<br>(SEQ ID NO: 7) | ‘Super” BMP-2 activity, partially inhibited by Noggin |
| 1b2b3b4b5a6b | AB2-013 | ATGCAAGCCAAACACAAACAGCGGAAACGCCTTAA<br>GTCCAGCTGTAAGAGACACCCTTTGTACGTGGACTTC<br>AGTGACGTGGGGTGGAATGACTGGATTGTGGCTCCC<br>CCGGGGTATCACGCCTTTTACTGCCACGGAGAATGC | M Q A K H K Q R K R L K S S C K R H P L Y V D F S D<br>V G W N D W I V A P P G Y H A F Y C H G E C P E P L<br>A D H L N S T N H A I V Q T L V N S V N S K I P K A<br>C C V P T K L R P M S M L Y Y D E N E K V V L K N Y | Activity comparable to BMP-2, inhibited by Noggin |

TABLE 1-continued

| BMP-2/activin constructs | Sample Designation | DNA Sequence | Protein Sequence | Exemplary Characteristics |
|---|---|---|---|---|
| | | CCTTTTCCTCTGGCTGATCATCTGAACTCCACTAATC<br>ATGCCATTGTTCAGACGTTGGTCAACTCTGTTAACTC<br>TAAGATTCCTAAGGCATGCTGTGTCCCGACCAAGCT<br>GAGACCCATGTCCATGTTGTACTATGATGAGAATGA<br>AAAGGTTGTATTAAAGAACTATCAGGACATGGTTGT<br>GGAGGGTTGTGGGTGTCGC<br>(SEQ ID NO: 10) | Q D M V V E G C G C R<br>(SEQ ID NO: 11) | |
| 1b2a3b4b5a6b | AB2-014 | ATGCAAGCCAAACACAAACAGCGGAAACGCCTTAA<br>GTCCAGCTGTAAGAGACACCCTTTGTACGTGGACTTC<br>AGTGACGTGGGGTGGAATGACTGGATCATTGCTCCC<br>TCTGGCTATCATGCCAACTACTGCGACGGAGAATGC<br>CCTTTTCCTCTGGCTGATCATCTGAACTCCACTAATC<br>ATGCCATTGTTCAGACGTTGGTCAACTCTGTTAACTC<br>TAAGATTCCTAAGGCATGCTGTGTCCCGACCAAGCT<br>GAGACCCATGTCCATGTTGTACCTTGACGAGAATGA<br>AAAGGTTGTATTAAAGAACTATCAGGACATGGTTGT<br>GGAGGGTTGTGGGTGTCGC<br>(SEQ ID NO: 32) | M Q A K H K Q R K R L K S S C K R H P L Y V D F S D<br>V G W N D W I I A P S G Y H A N Y C D G E C P F P L<br>A D H L N S T N H A I V Q T L V N S V N S K I P K A<br>C C V P T K L R P M S M L Y L D E N E K V V L K N Y<br>Q D M V V E G C G C R<br>(SEQ ID NO: 33) | Activity comparable to BMP-2, partially blocked by Noggin |
| 1b2a3b4b5b6a | AB2-015 | ATGCAAGCCAAACACAAACAGCGGAAACGCCTTAA<br>GTCCAGCTGTAAGAGACACCCTTTGTACGTGGACTTC<br>AGTGACGTGGGGTGGAATGACTGGATCATTGCTCCC<br>TCTGGCTATCATGCCAACTACTGCGACGGAGAATGC<br>CCTTTTCCTCTGGCTGATCATCTGAACTCCACTAATC<br>ATGCCATTGTTCAGACGTTGGTCAACTCTGTTAACTC<br>TAAGATTCCTAAGGCATGCTGTGTCCCGACAGAACT<br>CAGTGCTATCTCGATGTTGTACTATGATGATGGTCAA<br>AACATCATCAAAAAGGACATTCAGAACATGATCGTG<br>GAGGAGTGTGGGTGCTCA<br>(SEQ ID NO: 28) | M Q A K H K Q R K R L K S S C K R H P L Y V D F S D<br>V G W N D W I I A P S G Y H A N Y C D G E C P F P L<br>A D H L N S T N H A I V Q T L V N S V N S K I P K A<br>C C V P T E L S A I S M L Y Y D D G Q N I I K K D I<br>Q N M I V E E C G C S<br>(SEQ ID NO: 29) | ‘Super” BMP-2 activity, unable to be inhibited by Noggin |
| 1b,2a3b4b5b6b | AB2-016 | ATGCAAGCCAAACACAAACAGCGGAAGCGTCTTAAG<br>TCCAGCTGCAAAAGGCACCCTTTGTATGTGGACTTCA<br>GTGATGTGGGGTGGAATGACTGGATCATTGCTCCCT<br>CTGGCTATCATGCCAACTACTGCGAGGGAGAATGCC<br>CTTTTCCTCTGGCTGATCATCTGAACTCCACTAATCA<br>CGCCATTGTTCAGACGTTGGTCAACTCTGTTAACTCT<br>AAGATTCCTAAGGCATGCTGTGTCCCGACAGAACTC<br>AGTGCTATCTCGATGCTGTACCTTGACGAGAATGAA<br>AAGGTTGTATTAAAGAACTATCAGGACATGGTTGTG<br>GAGGGTTGCGGGTGTCGT<br>(SEQ ID NO: 111) | M Q A K H K Q R K R L K S S C K R H P L Y V D F S D<br>V G W N D W I I A P S G Y H A N Y C E G E C P F P L<br>A D H L N S T N H A I V Q T L V N S V N S K I P K A<br>C C V P T E L S A I S M L Y L D E N E K V V L K N Y<br>Q D M V V E G C G C R<br>(SEQ ID NO: 112) | Activity comparable to BMP-2, inhibited by Noggin |
| 1b2b3b4a5a6a | AB2-017 | ATGCAAGCCAAACACAAACAGCGGAAACGCCTTAA<br>GTCCAGCTGTAAGAGACACCCTTTGTACGTGGACTTC<br>AGTGACGTGGGGTGGAATGACTGGATTGTGGCTCCC<br>CCGGGGTATCACGCCTTTTACTGCCACGGAGAATGC<br>CCTTTTCCTCTGGCTGATCATCTGAACTCCACTAATC<br>ATGCCATTGTTCAGACGTTGGTCAACCACTACCGCAT | M Q A K H K Q R K R L K S S C K R H P L Y V D F S D<br>V G W N D W I V A P P G Y H A F Y C H G E C P F P L<br>A D H L N S T N H A I V Q T L V N H Y R M R G H S P<br>F A N L K S C C V P T K L R P M S M L Y Y D D G Q N<br>I I K K D I Q N M I V E E C G C S<br>(SEQ ID NO: 114) | |

TABLE 1-continued

| BMP-2/activin constructs | Sample Designation | DNA Sequence | Protein Sequence | Exemplary Characteristics |
|---|---|---|---|---|
| | | GCGGGGCCATAGCCCCTTTGCCAACCTCAAATCGTG<br>CTGTGTCCGACCAAGCTGAGACTGAGTCCATGTTG<br>TACTATGATGAGAATGTCAAAACATCATCAAAAGGAC<br>ATTCAGAACATGATCGTGGAGAGTGTGGGTGCTCA<br>(SEQ ID NO: 113) | | |
| 1b2b3b4a5b6b | AB2-018 | ATGCAAGCCAAACACAAACAGCGGAAACGCCTTAA<br>GTCCAGCTGTAAGAGACACCCCTTTGTACGTGGACTTC<br>AGTGACTGGGGTGGAATGACTGGATTGTGGCTCCC<br>CCGGGTATCACGCCTTTTACTGCCACGGAGAATGC<br>CCTTTTCCTCTGGCTGATCATCTGAACTCCACTAATC<br>ATGCCATTGTTCAGACGTTGGTCAACCACTACCGCAT<br>GCGGGGCCATAGCCCCTTTGCCAACCTCAAATCGTG<br>CTGTGTCCCGACAGAATGAGAACCAGTGCTATCTCGATACTG<br>TACCTTGACGAGAATGAAAAGGTTGTATTAAAGAAC<br>TATCAGGACATGGTTGTGGAGGGTTGCGGGTGTGCGC<br>(SEQ ID NO: 115) | M Q A K H K Q R K R L K S S C K R H P L Y V D F S D<br>V G W N D W I V A P P G Y H A F Y C H G E C P F P L<br>A D H L N S T N H A I V Q T L V N H Y R M R G H S P<br>F A N L K S S C V P T E L S A I S I L Y L D E N E K<br>V V L K N Y Q D M V V E G C G C R<br>(SEQ ID NO: 116) | |
| 1b2b3b4a5a6b | AB2-019 | ATGCAAGCCAAACACAAACAGCGGAAACGCCTTAA<br>GTCCAGCTGTAAGAGACACCCCTTTGTACGTGGACTTC<br>AGTGACTGGGGTGGAATGACTGGATTGTGGCTCCC<br>CCGGGTATCACGCCTTTTACTGCCACGGAGAATGC<br>CCTTTTCCTCTGGCTGATCATCTGAACTCCACTAATC<br>ATGCCATTGTTCAGACGTTGGTCAACCACTACCGCAT<br>GCGGGGCCATAGCCCCTTTGCCAACCTCAAATCGTG<br>CTGTGTCCCGACCAAGCTGAGACCAGTGCCATGTTG<br>TACTATGATGAGAATGAAAAGGTTGTATTAAAGAAC<br>TATCAGGACATGGTTGTGGAGGGTTGCGGGTGTGCGT<br>(SEQ ID NO: 117) | M Q A K H K Q R K R L K S S C K R H P L Y V D F S D<br>V G W N D W I V A P P G Y H A F Y C H G E C P F P L<br>A D H L N S T N H A I V Q T L V N H Y R M R G H S P<br>F A N L K S S C V P T K L R P M S M L Y Y D E N E K<br>V V L K N Y Q D M V V E G C G C R<br>(SEQ ID NO: 118) | |
| 1b2b3b4a5b6a | AB2-020 | ATGCAAGCCAAACACAAACAGCGGAAACGCCTTAA<br>GTCCAGCTGTAAGAGACACCCCTTTGTACGTGGACTTC<br>AGTGACTGGGGTGGAATGACTGGATTGTGGCTCCC<br>CCGGGTATCACGCCTTTTACTGCCACGGAGAATGC<br>CCTTTTCCTCTGGCTGATCATCTGAACTCCACTAATC<br>ATGCCATTGTTCAGACCCCCTTTGCCAACTACCGCAT<br>GCGGGGCCATAGCCCCTTTGCCAACCTCAAATCGTG<br>CTGTGTCCCGACAGAACTGGTCTATCTCGATGTTG<br>TACTATGATGAGAATGGTCAAAACATCATCAAAGGAC<br>ATTCAGAACATGATCGTGGAGAGTGTGGGTGCTCA<br>(SEQ ID NO: 119) | M Q A K H K Q R K R L K S S C K R H P L Y V D F S D<br>V G W N D W I V A P P G Y H A F Y C H G E C P F P L<br>A D H L N S T N H A I V Q T E L S A I S M L Y Y D D G Q N<br>F A N L K S S C V P T K L R P M S M L Y Y D D G Q N<br>I I K K D I Q N M I V E E C G C S<br>(SEQ ID NO: 120) | |
| 1b2b3a4a5a6b | AB2-021 | ATGCAAGCCAAACACAAACAGCGGAAACGCCTTAA<br>GTCCAGCTGTAAGAGACACCCCTTTGTATGTGACTTC<br>AGTGACTGGGGTGGAATGACTGGATTGTGGCTCCC<br>CCGGGTATCACGCCTTTTACTGCCAGGAGAATGC<br>CCTTCTCATATAGCAGGCACCTCCGGTCCTCACTGT<br>GGGCCATAGCCCCTTTGCCAACCTCAAATCGTG<br>GTCCCGACCAAGCTGAGACCCATGTCCATGTCTAC<br>(SEQ ID NO: 121) | M Q A K H K Q R K R L K S S C K R H P L Y V D F S D<br>V G W N D W I V A P P G Y H A F Y C H G E C P S H I<br>A G T S G S S L S F H S T L V R P M S P F<br>A N L K S C V P T K V Q D M V V E G C G C R<br>(SEQ ID NO: 122) | |

TABLE 1-continued

| BMP-2/activin constructs | Sample Designation | DNA Sequence | Protein Sequence | Exemplary Characteristics |
|---|---|---|---|---|
| | | CTTGACGAGAATGAAAAGGTTGTATTAAAGAACTAT CAGGACATGGTTGTGGAGGGTTGTGGGTGTCGC (SEQ ID NO: 121) | | |
| 1b2b3a4a5b6b | AB2-022 | ATGCAAGCCAAACACAAACAGCGGAAACGCCTTAA GTCCAGCTGTAAGAGACACCCTTTGTACGTGGACTTC AGTGACGTGGGGTGGAATGACTGGATTGTGGCTCCC CCGGGGTATCACGCCTTTTACTGCCACGGAGAATGC CCTTCTCATATAGCAGGCACGTCCGGGTCCTCACTGT CCTTCCACTCAACGTTGGTCAACCACTACCGCATGCG GGGCCATAGCCCCTTTGCCAACCTCAAATCGTCTGT GTCCCGACAACTCAGTGCTATCTCGATGTTGTACT ATGATGAGAATGAAAAGGTTGTATTAAAGAACTATC AGGACATGGTTGTGGAGGGTTGC (SEQ ID NO: 123) | M Q A K H K Q R K R L K S S C K R H P L Y V D F S D V G W N D W I V A P P G Y H A F Y C H G E C P S H I A G T D G S S L S F H S T L V N H Y R M R G H S P F P R E L S C C V P T E L S A I S M L Y L D E N E K V A N L K S C V P T E L S A I S M L Y L D E N E K V V L K N Y Q D M V V E G C R (SEQ ID NO: 124) | |
| 1b2b3a4b5b6b | AB2-023 | ATGCAAGCCAAACACAAACAGCGGAAACGCCTTAA GTCCAGCTGTAAGAGACACCCTTTGTACGTGGACTTC AGTGACGTGGGGTGGAATGACTGGATTGTGGCTCCC CCGGGGTATCACGCCTTTTACTGCCACGGAGAATGC CCTTCTCATATAGCAGGCACGTCCGGGTCCTCACTGT CCTTCCACTCAACGTTGGTCAACTCTGTTAACTCTAA GATTCCTAAGGCATGCTGTGTCCCGACAGAACTCAG TGCTATCTCGATGCTGTACCTTGACGAGAATGAAAA GGTTGTATTAAAGAACTATCAGGACATGGTTGTGTGA GGGTTGCGGGTGCGT (SEQ ID NO: 125) | M Q A K H K Q R K R L K S S C K R H P L Y V D F S D V G W N D W I V A P P G Y H A F Y C H G E C P S H I A G T S G S S L S F H S T L V N S V N E K V V L K N Y Q C V P T E L S A I S M L Y L D E N E K C R D M V V E G C R (SEQ ID NO: 126) | |
| 1b2b3a4b5b6a | AB2-024 | ATGCAAGCCAAACACAAACAGCGGAAACGCCTTAA GTCCAGCTGTAAGAGACACCCTTTGTACGTGGACTTC AGTGACGTGGGGTGGAATGACTGGATTGTGGCTCCC CCGGGGTATCACGCCTTTTACTGCCACGGAGAATGC CCTTCTCATATAGCAGGCACGTCCGGGTCCTCACTGT CCTTCCACTCAACGTTGGTCAACTCTGTTAACTCTAA GATTCCTAAGGCATGCTGTGTCTACTATGATGATGG TGCTATCTCGATGTTGTACTATGATGATGGTCAAAC ATCATCAAAAAGGACATTCAGAACATGATCGTGGAG GAGTGTGGGTGCTCA (SEQ ID NO: 127) | M Q A K H K Q R K R L K S S C K R H P L Y V D F S D V G W N D W I V A P P G Y H A F Y C H G E C P S H I A G T S G S S L S F H S T L V N S Y D D G Q N I I K K A C C V P T E L S A I S M L Y Y D D G Q N I I K K A C N M I V E E C G C S (SEQ ID NO: 128) | |
| 1b2b3a4b5a6a | AB2-025 | ATGCAAGCCAAACACAAACAGCGGAAACGCCTTAA GTCCAGCTGTAAGAGACACCCTTTGTACGTGGACTTC AGTGACGTGGGGTGGAATGACTGGATTGTGGCTCCC CCGGGGTATCACGCCTTTTACTGCCACGGAGAATGC CCTTCTCATATAGCAGGCACGTCCGGGTCCTCACTGT CCTTCCACTCAACGTTGGTCAACTCTGTTAACTCTAA GATTCCTAAGGCATGCTGTGTCCCGACCAAGCTGAG ACCATGTTCCATGTTGTACTATGATGATGGTCAAAC ATCATCAAAAAGGACATTCAGAACATGATCGTGGAG GAGTGTGGGTGCTCA (SEQ ID NO: 129) | M Q A K H K Q R K R L K S S C K R H P L Y V D F S D V G W N D W I V A P P G Y H A F Y C H G E C P S H I A G T S G S S L S F H S T L V N S Y D D G Q N I I K K D I Q C V P T K L R P M S M L Y Y D D G Q N I I K K D I Q N M I V E E C G C S (SEQ ID NO: 130) | |

TABLE 1-continued

| BMP-2/activin constructs | Sample Designation | DNA Sequence | Protein Sequence | Exemplary Characteristics |
|---|---|---|---|---|
| 1b2b3a4b5a6b | AB2-026 | ATGCAAGCCAAACACAAACAGCGGAAACGCCTTAA GTCCAGCTGTAAGAGACACCCTTTGTACGTGGACTTC AGTGACCTGGGGTGGAATGACTGGATTGTGGCTCCC CCGGGGTACACGCCTTTACTGCCACGAGAATGC CCTTCTCATATAGCAGGCACGTCCGGGTCCTCACTGT CCTTCCACTCAACGTTGGTCAACTCTGTTAACTCTAA GATTCCTAAGGCATGCTGTGTCCCGACCAAGCTGAG ACCCATGTCCATGTTGTACTATGATGAGAATGAAAA GGTTGTATTAAAGAACTATCAGGACATGGTTGTGA GGGTTGCGGGTGTCGT (SEQ ID NO: 131) | M Q A K H K Q R K R L K S S C K R H P L Y V D F S D V G W N D W I V A P P G Y H A F Y C H G E C P S H I A G T S G S S L F H S T L V N S K I P K A C C V P T K L R P M S M L Y Y D E N E K V V L K N Y Q D M V V E G C G R (SEQ ID NO: 132) | |
| 1b2a3a4b5b6b | AB2-027 | ATGCAAGCCAAACACAAACAGCGGAAACGCCTTAA GTCCAGCTGTAAGAGACACCCTTTGTACGTGGACTTC AGTGACCTGGGGTGGAATGACTGGATCATTGCTCCC TCTGGCTATCATGCCAACTACTGCGAGGGAGAATGC CCTTCTCATATAGCAGGCACGTCCGGGTCCTCACTGT CCTTCCACTCAACGTTGGTCAACTCTGTTAACTCTAA GATTCCTAAGGCATGCTGTGTCCGACAGAACTCAG TGCTATCTCGATGTTGTACCTTGACGAGAATGAAAA GGTTGTATTAAAGAACTATCAGGACATGGTTGTGA GGGTTGTGGGTGTCGC (SEQ ID NO: 133) | M Q A K H K Q R K R L K S S C K R H P L Y V D F S D V G W N D W I I A P S G Y H A N Y C E G E C P S H I A G T S G S S L F H S T L V N S V N S K I P K A C C V P T E L S A I S M L Y L D E N E K V V L K N Y Q D M V V E G C G R (SEQ ID NO: 134) | |
| 1b2a3a4b5b6a | AB2-028 | ATGCAAGCCAAACACAAACAGCGGAAACGCCTTAA GTCCAGCTGTAAGAGACACCCTTTGTACGTGGACTTC AGTGACCTGGGGTGGAATGACTGGATCATTGCTCCC TCTGGCTATCATGCCAACTACTGCGAGGGAGAATGC CCTTCTCATATAGCAGGCACGTCCGGGTCCTCACTGT CCTTCCACTCAACGTTGGTCAACTCTGTTAACTCTAA GATTCCTAAGGCATGCTGTGTCCGACAGAACTCAA TGCTATCTCGATGTTGTACTATGATGATGGTCAAAAA ATCATTAAAAAGGACATTCAGAACATGATCGTGGAG GAGTGTGGTGCTCA (SEQ ID NO: 135) | M Q A K H K Q R K R L K S S C K R H P L Y V D F S D V G W N D W I I A P S G Y H A N Y C E G E C P S H I A G T S G S S L F H S T L V N S V N S K I P K A C C V P T E L N A I S M L Y Y D D G Q N I I K K D I Q N M I V E E C G C S (SEQ ID NO: 136) | |
| 1b2a3a4b5a6a | AB2-030 | ATGCAAGCCAAACACAAACAGCGGAAACGCCTTAA GTCCAGCTGTAAGAGACACCCTTTGTACGTGGACTTC AGTGACCTGGGGTGGAATGACTGGATCATTGCTCCC TCTGGCTATCATGCCAACTACTGCGAGGGAGAATGC CCTTCTCATATAGCAGGCACGTCCGGGTCCTCACTGT CCTTCCACTCAACGTTGGTCAACTCTGTTAACTCTAA GATTCCTAAGGCATGCTGTGTCCGACCAAGCTGAG ACCCATGTCCATGTTGTACTATGATGATGGTCAAAAC ATCATCAAAAAGGACATTCAGAACATGATCGTGGAG GAGTGTGGTGCTCA (SEQ ID NO: 137) | M Q A K H K Q R K R L K S S C K R H P L Y V D F S D V G W N D W I I A P S G Y H A N Y C E G E C P S H I A G T S G S S L F H S T L V N S K I P K A C C V P T K L R P M S M L Y Y D D G Q N I I K K D I Q N M I V E E C G C S (SEQ ID NO: 138) | |

TABLE 1-continued

| BMP-2/activin constructs | Sample Designation | DNA Sequence | Protein Sequence | Exemplary Characteristics |
|---|---|---|---|---|
| 1b2a3b4a5a6a | AB2-031 | ATGCAAGCCAAACACAAACAGCGGAAACGCCTTAA GTCCAGCTGTAAGAGACACCCCTTTGTACGTGACTTC AGTGACTGGGGTGGAATGACTGGATCATTGCTCCC TCTGGCTATCATGCCAACTACTGCGAGGAGAATGC CCTTTTCCTCTGGCTGATCATCTGAACTCCACTAATC ATGCCATTGTTCAGACGTTGGTCAACCACTACCGCAT GCGGGGCCATAGCCCCTTTGCCAACCTCAAATCGTG CTGTGTCCCGACCAAGCTGAGACCCATGTCCATGTTG TACTATGATGATGGTCAAAACATCATCAAAAAGGAC ATTCAGAACATGATCGTGGAGGAGTGGGTGCTCA (SEQ ID NO: 139) | M Q A K H K Q R K R L K S S C K R H P L Y V D F S D V G W N D W I I A P S G Y H A N Y C E G E C P F P L A D H L N S T N H A I V Q T K L R P M S H Y R M R G H S P F A N L K S C C V P T K L R P M S M L Y Y D D G Q N I I K K D I Q N M I V E E C G C S (SEQ ID NO: 140) | |
| 1b2a3b4a5b6a | AB2-032 | ATGCAAGCCAAACACAAACAGCGGAAACGCCTTAA GTCCAGCTGTAAGAGACACCCCTTTGTACGTGACTTC AGTGACTGGGGTGGAATGACTGGATCATTGCTCCC TCTGGCTATCATGCCAACTACTGCGAGGAGAATGC CCTTTTCCTCTGGCTGATCATCTGAACTCCACTAATC ATGCCATTGTTCAGACGTTGGTCAACCACTACCGCAT GCGGGGCCATAGCCCCTTTGCCAACCTCAAATCGTG CTGTGTCCCGACAGAACTCAGTGCTATCTCGATGCTG TACCTTGACGAGAATGAAAAGTTGTATTAAAGAAC ATTCAGAACATGATCGTGGAGGAGTGGGTGCTCA (SEQ ID NO: 141) | M Q A K H K Q R K R L K S C K R H P L Y V D F S D V G W N D W I I A P S G Y H A N Y C E G E C P F P L A D H L N S T N H A I V Q T L V N H Y R M R G H S P F A N L K S C C V P T E L S A I S M L Y Y D D G Q N I I K K D I Q N M I V E E C G C S (SEQ ID NO: 142) | |
| 1b2a3b4a5b6b | AB2-033 | ATGCAAGCCAAACACAAACAGCGGAAACGCCTTAA GTCCAGCTGTAAGAGACACCCCTTTGTACGTGACTTC AGTGACTGGGGTGGAATGACTGGATCATTGCTCCC TCTGGCTATCATGCCAACTACTGCGAGGAGAATGC CCTTTTCCTCTGGCTGATCATCTGAACTCCACTAATC ATGCCATTGTTCAGACGTTGGTCAACCACTACCGCAT GCGGGGCCATAGCCCCTTTGCCAACCTCAAATCGTG CTGTGTCCCGACAGAACTCAGTGCTATCTCGATGCTG TACCTTGACGAGAATGAAAAGTTGTATTAAAGAAC TATCAGGACATGGTTGTGCGGGTTCGT (SEQ ID NO: 143) | M Q A K H K Q R K R L K S S C K R H P L Y V D F S D V G W N D W I I A P S G Y H A N Y C E G E C P F P L A D H L N S T N H A I V Q T L V N H Y R M L D E N E K F A N L K N Y Q D M V V E G G C R (SEQ ID NO: 144) | |
| 1b2a3b4a5a6b | AB2-034 | ATGCAAGCCAAACACAAACAGCGGAAGCGTCTTAAG TCCAGCTGCAAAAGGCACCCTTTGTATGTGGACTTCA GTGATGTGGGGTGGAATGACTGGATCATTGCTCCT GTGATTCATGCCAACTACTGCGACGGAGAATGCC CTTTTCCTCTGGCTGATCATCTGAACTCCACTAATCA TGCCATTGTTCAGACGTTGGTCAACCACTACCGCATG CGGGGCCACCAAGCTGAGACCCATGTCCATGTTGT ACTATGATGAGAATGAAAAGTTGTATTAAGAACT ATCAGGACATGGTTGTGGAGGGTTGCGGGTCGT (SEQ ID NO: 145) | M Q A K H K Q R K R L K S S C K R H P L Y V D F S D V G W N D W I I A P S G Y H A N Y C D G E C P F P L A D H L N S T N H A I V Q T L V N H Y R M L Y Y D E N E K F A N L K S C C V P T K L R P M S M L Y Y D E N E K V V L K N Y Q D M V V E G G C R (SEQ ID NO: 146) | |
| BMP-2$_{ma}$ | BMP-2$_{ma}$ | ATGGCTCAAGCCAAACAAACAGCGGAAACGCCTT AAGTCCAGCTGTAAGAGACACCCCTTTGTACGTGGAC | M A Q A K H K Q R K R L K S S C K R H P L Y V D F S D V G W N D W I V A P P G Y H A F Y C H G E C P F P | BMP-2$_{ma}$ contains two additional amino acids |

TABLE 1-continued

| BMP-2/activin constructs | Sample Designation | DNA Sequence | Protein Sequence | Exemplary Characteristics |
|---|---|---|---|---|
| | | TTCAGTGACGTGGGGTGGAATGACTGGATTCTGGCT CCCCCGGGTATCACGCCTTTTACTGCCACGAGAA TGCCCTTTCCTGGCTGATCATCTGAACTCCACTA ATCATGCCATTGTTCAGACGTTGGTCAACTCTGTTAA CTCTAAGATTCCTAAGGCATGCTGTGTCCCGACAGA ACTCAGTGCTATCTCGATGCTGTACCTTGACAGAAT GAAAAGGTTGTATTAAAGAACTATCAGGACATGGTT GTGGAGGGTTGTGGGTGTCGC (SEQ ID NO: 147) | L A D H L N S T N H A I V Q T L V N S V N S K I P K A C C V P T E L S A I S M L Y L D E N E K V V L K N Y Q D M V V E G C G C R (SEQ ID NO: 148) | (Met-Ala) at the N-terminal side of mature BMP-2 in nature (QAKH...). Met is often truncated during the folding process, but Ala remains as the N-terminus of the final product. Either form is regarded as BMP-2$_{ma}$. |
| 1b_BMP7 | NB2-BMP7 | ATGCAAGCCAAACACAAACAGCGGAAACGCCTTAA GTCCAGCTGTAAGAGACACCCTTTGTACGTGGACTTC AGTGACTGGGGTGGAATGACTGGATTATCGCGCT GAAGGCTACGCCGCCTACTACTGTGAGGGGCTGT GCCTTCCCTGAACTCCATGAACGCCACCAACC ACGCCATCGTGCAGACGCTGTCCACTTCATCAACC CGGAAACGGTGCCCAAGCCCTGCTGTGCCACGC AGCTCAATGCCATTCCGTCTCTACTTGATGACAG CTCCAACGTCATCCTGAAGAAATACAGAAACATGGT GGTCCGGGCCTGTGGCTGTCGC (SEQ ID NO: 34) | M Q A K H K Q R K R L K S S C K R H P L Y V D F S D V G W N D W I I A P E G Y A A Y Y C E G E C A F P L N S Y M N A T N H A I V Q T L V H F I N P E T V P K P C C A P T Q L N A I S V L Y F D D S S N V I L K K Y R N M V V R A C G C H (SEQ ID NO: 35) | |
| 1b_BMP9 | NB2-BMP9 | ATGCAAGCCAAACACAAACAGCGGAAACGCCTTAA GTCCAGCTGTAAGAGACACCCTTTGTACGTGGACTTC AGTGACTGGGGTGGAATGACTGGATTATTCCCCA AAAGGCTACGAGGCCGCCTACTACTGCGAGGGCTGT TTCTTTCCGCTGCCGACGATGTCAACCCGACCAAGC ACGCAATTGTCCAAACCTTAGTGCACCTGAAGTTCCC GTTATCTCCAATTAGCCGTGTGTGCCAACCAA GGCGTGCCGACGTTAAGATATCATTACGAGGCATG AGCGTCCCAGAGTGTGCTGCCGC (SEQ ID NO: 36) | M Q A K H K Q R K R L K S S C K R H P L Y V D F S D V G W N D W I I A P K K E Y E A A Y Y H L E C F F P L A D D V T P T K H A I V S Q T L V H L K F P T K V G K H Y E G M S V A E C G C R (SEQ ID NO: 37) | |
| 1b_GDF7 | NB2-GDF7 | ATGCAAGCCAAACACAAACAGCGGAAACGCCTTAA GTCCAGCTGTAAGAGACACCCTTTGTACGTGGACTTC AGTGACTGGGGTGGAATGACTGGATTATCGCGCCG CTGGAGGTCCACTTCGAACCTGACCTTATGC GATTTTCCTCGCGTTCGACTGCTCCACCACCAACC ATGCCATCATTCAGACGTTGGTCATCATGGCCACC AGACGCGGCGCCCATCAGCATCTTGTACTATGATGCC CCTGCAGCCCCATGCCTGTCTACAAGCAATACGAGGACTGTG GTGGAGCCTGTGGGTGTCGC (SEQ ID NO: 38) | M Q A K H K Q R K R L K S S C K R H P L Y V D F S D V G W N D W I I A P L D Y E A Y H C E G L C D F P L R S H L E P T N H A I I Q T L V N S M A P D A A P A S C C V P A R L S P I S I L Y Y D A A N N V V Y K Q Y E D M V V E A C G C R (SEQ ID NO: 39) | |
| 1b_GDF8 | NB2-GDF8 | ATGCAAGCCAAACACAAACAGCGGAAACGCCTTAA GTCCAGCTGTAAGAGACACCCTTTGTACGTGGACTTC | M Q A K H K Q R K R L K S S C K R H P L Y V D F S D V G W N D W I I A P K R Y K A N Y C S G E C E F V F | |

TABLE 1-continued

| BMP-2/activin constructs | Sample Designation | DNA Sequence | Protein Sequence | Exemplary Characteristics |
|---|---|---|---|---|
| | | AGTGACGTGGGGTGAATGACTGGATTATTGCACCC AAAAGATATAAGGCCAATTACTGTCTGGAGAGTGT GAATTTGTATTTTACAAAAATACCCTCACACTCATC TTGTGCACCAAGCAAACCCCAGAGGTTCAGCAGCC CCTGCTGTACTCCCCACAAAGATGTCTCCAATCAATAT GCTATATTTTAATGGCAAAGAACAAATAATTATGG GAAAATTCCAGCCATGGTAGTAGATCGCTGTGGGTG CTCA (SEQ ID NO: 40) | L Q K Y P H T H L V H Q A N P R G S A G P C C T P T K M S P I N M L Y F N G K E Q I I Y G K I P A M V V D R C G C S (SEQ ID NO: 41) | |
| BMP2/BMP6 | B2/B6 | BMP-2$_{wt}$ and BMP-6 are added together during the refolding to generate the BMP2/BMP6 heterodimer. BMP-2$_{wt}$ sequence herein is also reported as AB2-005. BMP-6 DNA sequence is: ATGCAACAGAGTCGTAATCGCTCTACCCAGTCCAG GACGTGCGCGGGTCTTCCAGTGCTTCAGATTACAAC AGCAGTGAATTGAAAACAGCCTGCAGGAAGCATGA GCTGTATGTGAGTTTCCAAGACCTGGGATGGCAGGA CTGGATCATTGCACCCAAGGGCTATGCTGCCAATTA CTGTGATGGAGAAGATGCTCCTTCCCACTCAACGACA CATGAATGCAACCAACCACGCGATTGTGCAGACCTT GGTTCACCTTATGAACCCCGAGTATGTCCCCAAACC GTGCTGTGCGCCAACTAAGCTAAATGCCATCTCGGTT CTTTACTTTGATGACAACTCCAATGTCATTCTGAAAA AATACAGGAATATGGTTGTAAGAGCTTGTGATGCC AC (SEQ ID NO: 149) | BMP-2$_{wt}$ sequence is reported above as AB2-005. BMP-6 amino acid sequence. Two amino acids, MA, are present in BMP-2$_{wt}$ in contrast to mature form of BMP-2 existent in nature. M Q Q S R N R S T Q S Q D V A R V S S A S D Y N S S E L K T A C R K H E L Y V S F Q D L G W Q D W I I A P K G Y A A N Y C D G E C S F P L N A H M N A T N H A I V Q T L V H L M N P E Y V P K P C C A P T K L N A I S V L Y F D D N S N V I L K K Y R N M V V R A C G C H (SEQ ID NO: 150) | Has increased SMAD-mediated signaling activity as compared to either BMP-2 or BMP-6. |

Protein Expression and Purification. The activin/BMP-2, 1b chimeras, and BMP-2$_{ma}$ chimeras were expressed using a typical *E. coli* expression system, and all 32 chimeras were found in the inclusion body fractions. The expressed inclusion bodies were isolated, purified, and refolded. The refolded ligands were purified using a Hi-trap heparin column (GE Healthcare) and reversed phase chromatography (GraceVydac). The ligands were lyophilized and re-suspended in 4 mM HCl, pH 1 for use in all cell based assays or 10 mM Na acetate, pH 4 for all biophysical assays. Activin-βA was expressed in a stably transfected CHO cell line and purified using techniques known in the art. Noggin was expressed and purified based on previously described protocols.

The activin/BMP-2 chimera inclusion bodies were seen as single bands on a reduced, SDS-PAGE gel and found at the expected size of ~13 kDa (FIG. 1a). To standardize the refoldings, all activin/BMP-2 chimeras were refolded in 100 mL volumes at a concentration of 50 mg/L. The concentration was chosen based on previously successful BMP-2, BMP-3, and GDF-5 refoldings. The volume was picked so that any dimer yield of 2% or greater would generate enough protein for biophysical activity assays, yet small enough to be manageable with the large number of samples. Following refolding, the activin/BMP-2 samples were analyzed for the formation of pure dimer, the desired product, after elution from Heparin column (FIG. 1b and c). Surprisingly, all 32 activin/BMP-2 samples showed the presence of some dimer and the chimeras were ranked based on their refolding efficiency (dimer yield) and grouped into 4 categories, from poor (<1%, −) to wild type (>10%, +++) (Table 2). To be classified as a 'successful' chimera, the ligand needed to have a refolding efficiency equal to or greater than 5%. This efficiency would yield 2.5 mg/L of dimeric protein from a standard 1 L refolding at 50 mg/L concentration, and would be considered suitable for experiments where large quantities are required, such as x-ray crystallography. When refolding efficiency was calculated, 24 out 32 (75%) of the activin/BMP-2 chimeras met this criteria (Table 2, supplemental, ++ or +++).

TABLE 2

| Construct | Name | Dimer Yield | Rating | Rating System | |
|---|---|---|---|---|---|
| 1b2b3a4a5a6a | AB2001 | 5% | ++ | +++ (wt) | >10% |
| 1b2b3a4a5b6a | AB2002 | 7% | ++ | ++ | 5-9% |
| 1b2a3a4a5b6a | AB2003 | 1% | − | + | 2-4% |
| 1b2a3b4b5b6a | AB2004 | 9% | ++ | − | <1% |
| 1b2b3b4b5b6b | AB2005 | >10% | +++ | | |
| 1b2a3a4a5a6b | AB2006 | 9% | ++ | | |
| 1b2a3a4a5a6b | AB2007 | >10% | +++ | | |
| 1b2a3a4a5a6a | AB2008 | >10% | +++ | | |
| 1b2a3a4a5a6a L66V/V67I | AB2009 | ~4% | + | | |
| 1b(1a_II)2a3a4a5a6a | AB2010 | 3% | + | | |
| 1b2b3b4b5a6a | AB2011 | >10% | +++ | | |
| 1b2b3b4b5b6a | AB2012 | >10% | +++ | | |
| 1b2b3b4b5b6b | AB2013 | >10% | +++ | | |
| 1b2a3b4b5a6b | AB2014 | >10% | +++ | | |
| 1b2a3b4b5b6a | AB2015 | >10% | +++ | | |
| 1b2a3b4b5b6b | AB2016 | >10% | +++ | | |
| 1b2b3b4a5a6a | AB2017 | 5% | ++ | | |
| 1b2b3b4a5b6b | AB2018 | 2% | + | | |
| 1b2b3b4a5a6b | AB2019 | 3% | + | | |
| 1b2b3b4a5b6a | AB2020 | 3% | + | | |
| 1b2b3a4a5a6a | AB2021 | 6% | ++ | | |
| 1b2b3a4a5b6b | AB2022 | 5% | ++ | | |
| 1b2b3a4b5b6b | AB2023 | 3% | + | | |
| 1b2b3a4b5b6a | AB2024 | 6% | ++ | | |
| 1b2b3a4b5a6a | AB2025 | 4% | + | | |
| 1b2b3a4b5a6b | AB2026 | 5% | ++ | | |

TABLE 2-continued

| Construct | Name | Dimer Yield | Rating | Rating System |
|---|---|---|---|---|
| 1b2a3a4b5b6b | AB2027 | >10% | +++ | |
| 1b2a3a4b5b6a | AB2028 | 4% | + | |
| 1b2a3a4b5a6b | AB2029 | 1% | − | |
| 1b2a3a4b5a6a | AB2030 | 2% | + | |
| 1b2a3b4a5a6a | AB2031 | 4% | + | |
| 1b2a3b4a5b6a | AB2032 | 4% | + | |
| 1b2a3b4a5b6b | AB2033 | 4% | + | |
| 1b2a3b4a5a6b | AB2034 | 1% | − | |

To be considered a successful ligand, the activin/BMP-2 chimeras not only have to be refoldable but they also need to display signaling characteristics. To test for these properties, all activin/BMP-2 chimeras, regardless of refolding efficiency, were initially subjected to activin activity assays. Activin-like signaling characteristics were tested using a whole cell luciferase reporter assay sensitive to Smad-2/3 activation (as described below). Activin-βA is known to signal through and activate the Smad-2/3 pathway, so if any of the activin/BMP-2 chimeras mimic activin-βA functionality, they should signal in a similar manner. Out of all 32 chimeras, only 1, 1b2a3a4a5a6a (AB2-008), signaled in an activin-like manner. AB2-008 activates the luciferase reporter in a dose dependent manner similar to activin-βA. When the potency of the AB2-008 chimera was determined, the EC$_{50}$ was calculated to be 64.5 pM. This value is ~2 fold lower than activin-βA with an $EC_{50}$ of 28.8 pM. To confirm that the luciferase results were a direct response to Smad-2 activation, phospho-Smad-2 was tested in the presence of AB2-008. Similar to activin-βA, the addition of AB2-008 promotes an increase in phospho-Smad-2 levels. As expected, AB2-008, along with activin-βA, does not stimulate phospho-Smad-1 production, indicating only activation of a specific signaling pathway. Interestingly, AB2-008 exhibits BMP-$2_{ma}$ refolding efficiency with >10% dimer yield (Table 2).

To fully test if AB2-008 possesses complete activin-βA functionality, additional biophysical assays were performed. Cripto is a known co-receptor for many of the TGF-β ligands and elicits a wide range of responses. For instance, the presence of Cripto is required for proper Nodal signaling, while it antagonizes TGF-β1 and activin signaling. Therefore, using the Smad-2/3 luciferase assay activin-βA and AB2-008 signaling were monitored in the presence or absence of Cripto. In the presence of Cripto, activin-βA signaling is decreased by ~43% compared activin-βA alone. The AB2-008 chimera exhibits a similar decrease in signaling of ~38% when Cripto is added to the assay. This result confirms that the AB2-008 chimera is a fully functioning activin mimic by being able to activate the activin signaling pathway as well having the ability to interact with other known activin binding partners.

Based on the results of AB2-008, 2 additional activin/BMP-2 chimeras were generated to see if the potency of the chimeras could be increased to wild type activin-βA levels. The first chimera, named 1b2a3a4a5a6a L66V/V67I (AB2-009), introduced a valine and iso-leucine into the chimera. These residues are found in the wild type sequence of activin-βA and were originally mutated to the corresponding BMP-2 residues due to experimental design constraints (FIG. 7*a*). The second chimera, named 1b(1a_II)2a3a4a5a6a (AB2-010), replaces the second half of the 1b section with the corresponding sequence from activin (FIG. 7*a*). This leaves only the 13 N-terminal residues preceding the first structurally conserved cysteine, Leu-66, and Val-67 as components from BMP-2 in this chimera construct. It is predicted that the introduction of additional activin residues into AB2-008 will improve its functional characteristics (i.e. potency). AB2-009 and AB2-010 were expressed and refolded as previously described for the other activin/BMP-2 chimeras. Unexpectedly, both of these new chimeras exhibited decreased refolding efficiency compared to AB2-008. AB2-009 and AB2-010 saw a decrease from >10% dimer yield to ~4% and ~3% for AB2-009 and AB2-010, respectively (Table 2). While this result may not be surprising for AB2-010 since an 11 residue section was mutated, the drastic decrease for AB2-009 was unexpected. Both the L66V and V67I mutations are very conservative changes with only a 1 carbon difference between the side chains of the mutated residues.

Following refolding, the new chimeras were subjected to the same Smad-2/3 luciferase assay as AB2-008 previously. AB2-009 activated the reporter in a dose dependent manner and displayed activity comparable to AB2-008 with an $EC_{50}$ of 79.4 pM. However, while AB2-010 also activated the reporter, it showed a significant decrease in activity with an $EC_{50}$ of 198.6 pM, or ~3-fold weaker than AB2-008 and ~7-fold weaker than activin-βA. As with AB2-008, both AB2-009 and AB2-0010 showed Smad-2 phosphorylation. Since AB2-009 and AB2-010 did not show enhanced signaling characteristics from AB2-008 in the luciferase assay, they were not subjected to Cripto binding assay.

While the Smad-2/3 luciferase, Smad-2 phosphorylation, and Cripto reporter assays indicate that AB2-008, AB2-009, and AB2-010 signal through the activin pathway and function very similarly to activin-βA, these assays only show function in an in vitro setting. Therefore, more physiologically relevant experiments are required to prove that these activin/BMP-2 chimeras will elicit a biological response similar activin-βA. One classical method used to test for proper activin function is a follicle stimulating hormone (FSH) release assay. Rat anterior pituitary cells are known to release FSH in response to the presence of activin in both in vivo and in vitro experiments. Therefore, rat anterior pituitary cells were exposed to increasing amounts of activin-βA or the activin/BMP-2 chimeras and FSH release was measured by radioimmunoassay. All three activin/BMP-2 chimeras showed a dose dependent increase in FSH release similar to activin-βA. The amount of FSH release stimulated by the chimeras was decreased in the presence of increasing amounts of Inhibin. Combined with the in vitro assay results, the FSH release assay confirms that AB2-008, AB2-009, and AB2-010 possess the complete activin-βA functional characteristics.

The chimeras were also tested to check for any additional signaling properties. BMP-2 is already used as a therapeutic agent for certain bone treatments and having chimeras with altered BMP-2 function may prove beneficial. To test if any of the activin/BMP-2 chimeras displayed unique signaling characteristics, a similar experiment to the activin-βA functional assay was performed. Here, a whole cell luciferase reporter assay sensitive to Smad-1/5 activation, the known BMP-2 signaling pathway, was used rather than a reporter sensitive to Smad-2/3 activation. Monitoring the luciferase response in a dose dependant manner, a number of activin/BMP-2 chimeras exhibit interesting traits. These activin/BMP-2 chimeras were identified and classified into 3 groups: Those with upregulated or 'super' BMP-2 activity; those with insensitivity to Noggin, a BMP-2 antagonist; or those with both 'super' BMP-2 activity and insensitivity to Noggin. Activin/BMP-2 chimeras 1b2a3b4b5a6a (AB2-004), 1b2b3b4b5a6a (AB2-011), 1b2b3b4b5b6a (AB2-012), and 1b2a3b4b5b6a (AB2-015) all fall into category of enhanced BMP-2 activity with Noggin insensitivity. In the Smad-1 luciferase assay, these ligands activate the reporter at the same level as $BMP-2_{wt}$ using 10× less protein (i.e., 10-fold higher activity). Grouped into the category of upregulated BMP-2 activity is 1b2b3b4b5a6b (AB2-013). This chimera shows the same 10-fold increase in activity as AB2-004, -011, -012, -015, but the signal is decreased down to background levels upon the addition of Noggin, similar to $BMP-2_{wt}$. Chimera, 1b2a3b4b5a6b (AB2-014), fell into the final category of ligands with normal BMP-2 signaling but with insensitivity. AB2-014 activates the luciferase reporter to the same level as $BMP-2_{wt}$ but its signal cannot be blocked by the addition Noggin. AB2-008 was also tested to see if it activated the Smad-1 pathway in addition to activating the Smad-2 pathway. AB2-008 did not show any Smad-1 activation, even up to levels of 1 µg/ml. This result confirms that AB2-008 is a specific activin mimic and does not exhibit non-specific signaling characteristics.

Figure 7A:
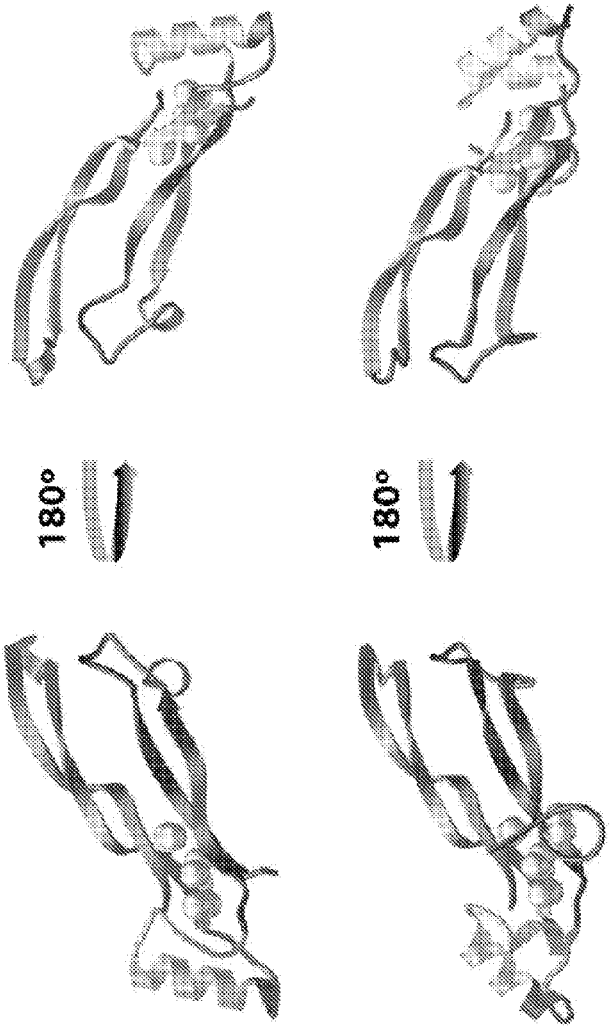
FIG. 7A shows a sequence alignment of BMP-2 and Activin-βA with the segments highlighted and labeled.

With the success of the AB2-008 chimera which refolds efficiently and possesses activin-like signaling characteristics, the 1b section was examined as a general tool to improve the refolding of other currently non-refoldable TGF-β ligands. As mentioned before, the 1b section is 30 a.a. long and comprises the N-terminus of BMP-2 as well as the residues forming the first beta strand of finger 1 (FIG. 7a). Based on analysis of the ternary structure of BMP-2/BMPRIa/ActRII, the majority of the residues found in section 1b do not form any contacts with either the Type I or Type II receptors. Indeed, of the few residues which do generate contacts with the Type I receptor, Val-26, Gly-27, and Trp-28, the tryptophan is invariant throughout the entire TGF-β superfamily, while the Gly-27 participates in a backbone interaction, and the valine is predominantly a non-polar amino acid at this position throughout the TGF-β superfamily. Based on this, it is possible that the 1b region, while not critical for contributing to ligand-receptor affinity and specificity, is very helpful in proper disulfide bond formation during the chemical refolding process. Therefore, the 1b section was cloned into the additional TGF-β ligands BMP-7, BMP-9, and GDF-8. As with the activin/BMP-2 chimeras, the 1b chimeras were expressed in an *E. coli* expression system and the inclusion bodies isolated to high purity.

Smad-1 Luciferase Assays in C2C12 Cells

Smad1-dependent luciferase assays were performed using techniques known in the art. In brief, C2C12 myoblast cells are cultured in Dulbecco's minimum essential medium (DMEM)+5% FBS supplemented with L-Glutamine and antibiotics. For luciferase reporter assays, cells were trypsinized, washed twice with PBS and plated into 48-well plates with DMEM+0.1% FBS. Twenty four hours later, cells were transfected with −1147Id1-luciferase construct containing the Smad binding sites (Id1-Luc), a Smad1 expression construct, and a CAGGS-LacZ plasmid by using Fugene6 (Roche) according to the manufacturer's instruction and cells were stimulated with increasing amounts of $BMP-2_{ma}$ or the various activin/BMP-2 chimeras added 24 hours post transfection. Luciferase activity was measured 24 hours after stimulation with ligands and the values were normalized for transfection efficiency by using beta-galactosidase activity. The activity of the luciferase reporter is expressed in fold-induction relative to control values that are obtained by using −927Id1-luciferase that lacks Smad binding domains (Id1-Luc mut). To test for the ability of Noggin to attenuate the Smad1 signaling of the ligands, the luciferase assays were repeated as described above, with a set dose of Noggin included in the assay.

Smad-2 Luciferase Assays in HEK293 Cells

HEK293T cells were seeded into 24-well plates coated with polylysine at a density of 150,000 cells/well. After 24 h cells were transfected overnight with a mixture of A3 Lux (25 ng) and β-galactosidase (25 ng) reporter plasmids, the transcription factor FAST2 (50 ng), and empty pCDNA3 vector (400 ng) using Perfectin® transfection reagent (GenLantis) according to the manufacturer's recommendations. Then the cells were treated with increasing doses of activin-βA or activin/BMP-2 chimeras for 16-24 h. The cells were harvested in ice-cold lysis buffer (1% Triton X-100 in 25 mM glycylglycine, 4 nM EGTA, 15 mM MgSO$_4$ containing 1 mM dithiothreitol) and assayed for luciferase and β-galactosidase activities using standard methods. To assess the ability of the activin/BMP-2 chimeras to bind' known TGF-β co-receptors, the HEK293T cells were treated with increasing doses of activin-βA or activin/BMP-2 chimeras in the presence or absence of transfected Cripto for 16-24 h (mouse Cripto construct was a generous gift from Malcolm Whitman (Department of Cell Biology, Harvard Medical School, Boston, Mass.)). Activity was then measures as previously described.

Follicle Stimulating Hormone (FSH) Release from Rat Interior Pituitary Cells The assay was performed as previously described in the art. Briefly, freshly isolated cells from male Sprague-Dawley rat interior pituitaries from several animals were combined and seeded into 96-well plates at a density of 50,000 cells/well in βPJ medium supplemented with 2% fetal bovine serum and appropriate growth factors. After 24 h cells were treated with increasing doses of activin-βA or activin/BMP-2 chimeras (0-40 nM). After 72 h, media were harvested and the concentration of the secreted FSH was determined by radioimmunoassay.

Surface Plasmon Resonance (BIAcore) Affinity Studies

The affinity of the ligands to BMPRIa, ActRII, and ActRIIb was monitored by using a Biacore 3000 (GE Healthcare) and the data were analyzed by using BIAevaluation software ver. 4.1 (GE Healthcare). Using primary amine coupling, receptor ECDs were immobilized on a CM5 chip. The receptors were immobilized independently on flow cells 2-4 for 10 minutes at a flow rate of 5 μL/min and a concentration of 20 μM in 10 mM Na acetate, pH 4.0. Flow cell 1 was left blank, no immobilized protein, as a negative control. The experiments were performed at a flow rate of 50 μL/min in 20 mM Tris-HCl pH 7.9, 250 mM NaCl, 0.36% 3-[(3-Cholamidopropyl)dimethylammonio]-1-propanesulfonate (CHAPS), and 0.005% Tween-20. A minimum of five concentrations, plus a zero concentration, were run per sample for kinetic analysis and the data were fit by using a global 1:1 Langmuir binding with mass transfer.

Example 2

Synthesis of the BMP Heterodimer Ligand

The crystal structure of BMP2-BMPRIa-ActRIIb has shown that each receptor molecule do not associate extracellularly and have 4 distinct ligand-receptor interface. This suggested that a heterodimer would have 2 distinct type I interfaces and 2 distinct type II interfaces. To characterize functional and other aspects of the BMP ligand recombinant heterodimers were synthesized. The purity of the protein was verified by sodium dodecyl sulfate-polyacrylamide gel electrophoresis (SDS-PAGE). FIG. 1a illustrates the migration of the BMP2/BMP6 heterodimer as a single band under non-reducing (lane 1) and as two distinct bands under reducing conditions (lane 3) on SDS-PAGE. The two distinct bands correlate to the two different monomer species (about 13 and 15 kDa respectively), of the BMP2/BMP6 heterodimer. This evidence is further supported with surface-enhanced laser desorption/ionization time-of-flight mass spectrometry (SELDI-TOF-MS) data. Three separate, purified samples of the BMP2 and BMP6 homodimers and the BMP2/BMP6 heterodimer were assayed on SELDI-TOF-MS. As FIG. 1b demonstrates, the three samples each correspond to their predicted mass with no other contaminating species. These assays indicate that a pure BMP2/BMP6 heterodimer was generated.

BMP Heterodimer Activity In Vitro

To assay the interactions between the BMP2/BMP6 heterodimer and type I and type II TGF-beta receptor ECDs, surface plasmon resonance was utilized to measure the in vitro affinity. The TGF-beta receptors were immobilized to a chip and the TGF-beta ligands were flowed over the surface while monitoring the interactions. Table 3 summarizes the ligands tested and the varying affinities for the type I and type II receptor ECDs. In the case of the BMP2/BMP6 heterodimer, it adopts the greater affinity from each of its BMP2 and BMP6 monomer subunits. As shown, the BMP2/BMP6 heterodimer has similar affinity for the type I receptor as the BMP2 homodimer. However, instead of adopting the type II receptor ECD affinity from the BMP2 subunit, the BMP2/BMP6 heterodimer has an affinity similar to the BMP6 homodimer for the type II receptor. This indicates that the high affinity for the type II receptor ECD is contributed by the BMP6 monomer subunit while the high affinity for the type I receptor ECD is contributed by the BMP2 monomer subunit.

TABLE 3

| | Ligand Affinity Data from BIAcore Analysis | | | |
|---|---|---|---|---|
| | Receptor BMPR-Ia | | Receptor ActRIIb | |
| Ligand | $k_{off}[1/s]/k_{on}[1/M * s]$ | $K_D$ [nM] | $k_{off}[1/s]/k_{on}[1/M * s]$ | $K_D$ [nM] |
| BMP2 | $1.11 \times 10^{-3}/8.52 \times 10^5$ | 1.31 | $2.57 \times 10^{-2}/6.68 \times 10^5$ | 38.5 |
| BMP6 | $9.37 \times 10^{-3}/1.50 \times 10^5$ | 62.8 | $1.82 \times 10^{-3}/2.73 \times 10^5$ | 6.68 |
| BMP2/BMP6 | $1.05 \times 10^{-3}/1.03 \times 10^6$ | 1.02 | $8.58/1.32 \times 10^9$ | 6.52 |

Ligand affinity data from BIAcore experiments. The BIAcore data is shown as the dissociation rate, $k_{off}$, and the association rate, $k_{on}$, based on a global fit using the kinetic model 1:1 Langmuir binding with mass transfer. The binding constant $K_D$ is calculated as $k_{off}/k_{on}$. The receptors were immobilized to the chip surface, with the ligands flowed over the surface.

Figure 2:
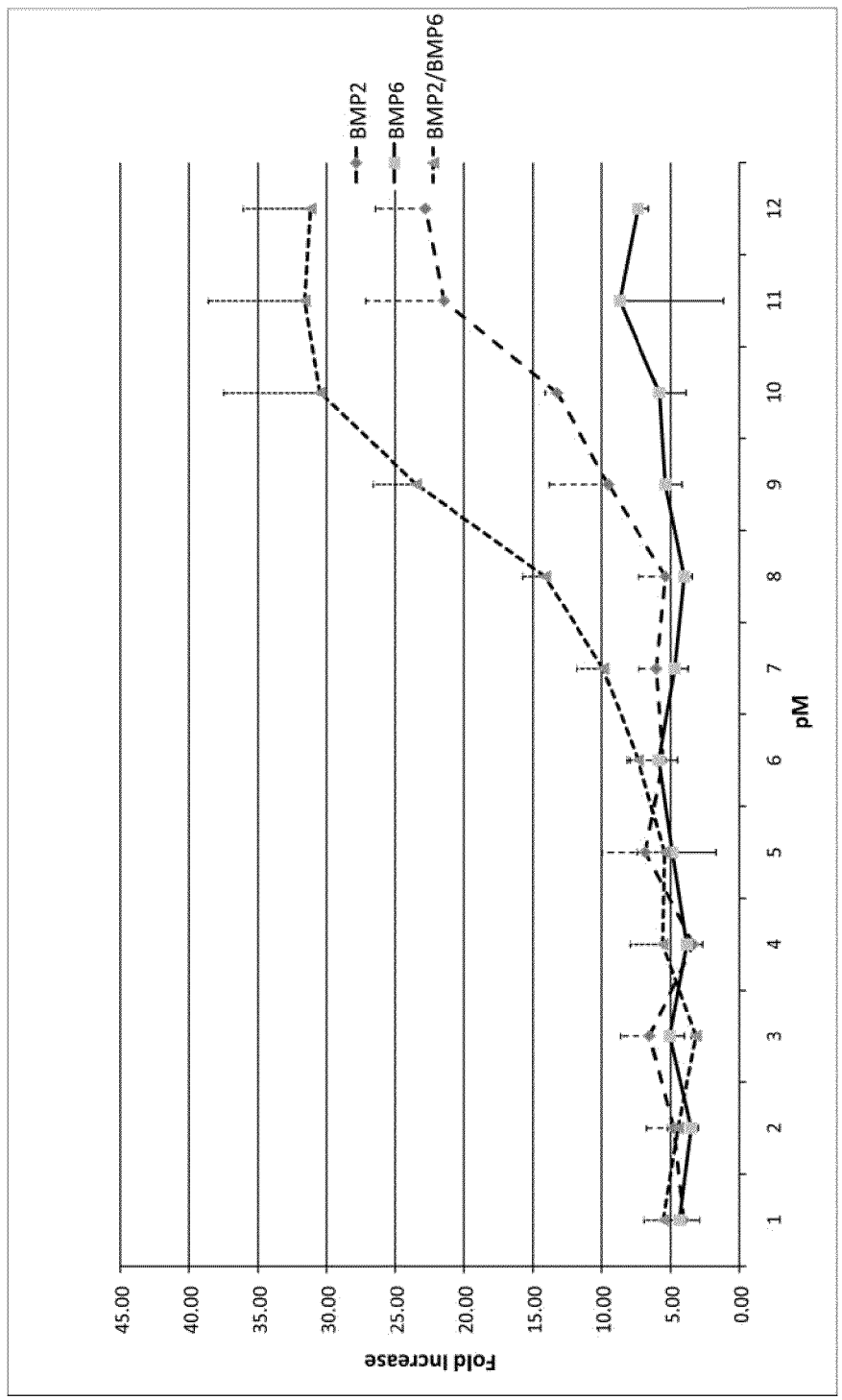
FIG. 2 shows $C_2C1_2$ whole cell Smad1-dependent reporter assay with wild type ligands. The solid black bars represent error.

To examine if receptor ECD affinity of the BMP2/BMP6 heterodimer correlates with signaling activity, a luciferase reporter assay was used. Using the C2C12 mouse myoblast cell line, the BMP ligands were quantitatively tested for the ability to activate a Smad1 dependent reporter gene. BMP2, BMP6 and BMP2/BMP6, all showed dose-dependent reporter activation. The BMP2/BMP6 heterodimer ligand showed further greater activation of the reporter gene than the BMP2 or BMP6 homodimer counterparts (FIG. 2). Up to 22-fold and 400-fold less BMP2/BMP6 was required to activate the reporter gene to an equivalent level as compared to the BMP2 and BMP6 homodimers respectively. Given that BMP2/BMP6 heterodimer has a high affinity to both type I and type II receptor ECDs, the results suggest that increased affinity to receptor correlates with level of intracellular signaling activity.

Figure 3:
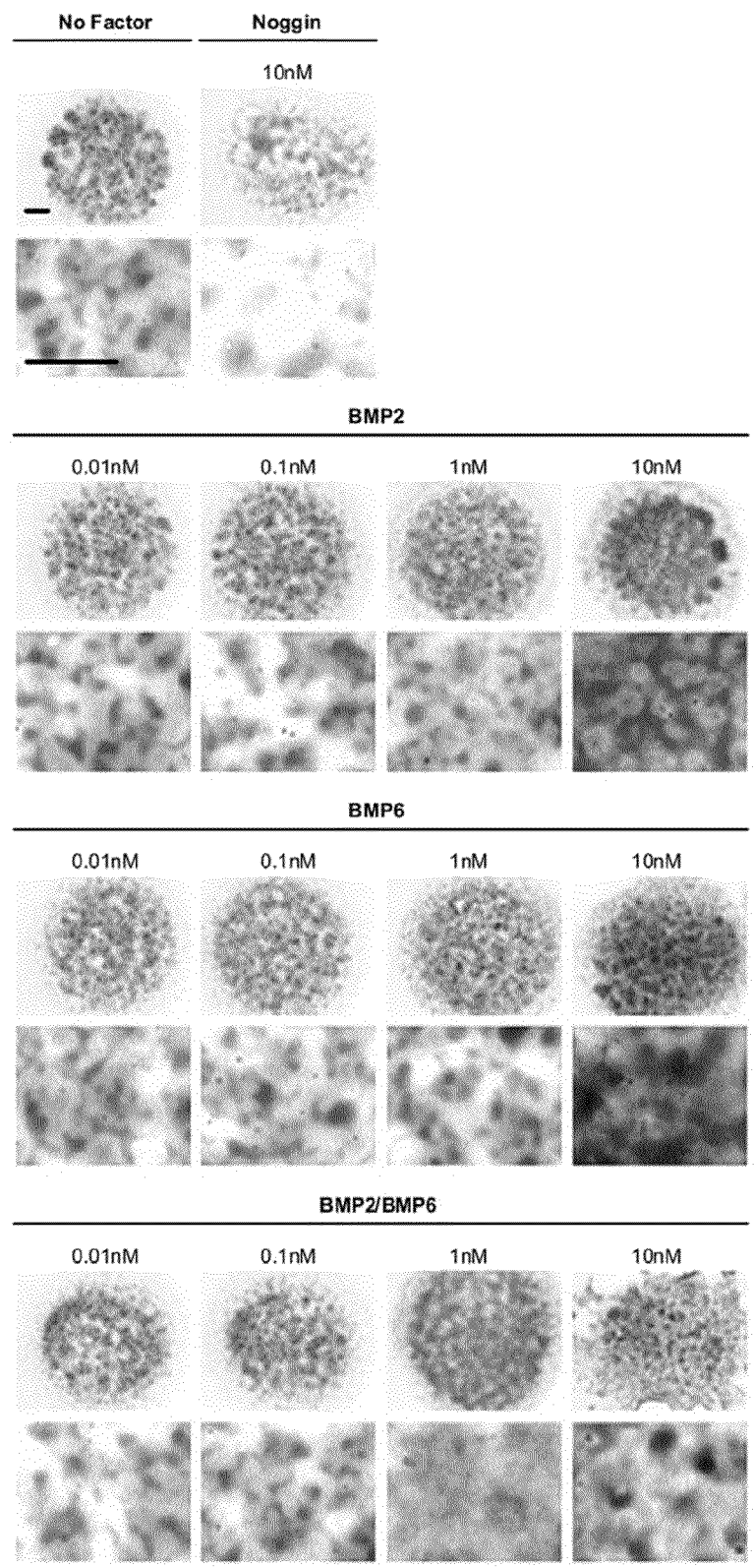
FIG. 3 shows a visualization of chick limb bud mesenchyme cell micromass culture chrondogenesis assays after 5 days. The top panel shows the culture with no factor and the extracellular antagonist Noggin. The bars in the micrographs represent 1 mm. The second through fourth panels show the culture with ligands BMP2, BMP6, and BMP2/BMP6 respectively.

To further characterize activities of BMP2/BMP6 heterodimer, an ex vivo assay using chick limb bud mesenchyme cells in micromass culture was used. Primary cultured limb bud mesenchymal cells undergo chondrogenesis in a BMP-dependent manner, and this system allows the characterization of homo and heterodimer in a biological process. FIG. 3 displays micrograph images of the staining of the chondrogenic nodules whose formation is known to be stimulated by BMPs. The extent of chondrogenesis is quantitated by measuring dye bound to the chondrogenic nodule. Similar to the reporter assay, a dose-dependent activation of chondrogenesis of limb bud mesenchymal cells by different BMP ligands. A unique aspect of this assay is that BMP6 has a slightly higher activity than BMP2, while its activity in the Smad-1-dependent reporter activation was significantly lower than that of BMP2. This likely involves Type II receptor-initiated distinct signaling such as the p38 pathway. Greater activity of BMP2/BMP6 heterodimer to activate chondrogenesis in this system was observed. BMP2/BMP6 activated chondrogenesis to the similar level of BMP2 and BMP6 homodimer at 10-fold concentration. The heterodimer ligand also induces a higher maximum response at the same concentration. This assay allows for the correlation of not only higher ligand-receptor affinity to higher signaling activity but extends this observation to an increase in biological activity.

Figure 5:
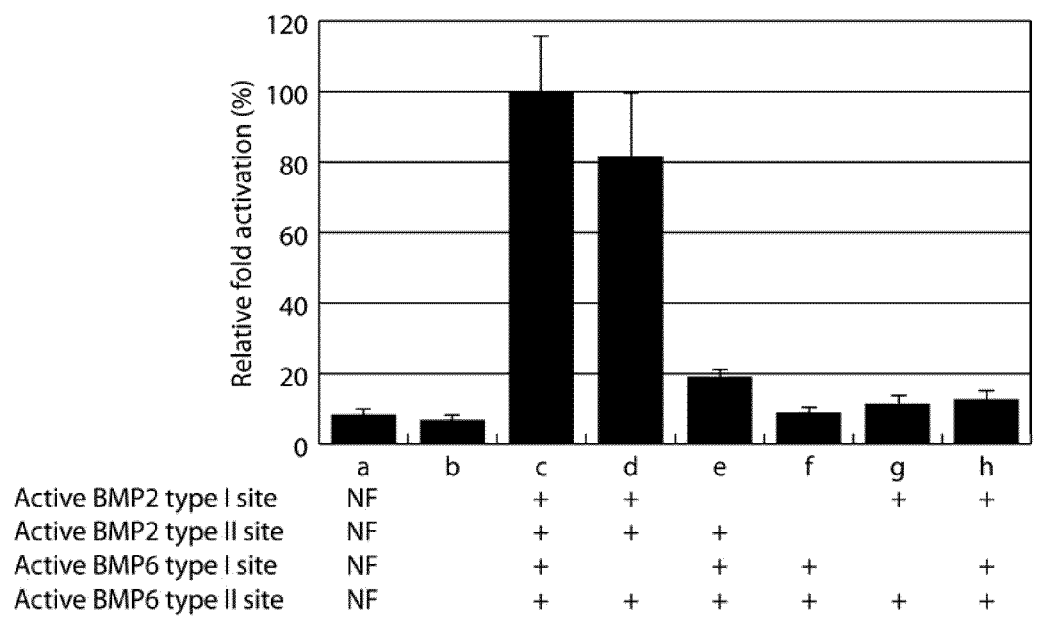
FIG. 5 shows Mutant BMP2/BMP6 heterodimers displaying activation of Smad1 reporter gene. Sample a contains no factor (background) and Sample b contains a BMP2 homodimer with no active receptor sites. All quantities are normalized to Sample c which is the fully active BMP2/BMP6 heterodimer (100% activation of reporter gene).

The data with ligand-receptor-ECD affinity, in vitro and ex vivo assays have demonstrated that a functional asymmetric BMP2/BMP6 dimer was generated. The asymmetric nature of the BMP2/BMP6 heterodimer allows for the manipulation of specific TGF-beta receptor sites of the ligand. FIG. 5 displays the specific mutagenesis of the BMP2/BMP6 heterodimer and the quantification of the ability of the different mutant variants to activate a Smad1 dependent reporter gene using the same system as described above (all factors are at 1 nM concentration). The quantified values are displayed as a percentage fold activation compared to the BMP2/BMP6 wild type heterodimer with no mutagenesis (normalized to 100% activation of the reporter gene). The BMP2/BMP6 heterodimer ligands with point mutations to only one of the two type I receptor interfaces with the two type II receptor interfaces intact (FIG. 5, samples d and e), are able to activate the reporter gene, although between 20-80% compared to the BMP2/BMP6 wild type heterodimer. In contrast, the BMP2/BMP6 heterodimer with point mutations to only one of the two type II receptor interfaces with the two type I interfaces intact (FIG. 5, sample f), can not activate the reporter gene. The BMP2/BMP6 heterodimer ligands with point mutations disrupting one each of the two type I receptor and type II receptor interfaces (FIG. 5, samples g and h), cannot activate the reporter gene. These results demonstrate that 2 type II sites are required for signaling activity, while only 1 type I site was sufficient for signaling. The difference of signaling activity between two ligands having 1 type I site mutation (d and e in FIG. 5) illustrates that Smad1 activation directly correlates with affinity of a type I site and type I receptor (Table 3).

Figure 6:
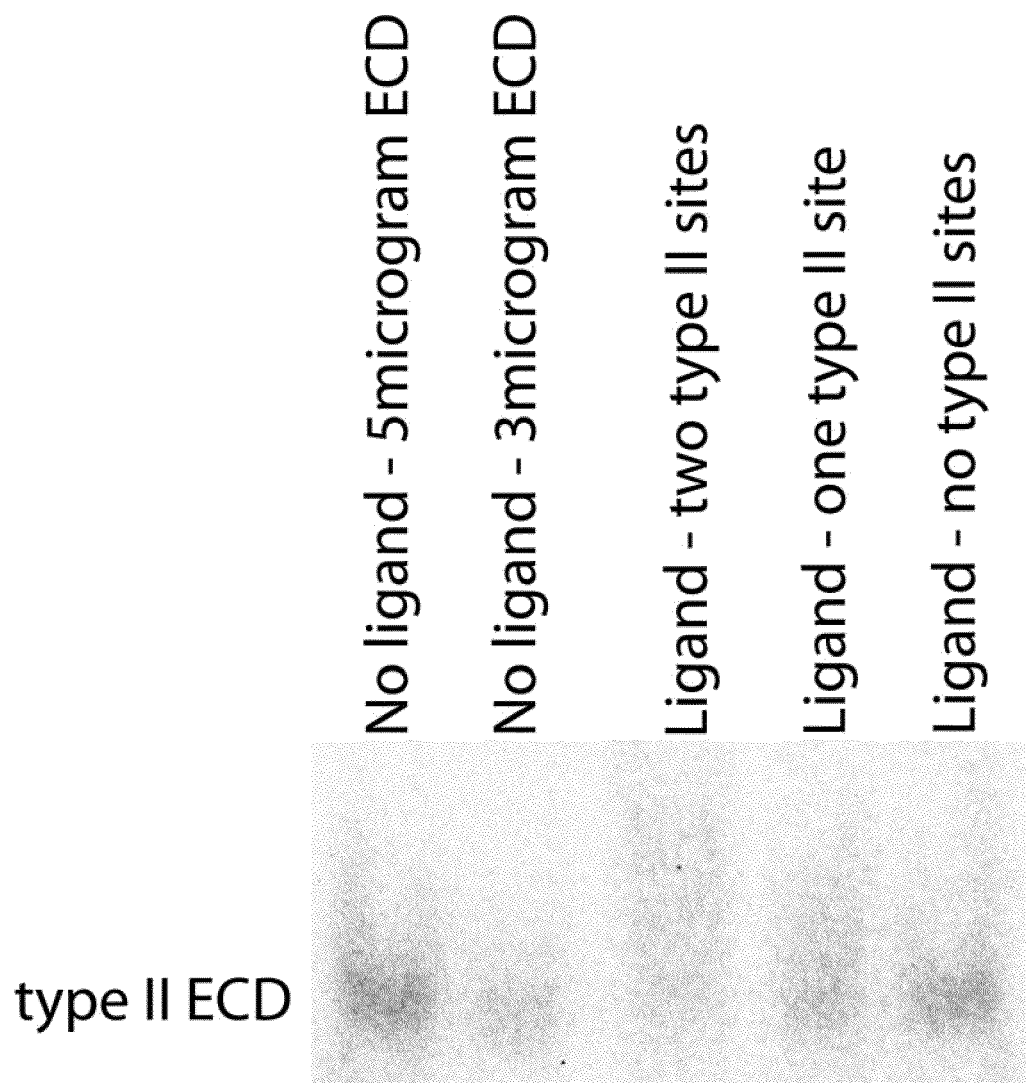
FIG. 6 shows a native-PAGE displaying the quantity of type II receptor ECD remaining after being saturated into a ligand-receptor complex with the specified ligands.

In further studies with the non-signaling BMP2/BMP6 heterodimer mutants, the ability of the ligands to bind receptor ECD was accessed. Despite the inability of the ligand with only one active type II receptor site to activate the reporter gene (FIG. 5, sample f), this ligand is still able to bind type II receptor ECD under native-PAGE conditions. FIG. 6 illustrates a type II receptor ECD saturation assay in which the receptor ECD is run on the native-PAGE both in the absence and presence of ligand. In comparing the lane with five micrograms of type II receptor ECD and no factor to the lane with ligand containing two active type II receptor binding sites, the intensity of the band is diminished by 9.0-fold, indicating that the receptor ECD has been incorporated in a ligand-receptor complex. This represents about half of the receptor ECD incorporated into a ligand-receptor complex when comparing the intensity of three micrograms receptor ECD run alone. In the next lane, a ligand with only one active type II receptor site shows an increase in the band intensity by 3.3-fold compared to the ligand with two active type II receptor sites. And in the final lane, a ligand with no active type II receptor sites increases the band intensity by 1.8-fold compared to the ligand with one active type II receptor site. As expected, the BMP2/BMP6 ligand with one active type II receptor site falls in between the ligand with two active type II receptor sites and that with no active type II receptor sites. The single intact type II receptor interface on the mutated BMP2/BMP6 heterodimer is still able to bind one type II TGF-beta receptor ECD, indicating that the extracellular signaling complex can assemble. The inability of the mutated ligand to signal lies further downstream from signaling complex assembly at the cell surface. This assay provides proof for an independent binding model of ligand-receptor complex formation where a single receptor ECD can bind to one of the four receptor sites on the ligand regardless of the affinity or functionality of the other three receptor sites on the ligand.

The results from the analysis of the recombinant BMP heterodimers prove that a purified homogeneous heterodimer sample can be synthesized (FIG. 1). The data further demonstrate that recombinant BMP heterodimers can be expressed in E. coli as inclusion bodies, refolded, and purified at a scalable level.

Figure 4:
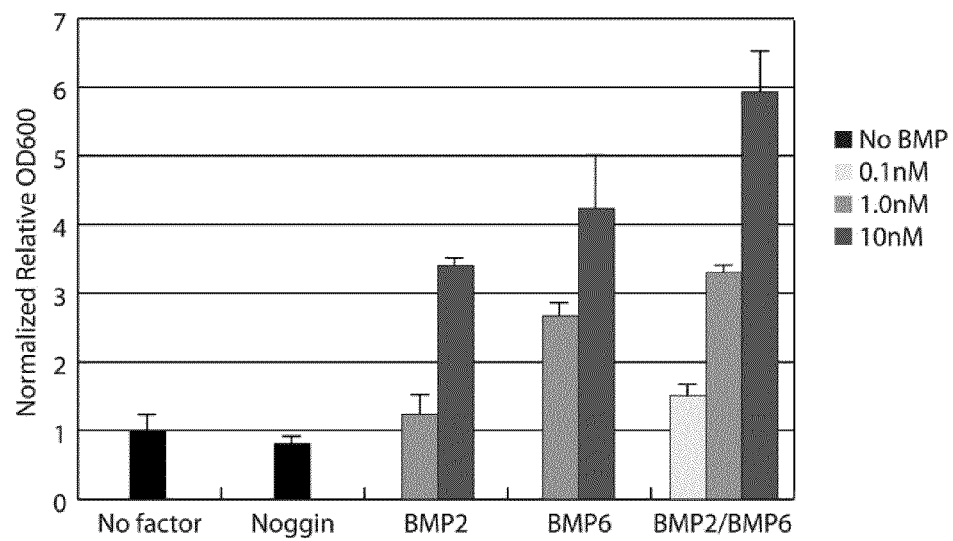
FIG. 4 shows quantification of chick limb bud mesenchyme cell micromass culture chrondogenesis assays after three days. The addition of the specified growth factor at different concentrations is indicated.

The data obtained from the surface plasmon resonance affinity studies (Table 3), shows that a BMP heterodimer is more potent in vivo and in vitro than the BMP homodimers. As compared to the homodimer counterparts, the BMP2/BMP6 heterodimer has the higher affinity receptor sites from each of its covalently linked monomer subunits. The BMP2/BMP6 heterodimer has a high affinity type I receptor site comparable with the BMP2 homodimer and a high affinity type II receptor site comparable with the BMP6 homodimer. Each of these homodimer ligands secondary receptor sites have lower affinity for the respective receptor compared to their primary receptor sites. This heterodimer ligand-receptor affinity data, for the first time, provides clear evidence for the mechanism of the high potency TGF-beta heterodimer ligands compared to their homodimer counterparts. With high affinity for both type I and type II receptor ECDs, the TGF-beta signaling complex can more readily assemble and remain assembled as the cell surface. The augmented affinity of the BMP heterodimer correlates directly to increased signaling in the whole cell reporter assays (FIG. 2). Additionally, the ex vivo data from the mesenchyme cell assays (FIGS. 3 and 4) demonstrates the ability of the BMP2/BMP6 heterodimer to be able to induce a response at a lower concentration and to a higher maximum than its homodimer counterparts. This data directly supports the correlation between increased ligand-receptor affinity, signaling activity, and biological activity.

While the high signaling activity of the BMP heterodimer was readily achieved in the whole cell reporter system (FIG. 2), elucidating the requirements of the TGF-beta signaling complex and mechanism of activation proved much more difficult. The BMP heterodimer constructs with just one type I receptor site and two type II receptor sites, were still able to activate the reporter gene, although to a lesser extent compared to the fully functional BMP heterodimer (FIG. 5). However, the BMP heterodimer constructs with two type I receptor sites and only one type II receptor site failed to activate the reporter gene (FIG. 5). This inconsistency between the number of required active type I and type II receptor sites on the ligand can not be readily explained. The data demonstrating complex formation under native-PAGE conditions (FIG. 6), illustrates that the type II receptor ECD can bind to the mutated heterodimer with only one active type II receptor interface. This indicates that the problem is not with signaling complex formation between ligand and receptor ECD at the cell surface. The complex with only one type II receptor forms as readily as the complex with one type I receptor, yet the complex with only one type II receptor does not initiate downstream signaling.

The data suggest that a type II receptor kinase phosphorylates it's partner type II receptor rather than itself, and such "cross-phosphorylation" is the molecular nature of the autophosphorylation. Alternatively, physical association of intracellular kinase domain between two type II receptor is required for "auto phosphorylation", although ECD does not associate one another. This initial step of the signaling cascade cannot occur in the absence of one type II receptor, and thus, no signal is transduced. The ability of some of the mutant BMP heterodimer ligands to form an active signaling complex with only one type I receptor present (FIG. 5), occurs because the two type II receptor kinases in the signaling complex are able to dimerize, autophosphorylate, and then transphosphorylate the single type I receptor kinase. No dimer of the type I receptor kinases is required because the kinase domain is simply transphosphorylated by the autophosphorylated dimer of type II receptor kinases.

The disclosure shows a truly independent ligand-receptor ECD binding model for the signaling complex formation at the cell surface. As stated above, mutated BMP2/BMP6 heterodimer ligand with only one active type II receptor site can still bind a single type II receptor ECD (FIG. 6). This evidence provides grounds for the assertion of the signaling complex's ability to form regardless of the affinity or functionality of the four individual receptor sites of the ligand. If each receptor site on the ligand is able to bind in this independent fashion, another layer of complexity is added to the TGF-beta signaling complex formation. With about forty genes encoding for ligands and many functional ligands possible because of heterodimers an intricate signaling mechanism must exist. With the ability to only signal through twelve receptors, this ligand driven signaling mechanism must rely on the affinity of ligand's individual receptor sites to the different receptors. This is only possible if each of the four receptor sites on the ligand act independently to recruit a receptor into the signaling complex. In order to elicit different biological functions through the same twelve receptors, the independent and individual affinities of each of the four receptor sites on the ligand is the key factor in fine tuning the biological response. In this point of view, a role of specific ligand (homodimer or heterodimer) is to assemble distinct set of type I and type II receptors with distinct affinity, which in turn, generate different level of signaling and complexity of TGF-b signaling.

The scalable generation of a novel BMP2/BMP6 construct with high activity in vitro and ex vivo has far reaching implications. This molecule served as the basis to determine the assembly of the TGF-beta superfamily ligand-receptor signaling complex and to demonstrate the direct correlation between ligand-receptor affinity, signaling activity, and biological activity. The differences in affinity between ligand and receptor are crucial and the asymmetric heterodimer ligand signaling adds further complexity to the biological activity of the TGF-beta molecules. The study with the BMP heteromider illustrates how each ligand-receptor interaction contributes to the activity of the TGF-beta superfamily.

Generation of Heterodimer

The mature domains of human BMP2 (residues 1-110) and human BMP6 (residues 1-132) were expressed in E. coli as inclusion bodies. Mutations to the wild type ligand sequences were based on previously published findings which disrupt the ligand-receptor interfaces (Keller et al., 2004; Kirsch et al., 2000). The expressed inclusion bodies were isolated, purified, and refolded. The refolded BMP2 and BMP6 homodimers, and BMP2/BMP6 heterodimer were purified using a HiTrap heparin column (GE Healthcare) and reversed phase chromatography (GraceVydac). The ligands were lyophilized and re-suspended in 10 mM sodium acetate pH 4.0. The ECDs of human BMPRIa (residues 1-129) and mouse ActRIIb (residues 1-98) were expressed in E. coli as thioredoxin fusion proteins. Mouse ActRII-ECD (residues 1-102) was expressed and purified from a P. pastoris expression system.

Surface Plasmon Resonance (BIAcore) Affinity Studies

The affinity of the ligands to BMPRIa, ActRII, and ACTRIIb was monitored by using a Biacore 3000 (GE Healthcare) and the data were analyzed by using BIAevaluation software ver. 4.1 (GE Healthcare). Using primary amine coupling, receptor ECDs were immobilized on a CM5 chip. The receptors were immobilized independently on flow cells 2-4 for 10 minutes at a flow rate of 5 μL/min and a concentration of 20 μM in 10 mM sodium acetate, pH 4.0. Flow cell 1 was left blank with no immobilized protein as a negative control. The experiments were performed at a flow rate of 50 μL/min in 20 mM Tris-HCl, pH 7.9, 250 mM NaCl, 0.36% 3-[(3-Cholamidopropyl)dimethylammonio]-1-propanesulfonate (CHAPS), and 0.005% Tween-20. At least five concentrations, plus a zero concentration, were run per sample for kinetic analysis and the data were fit by using a global 1:1 Langmuir binding with mass transfer.

Luciferase reporter assays. Smad1-dependent luciferase assays were performed. In brief, C2C12 cells are cultured in Dulbecco's minimum essential medium (DMEM)+5% FBS supplemented with L-glutamine and antibiotics. For luciferase reporter assays, cells were trypsinized, washed twice with PBS, and plated into 48-well plates with DMEM+ 0.1% FBS. Twenty-four hours later, cells were transfected with −1147Id1-luciferase construct containing the Smad binding sites (Id1-Luc) (Nakashima et al., 2001), a Smad-1 expression construct, and a CAGGS-LacZ plasmid using Fugene6 (Roche) according to the manufacturer's instruction. Luciferase activity was measured 24 h after stimulation with ligands, and the values were normalized for transfection efficiency using beta-galactosidase activity. The activity of the luciferase reporter is expressed in fold induction relative to control values that are obtained using −927Id1-luciferase that lacks Smad1 binding domains (Id1-Luc mut).

Chick Limb Bud Micromass Assays

Chick embryos at Hamburger-Hamilton stage 23-24 (Hamburger and Hamilton, 1951) were collected in Hanks solution containing Ca2+ and Mg2+, and distal ⅓ part of limb buds were dissected out. Ectodermal sheets were removed by trypsinization (0.5% in Hanks solution with Ca2+ and Mg2+) on ice for 30 min, and then mesenchymal tissues were recovered and incubated in $Ca^{2+}$ and $Mg^{2+}$-free Hanks solution at 37° C. for 15 min. The mesenchyme cells were dissociated into single cells by pipetting in OptiMEM medium (Invitrogen) containing 1% FBS. Cultures were seeded into 96-well plates at $4\times10^5$ cells/well. After 1 hour, media containing each ligand was added. Fresh media with ligands was changed daily, and cells were analyzed for chondrogenesis by Alcian blue staining to visualize cartilage nodule and quantification of chondrogenesis as described (Wada et al., 2003).

Native-PAGE Ligand-Receptor ECD Complex Formation

Five micrograms of purified ActRII-ECD alone and with ten micrograms of BMP2/BMP6, BMP2/BMP6 with a single active type II receptor interface, or BMP2 with no active type II receptor interfaces was loaded onto a native-PAGE gel in 50 mM Tris-HCl, pH 7.9, 700 mM NaCl, and 1.8% CHAPS. The Coomassie Brilliant Blue (Bio-Rad) stained gel was analyzed using the "Integrated Density" function with NIH ImageJ software (Abramoff et al., 2004).

Example 3

(1) Development of Stem Cell Media (Valera et al., 2010) Using AB2-008

Culturing human embryonic stem cells (hESC) in feeder free conditions requires the use of complex formulation media to Maintain pluripotency. Unfortunately, commercial media are very expensive since the growth factors required for the media are difficult to produce in mammalian cells. We have used mTeSR1 formulation to derive a new medium (CIVA medium or mCIVA) for culturing human embryonic stem (hES) cells, and deriving and culturing induced pluripotent stem (iPS) cells (see FIG. 2). CIVA medium substitutes TGFβ1 in mTeSR1 for AB2-008, a new chimeric protein with similar activity to Activin-A. hES cells cultured in this medium on matrigel coating maintain pluripotent morphology for more than 20 passages without karyotypic abnormalities. These cells are also positive for the pluripotency markers TRA-1-60 and SSEA-4, and differentiate in response to BMP-2 treatment. iPS cells cultured in this medium also retain morphological characteristics of pluripotency and expression of pluripotency markers. This new CIVA medium is also suitable to derivate iPS cells from human foreskin fibroblasts. CIVA medium has all the properties desired of other commercial media for hES cells but can be formulated for considerably less cost than currently available media. FIG. 2. Development of mCIVA formulation using H9 hES cell line.

Figure 9:
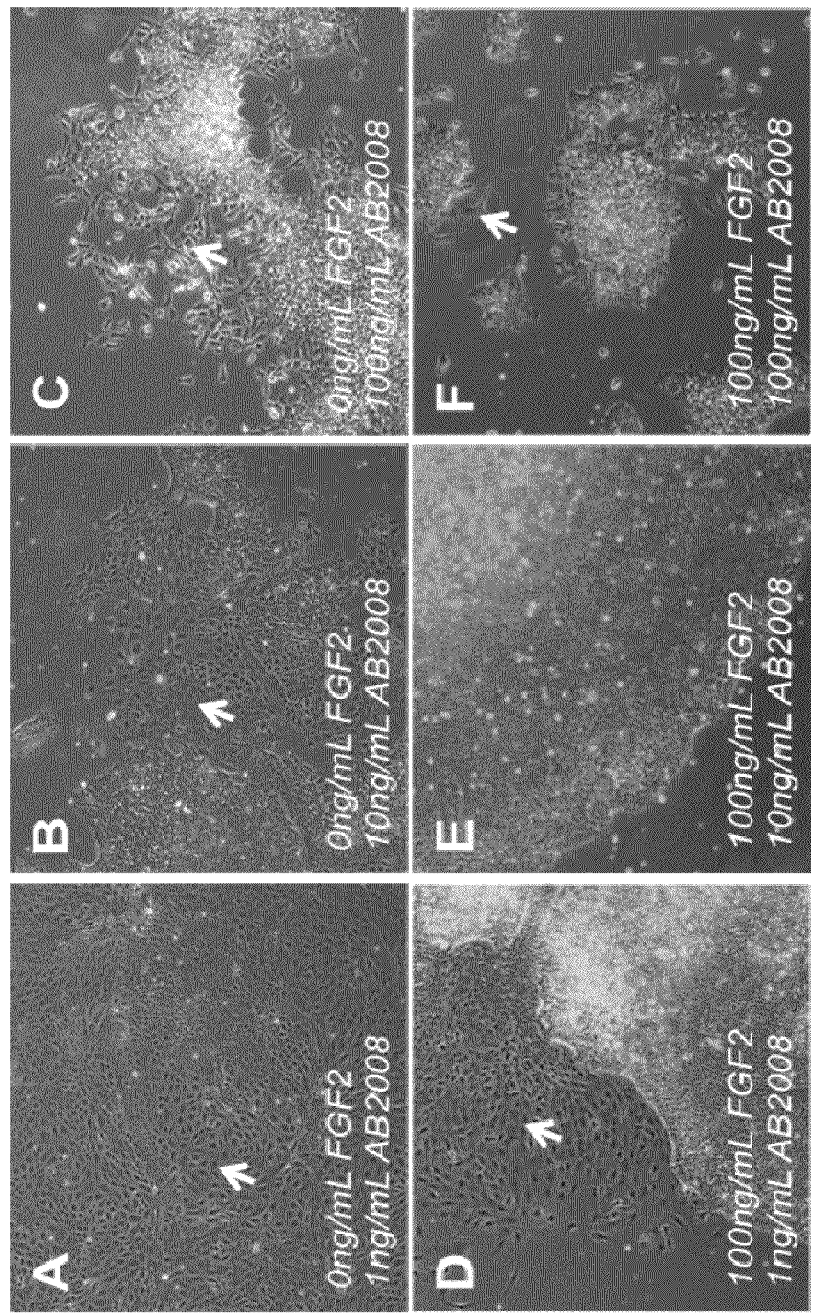
FIG. 9 shows H9 hES cells cultured in mCIVA using different concentrations of AB2-008 in the absence or presence of human FGF2.

FIG. 9 shows H9 hES cells cultured in mCIVA using different concentrations of AB2-008 in the absence or presence of human FGF2. A. Differentiated H9 cells after 3 passages (1 ng/mL, AB2-008; no FGF2). B. Differentiated H9 cells after 3 passages (10 ng/mL, AB2-008; no FGF2). C. Differentiated H9 cells after 11 passages (100 ng/mL, AB2-008; no FGF2). D. Differentiated H9 cells after 12 passages (1 ng/mL, AB2-008; 100 ng/mL, FGF2). E. H9 cells after 13 passages (10 ng/mL, AB2-008; 100 ng/mL, FGF2). F. Differentiated H9 cells after 9 passages (100 ng/mL, AB2-008; 100 ng/mL, FGF2). Differentiated cells are denoted by arrows.

(2) Mineralization Data of AB2-004, AB2-011, AB2-015 (Yoon et al., 2010

Figure 10:
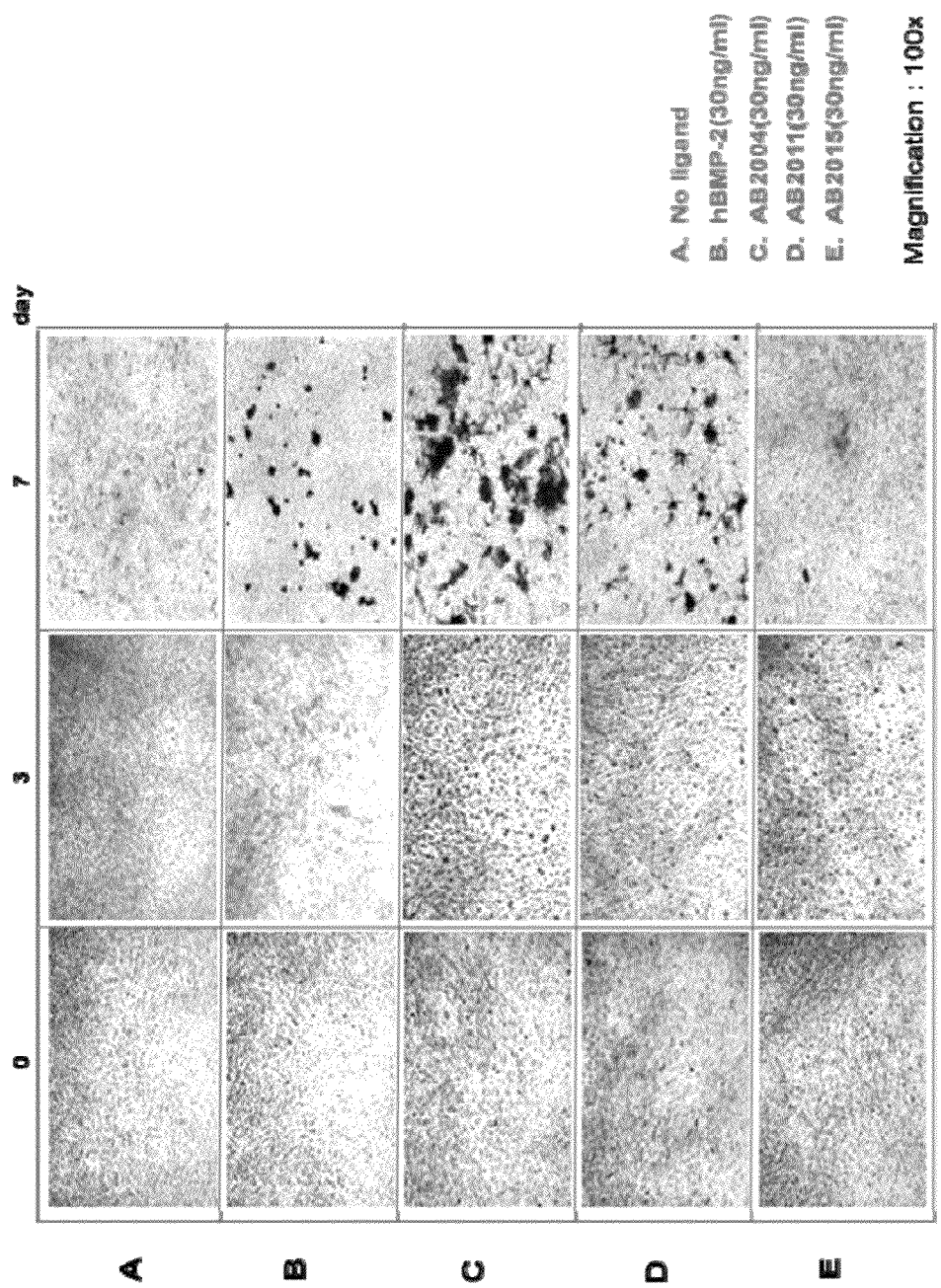
FIG. 10 shows mineralization shown by Von Kossa staining with (A) no ligand added, (B) recombinant BMP2 (30 ng/ml), C) AB2-004 (30 ng/ml), D) AB2-011 (30 ng/ml) and E) AB2-015 (30 ng/ml).

Von Kossa staining was used to monitor the development of pre-osteoblast cell line (MC3T3-E1) for extracellular mineralization by Ca deposition. AB2-004 and AB2-011 show dramatic increase of the stain of nearly 10 times or more intensity. AB2-015 shows the most increase but past 7 days period (not shown here). Control group (A) shows no appreciable mineralization, whereas the control ligand (BMP2) shows modest increase of Ca flux and deposition as shown in Row B, of FIG. 10.

(3) Adult Rat Regeneration by AB2-004 (in Collaboration

P3 digit of Adult rat was severed. Either BMP2 or AB2-004 soaked in an agarose gel bead were added at the sight of surgery. Bone regrowth was monitored. BMP2-treated tissue shows no bone recovery. AB2-004-treated digit shows full recovery.

(4) Smad2-Based Signaling (Luciferase) Assay by AB2-008, AB2-009, AB2-010 (Allendorph et al., 2010

Figure 11:
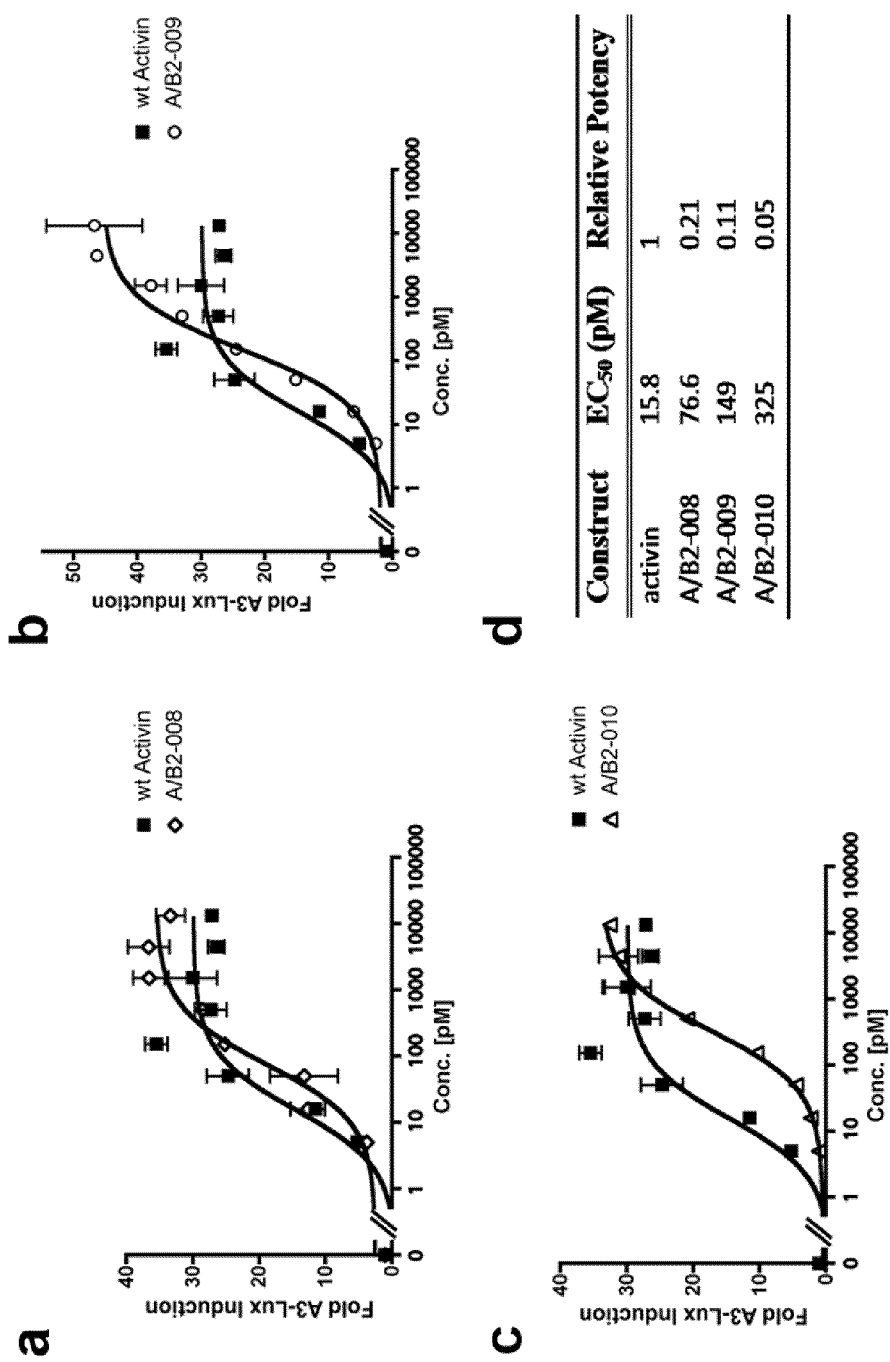
FIG. 11 shows the signaling activities of AB2-008, AB2-009, and AB2-010. (A) AB2-008 versus activin-βA (B) AB2-009 versus activin-βA (C) AB2-010 versus activin-βA (D) Relative signaling strength in comparison to activin-βA.
Figure 12:
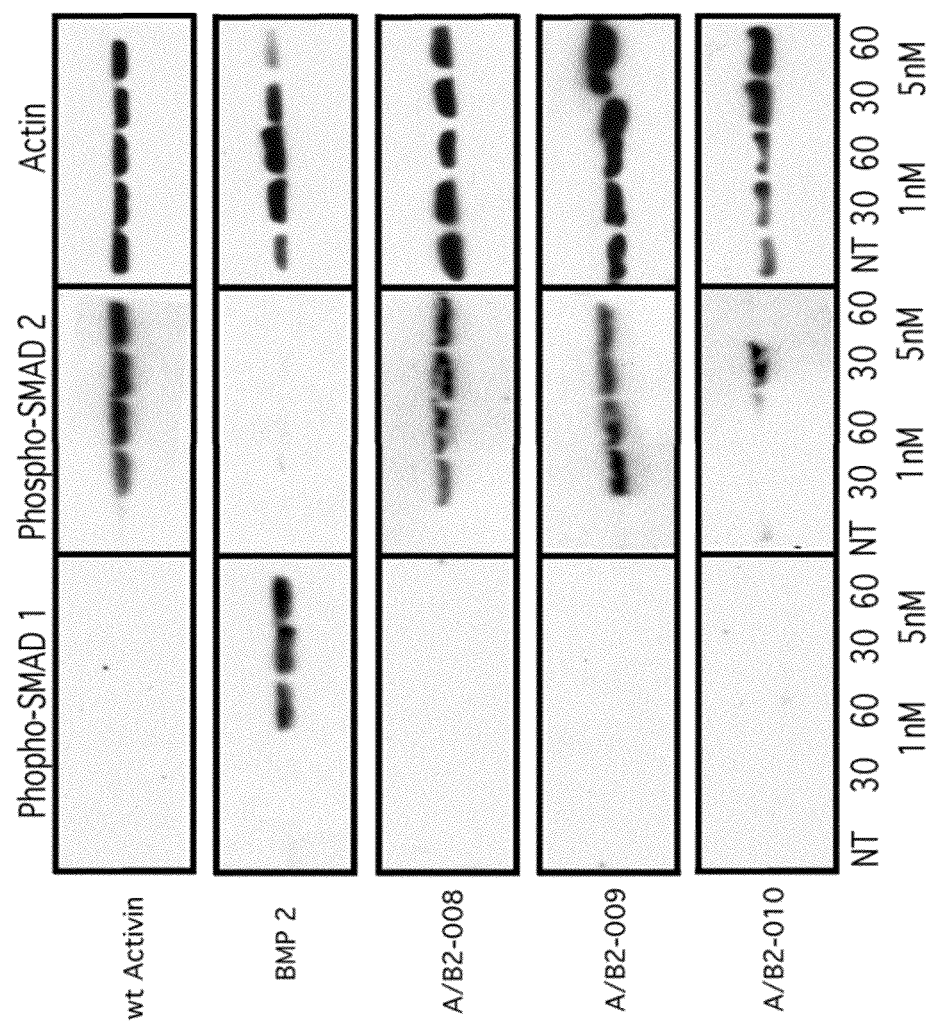
FIG. 12 shows phosphorylation by AB2-008, AB2-009, and AB2-010 in comparison to Activin-βA and BMP2. Activin-βA, AB2-008, and AB2-009 show comparable levels of phosphorylation of SMAD2, whereas BMP2 shows phosphorylation of SMAD1 specifically.
Figure 13:
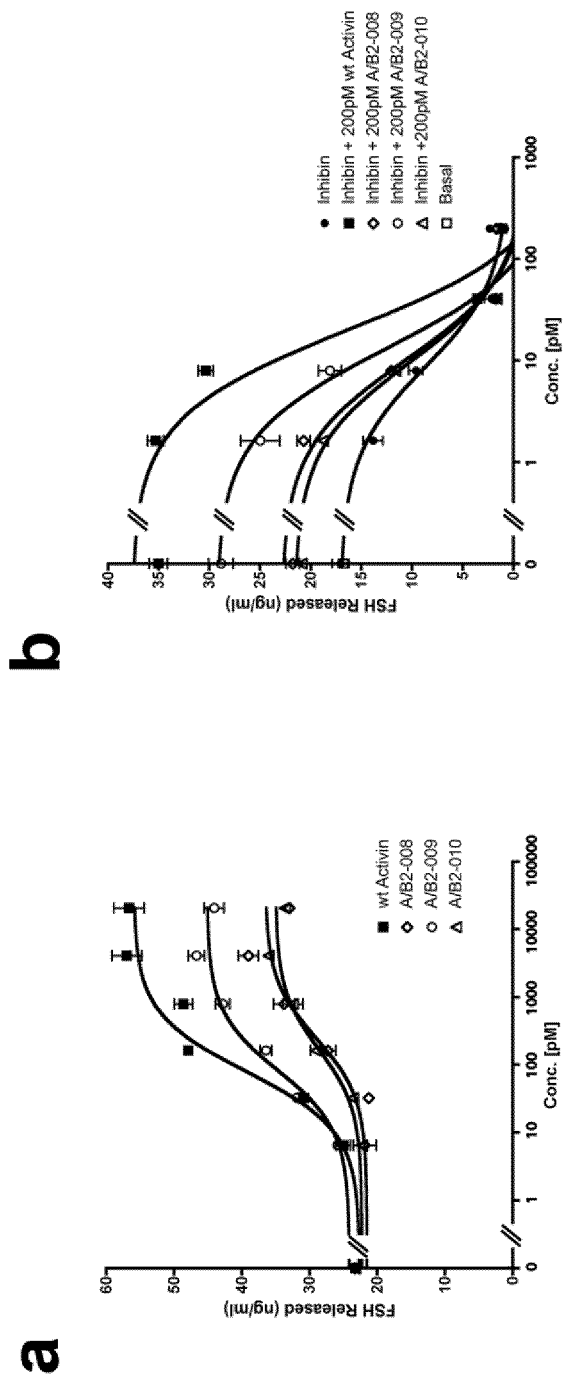
FIG. 13 depicts FSH release by Activin-βA, AB2-008, AB2-009, and AB2-010. (A) Dose dependent FSH stimulation without Inhibin, and (B) decreased release with Inhibin.

AB2-008, AB2-009, and AB2-010 activate the Smad2 pathway in a manner nearly undistinguishable from activin-βA. Potency for the chimeras is slightly reduced compared to activin-βA, from 5 to 20-fold (see FIG. 11).

(5) Phospho-Smad-2 Assays by AB2-008, AB2-009, and AB2-010

Activin-βA specifically phosphorylates Smad-2 and not Smad-1. This is in contrast to BMP-2 where we see specific phosphorylation of Smad-1 and not Smad-2. AB2-008, AB2-009, and AB2-010 display the same Smad-2 phosphorylation pattern as activin-βA. This confirms all three ligands stimulate the activin-βA signaling pathway in a manner similar to activin-βA (see FIG. 11).

(6) Follicle Stimulating Hormone Release by AB2-008, AB2-009, and AB2-010

When activin-βA is added to rat interior pituitary cells, it causes a dose dependent release of Follicle stimulating hormone (FSH). The activin-βA induced release of FSH can be blocked by the addition of the antagonist Inhibin. Similar to activin-βA, AB2-008, AB2-009, and AB2-010 cause the release of FSH and this stimulation is decreased in the presence of Inhibin.

(7) Co-Receptor Binding with Cripto by AB2-008

Addition of Cripto reduces both activin-βA and AB2-008 signaling by comparable levels. These data indicate that AB2-008 possesses ability to bind Cripto, activin-βA co-receptor, confirming the functional similarity between AB2-008 and activin-βA.

(8) AB2-008 and Activin-βA Receptor Affinity

AB2-008 shows the receptor binding profile similar to that of activin-βA, which has high affinity to ActRII and none for BMPRIa. Further, the two ligands have nearly the same binding affinity. AB2-008 is ~1.7 weaker than activin-βA.

TABLE 4

Receptor affinity of Activin-βA versus AB2-008
Receptor Affinity Data from BIAcore Experiments

| Ligand | BMPRIa-ECD | | ActRII-ECD | |
|---|---|---|---|---|
| | $k_{off}[1/s]/k_{on}[1/M * s]$ | $K_D$ [nM] | $k_{off}[1/s]/k_{on}[1/M * s]$ | $K_D$ [nM] |
| Activin-βA | No Binding | N.A. | $7.16 \times 10^{-4}/3.52 \times 10^6$ | 0.203 |
| AB2-008 | No Binding | N.A. | $8.24 \times 10^{-4}/2.39 \times 10^6$ | 0.344 |

The receptors were immobilized to the chip surface with the ligands flowed over the surface. The data were fit to a kinetic model (1:1 Langmuir binding with mass transfer) in which $K_D$ is calculated as $k_{off}/k_{on}$. The table reports data from a single trial. No Binding indicates that the interaction was not detectable.

(9) Signaling Activity of AB2-011, AB2-012, and AB2-015 by Smad-1 Pathway

AB2-004, AB2-011, AB2-012, and AB2-015 activate the Smad-1 pathway more potently than BMP-2. This activation is 3 to 8-fold higher than BMP-2 (FIG. 14).

(10) Receptor Binding Affinity of AB2-004, AB2-011, AB2-012, and AB2-015

AB2-004, AB2-011, AB2-012, and AB2-015 show similar binding affinity to ActRII as activin-βA. This is ~100 fold higher than the binding BMP-2 has for the same receptor. The type I receptor binding for the AB chimeras ranges from near BMP-2 levels (AB2-004) to activin-βA levels (no binding to BMPRIa for AB2-015).

TABLE 5

Receptor binding affinity of AB2-004, AB2-011, AB2-012, and AB2-015
Receptor Affinity Data from BIAcore Experiments

| Ligand | BMPRIa-ECD | | ActRII-ECD | |
|---|---|---|---|---|
| | $k_{off}[1/s]/k_{on}[1/M * s]$ | $K_D$ [nM] | $k_{off}[1/s]/k_{on}[1/M * s]$ | $K_D$ [nM] |
| BMP-2 | $7.54 \times 10^{-4}/3.60 \times 10^5$ | 2.09 | $4.05 \times 10^{-2}/1.10 \times 10^6$ | 36.8 |
| Activin-βA | No Binding | N.A. | $7.16 \times 10^{-4}/3.52 \times 10^6$ | 0.203 |
| AB2-004 | $1.85 \times 10^{-2}/1.13 \times 10^6$ | 16.4 | $1.87 \times 10^{-4}/4.91 \times 10^5$ | 0.381 |
| AB2-011 | $1.93 \times 10^{-2}/4.07 \times 10^5$ | 47.4 | $3.39 \times 10^{-4}/6.46 \times 10^5$ | 0.525 |
| AB2-015 | No Binding | N.A. | $3.71 \times 10^{-4}/1.61 \times 10^6$ | 0.230 |
| AB2-012 | $8.48 \times 10^{-2}/1.61 \times 10^5$ | 526 | $1.60 \times 10^{-3}/3.39 \times 10^6$ | 0.472 |

The receptors were immobilized to the chip surface with the ligands flowed over the surface. The data were fit to a kinetic model (1:1 Langmuir binding with mass transfer) in which $K_D$ is calculated as $k_{off}/k_{on}$. The table reports data from a single trial. No Binding indicates that the interaction was not detectable.

(11) Noggin Insensitivity of AB2-004, AB2-011, AB2-012, and AB2-015

Figure 15:
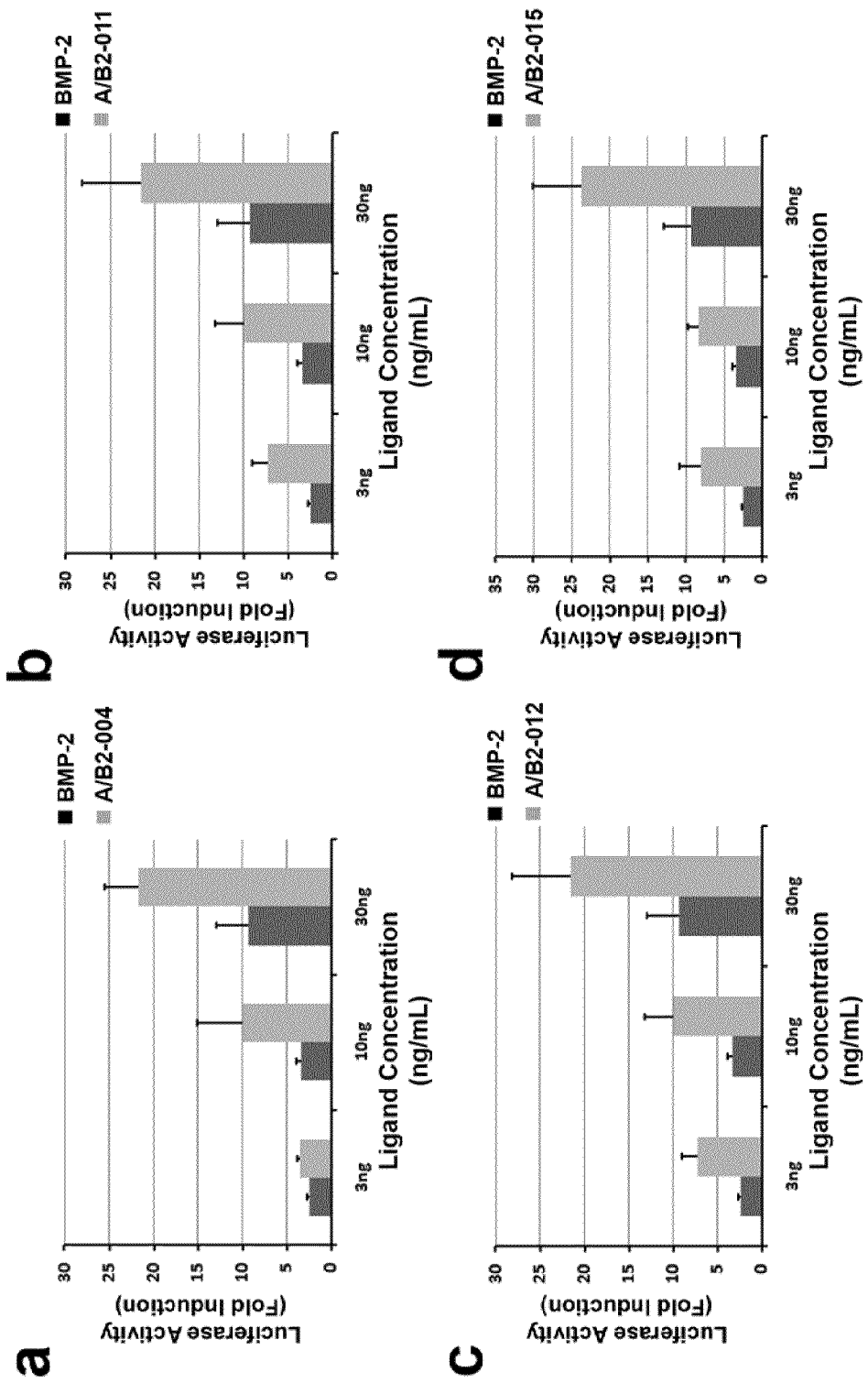
FIG. 15 shows signaling activity of AB2-011, AB2-012, and AB2-015 by Smad-1 pathway. (A) AB2-004 v.s. BMP2, (B) AB2-011 v.s. BMP2, (C) AB2-012 v.s. BMP2, and (D) AB2-015 v.s. BMP2, all in the concentration range of 3-30 ng/ml in culture media using Smad-1 Luciferase assay with C2C12 cells.
Figure 16:
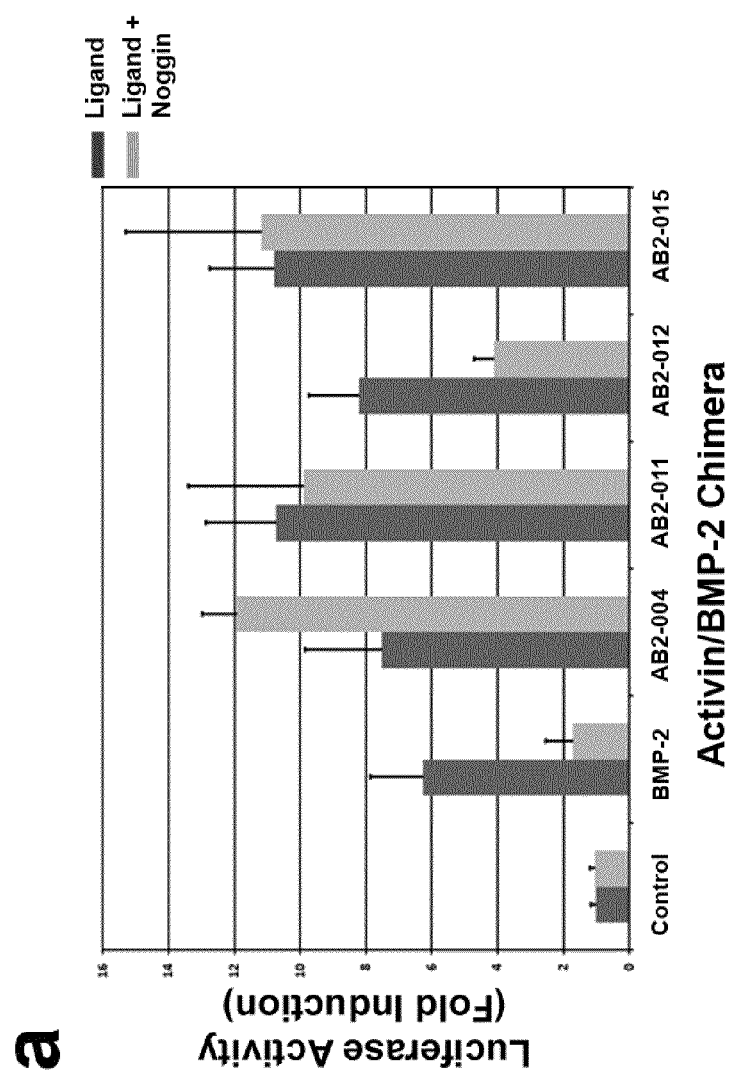
FIG. 16 shows Noggin sensitivity of BMP2, AB2-004, AB2-011, AB2-012, and AB2-015. Smad-1 luciferase signaling activity is measured with (light gray) and without (dark gray) Noggin.

Noggin suppresses the signaling activity by directly complexing with the ligand, and rendering it unable to bind its own receptors for signaling. In contrast to BMP-2 which is blocked to near background levels in the presence of Noggin, the higher signaling of AB2-004, AB2-011, and AB2-015 are not inhibited by Noggin. AB2-012 is partially insensitive to Noggin Inhibition, with a ~50% decrease in signaling with the addition of Noggin (FIG. 15). This property makes them particularly powerful in their cellular signaling ability in vivo, including bone regeneration.

(12) Production Efficiency

TABLE 6

Production efficiency of refolding from *E. coli* inclusion body.

| Construct | Dimer Yield | Rating |
|---|---|---|
| 1b2b3b4b5b6a | >10% | +++ |
| 1b2b3b4b5a6a | >10% | +++ |
| 1b2b3b4b5a6b | >10 | +++ |
| 1b2b3b4a5a6a | 5% | +++ |
| 1b2b3b4a5b6b | 2% | + |
| 1b2b3b4a5a6b | 3% | + |
| 1b2b3b4a5b6a | 3% | + |
| 1b2b3a4a5a6a | 5% | ++ |
| 1b2b3a4a5a6b | 6% | ++ |
| 1b2b3a4a5b6b | 5% | ++ |
| 1b2b3a4a5b6a | 7% | ++ |
| 1b2b3a4b5b6b | 3% | + |
| 1b2b3a4b5b6a | 6% | ++ |
| 1b2b3a4b5a6a | 4% | + |
| 1b2b3a4b5a6b | 5% | ++ |
| 1b2a3a4a5a6a | >10% | +++ |
| 1b2a3a4a5a6b | >10% | +++ |
| 1b2a3a4b5b6b | 9% | ++ |
| 1b2a3a4b5b6a | >10% | +++ |
| 1b2a3a4b5b6b | >10% | +++ |
| 1b2a3a4b5b6a | 4% | + |
| 1b2a3a4b5a6b | 1% | − |
| 1b2a3a4b5a6a | 2% | + |
| 1b2a3b4b5b6b | >10% | +++ |
| 1b2a3b4b5b6a | >10% | +++ |
| 1b2a3b4b5a6a | 9% | ++ |
| 1b2a3b4b5a6b | >10% | +++ |
| 1b2a3b4a5a6a | 4% | + |
| 1b2a3b4a5b6a | 4% | + |
| 1b2a3b4a5b6b | 4% | + |
| 1b2a3b4a5a6b | 1% | − |

TABLE 6-continued

Production efficiency of refolding from *E. coli* inclusion body.

| Construct | Dimer Yield | Rating |
|---|---|---|
| 1b2a3a4a5a6a L66V/V67I | 4% | + |
| 1b(1a_II)2a3a4a5a6a | 3% | + |

(13) Receptor Binding Affinity of BMP2/BMP6 Heterodimer (Isaacs et al., 2010

BMP2/BMP6 heterodimer has the binding characteristics of BMP2 for type I receptor BMPRIa and BMP6 for the type II receptor ActRIIb. Maintaining high affinity for each receptor type by the heterodimer ligand makes BMP2/BMP6 heterodimer stronger in signaling activities than its homodimeric couterparts, BMP2 and BMP6 homodimers (Table 7).

TABLE 7

Receptor binding affinity measured by Surface plasmon resonance.

| Ligand | Receptor BMPRIa $k_{off}[1/s]/k_{on}[1/M*s]$ | $K_D$ [nM] | Receptor ActRIIb $k_{off}[1/s]/k_{on}[1/M*s]$ | $K_D$ [nM] |
|---|---|---|---|---|
| BMP2 | $1.11 \times 10^{-3}/8.52 \times 10^5$ | 1.31 | $2.57 \times 10^{-2}/6.68 \times 10^5$ | 38.5 |
| BMP6 | $9.37 \times 10^{-3}/1.50 \times 10^5$ | 62.8 | $1.82 \times 10^{-3}/2.73 \times 10^5$ | 6.68 |
| BMP2/BMP6 | $1.05 \times 10^{-3}/1.03 \times 10^6$ | 1.02 | $8.61 \times 10^{-3}/1.32 \times 10^6$ | 6.52 |

(14) SMAD-1 Signaling Activity of BMP2/BMP6 Heterodimer

The BMP2/BMP6 heterodimer is much more active than either BMP2 or BMP6 alone. BMP2/BMP6 has an EC50 that is at least an order of magnitude higher than BMP2 or BMP6 alone. Further, the maximal response reached by BMP2/BMP6 is higher than the combination of maximum signal reached by BMP2 and BMP6 alone.

(15) Chick Limb Bud Micromass Assays for BMP2/BMP6 Heterodimer

BMP2/BMP6 induces chondrogenesis more potently than either BMP2 or BMP6 homodimers. In chick limb bud mesenchyme cell micromass culture chrondogenesis assays, after three days we see that BMP2/BMP6 induces chondrogenesis at both lower concentrations and to a higher level than either BMP2 or BMP6.

Example 4

Description of Subdomains (Building Blocks) for Generating Designer Ligand

In order to create the chimeras, a first step was deciding where to make the borders for each of the segments. The chimera library has been constructed using activin-βA and BMP-2 as two sequence sources. To design the cut-off regions (Junction) for the sections to make the activin/BMP-2 (AB) chimera, a structure-guided approach combined with protein sequence alignment was used. Initially, the 3-dimensional crystal structures of activin-βA (Harrington et al., 2006) and BMP-2 (Allendorph et al., 2006) were inspected structurally. From this analysis, the ligands were loosely divided into 6 distinct sections (see FIG. 7 for segments 1 through 6). The exact segment junctions were ultimately determined following a protein sequence alignment of the two ligands to minimize any sequence changes of either protein sequence as a result of joining the Junction. Further, the segmental boundaries were chosen to be located in structural regions away from receptor binding sites.

Detailed descriptions of Junctions: Between segments 1 and 2 (Junction 1): Focusing on the boundary of segment 1 and segment 2, we found a 10-residue region that is highly conserved between BMP-2 and activin-βA. Indeed, 8 of the 10 residues are identical and the other two are very conservative differences. This area is located in the tip region of Finger 1 and depending of the ligand, makes or is predicted to make limited contacts with either receptor type. Based on the ternary crystal structure of BMP-2/BMPRIa/ActRII (Allendorph et al., 2006), only Val-26, Gly-27, and Trp-28 (BMP-2 numbering) generate contacts with the type I receptor. Of these three residues, only Val-26 is different between the ligands, but it is a, very conservative change since the corresponding residue in activin-βA is Ile-23. Since the residues in this region are very similar and not involved in receptor binding, it makes for a good boundary point for segment 1 and 2.

Between segments 2 and 3 (Junction 2): Moving to the boundary region between segments 2 and 3, another good area for our boundary cut-off can be found. Here, a 4-residue sequence that is identical between activin-βA and BMP-2 exists. When the ligands are properly folded, this region is located in the center of the dimer, with both cyteines participating in the cystine knot. This is advantageous because the residues here are buried from the surface of the ligands and do not participate in any ligand-receptor interactions.

Between segments 4 and 5 (Junction 4): Similar to the segment 2/3 boundary, the segment 4/5 boundary is situated in an excellent location for the cut-off. Here, we find a 5-residue region of sequence identity and, as with the segment 2/3 boundary, this region is buried at the center of the ligand dimer. The 2 cysteine residues participate in both the cystine knot as well as the inter-monomer disulfide bond. Again, this location prevents the residues in this region from participating in receptor binding interactions.

Between segments 5 and 6 (Junction 5): To extend the design of BMP-2 and activin-βA chimeras, other boundary regions have been chosen to facilitate generating RASCH constructs using all members of the TGF-β superfamily. Along with sharing structural architecture, the TGF-β superfamily ligands seem to have certain regions in their protein sequences that are highly conserved. Interestingly, these regions coincide with the boundary regions chosen for making the BMP-2 and activin-βA chimeras. For example, in the boundary region of 4 and 5, most ligands share 3 out of the 4 residues that define the boundary domain. This high degree of similarity, coupled with these regions being isolated from the receptor binding sites, indicates RASCH as the universal strategy to create a library of Designer Ligands with new functionalities.

Between segments 3 and 4 ((Junction 3): The boundary between segments 3 and 4 is subject to structural variability between different subfamilies, in which ligand-receptor assembly mechanism can differ substantially. In that regard, segments 3 and 4 can be treated as one segmental piece such that two segments will be derived from the common parental strand to preserve their structural integrity.

The structural similarity among all TGF-beta superfamily ligands forms the rational basis for designing chimeric protein by exchanging (swapping) related segments of the sequences known to carry out certain functionality such as molecular recognition. Protein engineering of Antibody chain, or more specifically of antibody fragment (Fab), will be a prime example where the basic structural scaffold is built on the Core architecture of the light- and heavy chain sequences, for which six variable loops, three from each of the two chains, are responsible for the role of epitope-binding specificity. In the similar vein, the TGF-beta superfamily ligands share their structural framework as a butterfly-like architecture. A portion(s) of the sequence segments functionally equivalent to variable loop regions of Antibody can then be 'implanted' to transfer recognition specificity from one ligand to another. Our design principle distinguishes itself from the aforementioned 'functional transfer by sequence implantation'. The new chimeric library is created on the basis of structural feasibility of each subdomain as defined by each Junction. The junctions between the various domains of the TGF-beta family members used to generate the chimeras of the disclosure provide useful building blocks of the chimera library. By this reasoning, Junctions 1, 2, 4, and 5 are well defined to be broadly applicable to all TGF-beta superfamily members, whereas Junction 3 is not broadly applicable. The application of Junction 3 in the chimera design depends on the target sequences, in which case subdomain segments 3 and 4 can be treated instead as one segment in designing the chimera library. The approach maximizes the chance of producing such protein products that are foldable, for which functional characterization will then follow.

Table of Additional Sequences:

| TGF-β Ligand | DNA Sequence | Protein Sequence |
|---|---|---|
| BMP-2 | caagccaaacacaaacagcggaaacgccttaagtccagctgta agagacaccctttgtacgtggacttcagtgacgtggggtggaat gactggattgtggctcccccggggtatcacgccttttactgccac ggagaatgcccttttcctctggctgatcatctgaactccactaatc atgccattgttcagacgttggtcaactctgttaactctaagattcct aaggcatgctgtgtcccgacagaactcagtgctatctcgatgct gtaccttgacgagaatgaaaaggttgtattaaagaactatcagga catggttgtggagggttgtgggtgtcgc (SEQ ID NO: 1) | QAKHKQRKRLKSSCKRHPL YVDFSDVGWNDWIVAPPG YHAFYCHGECPFPLADHLN STNHAIVQTLVNSVNSKIPK ACCVPTELSAISMLYLDENE KVVLKNYQDMVVEGCGCR (SEQ ID NO: 2) |
| BMP-3 (osteogenin) | cagtggattgaacctcggaattgcgccaggagatacctcaaggt agactttgcagatattggctggagtgaatggattatctcccccaa gtcctttgatgcctattattgctctggagcatgccagttccccatgc caaagtctttgaagccatcaaatcatgctaccatccagagtatag tgagagctgtgggggtcgttcctgggattcctgagccttgctgtg taccagaaaagatgtcctcactcagtattttattctttgatgaaaat aagaatgtagtgcttaaagtataccctaacatgacagtagagtctt gcgcttgcaga (SEQ ID NO: 42) | QWIEPRNCARRYLKVDFAD IGWSEWIISPKSFDAYYCSG ACQFPMPKSLKPSNHATIQS IVRAVGVVPGIPEPCCVPEK MSSLSILFFDENKNVVLKV YPNMTVESCACR (SEQ ID NO: 43) |
| BMP-4 (BMP-2b) | agccctaagcatcactcacagcgggccaggaagaagaataag aactgccggcgccactcgctctatgtggacttcagcgatgtggg ctggaatgactggattgtggccccaccaggctaccaggccttct actgccatggggactgcccctttccactggctgaccacctcaac tcaaccaaccatgccattgtgcagaccctggtcaattctgtcaatt ccagtatccccaaagcctgttgtgtgcccactgaactgagtgcc atctccatgctgtacctggatgagtagataaggtggtactgaaaa attatcaggagatggtagtagagggatgtgggtgccgc (SEQ ID NO: 44) | SPKHHSQRARKKNKNCRR HSLYVDFSDVGWNDWIVA PPGYQAFYCHGDCPFPLAD HLNSTNHAIVQTLVNSVNS SIPKACCVPTELSAISMLYL DEYDKVVLKNYQEMVVEG CGCR (SEQ ID NO: 45) |
| BMP-5 | gcagccaacaaacgaaaaaatcaaaaccgcaataaatccagct ctcatcaggactcctccagaatgtccagtgttggagattataaca caagtgagcaaaaacaagcctgtaagaagcacgaactctatgt gagcttccgggatctgggatggcaggactggattatagcacca gaaggatacgctgcattttattgtgatggagaatgttcttttccactt aacgcccatatgaatgccaccaaccacgctatagttcagactct ggttcatctgatgtttcctgaccacgtaccaaagccttgttgtgctc caaccaaattaaatgccatctctgttctgtactttgatgacagctcc aatgtcattttgaaaaaatatagaaatatggtagtacgctcatgtg gctgccac (SEQ ID NO: 46) | AANQNRNKSSSHQDSSRMS SVGDYNTSEQKQACKKHEL YVSFRDLGWQDWIIAPEGY AAFYCDGECSFPLNAHMNA TNHAIVQTLVHLMFPDHVP KPCCAPTKLNAISVLYFDDS SNVILKKYRNMVVRSCGCH (SEQ ID NO: 47) |
| BMP-6 (Vgr-1) | caacagagtcgtaatcgctctacccagtcccaggacgtggcgc gggtctccagtgcttcagattacaacagcagtgaattgaaaaca gcctgcaggaagcatgagctgtatgtgagtttccaagacctggg atggcaggactggatcattgcacccaagggctatgctgccaatt actgtgatggagaatgctccttcccactcaacgcacacatgaat gcaaccaaccacgcgattgtgcagaccttggttcaccttatgaa ccccgagtatgtccccaaaccgtgctgtgcgccaactaagctaa atgccatctcggttctttactttgatgacaactccaatgtcattctga aaaaatacaggaatatggttgtaagagcttgtggatgccac (SEQ ID NO: 48) | QQSRNRSTQSQDVARVSSA SDYNSSELKTACRKHELYV SFQDLGWQDWIIAPKGYAA NYCDGECSFPLNAHMNAT NHAIVQTLVHLMNPEYVPK PCCAPTKLNAISVLYFDDNS NVILKKYRNMVVRACGCH (SEQ ID NO: 49) |
| BMP-7 (OP-1) | tccacggggagcaaacagcgcagccagaaccgctccaagac gcccaagaaccaggaagccctgcggatggccaacgtggcag agaacagcagcagcgaccagaggcaggcctgtaagaagcac gagctgtatgtcagcttccgagacctgggctggcaggactggat catcgcgcctgaaggctacgccgcctactactgtgagggggag tgtgccttccctctgaactcctacatgaacgccaccaaccacgc catcgtgcagacgctggtccacttcatcaacccggaaacggtg cccaagccctgctgtgcgcccacgcagctcaatgccatctccgt cctctacttcgatgacagctccaacgtcatcctgaagaaatacag aaacatggtggtccgggcctgtggctgccac (SEQ ID | STGSKQRSQNRSKTPKNQE ALRMANVAENSSSDQRQA CKKHELYVSFRDLGWQDW IIAPEGYAAYYCEGECAFPL NSYMNATNHAIVQTLVHFI NPETVPKPCCAPTQLNAISV LYFDDSSNVILKKYRNMVV RACGCH (SEQ ID NO: 51) |

-continued

| TGF-β Ligand | DNA Sequence | Protein Sequence |
|---|---|---|
| | NO: 50) | |
| BMP-8(OP-2) | gcagtgaggccactgaggaggaggcagccgaagaaaagcaa cgagctgccgcaggccaaccgactcccagggatctttgatgac gtccacggctcccacggccggcaggtctgccgtcggcacgag ctctacgtcagcttccaggacctcggctggctggactgggtcat cgctccccaaggctactccggcctattactgtgaggggagtgct ccttcccactggactcctgcatgaatgccaccaaccacgccatc ctgcagtccctggtgcacctgatgatgccagacgcagtcccca aggcgtgctgtgcacccaccaagctgagcgccacctctgtgct ctactatgacagcagcaacaatgtcatcctgcgcaagcaccgc aacatggtggtcaaggcctgcggctgccac (SEQ ID NO: 52) | AVRPLRRRQPKKSNELPQA NRLPGIFDDVHGSHGRQVC RRHELYVSFQDLGWLDWVI APQGYSAYYCEGECSFPLD SCMNATNHAILQSLVHLMK PNAVPKACCAPTKLSATSV LYYDSSNNVILRKHRNMVV KACGCH (SEQ ID NO: 53) |
| BMP-9(GDF-2) | agcgccggggctggcagccactgtcaaaagacctccctgcgg gtaaacttcgaggacatcggctgggacagctggatcattgcacc caaggagtatgaagcctacgagtgtaagggcggctgcttcttcc ccttggctgacgatgtgacgccgacgaaacacgctatcgtgca gaccctggtgcatctcaagttccccacaaaggtgggcaaggcc tgctgtgtgcccaccaaactgagccccatctccgtcctctacaag gatgacatgggggtgcccacccctcaagtaccattacgagggca tgagcgtggcagagtgtgggtgcaggtag (SEQ ID NO: 54) | SAGAGSHCQKTSLRVNFED IGWDSWIIAPKEYEAYECK GGCFFPLADDVTPTKHAIV QTLVHLKFPTKVGKACCVP TKLSPISVLYKDDMGVPTL KYHYEGMSVAECGCR (SEQ ID NO: 55) |
| BMP-10 | aacgccaaaggaaactactgtaagagaccccgctctacatcg acttcaaggagattgggtgggactcctggatcatcgctccgcct ggatacgaagcctatgaatgtcgtggttgttgtaactacccctg gcagagcatctcacacccacaaagcatgcaattatccaggcctt ggtccacctcaagaattcccagaaagcttccaaagcctgctgtg tgcccacaaagctagagcccatctccatcctctatttagacaaag gcgtcgtcacctacaagtttaaatacgaaggcatggccgtctcc gaatgtggctgtaga (SEQ ID NO: 56) | NAKGNYCKRTPLYIDFKEIG WDSWIIAPPGYEAYECRGV CNYPLAEHLTPTKHAIIQAL VHLKNSQKASKACCVPTKL EPISILYLDKGVVTYKFKYE GMAVSECGCR (SEQ ID NO: 57) |
| BMP-15(GDF-9b) | caagcagatggtatctcagctgaggttactgcctcttcctcaaaa catagcgggcctgaaaataacagtgttccctccaccctttccaa atcagctttccgccagctgggtttgggatcactggatcattgctccc ccttttctacaccccaaactactgtaaaggaacttgtctccgagtac tacgcgatggtctcaattcccccaatcacgccattattcagaacct tatcaatcagttggtggaccagagtgtccccggcccctcctgtgt cccgtataagtatgtcttccaattagtgtccttatgattgaggcaaatg ggagtattttgtacaaggagtatgagggtat gattgctgagtcttgtacatgcaga (SEQ ID NO: 58) | QADGISAEVTASSSKHSGPE NNQCSLHPFQISFRQLGWD HWIIAPPFYTPNYCKGTCLR VLRDGLNSPNHAIIQNLINQ LVDQSVPRPSCVPYKYVPIS VLMIEANGSILYKEYEGMIA ESCTCR (SEQ ID NO: 59) |
| GDF-1 | gacgccgaaccccgtgttggcggcggccccggggcgcttgt cgcgcgcggcggctgtacgtgagcttccgcgaggtgggctgg caccgctgggtcatcgcgccgcgcggcttcctggccaactact gccagggtcagtgcgcgctgcccgtcgcgctgtcggggtccg ggggcgccggcgctcaaccgcgctgtgctgcgcgcgcta tgcacggccgcccccgggagccgccgacctgccctgctgc gtgcccgcgcctgtcgccatctccgtgctcttcttcgacaac agcgacaacgtggtgctgcggcagtatgaggacatggtggtg gacgagtgcggctgccgc (SEQ ID NO: 60) | DAEPVLGGGPGGACRARRL YVSFREVGWHRWVIAPRGF LANYCQGQCALPVALSGSG GPPALNHAVLRALMHAAA PGAADLPCCVPARLSPISVL FFDNSDNVVLRQYEDMVV DECGC (SEQ ID NO: 61) |
| GDF-3(Vgr-2) | gcagccatccctgtccccaagctttcttgtaagaacctctgccac cgtcaccagctattcattaacttccgggacctggggttggcacaag tggatcattgccccccaagggggttcatggcaaattactgccatgg agagtgtcccttctcactgaccatctctctcaacagctccaattat gctttcatgcaagcccctgatgcatgccgttgacccagagatccc ccaggctgtgtgtatccccaccagctgtctcccatttccatgctc taccaggacaataatgacaatgtcattctacgacattatgaagac atggtagtcgatgaatgtgggtgtggg (SEQ ID NO: 62) | AAIPVPKLSCKNLCHRHQLF INFRDLGWHKWIIAPKGFM ANYCHGECPFSLTISLNSSN YAFMQALMHAVDPEIPQA VCIPTKLSPISMLYQDNNDN VILRHYEDMVVDECGCG (SEQ ID NO: 63) |
| GDF-5(BMP-14) | gccccactggccactcgccagggcaagcgacccagcaagaa ccttaaggctcgctgcagtcggaaggcactgcatgtcaacttca aggacatgggctgggacgactggatcatcgcacccctttagta cgaggctttccactgcgagggctgtgagttcccattgctgct cctgcacagcctggaacccacgaatcatgcagtcatccagaccctgat gaactccatggaccccgagtccacaccaccccacctgctgtgtg cccacgcggctgagtccatcagcatcctcttcattgactctgcc aacaacgtggtgtataagcagtatgaggacat ggtcgtggagtcgtgtggctgcagg (SEQ ID NO: 64) | APLATRQGKRPSKNLKARC SRKALHVNFKDMGWDDWI IAPLEYEAFHCEGLCEFPLR SHLEPTNHAVIQTLMNSMD PESTPPTCCVPTRLSPISILFI DSANNVVYKQYEDMVVES CGCR (SEQ ID NO: 65) |
| GDF-6(BMP-13) | acgcccttcgccagtcgccatggcaagcggcacggcaagaag tccaggctacgctgcagcaagaagcccctgcacgtgaacttca aggagctgggctggacgactggattatcgcgccctgagta cgaggcctatcactgcgagggtgtatgcgacttcccgctgcgct | TAFASRHGKRHGKKSRLRC SKKPLHVNFKELGWDDWII APLEYEAYHCEGVCDFPLR SHLEPTNHAIIQTLMNSMDP |

-continued

| TGF-β Ligand | DNA Sequence | Protein Sequence |
|---|---|---|
| | cgcacctggagcccaccaaccacgccatcatccagacgctgat gaactccatggaccccggctccaccccgcccagctgctgcgta cccaccaaattgactcccatcagcattctatacatcgacgcggg caataatgtggtctacaagcagtacgaggacatggtggtggagt cgtgcggctgcagg (SEQ ID NO: 66) | GSTPPSCCVPTKLTPISILYID AGNNVVYKQYEDMVVESC GCR (SEQ ID NO: 67) |
| GDF-7(BMP-12) | acggcgttggccgggacgcggacatcgcagggcagcggcg ggggcgcgggccggggccacgggcgcaggggccggagcc gctgcagccgcaagccgttgcacgtggacttcaaggagctcgg ctgggacgactggatcatcgcgccgctggactacgaggcgtac cactgcgagggcctttgcgacttcccttcgttcgcacctcgag cccaccaaccatgccatcattcagacgctgctcaactccatgc accagacgcggcgccggcctcctgctgtgtgccagcgcct cagccccatcagcatcctctacatcgacgccgccaacaacgttg tctacaagcaatacgaggacatggtggtggaggcctgcggctg cagg (SEQ ID NO: 68) | TALAGTRTSQGSGGGAGRG HGRRGRSRCSRKPLHVDFK ELGWDDWIIAPLDYEAYHC EGLCDFPLRSHLEPTNHAII QTLLNSMAPDAAPASCCVP ARLSPISILYIDAANNVVYK QYEDMVVEACGCR (SEQ ID NO: 69) |
| GDF-8(Myostatin) | gattttggtcttgactgtgatgagcactcaacagaatcacgatgct gtcgttaccctctaactgtggattttgaagcttttggatgggattgg attatcgctcctaaaagatataaggccaattactgctctggagagt gtgaatttgtattttacaaaaatatcctcatactcatcggtacacc aagcaaaccccagaggttcagcaggcccttgctgtactcccac aaagatgtctccaattaatatgctatattttaatggcaaagaacaa ataatatgtgggaaaattccagcgatggtagtagaccgctgtgg gtgctca (SEQ ID NO: 70) | DFGLDCDEHSTESRCCRYP LTVDFEAFGWDWIIAPKRY KANYCSGECEFVFLQKYPH THLVHQANPRGSAGPCCTP TKMSPINMLYFNGKEQIIYG KIPAMVVDRCGCS (SEQ ID NO: 71) |
| GDF-9 | ggtcaggaaactgtcagttctgaattgaagaagccctgggccc agcttccttcaatctgagtgaatacttcagacaatttcttcttcccca aaatgagtgtgagctccatgactttagacttagctttagtcagctg aagtgggacaactggattgtggctccgcacaggtacaaccctc gatactgtaaaggggactgtccaagggcagttggacatcggtat ggctcccagttcacaccatggtacagaacatcatctatgagaa gctggactcctcagtgccaagaccgtcatgtgtacctgccaaat acagccccttgagtgttttgaccattgagcccgatggctcaattg cctataaagagtacgaagatatgatagctacaaagtgcacctgt cgt (SEQ ID NO: 72) | GQETVSSELKKPLGPASFNL SEYFRQFLLPQNECELHDFR LSFSQLKWDNWIVAPHRYN PRYCKGDCPRAVGHRYGSP VHTMVQNIIYEKLDSSVPRP SCVPAKYSPLSVLTIEPDGSI AYKEYEDMIATKCTCR (SEQ ID NO: 73) |
| GDF-10(BMP-3b) | aagacgatgcagaaagcccggaggaagcagtgggatgagcc gagggtgtgctcccggaggtacctgaaggtggacttcgcagac atcggctggaatgaatggataatctcaccgaaatcttttgatgcct actactgcgcgggagcatgtgagttcccccatgcctaagatcgtt cgtccatccaaccatgccaccatccagagcattgtcagggctgt gggcatcatccctggcatcccagagccctgctgtgttcccgata agatgaactcccttgggtcctcttcctggatgagaat301cgg aatgtggttctgaaggtgtacccaacatgtccgtggacacctgt gcctgccggtga (SEQ ID NO: 74) | KTMQKARRKQWDEPRVCS RRYLKVDFADIGWNEWIISP KSFDAYYCAGACEFPMPKI VRPSNHATIQSIVRAVGIIPG IPEPCCVPDKMNSLGVLFLD ENRNVVLKVYPNMSVDTC ACR (SEQ ID NO: 75) |
| GDF-11(BMP-11) | aacctgggtctggactgcgacgagcactcaagcgagtcccgct gctgccgatatccctcacagtggactttgaggctttcggctggg actggatcatcgcacctaagcgctacaaggccaactactgctcc ggccagtgcgagtacatgttcatgcaaaaatatccgcataccca tttggtgcagcaggccaatccaagaggctctgctgggcctgtt gtaccccccaccaagatgtcccaatcaacatgctctacttcaatg acaagcagcagattatctacggcaagatccctggcatggtggtg gatcgctgtggctgctct (SEQ ID NO: 76) | NLGLDCDEHSSESRCCRYP LTVDFEAFGWDWIIAPKRY KANYCSGQCEYMFMQKYP HTHLVQQANPRGSAGPCCT PTKMSPINMLYFNDKQQIIY GKIPGMVVDRCGCS (SEQ ID NO: 77) |
| GDF-15 | gcgcgcaacggggaccactgtccgctcgggcccgggcgttgc tgccgtctgcacacggtccgcgcgtcgctggaagacctgggct gggccgattgggtgctgtgtcccgagccagttcgggcggcaaacat gtgcatcggcgcgtgcccgagccagttcgggcggcaaacat gcacgcgcagatcaagacgagcctgcaccgcctgaagcccg acacggtgccagcgcctgctgcgtgcccgcagctacaatcc catggtgctcattcaaaagaccgacaccggggtgtcgctccag acctatgatgacttgttagccaaagactgccactgcata (SEQ ID NO: 78) | ARNGDDCPLGPGRCCRLHT VRASLEDLGWADWVLSPR EVQVTMCIGACPSQFRAAN MHAQIKTSLHRLKPDTEPA PCCVPASYNPMVLIQKTDT GVSLQTYDDLLAKDCHCI (SEQ ID NO: 79) |
| Nodal | catcacttgccagacagaagtcaactgtgtcggaaggtcaagtt ccaggtggacttcaacctgatcggatgggctcctggatcatct acccccaagcagtacaacgcctatcgctgtgagggcgagtgtcc taatcctgttggggaggagtttcatccgaccaaccatgcatacat ccagagtctgctgaaacgttaccagcccaccgagtcccttcca cttgttgtgccccagtgaagaccaagccgctgagcatgctgtat gtggataatggcagagtgctcctagatcaccataaagacatgat cgtggaagaatgtgggtgcctc (SEQ ID NO: 80) | HHLPDRSQLCRKVKFQVDF NLIGWGSWIIYPKQYNAYR CEGECPNPVGEEFHPTNHA YIQSLLKRYQPHRVPSTCCA PVKTKPLSMLYVDNGRVLL DHHKDMIVEECGCL (SEQ ID NO: 81) |

-continued

| TGF-β Ligand | DNA Sequence | Protein Sequence |
|---|---|---|
| Activin-βA | ggcctggagtgcgacggcaaggtcaacatctgctgtaagaaac agttctttgtcagtttcaaggacatcggctggaatgactggtcat tgctccctctggctatcatgccaactactgcgagggtgagtgcc cgagccatatagcaggcacgtccgggtcctcactgtccttccac tcaacagtcatcaaccactacgcatgcggccatagcccctttgc caacctcaaatcgtgctgtgtgcccaccaagctgagacccatgt ccatgttgtactatgatgatggtcaaaacatcatcaaaaaggaca ttcagaacatgatcgtggaggagtgcgggtgctcc (SEQ ID NO: 82) | GLECDGKVNICCKKQFFVS FKDIGWNDWIIAPSGYHAN YCEGECPSHIAGTSGSSLSF HSTVINHYRMRGHSPFANL KSCCVPTKLRPMSMLYYDD GQNIIKKDIQNMIVEECGCS (SEQ ID NO: 83) |
| Activin-βB | ggcctggagtgcgatggccggaccaacctctgttgcaggcaac agttcttcattgacttccgcctcatcggctggaacgactggatcat agcaccaccggctactacggaactactgtgagggcagctgc ccagcctacctggcaggggtccccggctctgcctcctccttcca cacggctgtggtgaaccagtaccgcatgcgggggtctgaaccc ggcacggtgaactcctgctgcattcccaccaagctgagcaccat gtccatgctgtacttcgatgatgagtacaacatcgtcaagcggg acgtgcccaacatgattgtggaggagtgcggctgcgcc (SEQ ID NO: 84) | GLECDGRTNLCCRQQFFIDF RLIGWNDWIIAPTGYYGNY CEGSCPAYLAGVPGSASSF HTAVVNQYRMRGLNPGTV NSCCIPTKLSTMSMLYFDDE YNIVKRDVPNMIVEECGCA (SEQ ID NO: 85) |
| Activin-βC | ggcatcgactgccaaggagggtccaggatgtgctgtcgacaa gagtttttgtggacttccgtgagattggctggcacgactggatca tccagcctgagggctacgccatgaactctgcataggcagtgc ccactacacatagcaggcatgcctggtattgctgcctccttcac actgcagtgctcaatcttctcaaggccaacacagctgcaggcac cactggaggggctcatgctgtgtacccacgcccggcgccc cctgtctctgctctattatgacagggacagcaacattgtcaagact gacatacctgacatggtagtagaggcctgtgggtgcagt (SEQ ID NO: 86) | GIDCQGGSRMCCRQEFFVD FREIGWHDWIIQPEGYAMN FCIGGQCPLHIAGMPGIAASF HTAVLNLLKANTAAGGTTG GGSCCVPTARRPLSLLYYD RDSNIVKTDIPDMVVEACG CS (SEQ ID NO: 87) |
| Activin-βE | accccccacctgtgagcctgcgaccccctatgttgcaggcgag accattacgtagacttccaggaactgggatggcgggactggat actgcagcccgaggggtaccagctgaattactgcagtgggcag tgccctccccacctggctggcagcccaggcattgctgcctcttc cattctgccgtcttcagcctcctcaaagccaacaatccttggcct gccagtacctcctgttgtgtccctactgcccgaaggcccctctct ctcctctacctggatcataatgcaatgtggtcaagacggatgtg ccagatatggtggtggaggcctgtggctgcagc (SEQ ID NO: 88) | TPTCEPATPLCCRRDHYVD FQELGWRDWILQPEGYQLN YCSGQCPPHLAGSPGIAASF HSAVFSLLKANNPWPASTS CCVPTARRPLSLLYLDHNG NVVKTDVPDMVVEACGCS (SEQ ID NO: 89) |
| Inhibin-α | tcaactcccctgatgtcctggccttggtctccctctgctctgcgcc tgctgcagaggcctccggaggaaccggctgcccatgccaact gccacagagtagcactgaacatctccttccaggagctgggctg ggaacggtggatcgtgtaccctcccagtttcatcttccactactgt catggtggttgtgggctgcacatcccaccaaacctgtcccttca gtccctggggctcccctaccccagcccagccctactccttgct gccaggggcccagcccgtgtgctgctctcccaggaccatg aggcccctacatgtccgcaccacctcggatggaggttactctttc aagtatgagacagtgcccaaccttctcacgcagcactgtgcttgt atc (SEQ ID NO: 90) | STPLMSWPWSPSALRLLQR PPEEPAAHANCHRVALNISF QELGWERWIVYPPSFIFHYC HGGCGLHIPPNLSLPVPGAP PTPAQPYSLLPGAQPCCAAL PGTMRPLHVRTTSDGGYSF KYETVPNLLTQHCACI (SEQ ID NO: 91) |
| TGF-β1 | gccctggacaccaactattgcttcagctccacggagaagaactg ctgcgtgcggcagctgtacattgacttccgcaaggacctcggct ggaagtggatccacgagcccaagggctaccatgccaacttctg cctcgggcctgccctacatttggagcctggacacgcagtac agcaaggtcctggcctgtacaaccagcatccgggcgcct cggccgcgccgtgctgcgtgccgcaggcgctggagccgctg cccatcgtgtactacgtgggccgcaagcccaaggtggagcag ctgtccaacatgatcgtgcgctcctgcaagtgcagc (SEQ ID NO: 92) | ALDTNYCFSSTEKNCCVRQ LYIDFRKDLGWKWIHEPKG YHANFCLGPCPYIWSLDTQ YSKVLALYNQHNPGASAAP CCVPQALEPLPIVYYVGRKP KVEQLSNMIVRSCKCS (SEQ ID NO: 93) |
| TGF-β2 | gctttggatgcggcctattgctttagaaatgtgcaggataattgct gcctacgtccactttacattgatttcaagagggatctagggtgga atggatacacgaacccaaagggtacaatgccaacttctgtgct ggagcatgcccgtattggagttcaagcacacagcag ggtcctgagcttatataatacccataaatccagaagcatctgcttct ccttgctgcgtgtcccaagatttagaacctctaaccattctctacta cattggcaaaacacccaagattgaacagctttctaatatgattgta aagtcttgcaaatgcagc (SEQ ID NO: 94) | ALDAAYCFRNVQDNCCLRP LYIDFKRDLGWKWIHEPKG YNANFCAGACPYLWSSDT QHSRVLSLYNTINPEASASP CCVSQDLEPLTILYYIGKTP KIEQLSNMIVKSCKCS (SEQ ID NO: 95) |
| TGF-β3 | gctttggacaccaattactgcttccgcaacttggaggagaactgc tgtgtgcgccccctctacattgacttccgacaggatctgggctgg aagtgggtccatgaacctaagggctactatgccaacttctgctca ggcccttgcccataccttcgcagtgcagacacaacccacagca cggtgctgggactgtacaacactctgaacctgaagcatctgcc tcgccttgctgcgtgccccaggacctggagcccctgaccatcct | ALDTNYCFRNLEENCCVRP LYIDFRQDLGWKWVHEPK GYYANFCSGPCPYLRSADT THSTVLGLYNTLNPEASASP CCVPQDLEPLTILYYVGRTP KVEQLSNMVVKSCKCS |

| TGF-β Ligand DNA Sequence | Protein Sequence |
|---|---|
| gtactatgttgggaggacccccaaagtggagcagctctccaac atggtggtgaagtcttgtaaatgtagc (SEQ ID NO: 96) | (SEQ ID NO: 97) |

What is claimed is:

1. A recombinant TGF-β ligand polypeptide having at least 95% sequence identity to an amino acid sequence comprising
 a first segment of amino acid residues comprising amino acid residues 1 to 32 of SEQ ID NO:2 ("1b");
 a second segment of amino acid residues comprising amino acid residues 30 to 45 of SEQ ID NO:5 ("2a");
 a third segment of amino acid residues comprising amino acid residues 46 to $x_1$ of SEQ ID NO:5 ("3a"), or amino acid residues $x_2$ to $x_3$ of SEQ ID NO:2 ("3b"),
 wherein:
  $x_1$ is residue 61, 62, 63, or 64 of SEQ ID NO:5,
  $x_2$ is residue 45, 46, 47, or 48 of SEQ ID NO:2, and
  $x_3$ is residue 65, 66, 67, or 68 of SEQ ID NO:2; and
 a fourth segment of amino acid residues comprising amino acid residues $x_4$ to $x_5$ of SEQ ID NO:5 ("4a") or amino acid residues $x_6$ to $x_7$ of SEQ ID NO:2 ("4b"),
 wherein:
  $x_4$ is $x_1$ of SEQ ID NO: 5 if the third segment comprises 3b, or $x_4$ is $x_1$+1 of SEQ ID NO: 5 if the third segment comprises 3a,
  $x_5$ is residue 78, 79, 80, 81, 82, 83 or 84 of SEQ ID NO:5,
  $x_6$ is $x_3$ of SEQ ID NO: 2 if the third segment comprises 3a, or $x_6$ is $x_3$+1 of SEQ ID NO: 2 if the third segment comprises 3b,
  $x_7$ is residue 76, 77, 78, 79, 80, 81 or 82 of SEQ ID NO:2, and;
 a fifth segment of amino acid residues comprising amino acid residues $x_8$ to $x_9$ of SEQ ID NO:5 ("5a") or amino acid residues $x_{10}$ to $x_{11}$ of SEQ ID NO:2 ("5b"),
 wherein:
  $x_8$ is $x_5$ of SEQ ID NO: 5 if the fourth segment comprises 4b, or $x_8$ is $x_5$+1 of SEQ ID NO: 5 if the fourth segment comprises 4a,
  $x_9$ is residue 90, 91, 92, 93, 94, 95 or 96 of SEQ ID NO:5,
  $x_{10}$ is $x_7$ of SEQ ID NO: 2 if the fourth segment comprises 4a, or $x_{10}$ is $x_7$+1 of SEQ ID NO: 2 if the fourth segment comprises 4b,
  $x_{11}$ is residue 88, 89, 90, 91, 92, 93, or 94 of SEQ ID NO:2, and
 a sixth segment comprising amino acid residues $x_{12}$ to $x_{13}$ of SEQ ID NO:5 ("6a") or amino acid residues $x_{14}$ to $x_{15}$ of SEQ ID NO:2 ("6b"),
 wherein:
  $x_{12}$ is $x_9$ of SEQ ID NO: 5 if the fifth segment comprises 5b, or $x_{12}$ is $x_9$+1 of SEQ ID NO: 5 if the fifth segment comprises 5a,
  $x_{13}$ is residue 114, 115, or 116 or SEQ ID NO:5,
  $x_{14}$ is $x_{11}$ of SEQ ID NO: 2 if the fifth segment comprises 5a, or $x_{14}$ is $x_{11}$+1 of SEQ ID NO: 2 if the fifth segment comprises 5b,
  $x_{15}$ is residue 112, 113, or 114 or SEQ ID NO:2;
 wherein the recombinant TGF-β ligand polypeptide activates cell proliferation or activity associated with SMAD pathway.

2. The recombinant polypeptide of claim 1, wherein
 the third segment comprises amino acid residues $x_2$ to $x_3$ of SEQ ID NO:2 ("3b");

the fourth segment comprises amino acid residues $x_6$ to $x_7$ of SEQ ID NO:2 ("4b"), wherein $x_6$ is $x_3$+1 of SEQ ID NO: 2;

the fifth segment comprises amino acid residues $x_8$ to $x_9$ of SEQ ID NO:5 ("5a"), wherein $x_8$ is $x_5$ of SEQ ID NO: 5; and the sixth segment comprises amino acid residues $x_{12}$ to $x_{13}$ of SEQ ID NO:5 ("6a"), wherein $x_{12}$ is $x_9$+1 of SEQ ID NO: 5.

3. The recombinant polypeptide of claim 1, wherein the third segment comprises amino acid residue 46 to $x_1$ of SEQ ID NO:5 ("3a");

the fourth segment comprises amino acid residues $x_4$ to $x_5$ of SEQ ID NO:5 ("4a"), wherein $x_4$ is $x_1$+1 of SEQ ID NO: 5;

the fifth segment comprises amino acid residues $x_8$ to $x_9$ of SEQ ID NO:5 ("5a"), wherein $x_8$ is $x_5$+1 of SEQ ID NO: 5; and the sixth segment comprises amino acid residues $x_{12}$ to $x_{13}$ of SEQ ID NO:5 ("6a"), wherein $x_{12}$ is $x_9$+1 of SEQ ID NO: 5.

4. The recombinant polypeptide of claim 1, wherein the third segment comprises amino acid residues $x_2$ to $x_3$ of SEQ ID NO:2 ("3b");

the fourth segment comprises amino acid residues $x_6$ to $x_7$ of SEQ ID NO:2 ("4b"), wherein $x_6$ is $x_3$+1 of SEQ ID NO: 2;

the fifth segment comprises amino acid residues $x_{10}$ to $x_{11}$ of SEQ ID NO:2 ("5b"), wherein $x_{10}$ is $x_7$+1 of SEQ ID NO: 2; and the sixth segment comprises amino acid residues $x_{12}$ to $x_{13}$ of SEQ ID NO:5 ("6a"), wherein $x_{12}$ is $x_9$ of SEQ ID NO: 5.

5. The polypeptide of claim 1, wherein the polypeptide comprises a sequence selected from the group consisting of SEQ ID NO: 17, 19, 23, 25, 27, 29, 31, and 33.

6. The recombinant polypeptide of claim 1, wherein said polypeptide comprises the sequence as set forth in SEQ ID NO: 31.

7. The recombinant polypeptide of claim 1, wherein said polypeptide comprises the sequence as set forth in SEQ ID NO: 17.

8. The recombinant polypeptide of claim 1, wherein said polypeptide comprises the sequence as set forth in SEQ ID NO: 29.

9. The recombinant polypeptide of claim 1, wherein said polypeptide has at least 95% sequence identity to the sequence as set forth in SEQ ID NO: 31.

10. The recombinant TGF-β ligand polypeptide of claim 1, wherein the recombinant TGF-β ligand polypeptide has at least 97% sequence identity to the amino acid sequence comprising the first, the second, the third, the fourth, the fifth, and the sixth segments.

11. The recombinant TGF-β ligand polypeptide of claim 1, wherein the recombinant TGF-β ligand polypeptide has at least 98% sequence identity to the amino acid sequence comprising the first, the second, the third, the fourth, the fifth, and the sixth segments.

12. The recombinant TGF-β ligand polypeptide of claim 1, wherein the recombinant TGF-β ligand polypeptide has 100% sequence identity to the amino acid sequence comprising the first, the second, the third, the fourth, the fifth, and the sixth segments.

13. A polynucleotide comprising a sequence selected from the group consisting of SEQ ID NOs: 16, 18, 22, 24, 26, 28, 30, and 32.

14. The polynucleotide of claim 13, wherein said polynucleotide comprises the sequence as set forth in SEQ ID NO: 30.

15. The polynucleotide of claim 13, wherein said polynucleotide comprises the sequence as set forth in SEQ ID NO: 16.

16. The polynucleotide of claim 13, wherein said polynucleotide comprises the sequence as set forth in SEQ ID NO: 28.

* * * * *

SEQUENCE LISTING

<160> NUMBER OF SEQ ID NOS: 150

<210> SEQ ID NO 1
<211> LENGTH: 345
<212> TYPE: DNA
<213> ORGANISM: Artificial Sequence
<220> FEATURE:
<223> OTHER INFORMATION: BMP-2 polynucleotide coding sequence
<220> FEATURE:
<221> NAME/KEY: CDS
<222> LOCATION: (4)..(345)

<400> SEQUENCE: 1

```
atg caa gcc aaa cac aaa cag cgg aaa cgc ctt aag tcc agc tgt aag        48
    Gln Ala Lys His Lys Gln Arg Lys Arg Leu Lys Ser Ser Cys Lys
    1               5                   10                  15 aga cac cct ttg tac gtg gac ttc agt gac gtg ggg tgg aat gac tgg        96
Arg His Pro Leu Tyr Val Asp Phe Ser Asp Val Gly Trp Asn Asp Trp
                20                  25                  30 att gtg gct ccc ccg ggg tat cac gcc ttt tac tgc cac gga gaa tgc       144
Ile Val Ala Pro Pro Gly Tyr His Ala Phe Tyr Cys His Gly Glu Cys
            35                  40                  45 cct ttt cct ctg gct gat cat ctg aac tcc act aat cat gcc att gtt       192
Pro Phe Pro Leu Ala Asp His Leu Asn Ser Thr Asn His Ala Ile Val
        50                  55                  60 cag acg ttg gtc aac tct gtt aac tct aag att cct aag gca tgc tgt       240
Gln Thr Leu Val Asn Ser Val Asn Ser Lys Ile Pro Lys Ala Cys Cys
    65                  70                  75 gtc ccg aca gaa ctc agt gct atc tcg atg ctg tac ctt gac gag aat       288
Val Pro Thr Glu Leu Ser Ala Ile Ser Met Leu Tyr Leu Asp Glu Asn
80                  85                  90                  95 gaa aag gtt gta tta aag aac tat cag gac atg gtt gtg gag ggt tgt       336
Glu Lys Val Val Leu Lys Asn Tyr Gln Asp Met Val Val Glu Gly Cys
                100                 105                 110 ggg tgt cgc                                                           345
Gly Cys Arg
```

<210> SEQ ID NO 2
<211> LENGTH: 114
<212> TYPE: PRT
<213> ORGANISM: Artificial Sequence
<220> FEATURE:
<223> OTHER INFORMATION: Synthetic Construct

<400> SEQUENCE: 2

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60
```

```
Thr Leu Val Asn Ser Val Asn Ser Lys Ile Pro Lys Ala Cys Cys Val
 65                  70                  75                  80

Pro Thr Glu Leu Ser Ala Ile Ser Met Leu Tyr Leu Asp Glu Asn Glu
                 85                  90                  95

Lys Val Val Leu Lys Asn Tyr Gln Asp Met Val Val Glu Gly Cys Gly
            100                 105                 110

Cys Arg

<210> SEQ ID NO 3
<211> LENGTH: 1281
<212> TYPE: DNA
<213> ORGANISM: Homo Sapiens
<220> FEATURE:
<221> NAME/KEY: CDS
<222> LOCATION: (1)..(1281)

<400> SEQUENCE: 3 atg ccc ttg ctt tgg ctg aga gga ttt ctg ttg gca agt tgc tgg att      48
Met Pro Leu Leu Trp Leu Arg Gly Phe Leu Leu Ala Ser Cys Trp Ile
 1               5                  10                  15 ata gtg agg agt tcc ccc acc cca gga tcc gag ggg cac agc gcg gcc      96
Ile Val Arg Ser Ser Pro Thr Pro Gly Ser Glu Gly His Ser Ala Ala
             20                  25                  30 ccc gac tgt ccg tcc tgt gcg ctg gcc gcc ctc cca aag gat gta ccc     144
Pro Asp Cys Pro Ser Cys Ala Leu Ala Ala Leu Pro Lys Asp Val Pro
         35                  40                  45 aac tct cag cca gag atg gtg gag gcc gtc aag aag cac att tta aac     192
Asn Ser Gln Pro Glu Met Val Glu Ala Val Lys Lys His Ile Leu Asn
     50                  55                  60 atg ctg cac ttg aag aag aga ccc gat gtc acc cag ccg gta ccc aag     240
Met Leu His Leu Lys Lys Arg Pro Asp Val Thr Gln Pro Val Pro Lys
 65                  70                  75                  80 gcg gcg ctt ctg aac gcg atc aga aag ctt cat gtg ggc aaa gtc ggg     288
Ala Ala Leu Leu Asn Ala Ile Arg Lys Leu His Val Gly Lys Val Gly
                 85                  90                  95 gag aac ggg tat gtg gag ata gag gat gac att gga agg agg gca gaa     336
Glu Asn Gly Tyr Val Glu Ile Glu Asp Asp Ile Gly Arg Arg Ala Glu
            100                 105                 110 atg aat gaa ctt atg gag cag acc tcg gag atc atc acg ttt gcc gag     384
Met Asn Glu Leu Met Glu Gln Thr Ser Glu Ile Ile Thr Phe Ala Glu
        115                 120                 125 tca gga aca gcc agg aag acg ctg cac ttc gag att tcc aag gaa ggc     432
Ser Gly Thr Ala Arg Lys Thr Leu His Phe Glu Ile Ser Lys Glu Gly
    130                 135                 140 agt gac ctg tca gtg gtg gag cgt gca gaa gtc tgg ctc ttc cta aaa     480
Ser Asp Leu Ser Val Val Glu Arg Ala Glu Val Trp Leu Phe Leu Lys
145                 150                 155                 160 gtc ccc aag gcc aac agg acc agg acc aaa gtc acc atc cgc ctc ttc     528
Val Pro Lys Ala Asn Arg Thr Arg Thr Lys Val Thr Ile Arg Leu Phe
                165                 170                 175 cag cag cag aag cac ccg cag ggc agc ttg gac aca ggg gaa gag gcc     576
Gln Gln Gln Lys His Pro Gln Gly Ser Leu Asp Thr Gly Glu Glu Ala
            180                 185                 190 gag gaa gtg ggc tta aag ggg gag agg agt gaa ctg ttg ctc tct gaa     624
Glu Glu Val Gly Leu Lys Gly Glu Arg Ser Glu Leu Leu Leu Ser Glu
        195                 200                 205 aaa gta gta gac gct cgg aag agc acc tgg cat gtc ttc cct gtc tcc     672
Lys Val Val Asp Ala Arg Lys Ser Thr Trp His Val Phe Pro Val Ser
    210                 215                 220 agc agc atc cag cgg ttg ctg gac cag ggc aag agc tcc ctg gac gtt     720
```

```
Ser Ser Ile Gln Arg Leu Leu Asp Gln Gly Lys Ser Ser Leu Asp Val
225                 230                 235                 240 cgg att gcc tgt gag cag tgc cag gag agt ggc gcc agc ttg gtt ctc      768
Arg Ile Ala Cys Glu Gln Cys Gln Glu Ser Gly Ala Ser Leu Val Leu
                245                 250                 255 ctg ggc aag aag aag aag aaa gaa gag gag ggg gaa ggg aaa aag aag      816
Leu Gly Lys Lys Lys Lys Lys Glu Glu Glu Gly Glu Gly Lys Lys Lys
                260                 265                 270 ggc gga ggt gaa ggt ggg gca gga gca gat gag gaa aag gag cag tcg      864
Gly Gly Gly Glu Gly Gly Ala Gly Ala Asp Glu Glu Lys Glu Gln Ser
            275                 280                 285 cac aga cct ttc ctc atg ctg cag gcc cgg cag tct gaa gac cac cct      912
His Arg Pro Phe Leu Met Leu Gln Ala Arg Gln Ser Glu Asp His Pro
        290                 295                 300 cat cgc cgg cgt cgg cgg ggc ttg gag tgt gat ggc aag gtc aac atc      960
His Arg Arg Arg Arg Arg Gly Leu Glu Cys Asp Gly Lys Val Asn Ile
305                 310                 315                 320 tgt tgt aag aaa cag ttc ttt gtc agt ttc aag gac atc ggc tgg aat     1008
Cys Cys Lys Lys Gln Phe Phe Val Ser Phe Lys Asp Ile Gly Trp Asn
                325                 330                 335 gac tgg atc att gct ccc tct ggc tat cat gcc aac tac tgc gag ggt     1056
Asp Trp Ile Ile Ala Pro Ser Gly Tyr His Ala Asn Tyr Cys Glu Gly
                340                 345                 350 gag tgc ccg agc cat ata gca ggc acg tcc ggg tcc tca ctg tcc ttc     1104
Glu Cys Pro Ser His Ile Ala Gly Thr Ser Gly Ser Ser Leu Ser Phe
            355                 360                 365 cac tca aca gtc atc aac cac tac cgc atg cgg ggc cat agc ccc ttt     1152
His Ser Thr Val Ile Asn His Tyr Arg Met Arg Gly His Ser Pro Phe
        370                 375                 380 gcc aac ctc aaa tcg tgc tgt gtg ccc acc aag ctg aga ccc atg tcc     1200
Ala Asn Leu Lys Ser Cys Cys Val Pro Thr Lys Leu Arg Pro Met Ser
385                 390                 395                 400 atg ttg tac tat gat gat ggt caa aac atc atc aaa aag gac att cag     1248
Met Leu Tyr Tyr Asp Asp Gly Gln Asn Ile Ile Lys Lys Asp Ile Gln
                405                 410                 415 aac atg atc gtg gag gag tgt ggg tgc tca tag                         1281
Asn Met Ile Val Glu Glu Cys Gly Cys Ser
                420                 425
```

<210> SEQ ID NO 4
<211> LENGTH: 426
<212> TYPE: PRT
<213> ORGANISM: Homo Sapiens

<400> SEQUENCE: 4

```
Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
                20                  25                  30

Pro Asp Cys Pro Ser Cys Ala Leu Ala Ala Leu Pro Lys Asp Val Pro
            35                  40                  45

Asn Ser Gln Pro Glu Met Val Glu Ala Val Lys Lys His Ile Leu Asn
        50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
                100                 105                 110
```

```
Met Asn Glu Leu Met Glu Gln Thr Ser Glu Ile Ile Thr Phe Ala Glu
            115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
                180                 185                 190

Glu Glu Val Gly Leu Lys Gly Glu Arg Ser Glu Leu Leu Leu Ser Glu
            195                 200                 205

Lys Val Val Asp Ala Arg Lys Ser Thr Trp His Val Phe Pro Val Ser
210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Lys Glu Glu Gly Glu Gly Lys Lys Lys
                260                 265                 270

Gly Gly Gly Glu Gly Gly Ala Gly Ala Asp Glu Glu Lys Glu Gln Ser
            275                 280                 285

His Arg Pro Phe Leu Met Leu Gln Ala Arg Gln Ser Glu Asp His Pro
            290                 295                 300

His Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
                325                 330                 335

Asp Trp Ile Ile Ala Pro Ser Gly Tyr His Ala Asn Tyr Cys Glu Gly
                340                 345                 350

Glu Cys Pro Ser His Ile Ala Gly Thr Ser Gly Ser Ser Leu Ser Phe
            355                 360                 365

His Ser Thr Val Ile Asn His Tyr Arg Met Arg Gly His Ser Pro Phe
    370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
                405                 410                 415

Asn Met Ile Val Glu Glu Cys Gly Cys Ser
                420                 425

<210> SEQ ID NO 5
<211> LENGTH: 116
<212> TYPE: PRT
<213> ORGANISM: Artificial Sequence
<220> FEATURE:
<223> OTHER INFORMATION: Mature activin polypeptide homo sapiens

<400> SEQUENCE: 5

Gly Leu Glu Cys Asp Gly Lys Val Asn Ile Cys Cys Lys Gln Phe
1               5                   10                  15

Phe Val Ser Phe Lys Asp Ile Gly Trp Asn Asp Trp Ile Ile Ala Pro
                20                  25                  30

Ser Gly Tyr His Ala Asn Tyr Cys Glu Gly Glu Cys Pro Ser His Ile
            35                  40                  45
```

```
Ala Gly Thr Ser Gly Ser Ser Leu Ser Phe His Ser Thr Val Ile Asn
 50                  55                  60

His Tyr Arg Met Arg Gly His Ser Pro Phe Ala Asn Leu Lys Ser Cys
 65                  70                  75                  80

Cys Val Pro Thr Lys Leu Arg Pro Met Ser Met Leu Tyr Tyr Asp Asp
                 85                  90                  95

Gly Gln Asn Ile Ile Lys Lys Asp Ile Gln Asn Met Ile Val Glu Glu
            100                 105                 110

Cys Gly Cys Ser
        115
```

```
<210> SEQ ID NO 6
<211> LENGTH: 345
<212> TYPE: DNA
<213> ORGANISM: Artificial Sequence
<220> FEATURE:
<223> OTHER INFORMATION: Chimeric polypeptide
<220> FEATURE:
<221> NAME/KEY: CDS
<222> LOCATION: (1)..(345)

<400> SEQUENCE: 6
```

```
atg caa gcc aaa cac aaa cag cgg aaa cgc ctt aag tcc agc tgt aag     48
Met Gln Ala Lys His Lys Gln Arg Lys Arg Leu Lys Ser Ser Cys Lys
 1               5                  10                  15 aga cac cct ttg tac gtg gac ttc agt gac gtg ggg tgg aat gac tgg     96
Arg His Pro Leu Tyr Val Asp Phe Ser Asp Val Gly Trp Asn Asp Trp
             20                  25                  30 att gtg gct ccc ccg ggg tat cac gcc ttt tac tgc cac gga gaa tgc    144
Ile Val Ala Pro Pro Gly Tyr His Ala Phe Tyr Cys His Gly Glu Cys
         35                  40                  45 cct ttt cct ctg gct gat cat ctg aac tcc act aat cat gcc att gtt    192
Pro Phe Pro Leu Ala Asp His Leu Asn Ser Thr Asn His Ala Ile Val
 50                  55                  60 cag acg ttg gtc aac tct gtt aac tct aag att cct aag gca tgc tgt    240
Gln Thr Leu Val Asn Ser Val Asn Ser Lys Ile Pro Lys Ala Cys Cys
 65                  70                  75                  80 gtc ccg aca gaa ctc agt gct atc tcg atg ttg tac tat gat gat ggt    288
Val Pro Thr Glu Leu Ser Ala Ile Ser Met Leu Tyr Tyr Asp Asp Gly
                 85                  90                  95 cga aac atc atc aaa aag gac att cag aac atg atc gtg gag gag tgt    336
Arg Asn Ile Ile Lys Lys Asp Ile Gln Asn Met Ile Val Glu Glu Cys
            100                 105                 110 ggg tgc tca                                                        345
Gly Cys Ser
        115
```

```
<210> SEQ ID NO 7
<211> LENGTH: 115
<212> TYPE: PRT
<213> ORGANISM: Artificial Sequence
<220> FEATURE:
<223> OTHER INFORMATION: Synthetic Construct

<400> SEQUENCE: 7
```

```
Met Gln Ala Lys His Lys Gln Arg Lys Arg Leu Lys Ser Ser Cys Lys
 1               5                  10                  15

Arg His Pro Leu Tyr Val Asp Phe Ser Asp Val Gly Trp Asn Asp Trp
             20                  25                  30

Ile Val Ala Pro Pro Gly Tyr His Ala Phe Tyr Cys His Gly Glu Cys
         35                  40                  45
```

```
Pro Phe Pro Leu Ala Asp His Leu Asn Ser Thr Asn His Ala Ile Val
        50                  55                  60

Gln Thr Leu Val Asn Ser Val Asn Ser Lys Ile Pro Lys Ala Cys Cys
 65                  70                  75                  80

Val Pro Thr Glu Leu Ser Ala Ile Ser Met Leu Tyr Tyr Asp Asp Gly
                 85                  90                  95

Arg Asn Ile Ile Lys Lys Asp Ile Gln Asn Met Ile Val Glu Glu Cys
                100                 105                 110

Gly Cys Ser
        115

<210> SEQ ID NO 8
<211> LENGTH: 342
<212> TYPE: DNA
<213> ORGANISM: Artificial Sequence
<220> FEATURE:
<223> OTHER INFORMATION: Chimeric polypeptide
<220> FEATURE:
<221> NAME/KEY: CDS
<222> LOCATION: (1)..(342)

<400> SEQUENCE: 8 atg caa gcc aaa cac caa cag cgg aaa cgc ctt aag tcc agc tgt aag      48
Met Gln Ala Lys His Gln Gln Arg Lys Arg Leu Lys Ser Ser Cys Lys
 1               5                  10                  15 aga cac cct ttg tac gtg gac ttc agt gac gtg ggg tgg aat gac tgg      96
Arg His Pro Leu Tyr Val Asp Phe Ser Asp Val Gly Trp Asn Asp Trp
             20                  25                  30 att gtg gct ccc ccg ggg tat cac gcc ttt tac tgc cac gga gaa tgc     144
Ile Val Ala Pro Pro Gly Tyr His Ala Phe Tyr Cys His Gly Glu Cys
         35                  40                  45 cct ttt cct ctg gct gat cat ctg aac tcc act aat cat gcc att gtt     192
Pro Phe Pro Leu Ala Asp His Leu Asn Ser Thr Asn His Ala Ile Val
     50                  55                  60 cag acg ttg gtc aac tct gtt aac tct aag att cct aag gca tgc tgt     240
Gln Thr Leu Val Asn Ser Val Asn Ser Lys Ile Pro Lys Ala Cys Cys
 65                  70                  75                  80 gtc ccg acc aag ctg aga ccc tcc atg ttg tac tat gat gat ggt caa     288
Val Pro Thr Lys Leu Arg Pro Ser Met Leu Tyr Tyr Asp Asp Gly Gln
                 85                  90                  95 aac atc atc aaa aag gac att cag aac atg atc gtg gag gag tgt ggg     336
Asn Ile Ile Lys Lys Asp Ile Gln Asn Met Ile Val Glu Glu Cys Gly
                100                 105                 110 tgc tca                                                              342
Cys Ser <210> SEQ ID NO 9
<211> LENGTH: 114
<212> TYPE: PRT
<213> ORGANISM: Artificial Sequence
<220> FEATURE:
<223> OTHER INFORMATION: Synthetic Construct

<400> SEQUENCE: 9

Met Gln Ala Lys His Gln Gln Arg Lys Arg Leu Lys Ser Ser Cys Lys
 1               5                  10                  15

Arg His Pro Leu Tyr Val Asp Phe Ser Asp Val Gly Trp Asn Asp Trp
             20                  25                  30

Ile Val Ala Pro Pro Gly Tyr His Ala Phe Tyr Cys His Gly Glu Cys
         35                  40                  45
```

```
Pro Phe Pro Leu Ala Asp His Leu Asn Ser Thr Asn His Ala Ile Val
    50                  55                  60

Gln Thr Leu Val Asn Ser Val Asn Ser Lys Ile Pro Lys Ala Cys Cys
 65                  70                  75                  80

Val Pro Thr Lys Leu Arg Pro Ser Met Leu Tyr Tyr Asp Asp Gly Gln
                85                  90                  95

Asn Ile Ile Lys Lys Asp Ile Gln Asn Met Ile Val Glu Glu Cys Gly
            100                 105                 110

Cys Ser

<210> SEQ ID NO 10
<211> LENGTH: 345
<212> TYPE: DNA
<213> ORGANISM: Artificial Sequence
<220> FEATURE:
<223> OTHER INFORMATION: Chimeric polypeptide
<220> FEATURE:
<221> NAME/KEY: CDS
<222> LOCATION: (1)..(345)

<400> SEQUENCE: 10 atg caa gcc aaa cac aaa cag cgg aaa cgc ctt aag tcc agc tgt aag      48
Met Gln Ala Lys His Lys Gln Arg Lys Arg Leu Lys Ser Ser Cys Lys
  1               5                  10                  15 aga cac cct ttg tac gtg gac ttc agt gac gtg ggg tgg aat gac tgg      96
Arg His Pro Leu Tyr Val Asp Phe Ser Asp Val Gly Trp Asn Asp Trp
                20                  25                  30 att gtg gct ccc ccg ggg tat cac gcc ttt tac tgc cac gga gaa tgc     144
Ile Val Ala Pro Pro Gly Tyr His Ala Phe Tyr Cys His Gly Glu Cys
            35                  40                  45 cct ttt cct ctg gct gat cat ctg aac tcc act aat cat gcc att gtt     192
Pro Phe Pro Leu Ala Asp His Leu Asn Ser Thr Asn His Ala Ile Val
        50                  55                  60 cag acg ttg gtc aac tct gtt aac tct aag att cct aag gca tgc tgt     240
Gln Thr Leu Val Asn Ser Val Asn Ser Lys Ile Pro Lys Ala Cys Cys
 65                  70                  75                  80 gtc ccg acc aag ctg aga ccc atg tcc atg ttg tac tat gat gag aat     288
Val Pro Thr Lys Leu Arg Pro Met Ser Met Leu Tyr Tyr Asp Glu Asn
                85                  90                  95 gaa aag gtt gta tta aag aac tat cag gac atg gtt gtg gag ggt tgt     336
Glu Lys Val Val Leu Lys Asn Tyr Gln Asp Met Val Val Glu Gly Cys
            100                 105                 110 ggg tgt cgc                                                         345
Gly Cys Arg
        115

<210> SEQ ID NO 11
<211> LENGTH: 115
<212> TYPE: PRT
<213> ORGANISM: Artificial Sequence
<220> FEATURE:
<223> OTHER INFORMATION: Synthetic Construct

<400> SEQUENCE: 11

Met Gln Ala Lys His Lys Gln Arg Lys Arg Leu Lys Ser Ser Cys Lys
  1               5                  10                  15

Arg His Pro Leu Tyr Val Asp Phe Ser Asp Val Gly Trp Asn Asp Trp
                20                  25                  30

Ile Val Ala Pro Pro Gly Tyr His Ala Phe Tyr Cys His Gly Glu Cys
            35                  40                  45

Pro Phe Pro Leu Ala Asp His Leu Asn Ser Thr Asn His Ala Ile Val
```

```
            50                  55                  60
Gln Thr Leu Val Asn Ser Val Asn Ser Lys Ile Pro Lys Ala Cys Cys
 65                  70                  75                  80

Val Pro Thr Lys Leu Arg Pro Met Ser Met Leu Tyr Tyr Asp Glu Asn
                 85                  90                  95

Glu Lys Val Val Leu Lys Asn Tyr Gln Asp Met Val Val Glu Gly Cys
            100                 105                 110

Gly Cys Arg
        115

<210> SEQ ID NO 12
<211> LENGTH: 360
<212> TYPE: DNA
<213> ORGANISM: Artificial Sequence
<220> FEATURE:
<223> OTHER INFORMATION: Chimeric polypeptide
<220> FEATURE:
<221> NAME/KEY: CDS
<222> LOCATION: (1)..(360)

<400> SEQUENCE: 12 atg caa gcc aaa cac aaa cag cgg aaa cgc ctt aag tcc agc tgt aag      48
Met Gln Ala Lys His Lys Gln Arg Lys Arg Leu Lys Ser Ser Cys Lys
 1               5                  10                  15 aga cac cct ttg tac gtg gac ttc agt gac gtg ggg tgg aat gac tgg      96
Arg His Pro Leu Tyr Val Asp Phe Ser Asp Val Gly Trp Asn Asp Trp
                20                  25                  30 att gtg gct ccc ccg ggg tat cac gcc ttt tac tgc cac gga gaa tgc     144
Ile Val Ala Pro Pro Gly Tyr His Ala Phe Tyr Cys His Gly Glu Cys
            35                  40                  45 cct tct cat ata gca ggc acg tcc ggg tcc tca ctg tcc ttc cac tca     192
Pro Ser His Ile Ala Gly Thr Ser Gly Ser Ser Leu Ser Phe His Ser
        50                  55                  60 acg ttg gtc aac cac tac cgc atg cgg ggc cat agc ccc ttt gcc aac     240
Thr Leu Val Asn His Tyr Arg Met Arg Gly His Ser Pro Phe Ala Asn
 65                  70                  75                  80 ctc aaa tcg tgc tgt gtc ccg acc aag ctg aga ccc atg tcc atg ttg     288
Leu Lys Ser Cys Cys Val Pro Thr Lys Leu Arg Pro Met Ser Met Leu
                85                  90                  95 tac tat gat gat ggt caa aac atc atc aaa aag gac att cag aac atg     336
Tyr Tyr Asp Asp Gly Gln Asn Ile Ile Lys Lys Asp Ile Gln Asn Met
            100                 105                 110 atc gtg gag gag tgt ggg tgc tca                                     360
Ile Val Glu Glu Cys Gly Cys Ser
        115                 120

<210> SEQ ID NO 13
<211> LENGTH: 120
<212> TYPE: PRT
<213> ORGANISM: Artificial Sequence
<220> FEATURE:
<223> OTHER INFORMATION: Synthetic Construct

<400> SEQUENCE: 13

Met Gln Ala Lys His Lys Gln Arg Lys Arg Leu Lys Ser Ser Cys Lys
 1               5                  10                  15

Arg His Pro Leu Tyr Val Asp Phe Ser Asp Val Gly Trp Asn Asp Trp
                20                  25                  30

Ile Val Ala Pro Pro Gly Tyr His Ala Phe Tyr Cys His Gly Glu Cys
            35                  40                  45

Pro Ser His Ile Ala Gly Thr Ser Gly Ser Ser Leu Ser Phe His Ser
```

```
            50                  55                  60
Thr Leu Val Asn His Tyr Arg Met Arg Gly His Ser Pro Phe Ala Asn
 65                  70                  75                  80

Leu Lys Ser Cys Cys Val Pro Thr Lys Leu Arg Pro Met Ser Met Leu
                 85                  90                  95

Tyr Tyr Asp Asp Gly Gln Asn Ile Ile Lys Lys Asp Ile Gln Asn Met
            100                 105                 110

Ile Val Glu Glu Cys Gly Cys Ser
            115                 120

<210> SEQ ID NO 14
<211> LENGTH: 360
<212> TYPE: DNA
<213> ORGANISM: Artificial Sequence
<220> FEATURE:
<223> OTHER INFORMATION: Chimeric polypeptide
<220> FEATURE:
<221> NAME/KEY: CDS
<222> LOCATION: (1)..(360)

<400> SEQUENCE: 14 atg caa gcc aaa cac aaa cag cgg aaa cgc ctt aag tcc agc tgt aag    48
Met Gln Ala Lys His Lys Gln Arg Lys Arg Leu Lys Ser Ser Cys Lys
  1               5                  10                  15 aga cac cct ttg tac gtg gac ttc agt gac gtg ggg tgg aat gac tgg    96
Arg His Pro Leu Tyr Val Asp Phe Ser Asp Val Gly Trp Asn Asp Trp
                 20                  25                  30 att gtg gct ccc ccg ggg tat cac gcc ttt tac tgc cac gga gaa tgc   144
Ile Val Ala Pro Pro Gly Tyr His Ala Phe Tyr Cys His Gly Glu Cys
             35                  40                  45 cct tct cat ata gca ggc acg tcc ggg tcc tca ctg tcc tta cac tca   192
Pro Ser His Ile Ala Gly Thr Ser Gly Ser Ser Leu Ser Leu His Ser
         50                  55                  60 acg ttg gtc aac cac tac cgc atg cgg ggc cat agc ccc ttt gcc aac   240
Thr Leu Val Asn His Tyr Arg Met Arg Gly His Ser Pro Phe Ala Asn
 65                  70                  75                  80 ctc aaa tcg tgc tgt gtc ccg aca gag ctc agt gct atc tcg atg ttg   288
Leu Lys Ser Cys Cys Val Pro Thr Glu Leu Ser Ala Ile Ser Met Leu
                 85                  90                  95 tac tat gat gat ggt caa aac atc atc aaa aag gac att cag aac atg   336
Tyr Tyr Asp Asp Gly Gln Asn Ile Ile Lys Lys Asp Ile Gln Asn Met
            100                 105                 110 atc gtg gag gag tgt ggg tgc tca                                   360
Ile Val Glu Glu Cys Gly Cys Ser
            115                 120

<210> SEQ ID NO 15
<211> LENGTH: 120
<212> TYPE: PRT
<213> ORGANISM: Artificial Sequence
<220> FEATURE:
<223> OTHER INFORMATION: Synthetic Construct

<400> SEQUENCE: 15

Met Gln Ala Lys His Lys Gln Arg Lys Arg Leu Lys Ser Ser Cys Lys
  1               5                  10                  15

Arg His Pro Leu Tyr Val Asp Phe Ser Asp Val Gly Trp Asn Asp Trp
                 20                  25                  30

Ile Val Ala Pro Pro Gly Tyr His Ala Phe Tyr Cys His Gly Glu Cys
             35                  40                  45

Pro Ser His Ile Ala Gly Thr Ser Gly Ser Ser Leu Ser Leu His Ser
```

```
                      50                  55                  60
Thr Leu Val Asn His Tyr Arg Met Arg Gly His Ser Pro Phe Ala Asn
 65                  70                  75                  80

Leu Lys Ser Cys Cys Val Pro Thr Glu Leu Ser Ala Ile Ser Met Leu
                 85                  90                  95

Tyr Tyr Asp Asp Gly Gln Asn Ile Ile Lys Lys Asp Ile Gln Asn Met
            100                 105                 110

Ile Val Glu Glu Cys Gly Cys Ser
        115                 120

<210> SEQ ID NO 16
<211> LENGTH: 360
<212> TYPE: DNA
<213> ORGANISM: Artificial Sequence
<220> FEATURE:
<223> OTHER INFORMATION: Chimeric polypeptide
<220> FEATURE:
<221> NAME/KEY: CDS
<222> LOCATION: (1)..(360)

<400> SEQUENCE: 16 atg caa gcc aaa cac aaa cag cgg aaa cgc ctt aag tcc agc tgt aag      48
Met Gln Ala Lys His Lys Gln Arg Lys Arg Leu Lys Ser Ser Cys Lys
  1               5                  10                  15 aga cac cct ttg tac gtg gac ttc agt gac gtg ggg tgg aat gac tgg      96
Arg His Pro Leu Tyr Val Asp Phe Ser Asp Val Gly Trp Asn Asp Trp
                 20                  25                  30 atc att gct ccc tct ggc tat cat gcc aac tac tgc gag gga gaa tgc     144
Ile Ile Ala Pro Ser Gly Tyr His Ala Asn Tyr Cys Glu Gly Glu Cys
             35                  40                  45 cct tcc cat ata gca ggc acg tcc ggg tcc tca ctg tcc ttc cat tca     192
Pro Ser His Ile Ala Gly Thr Ser Gly Ser Ser Leu Ser Phe His Ser
         50                  55                  60 acg ttg gtc aac cac tac cgc atg cgg ggc cat agc ccc ttt gcc aac     240
Thr Leu Val Asn His Tyr Arg Met Arg Gly His Ser Pro Phe Ala Asn
 65                  70                  75                  80 ctc aaa tcg tgc tgt gtc ccg acc aag ctg aga ccc atg tcc atg ttg     288
Leu Lys Ser Cys Cys Val Pro Thr Lys Leu Arg Pro Met Ser Met Leu
                 85                  90                  95 tac tat gat gat ggt caa aac atc atc aaa aag gac att cag aac atg     336
Tyr Tyr Asp Asp Gly Gln Asn Ile Ile Lys Lys Asp Ile Gln Asn Met
            100                 105                 110 atc gtg gag gag tgt ggg tgc tca                                     360
Ile Val Glu Glu Cys Gly Cys Ser
        115                 120

<210> SEQ ID NO 17
<211> LENGTH: 120
<212> TYPE: PRT
<213> ORGANISM: Artificial Sequence
<220> FEATURE:
<223> OTHER INFORMATION: Synthetic Construct

<400> SEQUENCE: 17

Met Gln Ala Lys His Lys Gln Arg Lys Arg Leu Lys Ser Ser Cys Lys
  1               5                  10                  15

Arg His Pro Leu Tyr Val Asp Phe Ser Asp Val Gly Trp Asn Asp Trp
                 20                  25                  30

Ile Ile Ala Pro Ser Gly Tyr His Ala Asn Tyr Cys Glu Gly Glu Cys
             35                  40                  45

Pro Ser His Ile Ala Gly Thr Ser Gly Ser Ser Leu Ser Phe His Ser
```

```
                50                  55                  60
Thr Leu Val Asn His Tyr Arg Met Arg Gly His Ser Pro Phe Ala Asn
 65                  70                  75                  80

Leu Lys Ser Cys Cys Val Pro Thr Lys Leu Arg Pro Met Ser Met Leu
                 85                  90                  95

Tyr Tyr Asp Asp Gly Gln Asn Ile Ile Lys Lys Asp Ile Gln Asn Met
            100                 105                 110

Ile Val Glu Glu Cys Gly Cys Ser
        115                 120
```

<210> SEQ ID NO 18
<211> LENGTH: 360
<212> TYPE: DNA
<213> ORGANISM: Artificial Sequence
<220> FEATURE:
<223> OTHER INFORMATION: Chimeric polypeptide
<220> FEATURE:
<221> NAME/KEY: CDS
<222> LOCATION: (1)..(360)

<400> SEQUENCE: 18

```
atg caa gcc aaa cac aaa cag cgg aaa cgc ctt aag tcc agc tgt aag    48
Met Gln Ala Lys His Lys Gln Arg Lys Arg Leu Lys Ser Ser Cys Lys
 1               5                  10                  15 aga cac cct ttg tac gtg gac ttc agt gac gtg ggg tgg aat gac tgg    96
Arg His Pro Leu Tyr Val Asp Phe Ser Asp Val Gly Trp Asn Asp Trp
             20                  25                  30 atc att gct ccc tct ggc tat cat gcc aac tac tgc gag gga gaa tgc   144
Ile Ile Ala Pro Ser Gly Tyr His Ala Asn Tyr Cys Glu Gly Glu Cys
         35                  40                  45 cct tcc cat ata gca ggc acg tcc ggg tcc tca ctg tcc ttc cat tca   192
Pro Ser His Ile Ala Gly Thr Ser Gly Ser Ser Leu Ser Phe His Ser
     50                  55                  60 acg gtg atc aac cac tac cgc atg cgg ggc cat agc ccc ttt gcc aac   240
Thr Val Ile Asn His Tyr Arg Met Arg Gly His Ser Pro Phe Ala Asn
 65                  70                  75                  80 ctc aaa tcg tgc tgt gtc ccg acc aag ctg aga ccc atg tcc atg ttg   288
Leu Lys Ser Cys Cys Val Pro Thr Lys Leu Arg Pro Met Ser Met Leu
                 85                  90                  95 tac tat gat gat ggt caa aac atc atc aaa aag gac att cag aac atg   336
Tyr Tyr Asp Asp Gly Gln Asn Ile Ile Lys Lys Asp Ile Gln Asn Met
            100                 105                 110 atc gtg gag gag tgt ggg tgc tca                                   360
Ile Val Glu Glu Cys Gly Cys Ser
        115                 120
```

<210> SEQ ID NO 19
<211> LENGTH: 120
<212> TYPE: PRT
<213> ORGANISM: Artificial Sequence
<220> FEATURE:
<223> OTHER INFORMATION: Synthetic Construct

<400> SEQUENCE: 19

```
Met Gln Ala Lys His Lys Gln Arg Lys Arg Leu Lys Ser Ser Cys Lys
 1               5                  10                  15

Arg His Pro Leu Tyr Val Asp Phe Ser Asp Val Gly Trp Asn Asp Trp
             20                  25                  30

Ile Ile Ala Pro Ser Gly Tyr His Ala Asn Tyr Cys Glu Gly Glu Cys
         35                  40                  45

Pro Ser His Ile Ala Gly Thr Ser Gly Ser Ser Leu Ser Phe His Ser
```

```
                    50                  55                  60
Thr Val Ile Asn His Tyr Arg Met Arg Gly His Ser Pro Phe Ala Asn
 65                  70                  75                  80

Leu Lys Ser Cys Cys Val Pro Thr Lys Leu Arg Pro Met Ser Met Leu
                 85                  90                  95

Tyr Tyr Asp Asp Gly Gln Asn Ile Ile Lys Lys Asp Ile Gln Asn Met
            100                 105                 110

Ile Val Glu Glu Cys Gly Cys Ser
            115                 120

<210> SEQ ID NO 20
<211> LENGTH: 357
<212> TYPE: DNA
<213> ORGANISM: Artificial Sequence
<220> FEATURE:
<223> OTHER INFORMATION: Chimeric polypeptide
<220> FEATURE:
<221> NAME/KEY: CDS
<222> LOCATION: (1)..(357)

<400> SEQUENCE: 20 atg caa gcc aaa cac aaa cag cgg aaa cgc ctt aag tcc agc tgt aag      48
Met Gln Ala Lys His Lys Gln Arg Lys Arg Leu Lys Ser Ser Cys Lys
 1               5                  10                  15 aaa cag ttc ttt gtc agt ttc aag gac atc ggg tgg aat gac tgg atc      96
Lys Gln Phe Phe Val Ser Phe Lys Asp Ile Gly Trp Asn Asp Trp Ile
                 20                  25                  30 att gct ccc tct ggc tat cat gcc aac tac tgc gag gga gaa tgc cct     144
Ile Ala Pro Ser Gly Tyr His Ala Asn Tyr Cys Glu Gly Glu Cys Pro
             35                  40                  45 tcc cat ata gca ggc acg tcc ggg tcc tca ctg tcc ttc cat tca acg     192
Ser His Ile Ala Gly Thr Ser Gly Ser Ser Leu Ser Phe His Ser Thr
         50                  55                  60 ttg gtc aac cac tac cgc atg cgg ggc cat agc ccc ttt gcc aac ctc     240
Leu Val Asn His Tyr Arg Met Arg Gly His Ser Pro Phe Ala Asn Leu
 65                  70                  75                  80 aaa tcg tgc tgt gtc ccg acc aag ctg aga ccc atg tcc atg ttg tac     288
Lys Ser Cys Cys Val Pro Thr Lys Leu Arg Pro Met Ser Met Leu Tyr
                 85                  90                  95 tat gat gat ggt caa aac atc atc aaa aag gac att cag aac atg atc     336
Tyr Asp Asp Gly Gln Asn Ile Ile Lys Lys Asp Ile Gln Asn Met Ile
            100                 105                 110 gtg gag gag tgt ggg tgc tca                                          357
Val Glu Glu Cys Gly Cys Ser
            115

<210> SEQ ID NO 21
<211> LENGTH: 119
<212> TYPE: PRT
<213> ORGANISM: Artificial Sequence
<220> FEATURE:
<223> OTHER INFORMATION: Synthetic Construct

<400> SEQUENCE: 21

Met Gln Ala Lys His Lys Gln Arg Lys Arg Leu Lys Ser Ser Cys Lys
 1               5                  10                  15

Lys Gln Phe Phe Val Ser Phe Lys Asp Ile Gly Trp Asn Asp Trp Ile
                 20                  25                  30

Ile Ala Pro Ser Gly Tyr His Ala Asn Tyr Cys Glu Gly Glu Cys Pro
             35                  40                  45

Ser His Ile Ala Gly Thr Ser Gly Ser Ser Leu Ser Phe His Ser Thr
```

```
                    50                  55                  60
Leu Val Asn His Tyr Arg Met Arg Gly His Ser Pro Phe Ala Asn Leu
 65                  70                  75                  80

Lys Ser Cys Cys Val Pro Thr Lys Leu Arg Pro Met Ser Met Leu Tyr
                 85                  90                  95

Tyr Asp Asp Gly Gln Asn Ile Ile Lys Lys Asp Ile Gln Asn Met Ile
            100                 105                 110

Val Glu Glu Cys Gly Cys Ser
        115
```

<210> SEQ ID NO 22
<211> LENGTH: 360
<212> TYPE: DNA
<213> ORGANISM: Artificial Sequence
<220> FEATURE:
<223> OTHER INFORMATION: Chimeric polypeptide
<220> FEATURE:
<221> NAME/KEY: CDS
<222> LOCATION: (1)..(360)

<400> SEQUENCE: 22

```
atg caa gcc aaa cac aaa cag cgg aaa cgc ctt aag tcc agc tgt aag    48
Met Gln Ala Lys His Lys Gln Arg Lys Arg Leu Lys Ser Ser Cys Lys
 1               5                  10                  15 aga cac cct ttg tac gtg gac ttc agt gac gtg ggg tgg aat gac tgg    96
Arg His Pro Leu Tyr Val Asp Phe Ser Asp Val Gly Trp Asn Asp Trp
             20                  25                  30 atc att gct ccc tct ggc tat cat gcc aac tac tgc gag gga gaa tgc   144
Ile Ile Ala Pro Ser Gly Tyr His Ala Asn Tyr Cys Glu Gly Glu Cys
         35                  40                  45 cct tct cat ata gca ggc acg tcc ggg tcc tca ctg tcc ttc cac tca   192
Pro Ser His Ile Ala Gly Thr Ser Gly Ser Ser Leu Ser Phe His Ser
     50                  55                  60 acg ttg gtc aac cac tac cgc atg cgg ggc cat agc ccc ttt gcc aac   240
Thr Leu Val Asn His Tyr Arg Met Arg Gly His Ser Pro Phe Ala Asn
 65                  70                  75                  80 ctc aaa tcg tgc tgt gtc ccg acc aag ctg aga ccc atg tcc atg ttg   288
Leu Lys Ser Cys Cys Val Pro Thr Lys Leu Arg Pro Met Ser Met Leu
                 85                  90                  95 tac ctt gac gag aat gaa aag gtt gta tta aag aac tat cag gac atg   336
Tyr Leu Asp Glu Asn Glu Lys Val Val Leu Lys Asn Tyr Gln Asp Met
            100                 105                 110 gtt gtg gag ggt tgt ggg tgt cgc                                    360
Val Val Glu Gly Cys Gly Cys Arg
        115                 120
```

<210> SEQ ID NO 23
<211> LENGTH: 120
<212> TYPE: PRT
<213> ORGANISM: Artificial Sequence
<220> FEATURE:
<223> OTHER INFORMATION: Synthetic Construct

<400> SEQUENCE: 23

```
Met Gln Ala Lys His Lys Gln Arg Lys Arg Leu Lys Ser Ser Cys Lys
 1               5                  10                  15

Arg His Pro Leu Tyr Val Asp Phe Ser Asp Val Gly Trp Asn Asp Trp
             20                  25                  30

Ile Ile Ala Pro Ser Gly Tyr His Ala Asn Tyr Cys Glu Gly Glu Cys
         35                  40                  45

Pro Ser His Ile Ala Gly Thr Ser Gly Ser Ser Leu Ser Phe His Ser
```

```
                  50                  55                  60
Thr Leu Val Asn His Tyr Arg Met Arg Gly His Ser Pro Phe Ala Asn
 65                  70                  75                  80

Leu Lys Ser Cys Cys Val Pro Thr Lys Leu Arg Pro Met Ser Met Leu
                 85                  90                  95

Tyr Leu Asp Glu Asn Glu Lys Val Leu Lys Asn Tyr Gln Asp Met
            100                 105                 110

Val Val Glu Gly Cys Gly Cys Arg
        115                 120

<210> SEQ ID NO 24
<211> LENGTH: 360
<212> TYPE: DNA
<213> ORGANISM: Artificial Sequence
<220> FEATURE:
<223> OTHER INFORMATION: Chimeric polypeptide
<220> FEATURE:
<221> NAME/KEY: CDS
<222> LOCATION: (1)..(360)

<400> SEQUENCE: 24 atg caa gcc aaa cac aaa cag cgg aaa cgc ctt aag tcc agc tgt aag      48
Met Gln Ala Lys His Lys Gln Arg Lys Arg Leu Lys Ser Ser Cys Lys
 1               5                  10                  15 aga cac cct ttg tac gtg gac ttc agt gac gtg ggg tgg aat gac tgg      96
Arg His Pro Leu Tyr Val Asp Phe Ser Asp Val Gly Trp Asn Asp Trp
                20                  25                  30 atc att gct ccc tct ggc tat cat gcc aac tac tgc gag gga gaa tgc     144
Ile Ile Ala Pro Ser Gly Tyr His Ala Asn Tyr Cys Glu Gly Glu Cys
             35                  40                  45 cct tct cat ata gca ggc acg tcc ggg tcc tca ctg tcc ttc cac tca     192
Pro Ser His Ile Ala Gly Thr Ser Gly Ser Ser Leu Ser Phe His Ser
         50                  55                  60 acg ttg gtc aac cac tac cgc atg cgg ggc cat agc ccc ttt gcc aac     240
Thr Leu Val Asn His Tyr Arg Met Arg Gly His Ser Pro Phe Ala Asn
 65                  70                  75                  80 ctc aaa tcg tgc tgt gtc ccg aca gaa ctc agt gct atc tcg atg ttg     288
Leu Lys Ser Cys Cys Val Pro Thr Glu Leu Ser Ala Ile Ser Met Leu
                 85                  90                  95 tac ctt gac gag aat gaa aag gtt gta tta aag aac tat cag gac atg     336
Tyr Leu Asp Glu Asn Glu Lys Val Val Leu Lys Asn Tyr Gln Asp Met
            100                 105                 110 gtt gtg gag ggt tgt ggg tgt cgc                                      360
Val Val Glu Gly Cys Gly Cys Arg
        115                 120

<210> SEQ ID NO 25
<211> LENGTH: 120
<212> TYPE: PRT
<213> ORGANISM: Artificial Sequence
<220> FEATURE:
<223> OTHER INFORMATION: Synthetic Construct

<400> SEQUENCE: 25

Met Gln Ala Lys His Lys Gln Arg Lys Arg Leu Lys Ser Ser Cys Lys
 1               5                  10                  15

Arg His Pro Leu Tyr Val Asp Phe Ser Asp Val Gly Trp Asn Asp Trp
                20                  25                  30

Ile Ile Ala Pro Ser Gly Tyr His Ala Asn Tyr Cys Glu Gly Glu Cys
             35                  40                  45

Pro Ser His Ile Ala Gly Thr Ser Gly Ser Ser Leu Ser Phe His Ser
```

```
                50                  55                  60
Thr Leu Val Asn His Tyr Arg Met Arg Gly His Ser Pro Phe Ala Asn
 65                  70                  75                  80

Leu Lys Ser Cys Cys Val Pro Thr Glu Leu Ser Ala Ile Ser Met Leu
                 85                  90                  95

Tyr Leu Asp Glu Asn Glu Lys Val Val Leu Lys Asn Tyr Gln Asp Met
            100                 105                 110

Val Val Glu Gly Cys Gly Cys Arg
        115                 120
```

<210> SEQ ID NO 26
<211> LENGTH: 360
<212> TYPE: DNA
<213> ORGANISM: Artificial Sequence
<220> FEATURE:
<223> OTHER INFORMATION: Chimeric polypeptide
<220> FEATURE:
<221> NAME/KEY: CDS
<222> LOCATION: (1)..(360)

<400> SEQUENCE: 26

```
atg caa gcc aaa cac aaa cag cgg aaa cgc ctt aag tcc agc tgt aag      48
Met Gln Ala Lys His Lys Gln Arg Lys Arg Leu Lys Ser Ser Cys Lys
 1               5                  10                  15 aga cac cct ttg tac gtg gac ttc agt gac gtg ggg tgg aat gac tgg      96
Arg His Pro Leu Tyr Val Asp Phe Ser Asp Val Gly Trp Asn Asp Trp
                 20                  25                  30 atc att gct ccc tct ggc tat cat gcc aac tac tgc gag gga gaa tgc     144
Ile Ile Ala Pro Ser Gly Tyr His Ala Asn Tyr Cys Glu Gly Glu Cys
             35                  40                  45 cct tct cat ata gca ggc acg tcc ggg tcc tca ctg tcc ttc cac tca     192
Pro Ser His Ile Ala Gly Thr Ser Gly Ser Ser Leu Ser Phe His Ser
         50                  55                  60 acg ttg gtc aac cac tac cgc atg cgg ggc cat agc ccc ttt gcc aac     240
Thr Leu Val Asn His Tyr Arg Met Arg Gly His Ser Pro Phe Ala Asn
 65                  70                  75                  80 ctc aaa tcg tgc tgt gtc ccg aca gaa ctc agt gct atc tcg atg ttg     288
Leu Lys Ser Cys Cys Val Pro Thr Glu Leu Ser Ala Ile Ser Met Leu
                 85                  90                  95 tac tat gat gat ggt caa aac atc atc aaa aag gac att cag aac atg     336
Tyr Tyr Asp Asp Gly Gln Asn Ile Ile Lys Lys Asp Ile Gln Asn Met
            100                 105                 110 atc gtg gag gag tgt ggg tgc tca                                     360
Ile Val Glu Glu Cys Gly Cys Ser
        115                 120
```

<210> SEQ ID NO 27
<211> LENGTH: 120
<212> TYPE: PRT
<213> ORGANISM: Artificial Sequence
<220> FEATURE:
<223> OTHER INFORMATION: Synthetic Construct

<400> SEQUENCE: 27

```
Met Gln Ala Lys His Lys Gln Arg Lys Arg Leu Lys Ser Ser Cys Lys
 1               5                  10                  15

Arg His Pro Leu Tyr Val Asp Phe Ser Asp Val Gly Trp Asn Asp Trp
                 20                  25                  30

Ile Ile Ala Pro Ser Gly Tyr His Ala Asn Tyr Cys Glu Gly Glu Cys
             35                  40                  45

Pro Ser His Ile Ala Gly Thr Ser Gly Ser Ser Leu Ser Phe His Ser
```

```
            50                  55                  60
Thr Leu Val Asn His Tyr Arg Met Arg Gly His Ser Pro Phe Ala Asn
 65                  70                  75                  80

Leu Lys Ser Cys Cys Val Pro Thr Glu Leu Ser Ala Ile Ser Met Leu
                 85                  90                  95

Tyr Tyr Asp Asp Gly Gln Asn Ile Ile Lys Lys Asp Ile Gln Asn Met
            100                 105                 110

Ile Val Glu Glu Cys Gly Cys Ser
            115                 120
```

<210> SEQ ID NO 28
<211> LENGTH: 345
<212> TYPE: DNA
<213> ORGANISM: Artificial Sequence
<220> FEATURE:
<223> OTHER INFORMATION: Chimeric polypeptide
<220> FEATURE:
<221> NAME/KEY: CDS
<222> LOCATION: (1)..(345)

<400> SEQUENCE: 28

```
atg caa gcc aaa cac aaa cag cgg aaa cgc ctt aag tcc agc tgt aag     48
Met Gln Ala Lys His Lys Gln Arg Lys Arg Leu Lys Ser Ser Cys Lys
  1               5                  10                  15 aga cac cct ttg tac gtg gac ttc agt gac gtg ggg tgg aat gac tgg     96
Arg His Pro Leu Tyr Val Asp Phe Ser Asp Val Gly Trp Asn Asp Trp
                 20                  25                  30 atc att gct ccc tct ggc tat cat gcc aac tac tgc gac gga gaa tgc    144
Ile Ile Ala Pro Ser Gly Tyr His Ala Asn Tyr Cys Asp Gly Glu Cys
             35                  40                  45 cct ttt cct ctg gct gat cat ctg aac tcc act aat cat gcc att gtt    192
Pro Phe Pro Leu Ala Asp His Leu Asn Ser Thr Asn His Ala Ile Val
         50                  55                  60 cag acg ttg gtc aac tct gtt aac tct aag att cct aag gca tgc tgt    240
Gln Thr Leu Val Asn Ser Val Asn Ser Lys Ile Pro Lys Ala Cys Cys
 65                  70                  75                  80 gtc ccg aca gaa ctc agt gct atc tcg atg ttg tac tat gat gat ggt    288
Val Pro Thr Glu Leu Ser Ala Ile Ser Met Leu Tyr Tyr Asp Asp Gly
                 85                  90                  95 caa aac atc atc aaa aag gac att cag aac atg atc gtg gag gag tgt    336
Gln Asn Ile Ile Lys Lys Asp Ile Gln Asn Met Ile Val Glu Glu Cys
            100                 105                 110 ggg tgc tca                                                         345
Gly Cys Ser
        115
```

<210> SEQ ID NO 29
<211> LENGTH: 115
<212> TYPE: PRT
<213> ORGANISM: Artificial Sequence
<220> FEATURE:
<223> OTHER INFORMATION: Synthetic Construct

<400> SEQUENCE: 29

```
Met Gln Ala Lys His Lys Gln Arg Lys Arg Leu Lys Ser Ser Cys Lys
  1               5                  10                  15

Arg His Pro Leu Tyr Val Asp Phe Ser Asp Val Gly Trp Asn Asp Trp
                 20                  25                  30

Ile Ile Ala Pro Ser Gly Tyr His Ala Asn Tyr Cys Asp Gly Glu Cys
             35                  40                  45

Pro Phe Pro Leu Ala Asp His Leu Asn Ser Thr Asn His Ala Ile Val
```

```
                    50                  55                  60
Gln Thr Leu Val Asn Ser Val Asn Ser Lys Ile Pro Lys Ala Cys Cys
 65                  70                  75                  80

Val Pro Thr Glu Leu Ser Ala Ile Ser Met Leu Tyr Tyr Asp Asp Gly
                 85                  90                  95

Gln Asn Ile Ile Lys Lys Asp Ile Gln Asn Met Ile Val Glu Glu Cys
            100                 105                 110

Gly Cys Ser
        115

<210> SEQ ID NO 30
<211> LENGTH: 345
<212> TYPE: DNA
<213> ORGANISM: Artificial Sequence
<220> FEATURE:
<223> OTHER INFORMATION: Chimeric polypeptide
<220> FEATURE:
<221> NAME/KEY: CDS
<222> LOCATION: (1)..(345)

<400> SEQUENCE: 30
```

| | | |
|---|---|---|
| atg caa gcc aaa cac aaa cag cgg aag cgt ctt aag tcc agc tgc aaa<br>Met Gln Ala Lys His Lys Gln Arg Lys Arg Leu Lys Ser Ser Cys Lys<br>1               5                   10                  15 | | 48 |
| agg cac cct ttg tat gtg gac ttc agt gat gtg ggg tgg aat gac tgg<br>Arg His Pro Leu Tyr Val Asp Phe Ser Asp Val Gly Trp Asn Asp Trp<br>                20                  25                  30 | | 96 |
| atc att gct ccc tct ggc tat cat gcc aac tac tgc gac gga gaa tgc<br>Ile Ile Ala Pro Ser Gly Tyr His Ala Asn Tyr Cys Asp Gly Glu Cys<br>            35                  40                  45 | | 144 |
| cct ttt cct ctg gct gat cat ctg aac tcc act aat cat gcc att gtt<br>Pro Phe Pro Leu Ala Asp His Leu Asn Ser Thr Asn His Ala Ile Val<br>        50                  55                  60 | | 192 |
| cag acg ttg gtc aac tct gtt aac tct aag att cct aag gca tgc tgt<br>Gln Thr Leu Val Asn Ser Val Asn Ser Lys Ile Pro Lys Ala Cys Cys<br>65                  70                  75                  80 | | 240 |
| gtc ccg acc aag ctg aga ccc atg tcc atg ttg tac tat gat gat ggt<br>Val Pro Thr Lys Leu Arg Pro Met Ser Met Leu Tyr Tyr Asp Asp Gly<br>                85                  90                  95 | | 288 |
| caa aac atc atc aaa aag gac att cag aac atg atc gtg gag gag tgt<br>Gln Asn Ile Ile Lys Lys Asp Ile Gln Asn Met Ile Val Glu Glu Cys<br>            100                 105                 110 | | 336 |
| ggg tgc tca<br>Gly Cys Ser<br>        115 | | 345 |

```
<210> SEQ ID NO 31
<211> LENGTH: 115
<212> TYPE: PRT
<213> ORGANISM: Artificial Sequence
<220> FEATURE:
<223> OTHER INFORMATION: Synthetic Construct

<400> SEQUENCE: 31

Met Gln Ala Lys His Lys Gln Arg Lys Arg Leu Lys Ser Ser Cys Lys
1               5                   10                  15

Arg His Pro Leu Tyr Val Asp Phe Ser Asp Val Gly Trp Asn Asp Trp
                20                  25                  30

Ile Ile Ala Pro Ser Gly Tyr His Ala Asn Tyr Cys Asp Gly Glu Cys
            35                  40                  45

Pro Phe Pro Leu Ala Asp His Leu Asn Ser Thr Asn His Ala Ile Val
```

```
            50                  55                  60
Gln Thr Leu Val Asn Ser Val Asn Ser Lys Ile Pro Lys Ala Cys Cys
 65                  70                  75                  80

Val Pro Thr Lys Leu Arg Pro Met Ser Met Leu Tyr Tyr Asp Asp Gly
                 85                  90                  95

Gln Asn Ile Ile Lys Lys Asp Ile Gln Asn Met Ile Val Glu Glu Cys
                100                 105                 110

Gly Cys Ser
        115

<210> SEQ ID NO 32
<211> LENGTH: 345
<212> TYPE: DNA
<213> ORGANISM: Artificial Sequence
<220> FEATURE:
<223> OTHER INFORMATION: Chimeric polypeptide
<220> FEATURE:
<221> NAME/KEY: CDS
<222> LOCATION: (1)..(345)

<400> SEQUENCE: 32 atg caa gcc aaa cac aaa cag cgg aaa cgc ctt aag tcc agc tgt aag      48
Met Gln Ala Lys His Lys Gln Arg Lys Arg Leu Lys Ser Ser Cys Lys
 1               5                  10                  15 aga cac cct ttg tac gtg gac ttc agt gac gtg ggg tgg aat gac tgg      96
Arg His Pro Leu Tyr Val Asp Phe Ser Asp Val Gly Trp Asn Asp Trp
                 20                  25                  30 atc att gct ccc tct ggc tat cat gcc aac tac tgc gac gga gaa tgc     144
Ile Ile Ala Pro Ser Gly Tyr His Ala Asn Tyr Cys Asp Gly Glu Cys
             35                  40                  45 cct ttt cct ctg gct gat cat ctg aac tcc act aat cat gcc att gtt     192
Pro Phe Pro Leu Ala Asp His Leu Asn Ser Thr Asn His Ala Ile Val
         50                  55                  60 cag acg ttg gtc aac tct gtt aac tct aag att cct aag gca tgc tgt     240
Gln Thr Leu Val Asn Ser Val Asn Ser Lys Ile Pro Lys Ala Cys Cys
 65                  70                  75                  80 gtc ccg acc aag ctg aga ccc atg tcc atg ttg tac ctt gac gag aat     288
Val Pro Thr Lys Leu Arg Pro Met Ser Met Leu Tyr Leu Asp Glu Asn
                 85                  90                  95 gaa aag gtt gta tta aag aac tat cag gac atg gtt gtg gag ggt tgt     336
Glu Lys Val Val Leu Lys Asn Tyr Gln Asp Met Val Val Glu Gly Cys
                100                 105                 110 ggg tgt cgc                                                         345
Gly Cys Arg
        115

<210> SEQ ID NO 33
<211> LENGTH: 115
<212> TYPE: PRT
<213> ORGANISM: Artificial Sequence
<220> FEATURE:
<223> OTHER INFORMATION: Synthetic Construct

<400> SEQUENCE: 33

Met Gln Ala Lys His Lys Gln Arg Lys Arg Leu Lys Ser Ser Cys Lys
 1               5                  10                  15

Arg His Pro Leu Tyr Val Asp Phe Ser Asp Val Gly Trp Asn Asp Trp
                 20                  25                  30

Ile Ile Ala Pro Ser Gly Tyr His Ala Asn Tyr Cys Asp Gly Glu Cys
             35                  40                  45

Pro Phe Pro Leu Ala Asp His Leu Asn Ser Thr Asn His Ala Ile Val
```

```
                    50                  55                  60
Gln Thr Leu Val Asn Ser Val Asn Ser Lys Ile Pro Lys Ala Cys Cys
 65                  70                  75                  80

Val Pro Thr Lys Leu Arg Pro Met Ser Met Leu Tyr Leu Asp Glu Asn
                 85                  90                  95

Glu Lys Val Val Leu Lys Asn Tyr Gln Asp Met Val Val Glu Gly Cys
            100                 105                 110

Gly Cys Arg
        115

<210> SEQ ID NO 34
<211> LENGTH: 348
<212> TYPE: DNA
<213> ORGANISM: Artificial Sequence
<220> FEATURE:
<223> OTHER INFORMATION: Chimeric polypeptide
<220> FEATURE:
<221> NAME/KEY: CDS
<222> LOCATION: (1)..(348)

<400> SEQUENCE: 34 atg caa gcc aaa cac aaa cag cgg aaa cgc ctt aag tcc agc tgt aag      48
Met Gln Ala Lys His Lys Gln Arg Lys Arg Leu Lys Ser Ser Cys Lys
 1               5                  10                  15 aga cac cct ttg tac gtg gac ttc agt gac gtg ggg tgg aat gac tgg      96
Arg His Pro Leu Tyr Val Asp Phe Ser Asp Val Gly Trp Asn Asp Trp
                20                  25                  30 att atc gcg cct gaa ggc tac gcc gcc tac tac tgt gag ggg gag tgt     144
Ile Ile Ala Pro Glu Gly Tyr Ala Ala Tyr Tyr Cys Glu Gly Glu Cys
            35                  40                  45 gcc ttc cct ctg aac tcc tac atg aac gcc acc aac cac gcc atc gtg     192
Ala Phe Pro Leu Asn Ser Tyr Met Asn Ala Thr Asn His Ala Ile Val
        50                  55                  60 cag acg ctg gtc cac ttc atc aac ccg gaa acg gtg ccc aag ccc tgc     240
Gln Thr Leu Val His Phe Ile Asn Pro Glu Thr Val Pro Lys Pro Cys
 65                  70                  75                  80 tgt gcg ccc acg cag ctc aat gcc atc tcc gtc ctc tac ttc gat gac     288
Cys Ala Pro Thr Gln Leu Asn Ala Ile Ser Val Leu Tyr Phe Asp Asp
                 85                  90                  95 agc tcc aac gtc atc ctg aag aaa tac aga aac atg gtg gtc cgg gcc     336
Ser Ser Asn Val Ile Leu Lys Lys Tyr Arg Asn Met Val Val Arg Ala
            100                 105                 110 tgt ggc tgc cac                                                      348
Cys Gly Cys His
        115

<210> SEQ ID NO 35
<211> LENGTH: 116
<212> TYPE: PRT
<213> ORGANISM: Artificial Sequence
<220> FEATURE:
<223> OTHER INFORMATION: Synthetic Construct

<400> SEQUENCE: 35

Met Gln Ala Lys His Lys Gln Arg Lys Arg Leu Lys Ser Ser Cys Lys
 1               5                  10                  15

Arg His Pro Leu Tyr Val Asp Phe Ser Asp Val Gly Trp Asn Asp Trp
                20                  25                  30

Ile Ile Ala Pro Glu Gly Tyr Ala Ala Tyr Tyr Cys Glu Gly Glu Cys
            35                  40                  45

Ala Phe Pro Leu Asn Ser Tyr Met Asn Ala Thr Asn His Ala Ile Val
```

```
                    50                  55                  60
Gln Thr Leu Val His Phe Ile Asn Pro Glu Thr Val Pro Lys Pro Cys
 65                  70                  75                  80

Cys Ala Pro Thr Gln Leu Asn Ala Ile Ser Val Leu Tyr Phe Asp Asp
                 85                  90                  95

Ser Ser Asn Val Ile Leu Lys Lys Tyr Arg Asn Met Val Val Arg Ala
                100                 105                 110

Cys Gly Cys His
        115

<210> SEQ ID NO 36
<211> LENGTH: 351
<212> TYPE: DNA
<213> ORGANISM: Artificial Sequence
<220> FEATURE:
<223> OTHER INFORMATION: Chimeric polypeptide
<220> FEATURE:
<221> NAME/KEY: CDS
<222> LOCATION: (1)..(351)

<400> SEQUENCE: 36 atg caa gcc aaa cac aaa cag cgg aaa cgc ctt aag tcc agc tgt aag      48
Met Gln Ala Lys His Lys Gln Arg Lys Arg Leu Lys Ser Ser Cys Lys
 1               5                  10                  15 aga cac cct ttg tac gtg gac ttc agt gac gtg ggg tgg aat gac tgg      96
Arg His Pro Leu Tyr Val Asp Phe Ser Asp Val Gly Trp Asn Asp Trp
                 20                  25                  30 att att gcc cca aaa gag tac gag gca tac gag tgt aag ggc ggc tgt     144
Ile Ile Ala Pro Lys Glu Tyr Glu Ala Tyr Glu Cys Lys Gly Gly Cys
             35                  40                  45 ttc ttt ccg ctg gcc gac gat gtc acc ccg acc aag cac gca att gtc     192
Phe Phe Pro Leu Ala Asp Asp Val Thr Pro Thr Lys His Ala Ile Val
         50                  55                  60 caa acc tta gtg cac ctg aag ttc cca acg aaa gtg ggt aag gca tgt     240
Gln Thr Leu Val His Leu Lys Phe Pro Thr Lys Val Gly Lys Ala Cys
 65                  70                  75                  80 tgt gtg cca acc aag tta tct cca att agc gtg ctg tat aag gat gat     288
Cys Val Pro Thr Lys Leu Ser Pro Ile Ser Val Leu Tyr Lys Asp Asp
                 85                  90                  95 atg ggc gtg ccg acg tta aag tat cat tac gag ggc atg agc gtc gca     336
Met Gly Val Pro Thr Leu Lys Tyr His Tyr Glu Gly Met Ser Val Ala
                100                 105                 110 gag tgt ggc tgc cgc                                                 351
Glu Cys Gly Cys Arg
        115

<210> SEQ ID NO 37
<211> LENGTH: 117
<212> TYPE: PRT
<213> ORGANISM: Artificial Sequence
<220> FEATURE:
<223> OTHER INFORMATION: Synthetic Construct

<400> SEQUENCE: 37

Met Gln Ala Lys His Lys Gln Arg Lys Arg Leu Lys Ser Ser Cys Lys
 1               5                  10                  15

Arg His Pro Leu Tyr Val Asp Phe Ser Asp Val Gly Trp Asn Asp Trp
                 20                  25                  30

Ile Ile Ala Pro Lys Glu Tyr Glu Ala Tyr Glu Cys Lys Gly Gly Cys
             35                  40                  45

Phe Phe Pro Leu Ala Asp Asp Val Thr Pro Thr Lys His Ala Ile Val
```

```
                50                  55                  60
Gln Thr Leu Val His Leu Lys Phe Pro Thr Lys Val Gly Lys Ala Cys
 65                  70                  75                  80

Cys Val Pro Thr Lys Leu Ser Pro Ile Ser Val Leu Tyr Lys Asp Asp
                 85                  90                  95

Met Gly Val Pro Thr Leu Lys Tyr His Tyr Glu Gly Met Ser Val Ala
            100                 105                 110

Glu Cys Gly Cys Arg
        115

<210> SEQ ID NO 38
<211> LENGTH: 348
<212> TYPE: DNA
<213> ORGANISM: Artificial Sequence
<220> FEATURE:
<223> OTHER INFORMATION: Chimeric polypeptide
<220> FEATURE:
<221> NAME/KEY: CDS
<222> LOCATION: (1)..(348)

<400> SEQUENCE: 38 atg caa gcc aaa cac aaa cag cgg aaa cgc ctt aag tcc agc tgt aag    48
Met Gln Ala Lys His Lys Gln Arg Lys Arg Leu Lys Ser Ser Cys Lys
  1               5                  10                  15 aga cac cct ttg tac gtg gac ttc agt gac gtg ggg tgg aat gac tgg    96
Arg His Pro Leu Tyr Val Asp Phe Ser Asp Val Gly Trp Asn Asp Trp
                 20                  25                  30 att atc gcg ccg ctg gac tac gag gcg tac cac tgc gag ggc cta tgc   144
Ile Ile Ala Pro Leu Asp Tyr Glu Ala Tyr His Cys Glu Gly Leu Cys
             35                  40                  45 gat ttt cct ctg cgt tcg cac ctc gaa ccc acc aac cat gcc atc att   192
Asp Phe Pro Leu Arg Ser His Leu Glu Pro Thr Asn His Ala Ile Ile
         50                  55                  60 cag acg ttg gtc aac tcc atg gca cca gac gcg gcg ccg gcc tcc tgc   240
Gln Thr Leu Val Asn Ser Met Ala Pro Asp Ala Ala Pro Ala Ser Cys
 65                  70                  75                  80 tgt gtc ccg gcg cgc ctc agc ccc atc agc atc ttg tac tat gat gcc   288
Cys Val Pro Ala Arg Leu Ser Pro Ile Ser Ile Leu Tyr Tyr Asp Ala
                 85                  90                  95 gcc aac aac gtt gtc tac aag caa tac gag gac atg gtg gtg gag gcc   336
Ala Asn Asn Val Val Tyr Lys Gln Tyr Glu Asp Met Val Val Glu Ala
            100                 105                 110 tgt ggg tgt cgc                                                    348
Cys Gly Cys Arg
        115

<210> SEQ ID NO 39
<211> LENGTH: 116
<212> TYPE: PRT
<213> ORGANISM: Artificial Sequence
<220> FEATURE:
<223> OTHER INFORMATION: Synthetic Construct

<400> SEQUENCE: 39

Met Gln Ala Lys His Lys Gln Arg Lys Arg Leu Lys Ser Ser Cys Lys
  1               5                  10                  15

Arg His Pro Leu Tyr Val Asp Phe Ser Asp Val Gly Trp Asn Asp Trp
                 20                  25                  30

Ile Ile Ala Pro Leu Asp Tyr Glu Ala Tyr His Cys Glu Gly Leu Cys
             35                  40                  45

Asp Phe Pro Leu Arg Ser His Leu Glu Pro Thr Asn His Ala Ile Ile
```

```
            50                  55                  60
Gln Thr Leu Val Asn Ser Met Ala Pro Asp Ala Ala Pro Ala Ser Cys
 65                  70                  75                  80

Cys Val Pro Ala Arg Leu Ser Pro Ile Ser Ile Leu Tyr Tyr Asp Ala
                 85                  90                  95

Ala Asn Asn Val Val Tyr Lys Gln Tyr Glu Asp Met Val Val Glu Ala
                100                 105                 110

Cys Gly Cys Arg
            115

<210> SEQ ID NO 40
<211> LENGTH: 330
<212> TYPE: DNA
<213> ORGANISM: Artificial Sequence
<220> FEATURE:
<223> OTHER INFORMATION: Chimeric polypeptide
<220> FEATURE:
<221> NAME/KEY: CDS
<222> LOCATION: (1)..(330)

<400> SEQUENCE: 40 atg caa gcc aaa cac aaa cag cgg aaa cgc ctt aag tcc agc tgt aag     48
Met Gln Ala Lys His Lys Gln Arg Lys Arg Leu Lys Ser Ser Cys Lys
 1               5                  10                  15 aga cac cct ttg tac gtg gac ttc agt gac gtg ggg tgg aat gac tgg     96
Arg His Pro Leu Tyr Val Asp Phe Ser Asp Val Gly Trp Asn Asp Trp
                20                  25                  30 att att gca ccc aaa aga tat aag gcc aat tac tgc tct gga gag tgt    144
Ile Ile Ala Pro Lys Arg Tyr Lys Ala Asn Tyr Cys Ser Gly Glu Cys
             35                  40                  45 gaa ttt gta ttt tta caa aaa tac cct cac act cat ctt gtg cac caa    192
Glu Phe Val Phe Leu Gln Lys Tyr Pro His Thr His Leu Val His Gln
 50                  55                  60 gca aac ccc aga ggt tca gca ggc ccc tgc tgt act ccc aca aag atg    240
Ala Asn Pro Arg Gly Ser Ala Gly Pro Cys Cys Thr Pro Thr Lys Met
 65                  70                  75                  80 tct cca atc aat atg cta tat ttt aat ggc aaa gaa caa ata ata tat    288
Ser Pro Ile Asn Met Leu Tyr Phe Asn Gly Lys Glu Gln Ile Ile Tyr
                85                  90                  95 ggg aaa att cca gcc atg gta gta gat cgc tgt ggg tgc tca            330
Gly Lys Ile Pro Ala Met Val Val Asp Arg Cys Gly Cys Ser
                100                 105                 110

<210> SEQ ID NO 41
<211> LENGTH: 110
<212> TYPE: PRT
<213> ORGANISM: Artificial Sequence
<220> FEATURE:
<223> OTHER INFORMATION: Synthetic Construct

<400> SEQUENCE: 41

Met Gln Ala Lys His Lys Gln Arg Lys Arg Leu Lys Ser Ser Cys Lys
 1               5                  10                  15

Arg His Pro Leu Tyr Val Asp Phe Ser Asp Val Gly Trp Asn Asp Trp
                20                  25                  30

Ile Ile Ala Pro Lys Arg Tyr Lys Ala Asn Tyr Cys Ser Gly Glu Cys
             35                  40                  45

Glu Phe Val Phe Leu Gln Lys Tyr Pro His Thr His Leu Val His Gln
 50                  55                  60

Ala Asn Pro Arg Gly Ser Ala Gly Pro Cys Cys Thr Pro Thr Lys Met
 65                  70                  75                  80
```

```
Ser Pro Ile Asn Met Leu Tyr Phe Asn Gly Lys Glu Gln Ile Ile Tyr
                85                  90                  95

Gly Lys Ile Pro Ala Met Val Val Asp Arg Cys Gly Cys Ser
            100                 105                 110

<210> SEQ ID NO 42
<211> LENGTH: 330
<212> TYPE: DNA
<213> ORGANISM: homo sapiens
<220> FEATURE:
<221> NAME/KEY: CDS
<222> LOCATION: (1)..(330)

<400> SEQUENCE: 42 cag tgg att gaa cct cgg aat tgc gcc agg aga tac ctc aag gta gac      48
Gln Trp Ile Glu Pro Arg Asn Cys Ala Arg Arg Tyr Leu Lys Val Asp
1               5                   10                  15 ttt gca gat att ggc tgg agt gaa tgg att atc tcc ccc aag tcc ttt     96
Phe Ala Asp Ile Gly Trp Ser Glu Trp Ile Ile Ser Pro Lys Ser Phe
            20                  25                  30 gat gcc tat tat tgc tct gga gca tgc cag ttc ccc atg cca aag tct    144
Asp Ala Tyr Tyr Cys Ser Gly Ala Cys Gln Phe Pro Met Pro Lys Ser
        35                  40                  45 ttg aag cca tca aat cat gct acc atc cag agt ata gtg aga gct gtg    192
Leu Lys Pro Ser Asn His Ala Thr Ile Gln Ser Ile Val Arg Ala Val
    50                  55                  60 ggg gtc gtt cct ggg att cct gag cct tgc tgt gta cca gaa aag atg    240
Gly Val Val Pro Gly Ile Pro Glu Pro Cys Cys Val Pro Glu Lys Met
65                  70                  75                  80 tcc tca ctc agt att tta ttc ttt gat gaa aat aag aat gta gtg ctt    288
Ser Ser Leu Ser Ile Leu Phe Phe Asp Glu Asn Lys Asn Val Val Leu
                85                  90                  95 aaa gta tac cct aac atg aca gta gag tct tgc gct tgc aga             330
Lys Val Tyr Pro Asn Met Thr Val Glu Ser Cys Ala Cys Arg
            100                 105                 110

<210> SEQ ID NO 43
<211> LENGTH: 110
<212> TYPE: PRT
<213> ORGANISM: homo sapiens

<400> SEQUENCE: 43

Gln Trp Ile Glu Pro Arg Asn Cys Ala Arg Arg Tyr Leu Lys Val Asp
1               5                   10                  15

Phe Ala Asp Ile Gly Trp Ser Glu Trp Ile Ile Ser Pro Lys Ser Phe
            20                  25                  30

Asp Ala Tyr Tyr Cys Ser Gly Ala Cys Gln Phe Pro Met Pro Lys Ser
        35                  40                  45

Leu Lys Pro Ser Asn His Ala Thr Ile Gln Ser Ile Val Arg Ala Val
    50                  55                  60

Gly Val Val Pro Gly Ile Pro Glu Pro Cys Cys Val Pro Glu Lys Met
65                  70                  75                  80

Ser Ser Leu Ser Ile Leu Phe Phe Asp Glu Asn Lys Asn Val Val Leu
                85                  90                  95

Lys Val Tyr Pro Asn Met Thr Val Glu Ser Cys Ala Cys Arg
            100                 105                 110

<210> SEQ ID NO 44
<211> LENGTH: 348
<212> TYPE: DNA
```

<213> ORGANISM: Homo sapiens
<220> FEATURE:
<221> NAME/KEY: CDS
<222> LOCATION: (1)..(348)

<400> SEQUENCE: 44

```
agc cct aag cat cac tca cag cgg gcc agg aag aag aat aag aac tgc      48
Ser Pro Lys His His Ser Gln Arg Ala Arg Lys Lys Asn Lys Asn Cys
1               5                   10                  15 cgg cgc cac tcg ctc tat gtg gac ttc agc gat gtg ggc tgg aat gac      96
Arg Arg His Ser Leu Tyr Val Asp Phe Ser Asp Val Gly Trp Asn Asp
            20                  25                  30 tgg att gtg gcc cca cca ggc tac cag gcc ttc tac tgc cat ggg gac     144
Trp Ile Val Ala Pro Pro Gly Tyr Gln Ala Phe Tyr Cys His Gly Asp
        35                  40                  45 tgc ccc ttt cca ctg gct gac cac ctc aac tca acc aac cat gcc att     192
Cys Pro Phe Pro Leu Ala Asp His Leu Asn Ser Thr Asn His Ala Ile
    50                  55                  60 gtg cag acc ctg gtc aat tct gtc aat tcc agt atc ccc aaa gcc tgt     240
Val Gln Thr Leu Val Asn Ser Val Asn Ser Ser Ile Pro Lys Ala Cys
65                  70                  75                  80 tgt gtg ccc act gaa ctg agt gcc atc tcc atg ctg tac ctg gat gag     288
Cys Val Pro Thr Glu Leu Ser Ala Ile Ser Met Leu Tyr Leu Asp Glu
                85                  90                  95 tat gat aag gtg gta ctg aaa aat tat cag gag atg gta gta gag gga     336
Tyr Asp Lys Val Val Leu Lys Asn Tyr Gln Glu Met Val Val Glu Gly
            100                 105                 110 tgt ggg tgc cgc                                                     348
Cys Gly Cys Arg
        115
```

<210> SEQ ID NO 45
<211> LENGTH: 116
<212> TYPE: PRT
<213> ORGANISM: Homo sapiens

<400> SEQUENCE: 45

```
Ser Pro Lys His His Ser Gln Arg Ala Arg Lys Lys Asn Lys Asn Cys
1               5                   10                  15

Arg Arg His Ser Leu Tyr Val Asp Phe Ser Asp Val Gly Trp Asn Asp
            20                  25                  30

Trp Ile Val Ala Pro Pro Gly Tyr Gln Ala Phe Tyr Cys His Gly Asp
        35                  40                  45

Cys Pro Phe Pro Leu Ala Asp His Leu Asn Ser Thr Asn His Ala Ile
    50                  55                  60

Val Gln Thr Leu Val Asn Ser Val Asn Ser Ser Ile Pro Lys Ala Cys
65                  70                  75                  80

Cys Val Pro Thr Glu Leu Ser Ala Ile Ser Met Leu Tyr Leu Asp Glu
                85                  90                  95

Tyr Asp Lys Val Val Leu Lys Asn Tyr Gln Glu Met Val Val Glu Gly
            100                 105                 110

Cys Gly Cys Arg
        115
```

<210> SEQ ID NO 46
<211> LENGTH: 414
<212> TYPE: DNA
<213> ORGANISM: Homo sapiens
<220> FEATURE:
<221> NAME/KEY: CDS
<222> LOCATION: (1)..(414)

<400> SEQUENCE: 46

```
gca gcc aac aaa cga aaa aat caa aac cgc aat aaa tcc agc tct cat    48
Ala Ala Asn Lys Arg Lys Asn Gln Asn Arg Asn Lys Ser Ser Ser His
1               5                   10                  15 cag gac tcc tcc aga atg tcc agt gtt gga gat tat aac aca agt gag    96
Gln Asp Ser Ser Arg Met Ser Ser Val Gly Asp Tyr Asn Thr Ser Glu
                20                  25                  30 caa aaa caa gcc tgt aag aag cac gaa ctc tat gtg agc ttc cgg gat    144
Gln Lys Gln Ala Cys Lys Lys His Glu Leu Tyr Val Ser Phe Arg Asp
            35                  40                  45 ctg gga tgg cag gac tgg att ata gca cca gaa gga tac gct gca ttt    192
Leu Gly Trp Gln Asp Trp Ile Ile Ala Pro Glu Gly Tyr Ala Ala Phe
        50                  55                  60 tat tgt gat gga gaa tgt tct ttt cca ctt aac gcc cat atg aat gcc    240
Tyr Cys Asp Gly Glu Cys Ser Phe Pro Leu Asn Ala His Met Asn Ala
65                  70                  75                  80 acc aac cac gct ata gtt cag act ctg gtt cat ctg atg ttt cct gac    288
Thr Asn His Ala Ile Val Gln Thr Leu Val His Leu Met Phe Pro Asp
                85                  90                  95 cac gta cca aag cct tgt tgt gct cca acc aaa tta aat gcc atc tct    336
His Val Pro Lys Pro Cys Cys Ala Pro Thr Lys Leu Asn Ala Ile Ser
            100                 105                 110 gtt ctg tac ttt gat gac agc tcc aat gtc att ttg aaa aaa tat aga    384
Val Leu Tyr Phe Asp Asp Ser Ser Asn Val Ile Leu Lys Lys Tyr Arg
        115                 120                 125 aat atg gta gta cgc tca tgt ggc tgc cac                            414
Asn Met Val Val Arg Ser Cys Gly Cys His
    130                 135

<210> SEQ ID NO 47
<211> LENGTH: 138
<212> TYPE: PRT
<213> ORGANISM: Homo sapiens

<400> SEQUENCE: 47

Ala Ala Asn Lys Arg Lys Asn Gln Asn Arg Asn Lys Ser Ser Ser His
1               5                   10                  15

Gln Asp Ser Ser Arg Met Ser Ser Val Gly Asp Tyr Asn Thr Ser Glu
                20                  25                  30

Gln Lys Gln Ala Cys Lys Lys His Glu Leu Tyr Val Ser Phe Arg Asp
            35                  40                  45

Leu Gly Trp Gln Asp Trp Ile Ile Ala Pro Glu Gly Tyr Ala Ala Phe
        50                  55                  60

Tyr Cys Asp Gly Glu Cys Ser Phe Pro Leu Asn Ala His Met Asn Ala
65                  70                  75                  80

Thr Asn His Ala Ile Val Gln Thr Leu Val His Leu Met Phe Pro Asp
                85                  90                  95

His Val Pro Lys Pro Cys Cys Ala Pro Thr Lys Leu Asn Ala Ile Ser
            100                 105                 110

Val Leu Tyr Phe Asp Asp Ser Ser Asn Val Ile Leu Lys Lys Tyr Arg
        115                 120                 125

Asn Met Val Val Arg Ser Cys Gly Cys His
    130                 135

<210> SEQ ID NO 48
<211> LENGTH: 396
<212> TYPE: DNA
<213> ORGANISM: Homo sapiens
```

```
<220> FEATURE:
<221> NAME/KEY: CDS
<222> LOCATION: (1)..(396)

<400> SEQUENCE: 48 caa cag agt cgt aat cgc tct acc cag tcc cag gac gtg gcg cgg gtc     48
Gln Gln Ser Arg Asn Arg Ser Thr Gln Ser Gln Asp Val Ala Arg Val
1               5                   10                  15 tcc agt gct tca gat tac aac agc agt gaa ttg aaa aca gcc tgc agg     96
Ser Ser Ala Ser Asp Tyr Asn Ser Ser Glu Leu Lys Thr Ala Cys Arg
            20                  25                  30 aag cat gag ctg tat gtg agt ttc caa gac ctg gga tgg cag gac tgg    144
Lys His Glu Leu Tyr Val Ser Phe Gln Asp Leu Gly Trp Gln Asp Trp
        35                  40                  45 atc att gca ccc aag ggc tat gct gcc aat tac tgt gat gga gaa tgc    192
Ile Ile Ala Pro Lys Gly Tyr Ala Ala Asn Tyr Cys Asp Gly Glu Cys
    50                  55                  60 tcc ttc cca ctc aac gca cac atg aat gca acc aac cac gcg att gtg    240
Ser Phe Pro Leu Asn Ala His Met Asn Ala Thr Asn His Ala Ile Val
65                  70                  75                  80 cag acc ttg gtt cac ctt atg aac ccc gag tat gtc ccc aaa ccg tgc    288
Gln Thr Leu Val His Leu Met Asn Pro Glu Tyr Val Pro Lys Pro Cys
                85                  90                  95 tgt gcg cca act aag cta aat gcc atc tcg gtt ctt tac ttt gat gac    336
Cys Ala Pro Thr Lys Leu Asn Ala Ile Ser Val Leu Tyr Phe Asp Asp
            100                 105                 110 aac tcc aat gtc att ctg aaa aaa tac agg aat atg gtt gta aga gct    384
Asn Ser Asn Val Ile Leu Lys Lys Tyr Arg Asn Met Val Val Arg Ala
        115                 120                 125 tgt gga tgc cac                                                    396
Cys Gly Cys His
    130

<210> SEQ ID NO 49
<211> LENGTH: 132
<212> TYPE: PRT
<213> ORGANISM: Homo sapiens

<400> SEQUENCE: 49

Gln Gln Ser Arg Asn Arg Ser Thr Gln Ser Gln Asp Val Ala Arg Val
1               5                   10                  15

Ser Ser Ala Ser Asp Tyr Asn Ser Ser Glu Leu Lys Thr Ala Cys Arg
            20                  25                  30

Lys His Glu Leu Tyr Val Ser Phe Gln Asp Leu Gly Trp Gln Asp Trp
        35                  40                  45

Ile Ile Ala Pro Lys Gly Tyr Ala Ala Asn Tyr Cys Asp Gly Glu Cys
    50                  55                  60

Ser Phe Pro Leu Asn Ala His Met Asn Ala Thr Asn His Ala Ile Val
65                  70                  75                  80

Gln Thr Leu Val His Leu Met Asn Pro Glu Tyr Val Pro Lys Pro Cys
                85                  90                  95

Cys Ala Pro Thr Lys Leu Asn Ala Ile Ser Val Leu Tyr Phe Asp Asp
            100                 105                 110

Asn Ser Asn Val Ile Leu Lys Lys Tyr Arg Asn Met Val Val Arg Ala
        115                 120                 125

Cys Gly Cys His
    130

<210> SEQ ID NO 50
```

<211> LENGTH: 417
<212> TYPE: DNA
<213> ORGANISM: Homo sapiens
<220> FEATURE:
<221> NAME/KEY: CDS
<222> LOCATION: (1)..(417)

<400> SEQUENCE: 50

| tcc | acg | ggg | agc | aaa | cag | cgc | agc | cag | aac | cgc | tcc | aag | acg | ccc | aag | 48 |
|-----|-----|-----|-----|-----|-----|-----|-----|-----|-----|-----|-----|-----|-----|-----|-----|----|
| Ser | Thr | Gly | Ser | Lys | Gln | Arg | Ser | Gln | Asn | Arg | Ser | Lys | Thr | Pro | Lys | |
| 1 | | | | 5 | | | | | 10 | | | | | 15 | | |

| aac | cag | gaa | gcc | ctg | cgg | atg | gcc | aac | gtg | gca | gag | aac | agc | agc | agc | 96 |
| Asn | Gln | Glu | Ala | Leu | Arg | Met | Ala | Asn | Val | Ala | Glu | Asn | Ser | Ser | Ser | |
| | | 20 | | | | | 25 | | | | | 30 | | | | |

| gac | cag | agg | cag | gcc | tgt | aag | aag | cac | gag | ctg | tat | gtc | agc | ttc | cga | 144 |
| Asp | Gln | Arg | Gln | Ala | Cys | Lys | Lys | His | Glu | Leu | Tyr | Val | Ser | Phe | Arg | |
| | 35 | | | | | 40 | | | | | 45 | | | | | |

| gac | ctg | ggc | tgg | cag | gac | tgg | atc | atc | gcg | cct | gaa | ggc | tac | gcc | gcc | 192 |
| Asp | Leu | Gly | Trp | Gln | Asp | Trp | Ile | Ile | Ala | Pro | Glu | Gly | Tyr | Ala | Ala | |
| 50 | | | | | 55 | | | | | 60 | | | | | | |

| tac | tac | tgt | gag | ggg | gag | tgt | gcc | ttc | cct | ctg | aac | tcc | tac | atg | aac | 240 |
| Tyr | Tyr | Cys | Glu | Gly | Glu | Cys | Ala | Phe | Pro | Leu | Asn | Ser | Tyr | Met | Asn | |
| 65 | | | | 70 | | | | | 75 | | | | | 80 | | |

| gcc | acc | aac | cac | gcc | atc | gtg | cag | acg | ctg | gtc | cac | ttc | atc | aac | ccg | 288 |
| Ala | Thr | Asn | His | Ala | Ile | Val | Gln | Thr | Leu | Val | His | Phe | Ile | Asn | Pro | |
| | | | 85 | | | | | 90 | | | | | 95 | | | |

| gaa | acg | gtg | ccc | aag | ccc | tgt | gcg | ccc | acg | cag | ctc | aat | gcc | atc | | 336 |
| Glu | Thr | Val | Pro | Lys | Pro | Cys | Cys | Ala | Pro | Thr | Gln | Leu | Asn | Ala | Ile | |
| | | 100 | | | | | 105 | | | | | 110 | | | | |

| tcc | gtc | ctc | tac | ttc | gat | gac | agc | tcc | aac | gtc | atc | ctg | aag | aaa | tac | 384 |
| Ser | Val | Leu | Tyr | Phe | Asp | Asp | Ser | Ser | Asn | Val | Ile | Leu | Lys | Lys | Tyr | |
| | 115 | | | | | 120 | | | | | 125 | | | | | |

| aga | aac | atg | gtg | gtc | cgg | gcc | tgt | ggc | tgc | cac | | | | | | 417 |
| Arg | Asn | Met | Val | Val | Arg | Ala | Cys | Gly | Cys | His | | | | | | |
| | 130 | | | | | 135 | | | | | | | | | | |

<210> SEQ ID NO 51
<211> LENGTH: 139
<212> TYPE: PRT
<213> ORGANISM: Homo sapiens

<400> SEQUENCE: 51

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
        130                 135

```
<210> SEQ ID NO 52
<211> LENGTH: 417
<212> TYPE: DNA
<213> ORGANISM: Homo sapiens
<220> FEATURE:
<221> NAME/KEY: CDS
<222> LOCATION: (1)..(417)

<400> SEQUENCE: 52 gca agg agg cca ctg agg agg agg cag ccg aag aaa agc aac gag ctg      48
Ala Val Arg Pro Leu Arg Arg Arg Gln Pro Lys Lys Ser Asn Glu Leu
1               5                   10                  15 ccg cag gcc aac cga ctc cca ggg atc ttt gat gac gtc cac ggc tcc      96
Pro Gln Ala Asn Arg Leu Pro Gly Ile Phe Asp Asp Val His Gly Ser
            20                  25                  30 cac ggc cgg cag gtc tgc cgt cgg cac gag ctc tac gtc agc ttc cag     144
His Gly Arg Gln Val Cys Arg Arg His Glu Leu Tyr Val Ser Phe Gln
        35                  40                  45 gac ctc ggc tgg ctg gac tgg gtc atc gct ccc caa ggc tac tcg gcc     192
Asp Leu Gly Trp Leu Asp Trp Val Ile Ala Pro Gln Gly Tyr Ser Ala
    50                  55                  60 tat tac tgt gag ggg gag tgc tcc ttc cca ctg gac tcc tgc atg aat     240
Tyr Tyr Cys Glu Gly Glu Cys Ser Phe Pro Leu Asp Ser Cys Met Asn
65                  70                  75                  80 gcc acc aac cac gcc atc ctg cag tcc ctg gtg cac ctg atg atg cca     288
Ala Thr Asn His Ala Ile Leu Gln Ser Leu Val His Leu Met Met Pro
                85                  90                  95 gac gca gtc ccc aag gcg tgc tgt gca ccc acc aag ctg agc gcc acc     336
Asp Ala Val Pro Lys Ala Cys Cys Ala Pro Thr Lys Leu Ser Ala Thr
            100                 105                 110 tct gtg ctc tac tat gac agc agc aac aat gtc atc ctg cgc aag cac     384
Ser Val Leu Tyr Tyr Asp Ser Ser Asn Asn Val Ile Leu Arg Lys His
        115                 120                 125 cgc aac atg gtg gtc aag gcc tgc ggc tgc cac                         417
Arg Asn Met Val Val Lys Ala Cys Gly Cys His
    130                 135

<210> SEQ ID NO 53
<211> LENGTH: 139
<212> TYPE: PRT
<213> ORGANISM: Homo sapiens

<400> SEQUENCE: 53

Ala Val Arg Pro Leu Arg Arg Arg Gln Pro Lys Lys Ser Asn Glu Leu
1               5                   10                  15

Pro Gln Ala Asn Arg Leu Pro Gly Ile Phe Asp Asp Val His Gly Ser
            20                  25                  30

His Gly Arg Gln Val Cys Arg Arg His Glu Leu Tyr Val Ser Phe Gln
        35                  40                  45

Asp Leu Gly Trp Leu Asp Trp Val Ile Ala Pro Gln Gly Tyr Ser Ala
    50                  55                  60

Tyr Tyr Cys Glu Gly Glu Cys Ser Phe Pro Leu Asp Ser Cys Met Asn
65                  70                  75                  80

Ala Thr Asn His Ala Ile Leu Gln Ser Leu Val His Leu Met Met Pro
                85                  90                  95

Asp Ala Val Pro Lys Ala Cys Cys Ala Pro Thr Lys Leu Ser Ala Thr
            100                 105                 110

Ser Val Leu Tyr Tyr Asp Ser Ser Asn Asn Val Ile Leu Arg Lys His
        115                 120                 125
```

```
<210> SEQ ID NO 54
<211> LENGTH: 333
<212> TYPE: DNA
<213> ORGANISM: Homo sapiens
<220> FEATURE:
<221> NAME/KEY: CDS
<222> LOCATION: (1)..(333)

<400> SEQUENCE: 54
```

| agc | gcc | ggg | gct | ggc | agc | cac | tgt | caa | aag | acc | tcc | ctg | cgg | gta | aac | 48 |
|---|---|---|---|---|---|---|---|---|---|---|---|---|---|---|---|---|
| Ser | Ala | Gly | Ala | Gly | Ser | His | Cys | Gln | Lys | Thr | Ser | Leu | Arg | Val | Asn | |
| 1 | | | | 5 | | | | | 10 | | | | | 15 | | |

| ttc | gag | gac | atc | ggc | tgg | gac | agc | tgg | atc | att | gca | ccc | aag | gag | tat | 96 |
|---|---|---|---|---|---|---|---|---|---|---|---|---|---|---|---|---|
| Phe | Glu | Asp | Ile | Gly | Trp | Asp | Ser | Trp | Ile | Ile | Ala | Pro | Lys | Glu | Tyr | |
| | | | 20 | | | | | 25 | | | | | 30 | | | |

| gaa | gcc | tac | gag | tgt | aag | ggc | ggc | tgc | ttc | ttc | ccc | ttg | gct | gac | gat | 144 |
|---|---|---|---|---|---|---|---|---|---|---|---|---|---|---|---|---|
| Glu | Ala | Tyr | Glu | Cys | Lys | Gly | Gly | Cys | Phe | Phe | Pro | Leu | Ala | Asp | Asp | |
| | 35 | | | | | 40 | | | | | 45 | | | | | |

| gtg | acg | ccg | acg | aaa | cac | gct | atc | gtg | cag | acc | ctg | gtg | cat | ctc | aag | 192 |
|---|---|---|---|---|---|---|---|---|---|---|---|---|---|---|---|---|
| Val | Thr | Pro | Thr | Lys | His | Ala | Ile | Val | Gln | Thr | Leu | Val | His | Leu | Lys | |
| 50 | | | | | 55 | | | | | 60 | | | | | | |

| ttc | ccc | aca | aag | gtg | ggc | aag | gcc | tgc | tgt | gtg | ccc | acc | aaa | ctg | agc | 240 |
|---|---|---|---|---|---|---|---|---|---|---|---|---|---|---|---|---|
| Phe | Pro | Thr | Lys | Val | Gly | Lys | Ala | Cys | Cys | Val | Pro | Thr | Lys | Leu | Ser | |
| 65 | | | | 70 | | | | | 75 | | | | | 80 | | |

| ccc | atc | tcc | gtc | ctc | tac | aag | gat | gac | atg | ggg | gtg | ccc | acc | ctc | aag | 288 |
|---|---|---|---|---|---|---|---|---|---|---|---|---|---|---|---|---|
| Pro | Ile | Ser | Val | Leu | Tyr | Lys | Asp | Asp | Met | Gly | Val | Pro | Thr | Leu | Lys | |
| | | | | 85 | | | | | 90 | | | | | 95 | | |

| tac | cat | tac | gag | ggc | atg | agc | gtg | gca | gag | tgt | ggg | tgc | agg | tag | | 333 |
|---|---|---|---|---|---|---|---|---|---|---|---|---|---|---|---|---|
| Tyr | His | Tyr | Glu | Gly | Met | Ser | Val | Ala | Glu | Cys | Gly | Cys | Arg | | | |
| | | | 100 | | | | | 105 | | | | | 110 | | | |

```
<210> SEQ ID NO 55
<211> LENGTH: 110
<212> TYPE: PRT
<213> ORGANISM: Homo sapiens

<400> SEQUENCE: 55
```

Ser Ala Gly Ala Gly Ser His Cys Gln Lys Thr Ser Leu Arg Val Asn
1               5                   10                  15

Phe Glu Asp Ile Gly Trp Asp Ser Trp Ile Ile Ala Pro Lys Glu Tyr
            20                  25                  30

Glu Ala Tyr Glu Cys Lys Gly Gly Cys Phe Phe Pro Leu Ala Asp Asp
        35                  40                  45

Val Thr Pro Thr Lys His Ala Ile Val Gln Thr Leu Val His Leu Lys
    50                  55                  60

Phe Pro Thr Lys Val Gly Lys Ala Cys Cys Val Pro Thr Lys Leu Ser
65                  70                  75                  80

Pro Ile Ser Val Leu Tyr Lys Asp Asp Met Gly Val Pro Thr Leu Lys
                85                  90                  95

Tyr His Tyr Glu Gly Met Ser Val Ala Glu Cys Gly Cys Arg
            100                 105                 110

```
<210> SEQ ID NO 56
<211> LENGTH: 324
<212> TYPE: DNA
<213> ORGANISM: Homo sapiens
<220> FEATURE:
<221> NAME/KEY: CDS
```

<222> LOCATION: (1)..(324)

<400> SEQUENCE: 56

| aac | gcc | aaa | gga | aac | tac | tgt | aag | agg | acc | ccg | ctc | tac | atc | gac | ttc | 48 |
|-----|-----|-----|-----|-----|-----|-----|-----|-----|-----|-----|-----|-----|-----|-----|-----|----|
| Asn | Ala | Lys | Gly | Asn | Tyr | Cys | Lys | Arg | Thr | Pro | Leu | Tyr | Ile | Asp | Phe | |
| 1 | | | | 5 | | | | | 10 | | | | | 15 | | |

| aag | gag | att | ggg | tgg | gac | tcc | tgg | atc | atc | gct | ccg | cct | gga | tac | gaa | 96 |
| Lys | Glu | Ile | Gly | Trp | Asp | Ser | Trp | Ile | Ile | Ala | Pro | Pro | Gly | Tyr | Glu | |
| | | | 20 | | | | | 25 | | | | | 30 | | | |

| gcc | tat | gaa | tgc | cgt | ggt | gtt | tgt | aac | tac | ccc | ctg | gca | gag | cat | ctc | 144 |
| Ala | Tyr | Glu | Cys | Arg | Gly | Val | Cys | Asn | Tyr | Pro | Leu | Ala | Glu | His | Leu | |
| | | 35 | | | | | 40 | | | | | 45 | | | | |

| aca | ccc | aca | aag | cat | gca | att | atc | cag | gcc | ttg | gtc | cac | ctc | aag | aat | 192 |
| Thr | Pro | Thr | Lys | His | Ala | Ile | Ile | Gln | Ala | Leu | Val | His | Leu | Lys | Asn | |
| | 50 | | | | | 55 | | | | | 60 | | | | | |

| tcc | cag | aaa | gct | tcc | aaa | gcc | tgc | tgt | gtg | ccc | aca | aag | cta | gag | ccc | 240 |
| Ser | Gln | Lys | Ala | Ser | Lys | Ala | Cys | Cys | Val | Pro | Thr | Lys | Leu | Glu | Pro | |
| 65 | | | | | 70 | | | | | 75 | | | | | 80 | |

| atc | tcc | atc | ctc | tat | tta | gac | aaa | ggc | gtc | gtc | acc | tac | aag | ttt | aaa | 288 |
| Ile | Ser | Ile | Leu | Tyr | Leu | Asp | Lys | Gly | Val | Val | Thr | Tyr | Lys | Phe | Lys | |
| | | | | 85 | | | | | 90 | | | | | 95 | | |

| tac | gaa | ggc | atg | gcc | gtc | tcc | gaa | tgt | ggc | tgt | aga | | | | | 324 |
| Tyr | Glu | Gly | Met | Ala | Val | Ser | Glu | Cys | Gly | Cys | Arg | | | | | |
| | | | 100 | | | | | 105 | | | | | | | | |

<210> SEQ ID NO 57
<211> LENGTH: 108
<212> TYPE: PRT
<213> ORGANISM: Homo sapiens

<400> SEQUENCE: 57

Asn Ala Lys Gly Asn Tyr Cys Lys Arg Thr Pro Leu Tyr Ile Asp Phe
1               5                   10                  15

Lys Glu Ile Gly Trp Asp Ser Trp Ile Ile Ala Pro Pro Gly Tyr Glu
            20                  25                  30

Ala Tyr Glu Cys Arg Gly Val Cys Asn Tyr Pro Leu Ala Glu His Leu
        35                  40                  45

Thr Pro Thr Lys His Ala Ile Ile Gln Ala Leu Val His Leu Lys Asn
    50                  55                  60

Ser Gln Lys Ala Ser Lys Ala Cys Cys Val Pro Thr Lys Leu Glu Pro
65                  70                  75                  80

Ile Ser Ile Leu Tyr Leu Asp Lys Gly Val Val Thr Tyr Lys Phe Lys
                85                  90                  95

Tyr Glu Gly Met Ala Val Ser Glu Cys Gly Cys Arg
            100                 105

<210> SEQ ID NO 58
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 58

| caa | gca | gat | ggt | atc | tca | gct | gag | gtt | act | gcc | tct | tcc | tca | aaa | cat | 48 |
|-----|-----|-----|-----|-----|-----|-----|-----|-----|-----|-----|-----|-----|-----|-----|-----|----|
| Gln | Ala | Asp | Gly | Ile | Ser | Ala | Glu | Val | Thr | Ala | Ser | Ser | Ser | Lys | His | |
| 1 | | | | 5 | | | | | 10 | | | | | 15 | | |

| agc | ggg | cct | gaa | aat | aac | cag | tgt | tcc | ctc | cac | cct | ttc | caa | atc | agc | 96 |
| Ser | Gly | Pro | Glu | Asn | Asn | Gln | Cys | Ser | Leu | His | Pro | Phe | Gln | Ile | Ser | |
| | | | 20 | | | | | 25 | | | | | 30 | | | |

```
ttc cgc cag ctg ggt tgg gat cac tgg atc att gct ccc cct ttc tac      144
Phe Arg Gln Leu Gly Trp Asp His Trp Ile Ile Ala Pro Pro Phe Tyr
        35                  40                  45 acc cca aac tac tgt aaa gga act tgt ctc cga gta cta cgc gat ggt      192
Thr Pro Asn Tyr Cys Lys Gly Thr Cys Leu Arg Val Leu Arg Asp Gly
 50                  55                  60 ctc aat tcc ccc aat cac gcc att att cag aac ctt atc aat cag ttg      240
Leu Asn Ser Pro Asn His Ala Ile Ile Gln Asn Leu Ile Asn Gln Leu
65                  70                  75                  80 gtg gac cag agt gtc ccc cgg ccc tcc tgt gtc ccg tat aag tat gtt      288
Val Asp Gln Ser Val Pro Arg Pro Ser Cys Val Pro Tyr Lys Tyr Val
                85                  90                  95 cca att agt gtc ctt atg att gag gca aat ggg agt att ttg tac aag      336
Pro Ile Ser Val Leu Met Ile Glu Ala Asn Gly Ser Ile Leu Tyr Lys
            100                 105                 110 gag tat gag ggt atg att gct gag tct tgt aca tgc aga                  375
Glu Tyr Glu Gly Met Ile Ala Glu Ser Cys Thr Cys Arg
        115                 120                 125
```

<210> SEQ ID NO 59
<211> LENGTH: 125
<212> TYPE: PRT
<213> ORGANISM: Homo sapiens

<400> SEQUENCE: 59

```
Gln Ala Asp Gly Ile Ser Ala Glu Val Thr Ala Ser Ser Ser Lys His
1               5                   10                  15

Ser Gly Pro Glu Asn Asn Gln Cys Ser Leu His Pro Phe Gln Ile Ser
            20                  25                  30

Phe Arg Gln Leu Gly Trp Asp His Trp Ile Ile Ala Pro Pro Phe Tyr
        35                  40                  45

Thr Pro Asn Tyr Cys Lys Gly Thr Cys Leu Arg Val Leu Arg Asp Gly
 50                  55                  60

Leu Asn Ser Pro Asn His Ala Ile Ile Gln Asn Leu Ile Asn Gln Leu
65                  70                  75                  80

Val Asp Gln Ser Val Pro Arg Pro Ser Cys Val Pro Tyr Lys Tyr Val
                85                  90                  95

Pro Ile Ser Val Leu Met Ile Glu Ala Asn Gly Ser Ile Leu Tyr Lys
            100                 105                 110

Glu Tyr Glu Gly Met Ile Ala Glu Ser Cys Thr Cys Arg
        115                 120                 125
```

<210> SEQ ID NO 60
<211> LENGTH: 357
<212> TYPE: DNA
<213> ORGANISM: Homo sapiens
<220> FEATURE:
<221> NAME/KEY: CDS
<222> LOCATION: (1)..(357)

<400> SEQUENCE: 60

```
gac gcc gaa ccc gtg ttg ggc ggc ggc ccc ggg ggc gct tgt cgc gcg      48
Asp Ala Glu Pro Val Leu Gly Gly Gly Pro Gly Gly Ala Cys Arg Ala
1               5                   10                  15 cgg cgg ctg tac gtg agc ttc cgc gag gtg ggc tgg cac cgc tgg gtc      96
Arg Arg Leu Tyr Val Ser Phe Arg Glu Val Gly Trp His Arg Trp Val
            20                  25                  30 atc gcg ccg cgc ggc ttc ctg gcc aac tac tgc cag ggt cag tgc gcg     144
Ile Ala Pro Arg Gly Phe Leu Ala Asn Tyr Cys Gln Gly Gln Cys Ala
        35                  40                  45
```

```
ctg ccc gtc gcg ctg tcg ggg tcc ggg ggg ccg ccg gcg ctc aac cac      192
Leu Pro Val Ala Leu Ser Gly Ser Gly Gly Pro Pro Ala Leu Asn His
 50                  55                  60 gct gtg ctg cgc gcg ctc atg cac gcg gcc gcc ccg gga gcc gcc gac      240
Ala Val Leu Arg Ala Leu Met His Ala Ala Ala Pro Gly Ala Ala Asp
 65                  70                  75                  80 ctg ccc tgc tgc gtg ccc gcg cgc ctg tcg ccc atc tcc gtg ctc ttc      288
Leu Pro Cys Cys Val Pro Ala Arg Leu Ser Pro Ile Ser Val Leu Phe
                 85                  90                  95 ttt gac aac agc gac aac gtg gtg ctg cgg cag tat gag gac atg gtg      336
Phe Asp Asn Ser Asp Asn Val Val Leu Arg Gln Tyr Glu Asp Met Val
                100                 105                 110 gtg gac gag tgc ggc tgc cgc                                          357
Val Asp Glu Cys Gly Cys Arg
            115

<210> SEQ ID NO 61
<211> LENGTH: 119
<212> TYPE: PRT
<213> ORGANISM: Homo sapiens

<400> SEQUENCE: 61

Asp Ala Glu Pro Val Leu Gly Gly Gly Pro Gly Gly Ala Cys Arg Ala
 1               5                  10                  15

Arg Arg Leu Tyr Val Ser Phe Arg Glu Val Gly Trp His Arg Trp Val
                20                  25                  30

Ile Ala Pro Arg Gly Phe Leu Ala Asn Tyr Cys Gln Gly Gln Cys Ala
            35                  40                  45

Leu Pro Val Ala Leu Ser Gly Ser Gly Gly Pro Pro Ala Leu Asn His
 50                  55                  60

Ala Val Leu Arg Ala Leu Met His Ala Ala Ala Pro Gly Ala Ala Asp
 65                  70                  75                  80

Leu Pro Cys Cys Val Pro Ala Arg Leu Ser Pro Ile Ser Val Leu Phe
                 85                  90                  95

Phe Asp Asn Ser Asp Asn Val Val Leu Arg Gln Tyr Glu Asp Met Val
                100                 105                 110

Val Asp Glu Cys Gly Cys Arg
            115

<210> SEQ ID NO 62
<211> LENGTH: 342
<212> TYPE: DNA
<213> ORGANISM: Homo sapiens
<220> FEATURE:
<221> NAME/KEY: CDS
<222> LOCATION: (1)..(342)

<400> SEQUENCE: 62 gca gcc atc cct gtc ccc aag ctt tct tgt aag aac ctc tgc cac cgt       48
Ala Ala Ile Pro Val Pro Lys Leu Ser Cys Lys Asn Leu Cys His Arg
 1               5                  10                  15 cac cag cta ttc att aac ttc cgg gac ctg ggt tgg cac aag tgg atc       96
His Gln Leu Phe Ile Asn Phe Arg Asp Leu Gly Trp His Lys Trp Ile
                20                  25                  30 att gcc ccc aag ggg ttc atg gca aat tac tgc cat gga gag tgt ccc      144
Ile Ala Pro Lys Gly Phe Met Ala Asn Tyr Cys His Gly Glu Cys Pro
            35                  40                  45 ttc tca ctg acc atc tct ctc aac agc tcc aat tat gct ttc atg caa      192
Phe Ser Leu Thr Ile Ser Leu Asn Ser Ser Asn Tyr Ala Phe Met Gln
 50                  55                  60
```

```
gcc ctg atg cat gcc gtt gac cca gag atc ccc cag gct gtg tgt atc      240
Ala Leu Met His Ala Val Asp Pro Glu Ile Pro Gln Ala Val Cys Ile
 65              70                  75                  80 ccc acc aag ctg tct ccc att tcc atg ctc tac cag gac aat aat gac      288
Pro Thr Lys Leu Ser Pro Ile Ser Met Leu Tyr Gln Asp Asn Asn Asp
                 85                  90                  95 aat gtc att cta cga cat tat gaa gac atg gta gtc gat gaa tgt ggg      336
Asn Val Ile Leu Arg His Tyr Glu Asp Met Val Val Asp Glu Cys Gly
            100                 105                 110 tgt ggg                                                               342
Cys Gly <210> SEQ ID NO 63
<211> LENGTH: 114
<212> TYPE: PRT
<213> ORGANISM: Homo sapiens

<400> SEQUENCE: 63

Ala Ala Ile Pro Val Pro Lys Leu Ser Cys Lys Asn Leu Cys His Arg
  1               5                  10                  15

His Gln Leu Phe Ile Asn Phe Arg Asp Leu Gly Trp His Lys Trp Ile
                 20                  25                  30

Ile Ala Pro Lys Gly Phe Met Ala Asn Tyr Cys His Gly Glu Cys Pro
             35                  40                  45

Phe Ser Leu Thr Ile Ser Leu Asn Ser Ser Asn Tyr Ala Phe Met Gln
 50                  55                  60

Ala Leu Met His Ala Val Asp Pro Glu Ile Pro Gln Ala Val Cys Ile
 65              70                  75                  80

Pro Thr Lys Leu Ser Pro Ile Ser Met Leu Tyr Gln Asp Asn Asn Asp
                 85                  90                  95

Asn Val Ile Leu Arg His Tyr Glu Asp Met Val Val Asp Glu Cys Gly
            100                 105                 110

Cys Gly

<210> SEQ ID NO 64
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 64 gcc cca ctg gcc act cgc cag ggc aag cga ccc agc aag aac ctt aag       48
Ala Pro Leu Ala Thr Arg Gln Gly Lys Arg Pro Ser Lys Asn Leu Lys
  1               5                  10                  15 gct cgc tgc agt cgg aag gca ctg cat gtc aac ttc aag gac atg ggc       96
Ala Arg Cys Ser Arg Lys Ala Leu His Val Asn Phe Lys Asp Met Gly
                 20                  25                  30 tgg gac gac tgg atc atc gca ccc ctt gag tac gag gct ttc cac tgc      144
Trp Asp Asp Trp Ile Ile Ala Pro Leu Glu Tyr Glu Ala Phe His Cys
             35                  40                  45 gag ggc ctg tgc gag ttc cca ttg cgc tcc cac ctg gag ccc acg aat      192
Glu Gly Leu Cys Glu Phe Pro Leu Arg Ser His Leu Glu Pro Thr Asn
 50                  55                  60 cat gca gtc atc cag acc ctg atg aac tcc atg gac ccc gag tcc aca      240
His Ala Val Ile Gln Thr Leu Met Asn Ser Met Asp Pro Glu Ser Thr
 65              70                  75                  80 cca ccc acc tgc tgt gtg ccc acg cgg ctg agt ccc atc agc atc ctc      288
```

```
Pro Pro Thr Cys Cys Val Pro Thr Arg Leu Ser Pro Ile Ser Ile Leu
                85                  90                  95 ttc att gac tct gcc aac aac gtg gtg tat aag cag tat gag gac atg      336
Phe Ile Asp Ser Ala Asn Asn Val Val Tyr Lys Gln Tyr Glu Asp Met
            100                 105                 110 gtc gtg gag tcg tgt ggc tgc agg                                      360
Val Val Glu Ser Cys Gly Cys Arg
        115                 120

<210> SEQ ID NO 65
<211> LENGTH: 120
<212> TYPE: PRT
<213> ORGANISM: Homo sapiens

<400> SEQUENCE: 65

Ala Pro Leu Ala Thr Arg Gln Gly Lys Arg Pro Ser Lys Asn Leu Lys
1               5                   10                  15

Ala Arg Cys Ser Arg Lys Ala Leu His Val Asn Phe Lys Asp Met Gly
            20                  25                  30

Trp Asp Asp Trp Ile Ile Ala Pro Leu Glu Tyr Glu Ala Phe His Cys
        35                  40                  45

Glu Gly Leu Cys Glu Phe Pro Leu Arg Ser His Leu Glu Pro Thr Asn
    50                  55                  60

His Ala Val Ile Gln Thr Leu Met Asn Ser Met Asp Pro Glu Ser Thr
65                  70                  75                  80

Pro Pro Thr Cys Cys Val Pro Thr Arg Leu Ser Pro Ile Ser Ile Leu
                85                  90                  95

Phe Ile Asp Ser Ala Asn Asn Val Val Tyr Lys Gln Tyr Glu Asp Met
            100                 105                 110

Val Val Glu Ser Cys Gly Cys Arg
        115                 120

<210> SEQ ID NO 66
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 66 acg gcc ttc gcc agt cgc cat ggc aag cgg cac ggc aag aag tcc agg      48
Thr Ala Phe Ala Ser Arg His Gly Lys Arg His Gly Lys Lys Ser Arg
1               5                   10                  15 cta cgc tgc agc aag aag ccc ctg cac gtg aac ttc aag gag ctg ggc      96
Leu Arg Cys Ser Lys Lys Pro Leu His Val Asn Phe Lys Glu Leu Gly
            20                  25                  30 tgg gac gac tgg att atc gcg ccc ctg gag tac gag gcc tat cac tgc      144
Trp Asp Asp Trp Ile Ile Ala Pro Leu Glu Tyr Glu Ala Tyr His Cys
        35                  40                  45 gag ggt gta tgc gac ttc ccg ctg cgc tcg cac ctg gag ccc acc aac      192
Glu Gly Val Cys Asp Phe Pro Leu Arg Ser His Leu Glu Pro Thr Asn
    50                  55                  60 cac gcc atc atc cag acg ctg atg aac tcc atg gac ccc ggc tcc acc      240
His Ala Ile Ile Gln Thr Leu Met Asn Ser Met Asp Pro Gly Ser Thr
65                  70                  75                  80 ccg ccc agc tgc tgc gtg ccc acc aaa ttg act ccc atc agc att cta      288
Pro Pro Ser Cys Cys Val Pro Thr Lys Leu Thr Pro Ile Ser Ile Leu
                85                  90                  95 tac atc gac gcg ggc aat aat gtg gtc tac aag cag tac gag gac atg      336
```

```
Tyr Ile Asp Ala Gly Asn Asn Val Val Tyr Lys Gln Tyr Glu Asp Met
                100                 105                 110 gtg gtg gag tcg tgc ggc tgc agg                                      360
Val Val Glu Ser Cys Gly Cys Arg
        115                 120

<210> SEQ ID NO 67
<211> LENGTH: 120
<212> TYPE: PRT
<213> ORGANISM: Homo sapiens

<400> SEQUENCE: 67

Thr Ala Phe Ala Ser Arg His Gly Lys Arg His Gly Lys Lys Ser Arg
1               5                   10                  15

Leu Arg Cys Ser Lys Lys Pro Leu His Val Asn Phe Lys Glu Leu Gly
            20                  25                  30

Trp Asp Asp Trp Ile Ile Ala Pro Leu Glu Tyr Glu Ala Tyr His Cys
        35                  40                  45

Glu Gly Val Cys Asp Phe Pro Leu Arg Ser His Leu Glu Pro Thr Asn
    50                  55                  60

His Ala Ile Ile Gln Thr Leu Met Asn Ser Met Asp Pro Gly Ser Thr
65                  70                  75                  80

Pro Pro Ser Cys Cys Val Pro Thr Lys Leu Thr Pro Ile Ser Ile Leu
                85                  90                  95

Tyr Ile Asp Ala Gly Asn Asn Val Val Tyr Lys Gln Tyr Glu Asp Met
                100                 105                 110

Val Val Glu Ser Cys Gly Cys Arg
        115                 120

<210> SEQ ID NO 68
<211> LENGTH: 387
<212> TYPE: DNA
<213> ORGANISM: Homo sapiens
<220> FEATURE:
<221> NAME/KEY: CDS
<222> LOCATION: (1)..(387)

<400> SEQUENCE: 68 acg gcg ttg gcc ggg acg cgg aca tcg cag ggc agc ggc ggg ggc gcg    48
Thr Ala Leu Ala Gly Thr Arg Thr Ser Gln Gly Ser Gly Gly Gly Ala
1               5                   10                  15 ggc cgg ggc cac ggg cgc agg ggc cgg agc cgc tgc agc cgc aag ccg    96
Gly Arg Gly His Gly Arg Arg Gly Arg Ser Arg Cys Ser Arg Lys Pro
            20                  25                  30 ttg cac gtg gac ttc aag gag ctc ggc tgg gac gac tgg atc atc gcg   144
Leu His Val Asp Phe Lys Glu Leu Gly Trp Asp Asp Trp Ile Ile Ala
        35                  40                  45 ccg ctg gac tac gag gcg tac cac tgc gag ggc ctt tgc gac ttc cct   192
Pro Leu Asp Tyr Glu Ala Tyr His Cys Glu Gly Leu Cys Asp Phe Pro
    50                  55                  60 ttg cgt tcg cac ctc gag ccc acc aac cat gcc atc att cag acg ctg   240
Leu Arg Ser His Leu Glu Pro Thr Asn His Ala Ile Ile Gln Thr Leu
65                  70                  75                  80 ctc aac tcc atg gca cca gac gcg gcg ccg gcc tcc tgc tgt gtg cca   288
Leu Asn Ser Met Ala Pro Asp Ala Ala Pro Ala Ser Cys Cys Val Pro
                85                  90                  95 gcg cgc ctc agc ccc atc agc atc ctc tac atc gac gcc gcc aac aac   336
Ala Arg Leu Ser Pro Ile Ser Ile Leu Tyr Ile Asp Ala Ala Asn Asn
                100                 105                 110 gtt gtc tac aag caa tac gag gac atg gtg gtg gag gcc tgc ggc tgc   384
```

```
Val Val Tyr Lys Gln Tyr Glu Asp Met Val Val Glu Ala Cys Gly Cys
        115                 120                 125 agg                                                                    387
Arg
```

```
<210> SEQ ID NO 69
<211> LENGTH: 129
<212> TYPE: PRT
<213> ORGANISM: Homo sapiens

<400> SEQUENCE: 69
```

```
Thr Ala Leu Ala Gly Thr Arg Thr Ser Gln Gly Ser Gly Gly Gly Ala
1               5                   10                  15

Gly Arg Gly His Gly Arg Arg Gly Arg Ser Arg Cys Ser Arg Lys Pro
            20                  25                  30

Leu His Val Asp Phe Lys Glu Leu Gly Trp Asp Asp Trp Ile Ile Ala
        35                  40                  45

Pro Leu Asp Tyr Glu Ala Tyr His Cys Glu Gly Leu Cys Asp Phe Pro
    50                  55                  60

Leu Arg Ser His Leu Glu Pro Thr Asn His Ala Ile Ile Gln Thr Leu
65                  70                  75                  80

Leu Asn Ser Met Ala Pro Asp Ala Ala Pro Ala Ser Cys Cys Val Pro
                85                  90                  95

Ala Arg Leu Ser Pro Ile Ser Ile Leu Tyr Ile Asp Ala Ala Asn Asn
            100                 105                 110

Val Val Tyr Lys Gln Tyr Glu Asp Met Val Val Glu Ala Cys Gly Cys
        115                 120                 125

Arg
```

```
<210> SEQ ID NO 70
<211> LENGTH: 327
<212> TYPE: DNA
<213> ORGANISM: Homo sapiens
<220> FEATURE:
<221> NAME/KEY: CDS
<222> LOCATION: (1)..(327)

<400> SEQUENCE: 70
```

```
gat ttt ggt ctt gac tgt gat gag cac tca aca gaa tca cga tgc tgt    48
Asp Phe Gly Leu Asp Cys Asp Glu His Ser Thr Glu Ser Arg Cys Cys
1               5                   10                  15 cgt tac cct cta act gtg gat ttt gaa gct ttt gga tgg gat tgg att    96
Arg Tyr Pro Leu Thr Val Asp Phe Glu Ala Phe Gly Trp Asp Trp Ile
            20                  25                  30 atc gct cct aaa aga tat aag gcc aat tac tgc tct gga gag tgt gaa   144
Ile Ala Pro Lys Arg Tyr Lys Ala Asn Tyr Cys Ser Gly Glu Cys Glu
        35                  40                  45 ttt gta ttt tta caa aaa tat cct cat act cat ctg gta cac caa gca   192
Phe Val Phe Leu Gln Lys Tyr Pro His Thr His Leu Val His Gln Ala
    50                  55                  60 aac ccc aga ggt tca gca ggc cct tgc tgt act ccc aca aag atg tct   240
Asn Pro Arg Gly Ser Ala Gly Pro Cys Cys Thr Pro Thr Lys Met Ser
65                  70                  75                  80 cca att aat atg cta tat ttt aat ggc aaa gaa caa ata ata tat ggg   288
Pro Ile Asn Met Leu Tyr Phe Asn Gly Lys Glu Gln Ile Ile Tyr Gly
                85                  90                  95 aaa att cca gcg atg gta gta gac cgc tgt ggg tgc tca               327
Lys Ile Pro Ala Met Val Val Asp Arg Cys Gly Cys Ser
            100                 105
```

<210> SEQ ID NO 71
<211> LENGTH: 109
<212> TYPE: PRT
<213> ORGANISM: Homo sapiens

<400> SEQUENCE: 71

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105

<210> SEQ ID NO 72
<211> LENGTH: 405
<212> TYPE: DNA
<213> ORGANISM: Homo sapiens
<220> FEATURE:
<221> NAME/KEY: CDS
<222> LOCATION: (1)..(405)

<400> SEQUENCE: 72 ggt cag gaa act gtc agt tct gaa ttg aag aag ccc ttg ggc cca gct    48
Gly Gln Glu Thr Val Ser Ser Glu Leu Lys Lys Pro Leu Gly Pro Ala
1               5                   10                  15 tcc ttc aat ctg agt gaa tac ttc aga caa ttt ctt ctt ccc caa aat    96
Ser Phe Asn Leu Ser Glu Tyr Phe Arg Gln Phe Leu Leu Pro Gln Asn
            20                  25                  30 gag tgt gag ctc cat gac ttt aga ctt agc ttt agt cag ctg aag tgg    144
Glu Cys Glu Leu His Asp Phe Arg Leu Ser Phe Ser Gln Leu Lys Trp
        35                  40                  45 gac aac tgg att gtg gct ccg cac agg tac aac cct cga tac tgt aaa    192
Asp Asn Trp Ile Val Ala Pro His Arg Tyr Asn Pro Arg Tyr Cys Lys
50                  55                  60 ggg gac tgt cca agg gca gtt gga cat cgg tat ggc tct cca gtt cac    240
Gly Asp Cys Pro Arg Ala Val Gly His Arg Tyr Gly Ser Pro Val His
65                  70                  75                  80 acc atg gta cag aac atc atc tat gag aag ctg gac tcc tca gtg cca    288
Thr Met Val Gln Asn Ile Ile Tyr Glu Lys Leu Asp Ser Ser Val Pro
                85                  90                  95 aga ccg tca tgt gta cct gcc aaa tac agc ccc ttg agt gtt ttg acc    336
Arg Pro Ser Cys Val Pro Ala Lys Tyr Ser Pro Leu Ser Val Leu Thr
            100                 105                 110 att gag ccc gat ggc tca att gcc tat aaa gag tac gaa gat atg ata    384
Ile Glu Pro Asp Gly Ser Ile Ala Tyr Lys Glu Tyr Glu Asp Met Ile
        115                 120                 125 gct aca aag tgc acc tgt cgt                                        405
Ala Thr Lys Cys Thr Cys Arg
    130                 135

<210> SEQ ID NO 73
<211> LENGTH: 135

<212> TYPE: PRT
<213> ORGANISM: Homo sapiens

<400> SEQUENCE: 73

Gly Gln Glu Thr Val Ser Ser Glu Leu Lys Lys Pro Leu Gly Pro Ala
1               5                   10                  15

Ser Phe Asn Leu Ser Glu Tyr Phe Arg Gln Phe Leu Leu Pro Gln Asn
            20                  25                  30

Glu Cys Glu Leu His Asp Phe Arg Leu Ser Phe Ser Gln Leu Lys Trp
        35                  40                  45

Asp Asn Trp Ile Val Ala Pro His Arg Tyr Asn Pro Arg Tyr Cys Lys
    50                  55                  60

Gly Asp Cys Pro Arg Ala Val Gly His Arg Tyr Gly Ser Pro Val His
65                  70                  75                  80

Thr Met Val Gln Asn Ile Ile Tyr Glu Lys Leu Asp Ser Ser Val Pro
                85                  90                  95

Arg Pro Ser Cys Val Pro Ala Lys Tyr Ser Pro Leu Ser Val Leu Thr
            100                 105                 110

Ile Glu Pro Asp Gly Ser Ile Ala Tyr Lys Glu Tyr Glu Asp Met Ile
        115                 120                 125

Ala Thr Lys Cys Thr Cys Arg
    130                 135

<210> SEQ ID NO 74
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 74 aag acg atg cag aaa gcc cgg agg aag cag tgg gat gag ccg agg gtg      48
Lys Thr Met Gln Lys Ala Arg Arg Lys Gln Trp Asp Glu Pro Arg Val
1               5                   10                  15 tgc tcc cgg agg tac ctg aag gtg gac ttc gca gac atc ggc tgg aat      96
Cys Ser Arg Arg Tyr Leu Lys Val Asp Phe Ala Asp Ile Gly Trp Asn
            20                  25                  30 gaa tgg ata atc tca ccg aaa tct ttt gat gcc tac tac tgc gcg gga     144
Glu Trp Ile Ile Ser Pro Lys Ser Phe Asp Ala Tyr Tyr Cys Ala Gly
        35                  40                  45 gca tgt gag ttc ccc atg cct aag atc gtt cgt cca tcc aac cat gcc     192
Ala Cys Glu Phe Pro Met Pro Lys Ile Val Arg Pro Ser Asn His Ala
    50                  55                  60 acc atc cag agc att gtc agg gct gtg ggc atc atc cct ggc atc cca     240
Thr Ile Gln Ser Ile Val Arg Ala Val Gly Ile Ile Pro Gly Ile Pro
65                  70                  75                  80 gag ccc tgc tgt gtt ccc gat aag atg aac tcc ctt ggg gtc ctc ttc     288
Glu Pro Cys Cys Val Pro Asp Lys Met Asn Ser Leu Gly Val Leu Phe
                85                  90                  95 ctg gat gag aat cgg aat gtg gtt ctg aag gtg tac ccc aac atg tcc     336
Leu Asp Glu Asn Arg Asn Val Val Leu Lys Val Tyr Pro Asn Met Ser
            100                 105                 110 gtg gac acc tgt gcc tgc cgg tga                                     360
Val Asp Thr Cys Ala Cys Arg
        115

<210> SEQ ID NO 75
<211> LENGTH: 119
<212> TYPE: PRT

<213> ORGANISM: Homo sapiens

<400> SEQUENCE: 75

Lys Thr Met Gln Lys Ala Arg Arg Lys Gln Trp Asp Glu Pro Arg Val
1               5                   10                  15

Cys Ser Arg Arg Tyr Leu Lys Val Asp Phe Ala Asp Ile Gly Trp Asn
            20                  25                  30

Glu Trp Ile Ile Ser Pro Lys Ser Phe Asp Ala Tyr Tyr Cys Ala Gly
        35                  40                  45

Ala Cys Glu Phe Pro Met Pro Lys Ile Val Arg Pro Ser Asn His Ala
    50                  55                  60

Thr Ile Gln Ser Ile Val Arg Ala Val Gly Ile Ile Pro Gly Ile Pro
65                  70                  75                  80

Glu Pro Cys Cys Val Pro Asp Lys Met Asn Ser Leu Gly Val Leu Phe
                85                  90                  95

Leu Asp Glu Asn Arg Asn Val Val Leu Lys Val Tyr Pro Asn Met Ser
            100                 105                 110

Val Asp Thr Cys Ala Cys Arg
        115

<210> SEQ ID NO 76
<211> LENGTH: 327
<212> TYPE: DNA
<213> ORGANISM: Homo sapiens
<220> FEATURE:
<221> NAME/KEY: CDS
<222> LOCATION: (1)..(327)

<400> SEQUENCE: 76 aac ctg ggt ctg gac tgc gac gag cac tca agc gag tcc cgc tgc tgc    48
Asn Leu Gly Leu Asp Cys Asp Glu His Ser Ser Glu Ser Arg Cys Cys
1               5                   10                  15 cga tat ccc ctc aca gtg gac ttt gag gct ttc ggc tgg gac tgg atc    96
Arg Tyr Pro Leu Thr Val Asp Phe Glu Ala Phe Gly Trp Asp Trp Ile
            20                  25                  30 atc gca cct aag cgc tac aag gcc aac tac tgc tcc ggc cag tgc gag   144
Ile Ala Pro Lys Arg Tyr Lys Ala Asn Tyr Cys Ser Gly Gln Cys Glu
        35                  40                  45 tac atg ttc atg caa aaa tat ccg cat acc cat ttg gtg cag cag gcc   192
Tyr Met Phe Met Gln Lys Tyr Pro His Thr His Leu Val Gln Gln Ala
    50                  55                  60 aat cca aga ggc tct gct ggg ccc tgt tgt acc ccc acc aag atg tcc   240
Asn Pro Arg Gly Ser Ala Gly Pro Cys Cys Thr Pro Thr Lys Met Ser
65                  70                  75                  80 cca atc aac atg ctc tac ttc aat gac aag cag cag att atc tac ggc   288
Pro Ile Asn Met Leu Tyr Phe Asn Asp Lys Gln Gln Ile Ile Tyr Gly
                85                  90                  95 aag atc cct ggc atg gtg gtg gat cgc tgt ggc tgc tct               327
Lys Ile Pro Gly Met Val Val Asp Arg Cys Gly Cys Ser
            100                 105

<210> SEQ ID NO 77
<211> LENGTH: 109
<212> TYPE: PRT
<213> ORGANISM: Homo sapiens

<400> SEQUENCE: 77

Asn Leu Gly Leu Asp Cys Asp Glu His Ser Ser Glu Ser Arg Cys Cys
1               5                   10                  15

Arg Tyr Pro Leu Thr Val Asp Phe Glu Ala Phe Gly Trp Asp Trp Ile

```
            20                  25                  30
Ile Ala Pro Lys Arg Tyr Lys Ala Asn Tyr Cys Ser Gly Gln Cys Glu
            35                  40                  45

Tyr Met Phe Met Gln Lys Tyr Pro His Thr His Leu Val Gln Gln Ala
        50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Asp Lys Gln Gln Ile Ile Tyr Gly
                85                  90                  95

Lys Ile Pro Gly Met Val Val Asp Arg Cys Gly Cys Ser
            100                 105

<210> SEQ ID NO 78
<211> LENGTH: 336
<212> TYPE: DNA
<213> ORGANISM: Homo sapiens
<220> FEATURE:
<221> NAME/KEY: CDS
<222> LOCATION: (1)..(336)

<400> SEQUENCE: 78 gcg cgc aac ggg gac cac tgt ccg ctc ggg ccc ggg cgt tgc tgc cgt    48
Ala Arg Asn Gly Asp His Cys Pro Leu Gly Pro Gly Arg Cys Cys Arg
1               5                   10                  15 ctg cac acg gtc cgc gcg tcg ctg gaa gac ctg ggc tgg gcc gat tgg    96
Leu His Thr Val Arg Ala Ser Leu Glu Asp Leu Gly Trp Ala Asp Trp
                20                  25                  30 gtg ctg tcg cca cgg gag gtg caa gtg acc atg tgc atc ggc gcg tgc   144
Val Leu Ser Pro Arg Glu Val Gln Val Thr Met Cys Ile Gly Ala Cys
            35                  40                  45 ccg agc cag ttc cgg gcg gca aac atg cac gcg cag atc aag acg agc   192
Pro Ser Gln Phe Arg Ala Ala Asn Met His Ala Gln Ile Lys Thr Ser
        50                  55                  60 ctg cac cgc ctg aag ccc gac acg gtg cca gcg ccc tgc tgc gtg ccc   240
Leu His Arg Leu Lys Pro Asp Thr Val Pro Ala Pro Cys Cys Val Pro
65                  70                  75                  80 gcc agc tac aat ccc atg gtg ctc att caa aag acc gac acc ggg gtg   288
Ala Ser Tyr Asn Pro Met Val Leu Ile Gln Lys Thr Asp Thr Gly Val
                85                  90                  95 tcg ctc cag acc tat gat gac ttg tta gcc aaa gac tgc cac tgc ata   336
Ser Leu Gln Thr Tyr Asp Asp Leu Leu Ala Lys Asp Cys His Cys Ile
            100                 105                 110

<210> SEQ ID NO 79
<211> LENGTH: 112
<212> TYPE: PRT
<213> ORGANISM: Homo sapiens

<400> SEQUENCE: 79

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
        50                  55                  60

Leu His Arg Leu Lys Pro Asp Thr Val Pro Ala Pro Cys Cys Val Pro
65                  70                  75                  80
```

```
Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 80
<211> LENGTH: 330
<212> TYPE: DNA
<213> ORGANISM: Homo sapiens
<220> FEATURE:
<221> NAME/KEY: CDS
<222> LOCATION: (1)..(330)

<400> SEQUENCE: 80

```
cat cac ttg cca gac aga agt caa ctg tgt cgg aag gtc aag ttc cag      48
His His Leu Pro Asp Arg Ser Gln Leu Cys Arg Lys Val Lys Phe Gln
1               5                   10                  15 gtg gac ttc aac ctg atc gga tgg ggc tcc tgg atc atc tac ccc aag      96
Val Asp Phe Asn Leu Ile Gly Trp Gly Ser Trp Ile Ile Tyr Pro Lys
            20                  25                  30 cag tac aac gcc tat cgc tgt gag ggc gag tgt cct aat cct gtt ggg     144
Gln Tyr Asn Ala Tyr Arg Cys Glu Gly Glu Cys Pro Asn Pro Val Gly
        35                  40                  45 gag gag ttt cat ccg acc aac cat gca tac atc cag agt ctg ctg aaa     192
Glu Glu Phe His Pro Thr Asn His Ala Tyr Ile Gln Ser Leu Leu Lys
    50                  55                  60 cgt tac cag ccc cac cga gtc cct tcc act tgt tgt gcc cca gtg aag     240
Arg Tyr Gln Pro His Arg Val Pro Ser Thr Cys Cys Ala Pro Val Lys
65                  70                  75                  80 acc aag ccg ctg agc atg ctg tat gtg gat aat ggc aga gtg ctc cta     288
Thr Lys Pro Leu Ser Met Leu Tyr Val Asp Asn Gly Arg Val Leu Leu
                85                  90                  95 gat cac cat aaa gac atg atc gtg gaa gaa tgt ggg tgc ctc              330
Asp His His Lys Asp Met Ile Val Glu Glu Cys Gly Cys Leu
            100                 105                 110
```

<210> SEQ ID NO 81
<211> LENGTH: 110
<212> TYPE: PRT
<213> ORGANISM: Homo sapiens

<400> SEQUENCE: 81

```
His His Leu Pro Asp Arg Ser Gln Leu Cys Arg Lys Val Lys Phe Gln
1               5                   10                  15

Val Asp Phe Asn Leu Ile Gly Trp Gly Ser Trp Ile Ile Tyr Pro Lys
            20                  25                  30

Gln Tyr Asn Ala Tyr Arg Cys Glu Gly Glu Cys Pro Asn Pro Val Gly
        35                  40                  45

Glu Glu Phe His Pro Thr Asn His Ala Tyr Ile Gln Ser Leu Leu Lys
    50                  55                  60

Arg Tyr Gln Pro His Arg Val Pro Ser Thr Cys Cys Ala Pro Val Lys
65                  70                  75                  80

Thr Lys Pro Leu Ser Met Leu Tyr Val Asp Asn Gly Arg Val Leu Leu
                85                  90                  95

Asp His His Lys Asp Met Ile Val Glu Glu Cys Gly Cys Leu
            100                 105                 110
```

<210> SEQ ID NO 82
<211> LENGTH: 345
<212> TYPE: DNA
<213> ORGANISM: Homo sapiens

```
<220> FEATURE:
<221> NAME/KEY: CDS
<222> LOCATION: (1)..(345)

<400> SEQUENCE: 82 ggc ctg gag tgc gac ggc aag gtc aac atc tgc tgt aag aaa cag ttc      48
Gly Leu Glu Cys Asp Gly Lys Val Asn Ile Cys Cys Lys Lys Gln Phe
1               5                   10                  15 ttt gtc agt ttc aag gac atc ggc tgg aat gac tgg atc att gct ccc      96
Phe Val Ser Phe Lys Asp Ile Gly Trp Asn Asp Trp Ile Ile Ala Pro
            20                  25                  30 tct ggc tat cat gcc aac tac tgc gag ggt gag tgc ccg agc cat ata     144
Ser Gly Tyr His Ala Asn Tyr Cys Glu Gly Glu Cys Pro Ser His Ile
        35                  40                  45 gca ggc acg tcc ggg tcc tca ctg tcc ttc cac tca aca gtc atc aac     192
Ala Gly Thr Ser Gly Ser Ser Leu Ser Phe His Ser Thr Val Ile Asn
50                  55                  60 cac tac gca tgc ggc cat agc ccc ttt gcc aac ctc aaa tcg tgc tgt     240
His Tyr Ala Cys Gly His Ser Pro Phe Ala Asn Leu Lys Ser Cys Cys
65                  70                  75                  80 gtg ccc acc aag ctg aga ccc atg tcc atg ttg tac tat gat gat ggt     288
Val Pro Thr Lys Leu Arg Pro Met Ser Met Leu Tyr Tyr Asp Asp Gly
                85                  90                  95 caa aac atc atc aaa aag gac att cag aac atg atc gtg gag gag tgc     336
Gln Asn Ile Ile Lys Lys Asp Ile Gln Asn Met Ile Val Glu Glu Cys
            100                 105                 110 ggg tgc tcc                                                         345
Gly Cys Ser
        115

<210> SEQ ID NO 83
<211> LENGTH: 115
<212> TYPE: PRT
<213> ORGANISM: Homo sapiens

<400> SEQUENCE: 83

Gly Leu Glu Cys Asp Gly Lys Val Asn Ile Cys Cys Lys Lys Gln Phe
1               5                   10                  15

Phe Val Ser Phe Lys Asp Ile Gly Trp Asn Asp Trp Ile Ile Ala Pro
            20                  25                  30

Ser Gly Tyr His Ala Asn Tyr Cys Glu Gly Glu Cys Pro Ser His Ile
        35                  40                  45

Ala Gly Thr Ser Gly Ser Ser Leu Ser Phe His Ser Thr Val Ile Asn
50                  55                  60

His Tyr Ala Cys Gly His Ser Pro Phe Ala Asn Leu Lys Ser Cys Cys
65                  70                  75                  80

Val Pro Thr Lys Leu Arg Pro Met Ser Met Leu Tyr Tyr Asp Asp Gly
                85                  90                  95

Gln Asn Ile Ile Lys Lys Asp Ile Gln Asn Met Ile Val Glu Glu Cys
            100                 105                 110

Gly Cys Ser
        115

<210> SEQ ID NO 84
<211> LENGTH: 345
<212> TYPE: DNA
<213> ORGANISM: Homo sapiens
<220> FEATURE:
<221> NAME/KEY: CDS
<222> LOCATION: (1)..(345)
```

<400> SEQUENCE: 84

```
ggc ctg gag tgc gat ggc cgg acc aac ctc tgt tgc agg caa cag ttc      48
Gly Leu Glu Cys Asp Gly Arg Thr Asn Leu Cys Cys Arg Gln Gln Phe
1               5                   10                  15 ttc att gac ttc cgc ctc atc ggc tgg aac gac tgg atc ata gca ccc      96
Phe Ile Asp Phe Arg Leu Ile Gly Trp Asn Asp Trp Ile Ile Ala Pro
            20                  25                  30 acc ggc tac tac ggc aac tac tgt gag ggc agc tgc cca gcc tac ctg     144
Thr Gly Tyr Tyr Gly Asn Tyr Cys Glu Gly Ser Cys Pro Ala Tyr Leu
        35                  40                  45 gca ggg gtc ccc ggc tct gcc tcc tcc ttc cac acg gct gtg gtg aac     192
Ala Gly Val Pro Gly Ser Ala Ser Ser Phe His Thr Ala Val Val Asn
    50                  55                  60 cag tac cgc atg cgg ggt ctg aac ccc ggc acg gtg aac tcc tgc tgc     240
Gln Tyr Arg Met Arg Gly Leu Asn Pro Gly Thr Val Asn Ser Cys Cys
65                  70                  75                  80 att ccc acc aag ctg agc acc atg tcc atg ctg tac ttc gat gat gag     288
Ile Pro Thr Lys Leu Ser Thr Met Ser Met Leu Tyr Phe Asp Asp Glu
                85                  90                  95 tac aac atc gtc aag cgg gac gtg ccc aac atg att gtg gag gag tgc     336
Tyr Asn Ile Val Lys Arg Asp Val Pro Asn Met Ile Val Glu Glu Cys
            100                 105                 110 ggc tgc gcc                                                         345
Gly Cys Ala
        115
```

<210> SEQ ID NO 85
<211> LENGTH: 115
<212> TYPE: PRT
<213> ORGANISM: Homo sapiens

<400> SEQUENCE: 85

```
Gly Leu Glu Cys Asp Gly Arg Thr Asn Leu Cys Cys Arg Gln Gln Phe
1               5                   10                  15

Phe Ile Asp Phe Arg Leu Ile Gly Trp Asn Asp Trp Ile Ile Ala Pro
            20                  25                  30

Thr Gly Tyr Tyr Gly Asn Tyr Cys Glu Gly Ser Cys Pro Ala Tyr Leu
        35                  40                  45

Ala Gly Val Pro Gly Ser Ala Ser Ser Phe His Thr Ala Val Val Asn
    50                  55                  60

Gln Tyr Arg Met Arg Gly Leu Asn Pro Gly Thr Val Asn Ser Cys Cys
65                  70                  75                  80

Ile Pro Thr Lys Leu Ser Thr Met Ser Met Leu Tyr Phe Asp Asp Glu
                85                  90                  95

Tyr Asn Ile Val Lys Arg Asp Val Pro Asn Met Ile Val Glu Glu Cys
            100                 105                 110

Gly Cys Ala
        115
```

<210> SEQ ID NO 86
<211> LENGTH: 348
<212> TYPE: DNA
<213> ORGANISM: Homo sapiens
<220> FEATURE:
<221> NAME/KEY: CDS
<222> LOCATION: (1)..(348)

<400> SEQUENCE: 86

```
ggc atc gac tgc caa gga ggg tcc agg atg tgc tgt cga caa gag ttt      48
Gly Ile Asp Cys Gln Gly Gly Ser Arg Met Cys Cys Arg Gln Glu Phe
```

```
1               5                   10                  15 ttt gtg gac ttc cgt gag att ggc tgg cac gac tgg atc atc cag cct     96
Phe Val Asp Phe Arg Glu Ile Gly Trp His Asp Trp Ile Ile Gln Pro
             20                  25                  30 gag ggc tac gcc atg aac ttc tgc ata ggg cag tgc cca cta cac ata    144
Glu Gly Tyr Ala Met Asn Phe Cys Ile Gly Gln Cys Pro Leu His Ile
         35                  40                  45 gca ggc atg cct ggt att gct gcc tcc ttt cac act gca gtg ctc aat    192
Ala Gly Met Pro Gly Ile Ala Ala Ser Phe His Thr Ala Val Leu Asn
     50                  55                  60 ctt ctc aag gcc aac aca gct gca ggc acc act gga ggg ggc tca tgc    240
Leu Leu Lys Ala Asn Thr Ala Ala Gly Thr Thr Gly Gly Gly Ser Cys
65                  70                  75                  80 tgt gta ccc acg gcc cgg cgc ccc ctg tct ctg ctc tat tat gac agg    288
Cys Val Pro Thr Ala Arg Arg Pro Leu Ser Leu Leu Tyr Tyr Asp Arg
                 85                  90                  95 gac agc aac att gtc aag act gac ata cct gac atg gta gta gag gcc    336
Asp Ser Asn Ile Val Lys Thr Asp Ile Pro Asp Met Val Val Glu Ala
             100                 105                 110 tgt ggg tgc agt                                                    348
Cys Gly Cys Ser
        115

<210> SEQ ID NO 87
<211> LENGTH: 116
<212> TYPE: PRT
<213> ORGANISM: Homo sapiens

<400> SEQUENCE: 87

Gly Ile Asp Cys Gln Gly Gly Ser Arg Met Cys Cys Arg Gln Glu Phe
1               5                   10                  15

Phe Val Asp Phe Arg Glu Ile Gly Trp His Asp Trp Ile Ile Gln Pro
             20                  25                  30

Glu Gly Tyr Ala Met Asn Phe Cys Ile Gly Gln Cys Pro Leu His Ile
         35                  40                  45

Ala Gly Met Pro Gly Ile Ala Ala Ser Phe His Thr Ala Val Leu Asn
     50                  55                  60

Leu Leu Lys Ala Asn Thr Ala Ala Gly Thr Thr Gly Gly Gly Ser Cys
65                  70                  75                  80

Cys Val Pro Thr Ala Arg Arg Pro Leu Ser Leu Leu Tyr Tyr Asp Arg
                 85                  90                  95

Asp Ser Asn Ile Val Lys Thr Asp Ile Pro Asp Met Val Val Glu Ala
             100                 105                 110

Cys Gly Cys Ser
        115

<210> SEQ ID NO 88
<211> LENGTH: 342
<212> TYPE: DNA
<213> ORGANISM: Homo sapiens
<220> FEATURE:
<221> NAME/KEY: CDS
<222> LOCATION: (1)..(342)

<400> SEQUENCE: 88 acc ccc acc tgt gag cct gcg acc ccc tta tgt tgc agg cga gac cat     48
Thr Pro Thr Cys Glu Pro Ala Thr Pro Leu Cys Cys Arg Arg Asp His
1               5                   10                  15 tac gta gac ttc cag gaa ctg gga tgg cgg gac tgg ata ctg cag ccc     96
Tyr Val Asp Phe Gln Glu Leu Gly Trp Arg Asp Trp Ile Leu Gln Pro
```

```
            20                  25                  30
gag ggg tac cag ctg aat tac tgc agt ggg cag tgc cct ccc cac ctg      144
Glu Gly Tyr Gln Leu Asn Tyr Cys Ser Gly Gln Cys Pro Pro His Leu
         35                  40                  45 gct ggc agc cca ggc att gct gcc tct ttc cat tct gcc gtc ttc agc      192
Ala Gly Ser Pro Gly Ile Ala Ala Ser Phe His Ser Ala Val Phe Ser
 50                  55                  60 ctc ctc aaa gcc aac aat cct tgg cct gcc agt acc tcc tgt tgt gtc      240
Leu Leu Lys Ala Asn Asn Pro Trp Pro Ala Ser Thr Ser Cys Cys Val
 65                  70                  75                  80 cct act gcc cga agg ccc ctc tct ctc ctc tac ctg gat cat aat ggc      288
Pro Thr Ala Arg Arg Pro Leu Ser Leu Leu Tyr Leu Asp His Asn Gly
                 85                  90                  95 aat gtg gtc aag acg gat gtg cca gat atg gtg gtg gag gcc tgt ggc      336
Asn Val Val Lys Thr Asp Val Pro Asp Met Val Val Glu Ala Cys Gly
            100                 105                 110 tgc agc                                                               342
Cys Ser <210> SEQ ID NO 89
<211> LENGTH: 114
<212> TYPE: PRT
<213> ORGANISM: Homo sapiens

<400> SEQUENCE: 89

Thr Pro Thr Cys Glu Pro Ala Thr Pro Leu Cys Cys Arg Arg Asp His
 1               5                  10                  15

Tyr Val Asp Phe Gln Glu Leu Gly Trp Arg Asp Trp Ile Leu Gln Pro
             20                  25                  30

Glu Gly Tyr Gln Leu Asn Tyr Cys Ser Gly Gln Cys Pro Pro His Leu
         35                  40                  45

Ala Gly Ser Pro Gly Ile Ala Ala Ser Phe His Ser Ala Val Phe Ser
 50                  55                  60

Leu Leu Lys Ala Asn Asn Pro Trp Pro Ala Ser Thr Ser Cys Cys Val
 65                  70                  75                  80

Pro Thr Ala Arg Arg Pro Leu Ser Leu Leu Tyr Leu Asp His Asn Gly
                 85                  90                  95

Asn Val Val Lys Thr Asp Val Pro Asp Met Val Val Glu Ala Cys Gly
            100                 105                 110

Cys Ser

<210> SEQ ID NO 90
<211> LENGTH: 402
<212> TYPE: DNA
<213> ORGANISM: Homo sapiens
<220> FEATURE:
<221> NAME/KEY: CDS
<222> LOCATION: (1)..(402)

<400> SEQUENCE: 90 tca act ccc ctg atg tcc tgg cct tgg tct ccc tct gct ctg cgc ctg       48
Ser Thr Pro Leu Met Ser Trp Pro Trp Ser Pro Ser Ala Leu Arg Leu
 1               5                  10                  15 ctg cag agg cct ccg gag gaa ccg gct gcc cat gcc aac tgc cac aga       96
Leu Gln Arg Pro Pro Glu Glu Pro Ala Ala His Ala Asn Cys His Arg
             20                  25                  30 gta gca ctg aac atc tcc ttc cag gag ctg ggc tgg gaa cgg tgg atc      144
Val Ala Leu Asn Ile Ser Phe Gln Glu Leu Gly Trp Glu Arg Trp Ile
         35                  40                  45
```

| | | | | | | | | | | | | | | | | |
|---|---|---|---|---|---|---|---|---|---|---|---|---|---|---|---|---|
| gtg | tac | cct | ccc | agt | ttc | atc | ttc | cac | tac | tgt | cat | ggt | ggt | tgt | ggg | 192 |
| Val | Tyr | Pro | Pro | Ser | Phe | Ile | Phe | His | Tyr | Cys | His | Gly | Gly | Cys | Gly | |
| | 50 | | | | 55 | | | | 60 | | | | | | | |
| ctg | cac | atc | cca | cca | aac | ctg | tcc | ctt | cca | gtc | cct | ggg | gct | ccc | cct | 240 |
| Leu | His | Ile | Pro | Pro | Asn | Leu | Ser | Leu | Pro | Val | Pro | Gly | Ala | Pro | Pro | |
| 65 | | | | | 70 | | | | | 75 | | | | | 80 | |
| acc | cca | gcc | cag | ccc | tac | tcc | ttg | ctg | cca | ggg | gcc | cag | ccc | tgc | tgt | 288 |
| Thr | Pro | Ala | Gln | Pro | Tyr | Ser | Leu | Leu | Pro | Gly | Ala | Gln | Pro | Cys | Cys | |
| | | | | 85 | | | | | 90 | | | | | 95 | | |
| gct | gct | ctc | cca | ggg | acc | atg | agg | ccc | cta | cat | gtc | cgc | acc | acc | tcg | 336 |
| Ala | Ala | Leu | Pro | Gly | Thr | Met | Arg | Pro | Leu | His | Val | Arg | Thr | Thr | Ser | |
| | | | | 100 | | | | | 105 | | | | | 110 | | |
| gat | gga | ggt | tac | tct | ttc | aag | tat | gag | aca | gtg | ccc | aac | ctt | ctc | acg | 384 |
| Asp | Gly | Gly | Tyr | Ser | Phe | Lys | Tyr | Glu | Thr | Val | Pro | Asn | Leu | Leu | Thr | |
| | | | 115 | | | | | 120 | | | | | 125 | | | |
| cag | cac | tgt | gct | tgt | atc | | | | | | | | | | | 402 |
| Gln | His | Cys | Ala | Cys | Ile | | | | | | | | | | | |
| | 130 | | | | | | | | | | | | | | | |

<210> SEQ ID NO 91
<211> LENGTH: 134
<212> TYPE: PRT
<213> ORGANISM: Homo sapiens

<400> SEQUENCE: 91

Ser Thr Pro Leu Met Ser Trp Pro Trp Ser Pro Ser Ala Leu Arg Leu
1               5                   10                  15

Leu Gln Arg Pro Pro Glu Glu Pro Ala Ala His Ala Asn Cys His Arg
            20                  25                  30

Val Ala Leu Asn Ile Ser Phe Gln Glu Leu Gly Trp Glu Arg Trp Ile
        35                  40                  45

Val Tyr Pro Pro Ser Phe Ile Phe His Tyr Cys His Gly Gly Cys Gly
    50                  55                  60

Leu His Ile Pro Pro Asn Leu Ser Leu Pro Val Pro Gly Ala Pro Pro
65                  70                  75                  80

Thr Pro Ala Gln Pro Tyr Ser Leu Leu Pro Gly Ala Gln Pro Cys Cys
                85                  90                  95

Ala Ala Leu Pro Gly Thr Met Arg Pro Leu His Val Arg Thr Thr Ser
            100                 105                 110

Asp Gly Gly Tyr Ser Phe Lys Tyr Glu Thr Val Pro Asn Leu Leu Thr
        115                 120                 125

Gln His Cys Ala Cys Ile
    130

<210> SEQ ID NO 92
<211> LENGTH: 336
<212> TYPE: DNA
<213> ORGANISM: Homo sapiens
<220> FEATURE:
<221> NAME/KEY: CDS
<222> LOCATION: (1)..(336)

<400> SEQUENCE: 92

| | | | | | | | | | | | | | | | | |
|---|---|---|---|---|---|---|---|---|---|---|---|---|---|---|---|---|
| gcc | ctg | gac | acc | aac | tat | tgc | ttc | agc | tcc | acg | gag | aag | aac | tgc | tgc | 48 |
| Ala | Leu | Asp | Thr | Asn | Tyr | Cys | Phe | Ser | Ser | Thr | Glu | Lys | Asn | Cys | Cys | |
| 1 | | | | 5 | | | | | 10 | | | | | 15 | | |
| gtg | cgg | cag | ctg | tac | att | gac | ttc | cgc | aag | gac | ctc | ggc | tgg | aag | tgg | 96 |
| Val | Arg | Gln | Leu | Tyr | Ile | Asp | Phe | Arg | Lys | Asp | Leu | Gly | Trp | Lys | Trp | |
| | | | 20 | | | | | 25 | | | | | 30 | | | |
| atc | cac | gag | ccc | aag | ggc | tac | cat | gcc | aac | ttc | tgc | ctc | ggg | ccc | tgc | 144 |

```
ccc tac att tgg agc ctg gac acg cag tac agc aag gtc ctg gcc ctg        192
Pro Tyr Ile Trp Ser Leu Asp Thr Gln Tyr Ser Lys Val Leu Ala Leu
    50                  55                  60 tac aac cag cat aac ccg ggc gcc tcg gcg gcg ccg tgc tgc gtg ccg        240
Tyr Asn Gln His Asn Pro Gly Ala Ser Ala Ala Pro Cys Cys Val Pro
65                  70                  75                  80 cag gcg ctg gag ccg ctg ccc atc gtg tac tac gtg ggc cgc aag ccc        288
Gln Ala Leu Glu Pro Leu Pro Ile Val Tyr Tyr Val Gly Arg Lys Pro
                85                  90                  95 aag gtg gag cag ctg tcc aac atg atc gtg cgc tcc tgc aag tgc agc        336
Lys Val Glu Gln Leu Ser Asn Met Ile Val Arg Ser Cys Lys Cys Ser
            100                 105                 110
```

<210> SEQ ID NO 93
<211> LENGTH: 112
<212> TYPE: PRT
<213> ORGANISM: Homo sapiens

<400> SEQUENCE: 93

```
Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
                20                  25                  30

Ile His Glu Pro Lys Gly Tyr His Ala Asn Phe Cys Leu Gly Pro Cys
            35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110
```

<210> SEQ ID NO 94
<211> LENGTH: 336
<212> TYPE: DNA
<213> ORGANISM: Homo sapiens
<220> FEATURE:
<221> NAME/KEY: CDS
<222> LOCATION: (1)..(336)

<400> SEQUENCE: 94

```
gct ttg gat gcg gcc tat tgc ttt aga aat gtg cag gat aat tgc tgc        48
Ala Leu Asp Ala Ala Tyr Cys Phe Arg Asn Val Gln Asp Asn Cys Cys
1               5                   10                  15 cta cgt cca ctt tac att gat ttc aag agg gat cta ggg tgg aaa tgg        96
Leu Arg Pro Leu Tyr Ile Asp Phe Lys Arg Asp Leu Gly Trp Lys Trp
                20                  25                  30 ata cac gaa ccc aaa ggg tac aat gcc aac ttc tgt gct gga gca tgc        144
Ile His Glu Pro Lys Gly Tyr Asn Ala Asn Phe Cys Ala Gly Ala Cys
            35                  40                  45 ccg tat tta tgg agt tca gac act cag cac agc agg gtc ctg agc tta        192
Pro Tyr Leu Trp Ser Ser Asp Thr Gln His Ser Arg Val Leu Ser Leu
    50                  55                  60 tat aat acc ata aat cca gaa gca tct gct tct cct tgc tgc gtg tcc        240
Tyr Asn Thr Ile Asn Pro Glu Ala Ser Ala Ser Pro Cys Cys Val Ser
65                  70                  75                  80
```

-continued

```
caa gat tta gaa cct cta acc att ctc tac tac att ggc aaa aca ccc      288
Gln Asp Leu Glu Pro Leu Thr Ile Leu Tyr Tyr Ile Gly Lys Thr Pro
                85                  90                  95 aag att gaa cag ctt tct aat atg att gta aag tct tgc aaa tgc agc      336
Lys Ile Glu Gln Leu Ser Asn Met Ile Val Lys Ser Cys Lys Cys Ser
            100                 105                 110

<210> SEQ ID NO 95
<211> LENGTH: 112
<212> TYPE: PRT
<213> ORGANISM: Homo sapiens

<400> SEQUENCE: 95

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
                20                  25                  30

Ile His Glu Pro Lys Gly Tyr Asn Ala Asn Phe Cys Ala Gly Ala Cys
            35                  40                  45

Pro Tyr Leu Trp Ser Ser Asp Thr Gln His Ser Arg Val Leu Ser Leu
        50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

<210> SEQ ID NO 96
<211> LENGTH: 336
<212> TYPE: DNA
<213> ORGANISM: Homo sapiens
<220> FEATURE:
<221> NAME/KEY: CDS
<222> LOCATION: (1)..(336)

<400> SEQUENCE: 96 gct ttg gac acc aat tac tgc ttc cgc aac ttg gag gag aac tgc tgt      48
Ala Leu Asp Thr Asn Tyr Cys Phe Arg Asn Leu Glu Glu Asn Cys Cys
1               5                   10                  15 gtg cgc ccc ctc tac att gac ttc cga cag gat ctg ggc tgg aag tgg      96
Val Arg Pro Leu Tyr Ile Asp Phe Arg Gln Asp Leu Gly Trp Lys Trp
                20                  25                  30 gtc cat gaa cct aag ggc tac tat gcc aac ttc tgc tca ggc cct tgc      144
Val His Glu Pro Lys Gly Tyr Tyr Ala Asn Phe Cys Ser Gly Pro Cys
            35                  40                  45 cca tac ctc cgc agt gca gac aca acc cac agc acg gtg ctg gga ctg      192
Pro Tyr Leu Arg Ser Ala Asp Thr Thr His Ser Thr Val Leu Gly Leu
        50                  55                  60 tac aac act ctg aac cct gaa gca tct gcc tcg cct tgc tgc gtg ccc      240
Tyr Asn Thr Leu Asn Pro Glu Ala Ser Ala Ser Pro Cys Cys Val Pro
65                  70                  75                  80 cag gac ctg gag ccc ctg acc atc ctg tac tat gtt ggg agg acc ccc      288
Gln Asp Leu Glu Pro Leu Thr Ile Leu Tyr Tyr Val Gly Arg Thr Pro
                85                  90                  95 aaa gtg gag cag ctc tcc aac atg gtg gtg aag tct tgt aaa tgt agc      336
Lys Val Glu Gln Leu Ser Asn Met Val Val Lys Ser Cys Lys Cys Ser
            100                 105                 110

<210> SEQ ID NO 97
<211> LENGTH: 112
```

```
<212> TYPE: PRT
<213> ORGANISM: Homo sapiens

<400> SEQUENCE: 97

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110

<210> SEQ ID NO 98
<211> LENGTH: 30
<212> TYPE: PRT
<213> ORGANISM: Artificial Sequence
<220> FEATURE:
<223> OTHER INFORMATION: Section 1 of BMP-2

<400> SEQUENCE: 98

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp
            20                  25                  30

<210> SEQ ID NO 99
<211> LENGTH: 18
<212> TYPE: PRT
<213> ORGANISM: Artificial Sequence
<220> FEATURE:
<223> OTHER INFORMATION: Section 2 of BMP-2

<400> SEQUENCE: 99

Trp Ile Val Ala Pro Pro Gly Tyr His Ala Phe Tyr Cys His Gly Glu
1               5                   10                  15

Cys Pro

<210> SEQ ID NO 100
<211> LENGTH: 20
<212> TYPE: PRT
<213> ORGANISM: Artificial Sequence
<220> FEATURE:
<223> OTHER INFORMATION: Section 3 of BMP-2

<400> SEQUENCE: 100

Phe Pro Leu Ala Asp His Leu Asn Ser Thr Asn His Ala Ile Val Gln
1               5                   10                  15

Thr Leu Val Asn
            20

<210> SEQ ID NO 101
<211> LENGTH: 13
<212> TYPE: PRT
<213> ORGANISM: Artificial Sequence
<220> FEATURE:
```

<223> OTHER INFORMATION: Section 4 of BMP-2

<400> SEQUENCE: 101

Ser Val Asn Ser Lys Ile Pro Lys Ala Cys Cys Val Pro
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Section 5 of BMP-2

<400> SEQUENCE: 102

Thr Glu Leu Ser Ala Ile Ser Met Leu Tyr Tyr Asp
1               5                   10

<210> SEQ ID NO 103
<211> LENGTH: 21
<212> TYPE: PRT
<213> ORGANISM: Artificial Sequence
<220> FEATURE:
<223> OTHER INFORMATION: Section 6 of BMP-2

<400> SEQUENCE: 103

Glu Asn Glu Lys Val Val Leu Lys Asn Tyr Gln Asp Met Val Val Glu
1               5                   10                  15

Gly Cys Gly Cys Arg
            20

<210> SEQ ID NO 104
<211> LENGTH: 29
<212> TYPE: PRT
<213> ORGANISM: Artificial Sequence
<220> FEATURE:
<223> OTHER INFORMATION: Section 1 of activin-betaA

<400> SEQUENCE: 104

Arg Gly Leu Glu Cys Asp Gly Lys Val Asn Ile Cys Cys Lys Lys Gln
1               5                   10                  15

Phe Phe Val Ser Phe Lys Asp Ile Gly Trp Asn Asp Trp
            20                  25

<210> SEQ ID NO 105
<211> LENGTH: 18
<212> TYPE: PRT
<213> ORGANISM: Artificial Sequence
<220> FEATURE:
<223> OTHER INFORMATION: Section 2 of activin-betaA

<400> SEQUENCE: 105

Trp Ile Ile Ala Pro Ser Gly Tyr His Ala Asn Tyr Cys Glu Gly Glu
1               5                   10                  15

Cys Pro

<210> SEQ ID NO 106
<211> LENGTH: 19
<212> TYPE: PRT
<213> ORGANISM: Artificial Sequence
<220> FEATURE:
<223> OTHER INFORMATION: Section 3 of activin-betaA

<400> SEQUENCE: 106

Ser His Ile Ala Gly Thr Ser Gly Ser Ser Leu Ser Phe His Ser Thr
1               5                   10                  15

Leu Val Asn

<210> SEQ ID NO 107
<211> LENGTH: 19
<212> TYPE: PRT
<213> ORGANISM: Artificial Sequence
<220> FEATURE:
<223> OTHER INFORMATION: Section 4 of activin-betaA

<400> SEQUENCE: 107

His Tyr Arg Met Arg Gly His Ser Pro Phe Ala Asn Leu Lys Ser Cys
1               5                   10                  15

Cys Val Pro

<210> SEQ ID NO 108
<211> LENGTH: 12
<212> TYPE: PRT
<213> ORGANISM: Artificial Sequence
<220> FEATURE:
<223> OTHER INFORMATION: Section 5 of activin-betaA

<400> SEQUENCE: 108

Thr Lys Leu Arg Pro Met Ser Met Leu Tyr Tyr Asp
1               5                   10

<210> SEQ ID NO 109
<211> LENGTH: 21
<212> TYPE: PRT
<213> ORGANISM: Artificial Sequence
<220> FEATURE:
<223> OTHER INFORMATION: Section 6 of activin-betaA

<400> SEQUENCE: 109

Asp Gly Gln Asn Ile Ile Lys Lys Asp Ile Gln Asn Met Ile Val Glu
1               5                   10                  15

Glu Cys Gly Cys Ser
            20

<210> SEQ ID NO 110
<211> LENGTH: 32
<212> TYPE: PRT
<213> ORGANISM: Artificial Sequence
<220> FEATURE:
<223> OTHER INFORMATION: BMP-2 Sequence

<400> SEQUENCE: 110

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Ile Ile
            20                  25                  30

<210> SEQ ID NO 111
<211> LENGTH: 345
<212> TYPE: DNA
<213> ORGANISM: Artificial Sequence
<220> FEATURE:
<223> OTHER INFORMATION: AB2-016

<400> SEQUENCE: 111
atgcaagcca aacacaaaca gcggaagcgt cttaagtcca gctgcaaaag gcacccttg      60 tatgtggact tcagtgatgt ggggtggaat gactggatca ttgctccctc tggctatcat   120
gccaactact gcgagggaga atgccctttt cctctggctg atcatctgaa ctccactaat   180

```
cacgccattg ttcagacgtt ggtcaactct gttaactcta agattcctaa ggcatgctgt    240
gtcccgacag aactcagtgc tatctcgatg ctgtaccttg acgagaatga aaaggttgta    300
ttaaagaact atcaggacat ggttgtggag ggttgcgggt gtcgt                    345
```

```
<210> SEQ ID NO 112
<211> LENGTH: 115
<212> TYPE: PRT
<213> ORGANISM: Artificial Sequence
<220> FEATURE:
<223> OTHER INFORMATION: AB2-016

<400> SEQUENCE: 112
```

| Met | Gln | Ala | Lys | His | Lys | Gln | Arg | Lys | Arg | Leu | Lys | Ser | Ser | Cys | Lys |
|---|---|---|---|---|---|---|---|---|---|---|---|---|---|---|---|
| 1 | | | | 5 | | | | | 10 | | | | | 15 | |

| Arg | His | Pro | Leu | Tyr | Val | Asp | Phe | Ser | Asp | Val | Gly | Trp | Asn | Asp | Trp |
|---|---|---|---|---|---|---|---|---|---|---|---|---|---|---|---|
| | | | 20 | | | | | 25 | | | | | 30 | | |

| Ile | Ile | Ala | Pro | Ser | Gly | Tyr | His | Ala | Asn | Tyr | Cys | Glu | Gly | Glu | Cys |
|---|---|---|---|---|---|---|---|---|---|---|---|---|---|---|---|
| | | 35 | | | | | 40 | | | | | 45 | | | |

| Pro | Phe | Pro | Leu | Ala | Asp | His | Leu | Asn | Ser | Thr | Asn | His | Ala | Ile | Val |
|---|---|---|---|---|---|---|---|---|---|---|---|---|---|---|---|
| | 50 | | | | | 55 | | | | | 60 | | | | |

| Gln | Thr | Leu | Val | Asn | Ser | Val | Asn | Ser | Lys | Ile | Pro | Lys | Ala | Cys | Cys |
|---|---|---|---|---|---|---|---|---|---|---|---|---|---|---|---|
| 65 | | | | | 70 | | | | | 75 | | | | | 80 |

| Val | Pro | Thr | Glu | Leu | Ser | Ala | Ile | Ser | Met | Leu | Tyr | Leu | Asp | Glu | Asn |
|---|---|---|---|---|---|---|---|---|---|---|---|---|---|---|---|
| | | | | 85 | | | | | 90 | | | | | 95 | |

| Glu | Lys | Val | Val | Leu | Lys | Asn | Tyr | Gln | Asp | Met | Val | Val | Glu | Gly | Cys |
|---|---|---|---|---|---|---|---|---|---|---|---|---|---|---|---|
| | | | 100 | | | | | 105 | | | | | 110 | | |

| Gly | Cys | Arg |
|---|---|---|
| | | 115 |

```
<210> SEQ ID NO 113
<211> LENGTH: 363
<212> TYPE: DNA
<213> ORGANISM: Artificial Sequence
<220> FEATURE:
<223> OTHER INFORMATION: AB2-017

<400> SEQUENCE: 113
```

```
atgcaagcca aacacaaaca gcggaaacgc cttaagtcca gctgtaagag acacccttttg   60 tacgtggact tcagtgacgt ggggtggaat gactggattg tggctccccc ggggtatcac   120 gcctttttact gccacggaga atgccctttt cctctggctg atcatctgaa ctccactaat   180
catgccattg ttcagacgtt ggtcaaccac taccgcatgc ggggccatag ccccttttgcc   240 aacctcaaat cgtgctgtgt cccgaccaag ctgagaccca tgtccatgtt gtactatgat   300
gatggtcaaa acatcatcaa aaaggacatt cagaacatga tcgtggagga gtgtgggtgc   360
tca                                                                   363
```

```
<210> SEQ ID NO 114
<211> LENGTH: 121
<212> TYPE: PRT
<213> ORGANISM: Artificial Sequence
<220> FEATURE:
<223> OTHER INFORMATION: AB2-017

<400> SEQUENCE: 114
```

| Met | Gln | Ala | Lys | His | Lys | Gln | Arg | Lys | Arg | Leu | Lys | Ser | Ser | Cys | Lys |
|---|---|---|---|---|---|---|---|---|---|---|---|---|---|---|---|
| 1 | | | | 5 | | | | | 10 | | | | | 15 | |

| Arg | His | Pro | Leu | Tyr | Val | Asp | Phe | Ser | Asp | Val | Gly | Trp | Asn | Asp | Trp |
|---|---|---|---|---|---|---|---|---|---|---|---|---|---|---|---|
| | | | 20 | | | | | 25 | | | | | 30 | | |

```
Ile Val Ala Pro Pro Gly Tyr His Ala Phe Tyr Cys His Gly Glu Cys
            35                  40                  45

Pro Phe Pro Leu Ala Asp His Leu Asn Ser Thr Asn His Ala Ile Val
 50                  55                  60

Gln Thr Leu Val Asn His Tyr Arg Met Arg Gly His Ser Pro Phe Ala
 65                  70                  75                  80

Asn Leu Lys Ser Cys Cys Val Pro Thr Lys Leu Arg Pro Met Ser Met
                 85                  90                  95

Leu Tyr Tyr Asp Asp Gly Gln Asn Ile Ile Lys Lys Asp Ile Gln Asn
                100                 105                 110

Met Ile Val Glu Glu Cys Gly Cys Ser
            115                 120

<210> SEQ ID NO 115
<211> LENGTH: 363
<212> TYPE: DNA
<213> ORGANISM: Artificial Sequence
<220> FEATURE:
<223> OTHER INFORMATION: AB2-018

<400> SEQUENCE: 115
atgcaagcca aacacaaaca gcggaaacgc cttaagtcca gctgtaagag acacccttg      60 tacgtggact tcagtgacgt ggggtggaat gactggattg tggctccccc ggggtatcac    120
gccttttact gccacggaga atgcccttt cctctggctg atcatctgaa ctccactaat     180
catgccattg ttcagacgtt ggtcaaccac taccgcatgc ggggccatag ccccttgcc    240 aacctcaaat cgtgctgtgt cccgacagaa ctcagtgcta tctcgatact gtaccttgac   300
gagaatgaaa aggttgtatt aaagaactat caggacatgg ttgtggaggg ttgtgggtgt   360
cgc                                                                  363

<210> SEQ ID NO 116
<211> LENGTH: 121
<212> TYPE: PRT
<213> ORGANISM: Artificial Sequence
<220> FEATURE:
<223> OTHER INFORMATION: AB2-018

<400> SEQUENCE: 116

Met Gln Ala Lys His Lys Gln Arg Lys Arg Leu Lys Ser Ser Cys Lys
 1               5                  10                  15

Arg His Pro Leu Tyr Val Asp Phe Ser Asp Val Gly Trp Asn Asp Trp
                 20                  25                  30

Ile Val Ala Pro Pro Gly Tyr His Ala Phe Tyr Cys His Gly Glu Cys
            35                  40                  45

Pro Phe Pro Leu Ala Asp His Leu Asn Ser Thr Asn His Ala Ile Val
 50                  55                  60

Gln Thr Leu Val Asn His Tyr Arg Met Arg Gly His Ser Pro Phe Ala
 65                  70                  75                  80

Asn Leu Lys Ser Cys Cys Val Pro Thr Glu Leu Ser Ala Ile Ser Ile
                 85                  90                  95

Leu Tyr Leu Asp Glu Asn Glu Lys Val Val Leu Lys Asn Tyr Gln Asp
                100                 105                 110

Met Val Val Glu Gly Cys Gly Cys Arg
            115                 120

<210> SEQ ID NO 117
```

```
<211> LENGTH: 363
<212> TYPE: DNA
<213> ORGANISM: Artificial Sequence
<220> FEATURE:
<223> OTHER INFORMATION: AB2-019

<400> SEQUENCE: 117
atgcaagcca aacacaaaca gcggaaacgc cttaagtcca gctgtaagag acacccttttg    60 tacgtggact tcagtgacgt ggggtggaat gactggattg tggctccccc ggggtatcac   120 gcctttttact gccacggaga atgcccttttt cctctggctg atcatctgaa ctccactaat   180
catgccattg ttcagacgtt ggtcaaccac taccgcatgc ggggccatag cccctttgcc   240
aacctcaaat cgtgctgtgt cccgaccaag ctgagaccca tgtccatgtt gtactatgat   300
gagaatgaaa aggttgtatt aaagaactat caggacatgg ttgtggaggg ttgcgggtgt   360
cgt                                                                 363

<210> SEQ ID NO 118
<211> LENGTH: 121
<212> TYPE: PRT
<213> ORGANISM: Artificial Sequence
<220> FEATURE:
<223> OTHER INFORMATION: AB2-019

<400> SEQUENCE: 118

Met Gln Ala Lys His Lys Gln Arg Lys Arg Leu Lys Ser Ser Cys Lys
1               5                   10                  15

Arg His Pro Leu Tyr Val Asp Phe Ser Asp Val Gly Trp Asn Asp Trp
                20                  25                  30

Ile Val Ala Pro Pro Gly Tyr His Ala Phe Tyr Cys His Gly Glu Cys
            35                  40                  45

Pro Phe Pro Leu Ala Asp His Leu Asn Ser Thr Asn His Ala Ile Val
        50                  55                  60

Gln Thr Leu Val Asn His Tyr Arg Met Arg Gly His Ser Pro Phe Ala
65                  70                  75                  80

Asn Leu Lys Ser Cys Cys Val Pro Thr Lys Leu Arg Pro Met Ser Met
                85                  90                  95

Leu Tyr Tyr Asp Glu Asn Glu Lys Val Val Leu Lys Asn Tyr Gln Asp
                100                 105                 110

Met Val Val Glu Gly Cys Gly Cys Arg
            115                 120

<210> SEQ ID NO 119
<211> LENGTH: 363
<212> TYPE: DNA
<213> ORGANISM: Artificial Sequence
<220> FEATURE:
<223> OTHER INFORMATION: AB2-020

<400> SEQUENCE: 119
atgcaagcca aacacaaaca gcggaaacgc cttaagtcca gctgtaagag acacccttttg    60 tacgtggact tcagtgacgt ggggtggaat gactggattg tggctccccc ggggtatcac   120 gcctttttact gccacggaga atgcccttttt cctctggctg atcatctgaa ctccactaat   180
catgccattg ttcagacgtt ggtcaaccac taccgcatgc ggggccatag cccctttgcc   240
aacctcaaat cgtgctgtgt cccgacagaa ctcagtgcta tctcgatgtt gtactatgat   300
gatggtcaaa acatcatcaa aaaggacatt cagaacatga tcgtggagga gtgtgggtgc   360
tca                                                                 363
```

<210> SEQ ID NO 120
<211> LENGTH: 121
<212> TYPE: PRT
<213> ORGANISM: Artificial Sequence
<220> FEATURE:
<223> OTHER INFORMATION: AB2-020

<400> SEQUENCE: 120

```
Met Gln Ala Lys His Lys Gln Arg Lys Arg Leu Lys Ser Ser Cys Lys
1               5                   10                  15

Arg His Pro Leu Tyr Val Asp Phe Ser Asp Val Gly Trp Asn Asp Trp
            20                  25                  30

Ile Val Ala Pro Pro Gly Tyr His Ala Phe Tyr Cys His Gly Glu Cys
        35                  40                  45

Pro Phe Pro Leu Ala Asp His Leu Asn Ser Thr Asn His Ala Ile Val
    50                  55                  60

Gln Thr Leu Val Asn His Tyr Arg Met Arg Gly His Ser Pro Phe Ala
65                  70                  75                  80

Asn Leu Lys Ser Cys Cys Val Pro Thr Glu Leu Ser Ala Ile Ser Met
                85                  90                  95

Leu Tyr Tyr Asp Asp Gly Gln Asn Ile Ile Lys Lys Asp Ile Gln Asn
            100                 105                 110

Met Ile Val Glu Glu Cys Gly Cys Ser
        115                 120
```

<210> SEQ ID NO 121
<211> LENGTH: 360
<212> TYPE: DNA
<213> ORGANISM: Artificial Sequence
<220> FEATURE:
<223> OTHER INFORMATION: AB2-021

<400> SEQUENCE: 121

```
atgcaagcca aacacaaaca gcggaaacgc cttaagtcca gctgtaagag acacccttg      60
tatgtggact tcagtgacgt ggggtggaat gactggattg tggctccccc ggggtatcac    120
gccttttact gccacggaga atgcccttct catatagcag gcacgtccgg gtcctcactg    180
tccttccact caacgttggt caaccactac cgcatgcggg ccatagcccc ctttgccaac    240
ctcaaatcgt gctgtgtccc gaccaagctg agacccatgt ccatgttgta ccttgacgag    300
aatgaaaagg ttgtattaaa gaactatcag gacatggttg tggagggttg tgggtgtcgc    360
```

<210> SEQ ID NO 122
<211> LENGTH: 120
<212> TYPE: PRT
<213> ORGANISM: Artificial Sequence
<220> FEATURE:
<223> OTHER INFORMATION: AB2-021

<400> SEQUENCE: 122

```
Met Gln Ala Lys His Lys Gln Arg Lys Arg Leu Lys Ser Ser Cys Lys
1               5                   10                  15

Arg His Pro Leu Tyr Val Asp Phe Ser Asp Val Gly Trp Asn Asp Trp
            20                  25                  30

Ile Val Ala Pro Pro Gly Tyr His Ala Phe Tyr Cys His Gly Glu Cys
        35                  40                  45

Pro Ser His Ile Ala Gly Thr Ser Gly Ser Ser Leu Ser Phe His Ser
    50                  55                  60
```

```
Thr Leu Val Asn His Tyr Arg Met Arg Gly His Ser Pro Phe Ala Asn
 65                  70                  75                  80

Leu Lys Ser Cys Cys Val Pro Thr Lys Leu Arg Pro Met Ser Met Leu
                 85                  90                  95

Tyr Leu Asp Glu Asn Glu Lys Val Val Leu Lys Asn Tyr Gln Asp Met
            100                 105                 110

Val Val Glu Gly Cys Gly Cys Arg
        115                 120

<210> SEQ ID NO 123
<211> LENGTH: 351
<212> TYPE: DNA
<213> ORGANISM: Artificial Sequence
<220> FEATURE:
<223> OTHER INFORMATION: AB2-022

<400> SEQUENCE: 123
atgcaagcca aacacaaaca gcggaaacgc cttaagtcca gctgtaagag acacccttttg      60 tacgtggact tcagtgacgt ggggtggaat gactggattg tggctccccc ggggtatcac     120
gccttttact gccacggaga atgcccttct catatagcag gcacgtccgg gtcctcactg     180
tccttccact caacgttggt caaccactac cgcatgcggg ccatagccc ctttgccaac     240 ctcaaatcgt gctgtgtccc gacagaactc agtgctatct cgatgttgta ctatgatgag     300
aatgaaaagg ttgtattaaa gaactatcag gacatggttg tggagggttg c             351

<210> SEQ ID NO 124
<211> LENGTH: 120
<212> TYPE: PRT
<213> ORGANISM: Artificial Sequence
<220> FEATURE:
<223> OTHER INFORMATION: AB2-022

<400> SEQUENCE: 124

Met Gln Ala Lys His Lys Gln Arg Lys Arg Leu Lys Ser Ser Cys Lys
  1               5                  10                  15

Arg His Pro Leu Tyr Val Asp Phe Ser Asp Val Gly Trp Asn Asp Trp
                20                  25                  30

Ile Val Ala Pro Pro Gly Tyr His Ala Phe Tyr Cys His Gly Glu Cys
             35                  40                  45

Pro Ser His Ile Ala Gly Thr Ser Gly Ser Ser Leu Ser Phe His Ser
         50                  55                  60

Thr Leu Val Asn His Tyr Arg Met Arg Gly His Ser Pro Phe Ala Asn
 65                  70                  75                  80

Leu Lys Ser Cys Cys Val Pro Thr Glu Leu Ser Ala Ile Ser Met Leu
                 85                  90                  95

Tyr Leu Asp Glu Asn Glu Lys Val Val Leu Lys Asn Tyr Gln Asp Met
            100                 105                 110

Val Val Glu Gly Cys Gly Cys Arg
        115                 120

<210> SEQ ID NO 125
<211> LENGTH: 342
<212> TYPE: DNA
<213> ORGANISM: Artificial Sequence
<220> FEATURE:
<223> OTHER INFORMATION: AB2-023

<400> SEQUENCE: 125
atgcaagcca aacacaaaca gcggaaacgc cttaagtcca gctgtaagag acacccttttg      60
```

```
tacgtggact tcagtgacgt ggggtggaat gactggattg tggctccccc ggggtatcac    120 gcctttact gccacggaga atgcccttct catatagcag gcacgtccgg gtcctcactg     180
tccttccact caacgttggt caactctgtt aactctaaga ttcctaaggc atgctgtgtc    240
ccgacagaac tcagtgctat ctcgatgctg taccttgacg agaatgaaaa ggttgtatta    300
aagaactatc aggacatggt tgtggagggt tgcgggtgtc gt                      342
```

<210> SEQ ID NO 126
<211> LENGTH: 114
<212> TYPE: PRT
<213> ORGANISM: Artificial Sequence
<220> FEATURE:
<223> OTHER INFORMATION: AB2-023

<400> SEQUENCE: 126

```
Met Gln Ala Lys His Lys Gln Arg Lys Arg Leu Lys Ser Ser Cys Lys
1               5                   10                  15

Arg His Pro Leu Tyr Val Asp Phe Ser Asp Val Gly Trp Asn Asp Trp
            20                  25                  30

Ile Val Ala Pro Pro Gly Tyr His Ala Phe Tyr Cys His Gly Glu Cys
        35                  40                  45

Pro Ser His Ile Ala Gly Thr Ser Gly Ser Ser Leu Ser Phe His Ser
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg
```

<210> SEQ ID NO 127
<211> LENGTH: 342
<212> TYPE: DNA
<213> ORGANISM: Artificial Sequence
<220> FEATURE:
<223> OTHER INFORMATION: AB2-024

<400> SEQUENCE: 127

```
atgcaagcca aacacaaaca gcggaaacgc cttaagtcca gctgtaagag acacccttg     60 tacgtggact tcagtgacgt ggggtggaat gactggattg tggctccccc ggggtatcac    120 gcctttact gccacggaga atgcccttct catatagcag gcacgtccgg gtcctcactg     180
tccttccact caacgttggt caactctgtt aactctaaga ttcctaaggc atgctgtgtc    240
ccgacagaac tcagtgctat ctcgatgttg tactatgatg atggtcaaaa catcatcaaa    300
aaggacattc agaacatgat cgtggaggag tgtgggtgct ca                      342
```

<210> SEQ ID NO 128
<211> LENGTH: 114
<212> TYPE: PRT
<213> ORGANISM: Artificial Sequence
<220> FEATURE:
<223> OTHER INFORMATION: AB2-024

<400> SEQUENCE: 128

```
Met Gln Ala Lys His Lys Gln Arg Lys Arg Leu Lys Ser Ser Cys Lys
1               5                   10                  15
```

Arg His Pro Leu Tyr Val Asp Phe Ser Asp Val Gly Trp Asn Asp Trp
            20                  25                  30

Ile Val Ala Pro Pro Gly Tyr His Ala Phe Tyr Cys His Gly Glu Cys
             35                  40                  45

Pro Ser His Ile Ala Gly Thr Ser Gly Ser Ser Leu Ser Phe His Ser
         50                  55                  60

Thr Leu Val Asn Ser Val Asn Ser Lys Ile Pro Lys Ala Cys Cys Val
 65                  70                  75                  80

Pro Thr Glu Leu Ser Ala Ile Ser Met Leu Tyr Tyr Asp Asp Gly Gln
                 85                  90                  95

Asn Ile Ile Lys Lys Asp Ile Gln Asn Met Ile Val Glu Glu Cys Gly
            100                 105                 110

Cys Ser

<210> SEQ ID NO 129
<211> LENGTH: 342
<212> TYPE: DNA
<213> ORGANISM: Artificial Sequence
<220> FEATURE:
<223> OTHER INFORMATION: AB2-025

<400> SEQUENCE: 129
atgcaagcca aacacaaaca gcggaaacgc cttaagtcca gctgtaagag acacccttg      60 tacgtggact tcagtgacgt ggggtggaat gactggattg tggctccccc ggggtatcac    120 gcctttact gccacggaga atgcccttct catatagcag gcacgtccgg gtcctcactg     180
tccttccact caacgttggt caactctgtt aactctaaga ttcctaaggc atgctgtgtc    240
ccgaccaagc tgagacccat gtccatgttg tactatgatg atggtcaaaa catcatcaaa    300
aaggacattc agaacatgat cgtggaggag tgtgggtgct ca                      342

<210> SEQ ID NO 130
<211> LENGTH: 114
<212> TYPE: PRT
<213> ORGANISM: Artificial Sequence
<220> FEATURE:
<223> OTHER INFORMATION: AB2-025

<400> SEQUENCE: 130

Met Gln Ala Lys His Lys Gln Arg Lys Arg Leu Lys Ser Ser Cys Lys
 1               5                  10                  15

Arg His Pro Leu Tyr Val Asp Phe Ser Asp Val Gly Trp Asn Asp Trp
            20                  25                  30

Ile Val Ala Pro Pro Gly Tyr His Ala Phe Tyr Cys His Gly Glu Cys
         35                  40                  45

Pro Ser His Ile Ala Gly Thr Ser Gly Ser Ser Leu Ser Phe His Ser
     50                  55                  60

Thr Leu Val Asn Ser Val Asn Ser Lys Ile Pro Lys Ala Cys Cys Val
 65                  70                  75                  80

Pro Thr Lys Leu Arg Pro Met Ser Met Leu Tyr Tyr Asp Asp Gly Gln
                 85                  90                  95

Asn Ile Ile Lys Lys Asp Ile Gln Asn Met Ile Val Glu Glu Cys Gly
            100                 105                 110

Cys Ser

<210> SEQ ID NO 131
<211> LENGTH: 342
<212> TYPE: DNA

<213> ORGANISM: Artificial Sequence
<220> FEATURE:
<223> OTHER INFORMATION: AB2-026

<400> SEQUENCE: 131

```
atgcaagcca aacacaaaca gcggaaacgc cttaagtcca gctgtaagag acacccttg      60
tacgtggact tcagtgacgt ggggtggaat gactggattg tggctccccc ggggtatcac    120
gcctttact gccacggaga atgcccttct catatagcag gcacgtccgg gtcctcactg     180
tccttccact caacgttggt caactctgtt aactctaaga ttcctaaggc atgctgtgtc    240
ccgaccaagc tgagacccat gtccatgttg tactatgatg agaatgaaaa ggttgtatta    300
agaactatc aggacatggt tgtggagggt tgcgggtgtc gt                        342
```

<210> SEQ ID NO 132
<211> LENGTH: 114
<212> TYPE: PRT
<213> ORGANISM: Artificial Sequence
<220> FEATURE:
<223> OTHER INFORMATION: AB2-026

<400> SEQUENCE: 132

```
Met Gln Ala Lys His Lys Gln Arg Lys Arg Leu Lys Ser Ser Cys Lys
  1               5                  10                  15
Arg His Pro Leu Tyr Val Asp Phe Ser Asp Val Gly Trp Asn Asp Trp
             20                  25                  30
Ile Val Ala Pro Pro Gly Tyr His Ala Phe Tyr Cys His Gly Glu Cys
         35                  40                  45
Pro Ser His Ile Ala Gly Thr Ser Gly Ser Ser Leu Ser Phe His Ser
     50                  55                  60
Thr Leu Val Asn Ser Val Asn Ser Lys Ile Pro Lys Ala Cys Cys Val
 65                  70                  75                  80
Pro Thr Lys Leu Arg Pro Met Ser Met Leu Tyr Tyr Asp Glu Asn Glu
                 85                  90                  95
Lys Val Val Leu Lys Asn Tyr Gln Asp Met Val Val Glu Gly Cys Gly
            100                 105                 110
Cys Arg
```

<210> SEQ ID NO 133
<211> LENGTH: 342
<212> TYPE: DNA
<213> ORGANISM: Artificial Sequence
<220> FEATURE:
<223> OTHER INFORMATION: AB2-027

<400> SEQUENCE: 133

```
atgcaagcca aacacaaaca gcggaaacgc cttaagtcca gctgtaagag acacccttg      60
tacgtggact tcagtgacgt ggggtggaat gactggatca ttgctccctc tggctatcat    120
gccaactact gcgagggaga atgcccttct catatagcag gcacgtccgg gtcctcactg    180
tccttccact caacgttggt caactctgtt aactctaaga ttcctaaggc atgctgtgtc    240
ccgacagaac tcagtgctat ctcgatgttg taccttgacg agaatgaaaa ggttgtatta    300
agaactatc aggacatggt tgtggagggt tgtgggtgtc gc                        342
```

<210> SEQ ID NO 134
<211> LENGTH: 114
<212> TYPE: PRT
<213> ORGANISM: Artificial Sequence
<220> FEATURE:

<223> OTHER INFORMATION: AB2-027

<400> SEQUENCE: 134

Met Gln Ala Lys His Lys Gln Arg Lys Arg Leu Lys Ser Ser Cys Lys
1               5                   10                  15

Arg His Pro Leu Tyr Val Asp Phe Ser Asp Val Gly Trp Asn Asp Trp
            20                  25                  30

Ile Ile Ala Pro Ser Gly Tyr His Ala Asn Tyr Cys Glu Gly Glu Cys
        35                  40                  45

Pro Ser His Ile Ala Gly Thr Ser Gly Ser Ser Leu Ser Phe His Ser
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg

<210> SEQ ID NO 135
<211> LENGTH: 342
<212> TYPE: DNA
<213> ORGANISM: Artificial Sequence
<220> FEATURE:
<223> OTHER INFORMATION: AB2-028

<400> SEQUENCE: 135
atgcaagcca aacacaaaca gcggaaacgc cttaagtcca gctgtaagag acacccttg      60 tacgtggact tcagtgacgt ggggtggaat gactggatca ttgctccctc tggctatcat    120
gccaactact gcgagggaga atgcccttct catatagcag gcacgtccgg gtcctcactg    180
tccttccact caacgttggt caactctgtt aactctaaga ttcctaaggc atgctgtgtc    240
ccgacagaac tcaatgctat ctcgatgttg tactatgatg atggtcaaaa catcattaaa    300
aaggacattc agaacatgat cgtggaggag tgtgggtgct ca                       342

<210> SEQ ID NO 136
<211> LENGTH: 114
<212> TYPE: PRT
<213> ORGANISM: Artificial Sequence
<220> FEATURE:
<223> OTHER INFORMATION: AB2-028

<400> SEQUENCE: 136

Met Gln Ala Lys His Lys Gln Arg Lys Arg Leu Lys Ser Ser Cys Lys
1               5                   10                  15

Arg His Pro Leu Tyr Val Asp Phe Ser Asp Val Gly Trp Asn Asp Trp
            20                  25                  30

Ile Ile Ala Pro Ser Gly Tyr His Ala Asn Tyr Cys Glu Gly Glu Cys
        35                  40                  45

Pro Ser His Ile Ala Gly Thr Ser Gly Ser Ser Leu Ser Phe His Ser
    50                  55                  60

Thr Leu Val Asn Ser Val Asn Ser Lys Ile Pro Lys Ala Cys Cys Val
65                  70                  75                  80

Pro Thr Glu Leu Asn Ala Ile Ser Met Leu Tyr Tyr Asp Asp Gly Gln
                85                  90                  95

Asn Ile Ile Lys Lys Asp Ile Gln Asn Met Ile Val Glu Glu Cys Gly
            100                 105                 110

Cys Ser

<210> SEQ ID NO 137
<211> LENGTH: 342
<212> TYPE: DNA
<213> ORGANISM: Artificial Sequence
<220> FEATURE:
<223> OTHER INFORMATION: AB2-030

<400> SEQUENCE: 137

```
atgcaagcca aacacaaaca gcggaaacgc cttaagtcca gctgtaagag acacccttg      60
tacgtggact tcagtgacgt ggggtggaat gactggatca ttgctccctc tggctatcat    120
gccaactact gcgagggaga atgcccttct catatagcag gcacgtccgg gtcctcactg    180
tccttccact caacgttggt caactctgtt aactctaaga ttcctaaggc atgctgtgtc    240
ccgaccaagc tgagacccat gtccatgttg tactatgatg atggtcaaaa catcatcaaa    300
aaggacattc agaacatgat cgtggaggag tgtgggtgct ca                       342
```

<210> SEQ ID NO 138
<211> LENGTH: 114
<212> TYPE: PRT
<213> ORGANISM: Artificial Sequence
<220> FEATURE:
<223> OTHER INFORMATION: AB2-030

<400> SEQUENCE: 138

Met Gln Ala Lys His Lys Gln Arg Lys Arg Leu Lys Ser Ser Cys Lys
1               5                   10                  15

Arg His Pro Leu Tyr Val Asp Phe Ser Asp Val Gly Trp Asn Asp Trp
            20                  25                  30

Ile Ile Ala Pro Ser Gly Tyr His Ala Asn Tyr Cys Glu Gly Glu Cys
        35                  40                  45

Pro Ser His Ile Ala Gly Thr Ser Gly Ser Ser Leu Ser Phe His Ser
    50                  55                  60

Thr Leu Val Asn Ser Val Asn Ser Lys Ile Pro Lys Ala Cys Cys Val
65                  70                  75                  80

Pro Thr Lys Leu Arg Pro Met Ser Met Leu Tyr Tyr Asp Asp Gly Gln
                85                  90                  95

Asn Ile Ile Lys Lys Asp Ile Gln Asn Met Ile Val Glu Glu Cys Gly
            100                 105                 110

Cys Ser

<210> SEQ ID NO 139
<211> LENGTH: 363
<212> TYPE: DNA
<213> ORGANISM: Artificial Sequence
<220> FEATURE:
<223> OTHER INFORMATION: AB2-031

<400> SEQUENCE: 139

```
atgcaagcca aacacaaaca gcggaaacgc cttaagtcca gctgtaagag acacccttg      60
tacgtggact tcagtgacgt ggggtggaat gactggatca ttgctccctc tggctatcat    120
gccaactact gcgagggaga atgccctttt cctctggctg atcatctgaa ctccactaat    180
catgccattg ttcagacgtt ggtcaaccac taccgcatgc ggggccatag ccccttgcc     240
aacctcaaat cgtgctgtgt cccgaccaag ctgagaccca tgtccatgtt gtactatgat    300
gatggtcaaa acatcatcaa aaaggacatt cagaacatga tcgtggagga gtgtgggtgc    360
```

```
tca                                                                   363
```

<210> SEQ ID NO 140
<211> LENGTH: 121
<212> TYPE: PRT
<213> ORGANISM: Artificial Sequence
<220> FEATURE:
<223> OTHER INFORMATION: AB2-031

<400> SEQUENCE: 140

Met Gln Ala Lys His Lys Gln Arg Lys Arg Leu Lys Ser Ser Cys Lys
1               5                   10                  15

Arg His Pro Leu Tyr Val Asp Phe Ser Asp Val Gly Trp Asn Asp Trp
            20                  25                  30

Ile Ile Ala Pro Ser Gly Tyr His Ala Asn Tyr Cys Glu Gly Glu Cys
        35                  40                  45

Pro Phe Pro Leu Ala Asp His Leu Asn Ser Thr Asn His Ala Ile Val
    50                  55                  60

Gln Thr Leu Val Asn His Tyr Arg Met Arg Gly His Ser Pro Phe Ala
65                  70                  75                  80

Asn Leu Lys Ser Cys Cys Val Pro Thr Lys Leu Arg Pro Met Ser Met
                85                  90                  95

Leu Tyr Tyr Asp Asp Gly Gln Asn Ile Ile Lys Lys Asp Ile Gln Asn
            100                 105                 110

Met Ile Val Glu Glu Cys Gly Cys Ser
        115                 120

<210> SEQ ID NO 141
<211> LENGTH: 363
<212> TYPE: DNA
<213> ORGANISM: Artificial Sequence
<220> FEATURE:
<223> OTHER INFORMATION: AB2-032

<400> SEQUENCE: 141

```
atgcaagcca  acacaaaca  gcggaaacgc  cttaagtcca  gctgtaagag  acacccttg    60
tacgtggact  tcagtgacgt  ggggtggaat  gactggatca  ttgctccctc  tggctatcat  120
gccaactact  gcgagggaga  atgccctttt  cctctggctg  atcatctgaa  ctccactaat  180
catgccattg  ttcagacgtt  ggtcaaccac  taccgcatgc  ggggccatag  cccctttgcc  240
aacctcaaat  cgtgctgtgt  cccgacagaa  ctcagtgcta  tctcgatgct  gtaccttgac  300
gatggtcaaa  acatcatcaa  aaaggacatt  cagaacatga  tcgtggagga  gtgtgggtgc  360
tca                                                                   363
```

<210> SEQ ID NO 142
<211> LENGTH: 121
<212> TYPE: PRT
<213> ORGANISM: Artificial Sequence
<220> FEATURE:
<223> OTHER INFORMATION: AB2-032

<400> SEQUENCE: 142

Met Gln Ala Lys His Lys Gln Arg Lys Arg Leu Lys Ser Ser Cys Lys
1               5                   10                  15

Arg His Pro Leu Tyr Val Asp Phe Ser Asp Val Gly Trp Asn Asp Trp
            20                  25                  30

Ile Ile Ala Pro Ser Gly Tyr His Ala Asn Tyr Cys Glu Gly Glu Cys
        35                  40                  45

```
Pro Phe Pro Leu Ala Asp His Leu Asn Ser Thr Asn His Ala Ile Val
    50                  55                  60

Gln Thr Leu Val Asn His Tyr Arg Met Arg Gly His Ser Pro Phe Ala
 65                  70                  75                  80

Asn Leu Lys Ser Cys Cys Val Pro Thr Glu Leu Ser Ala Ile Ser Met
                 85                  90                  95

Leu Tyr Tyr Asp Asp Gly Gln Asn Ile Ile Lys Lys Asp Ile Gln Asn
            100                 105                 110

Met Ile Val Glu Glu Cys Gly Cys Ser
            115                 120

<210> SEQ ID NO 143
<211> LENGTH: 363
<212> TYPE: DNA
<213> ORGANISM: Artificial Sequence
<220> FEATURE:
<223> OTHER INFORMATION: AB2-033

<400> SEQUENCE: 143
atgcaagcca aacacaaaca gcggaaacgc cttaagtcca gctgtaagag acaccctttg      60
tacgtggact tcagtgacgt gggtggaat gactggatca ttgctccctc tggctatcat     120
gccaactact gcgagggaga atgccctttt cctctggctg atcatctgaa ctctactaat     180
catgccattg ttcagacgtt ggtcaaccac taccgcatgc ggggccatag ccccttgcc     240 aacctcaaat cgtgctgtgt cccgacagaa ctcagtgcta tctcgatgct gtaccttgac     300
gagaatgaaa aggttgtatt aaagaactat caggacatgg ttgtggaggg ttgcgggtgt     360
cgt                                                                   363

<210> SEQ ID NO 144
<211> LENGTH: 121
<212> TYPE: PRT
<213> ORGANISM: Artificial Sequence
<220> FEATURE:
<223> OTHER INFORMATION: AB2-033

<400> SEQUENCE: 144

Met Gln Ala Lys His Lys Gln Arg Lys Arg Leu Lys Ser Ser Cys Lys
 1               5                  10                  15

Arg His Pro Leu Tyr Val Asp Phe Ser Asp Val Gly Trp Asn Asp Trp
                20                  25                  30

Ile Ile Ala Pro Ser Gly Tyr His Ala Asn Tyr Cys Glu Gly Glu Cys
            35                  40                  45

Pro Phe Pro Leu Ala Asp His Leu Asn Ser Thr Asn His Ala Ile Val
    50                  55                  60

Gln Thr Leu Val Asn His Tyr Arg Met Arg Gly His Ser Pro Phe Ala
 65                  70                  75                  80

Asn Leu Lys Ser Cys Cys Val Pro Thr Glu Leu Ser Ala Ile Ser Met
                 85                  90                  95

Leu Tyr Leu Asp Glu Asn Glu Lys Val Val Leu Lys Asn Tyr Gln Asp
            100                 105                 110

Met Val Val Glu Gly Cys Gly Cys Arg
            115                 120

<210> SEQ ID NO 145
<211> LENGTH: 363
<212> TYPE: DNA
<213> ORGANISM: Artificial Sequence
```

<220> FEATURE:
<223> OTHER INFORMATION: AB2-034

<400> SEQUENCE: 145

```
atgcaagcca aacacaaaca gcggaagcgt cttaagtcca gctgcaaaag gcaccctttg      60
tatgtggact tcagtgatgt ggggtggaat gactggatca ttgctccctc tggctatcat     120
gccaactact gcgacggaga atgccctttt cctctggctg atcatctgaa ctccactaat     180
catgccattg ttcagacgtt ggtcaaccac taccgcatgc ggggccatag ccccttttgcc    240
aacctcaaat catgctgtgt cccgaccaag ctgagaccca tgtccatgtt gtactatgat    300
gagaatgaaa aggttgtatt aaagaactat caggacatgg ttgtggaggg ttgcgggtgt    360
cgt                                                                   363
```

<210> SEQ ID NO 146
<211> LENGTH: 121
<212> TYPE: PRT
<213> ORGANISM: Artificial Sequence
<220> FEATURE:
<223> OTHER INFORMATION: AB2-034

<400> SEQUENCE: 146

```
Met Gln Ala Lys His Lys Gln Arg Lys Arg Leu Lys Ser Ser Cys Lys
1               5                   10                  15
Arg His Pro Leu Tyr Val Asp Phe Ser Asp Val Gly Trp Asn Asp Trp
            20                  25                  30
Ile Ile Ala Pro Ser Gly Tyr His Ala Asn Tyr Cys Asp Gly Glu Cys
        35                  40                  45
Pro Phe Pro Leu Ala Asp His Leu Asn Ser Thr Asn His Ala Ile Val
    50                  55                  60
Gln Thr Leu Val Asn His Tyr Arg Met Arg Gly His Ser Pro Phe Ala
65                  70                  75                  80
Asn Leu Lys Ser Cys Cys Val Pro Thr Lys Leu Arg Pro Met Ser Met
                85                  90                  95
Leu Tyr Tyr Asp Glu Asn Glu Lys Val Val Leu Lys Asn Tyr Gln Asp
            100                 105                 110
Met Val Val Glu Gly Cys Gly Cys Arg
        115                 120
```

<210> SEQ ID NO 147
<211> LENGTH: 348
<212> TYPE: DNA
<213> ORGANISM: Artificial Sequence
<220> FEATURE:
<223> OTHER INFORMATION: BMP-2ma

<400> SEQUENCE: 147

```
atggctcaag ccaaacacaa acagcggaaa cgccttaagt ccagctgtaa agacaccct      60
ttgtacgtgg acttcagtga cgtggggtgg aatgactgga ttgtggctcc ccgggggtat    120
cacgcctttt actgccacgg agaatgccct tttcctctgg ctgatcatct gaactccact    180
aatcatgcca ttgttcagac gttggtcaac tctgttaact ctaagattcc taaggcatgc    240
tgtgtcccga cagaactcag tgctatctcg atgctgtacc ttgacgagaa tgaaaaggtt    300
gtattaaaga actatcagga catggttgtg gagggttgtg ggtgtcgc                 348
```

<210> SEQ ID NO 148
<211> LENGTH: 116
<212> TYPE: PRT

<213> ORGANISM: Artificial Sequence
<220> FEATURE:
<223> OTHER INFORMATION: BMP-2ma

<400> SEQUENCE: 148

```
Met Ala Gln Ala Lys His Lys Gln Arg Lys Arg Leu Lys Ser Ser Cys
1               5                   10                  15
Lys Arg His Pro Leu Tyr Val Asp Phe Ser Asp Val Gly Trp Asn Asp
            20                  25                  30
Trp Ile Val Ala Pro Pro Gly Tyr His Ala Phe Tyr Cys His Gly Glu
        35                  40                  45
Cys Pro Phe Pro Leu Ala Asp His Leu Asn Ser Thr Asn His Ala Ile
    50                  55                  60
Val Gln Thr Leu Val Asn Ser Val Asn Ser Lys Ile Pro Lys Ala Cys
65                  70                  75                  80
Cys Val Pro Thr Glu Leu Ser Ala Ile Ser Met Leu Tyr Leu Asp Glu
                85                  90                  95
Asn Glu Lys Val Val Leu Lys Asn Tyr Gln Asp Met Val Val Glu Gly
            100                 105                 110
Cys Gly Cys Arg
        115
```

<210> SEQ ID NO 149
<211> LENGTH: 399
<212> TYPE: DNA
<213> ORGANISM: Artificial Sequence
<220> FEATURE:
<223> OTHER INFORMATION: BMP2/BMP6

<400> SEQUENCE: 149

```
atgcaacaga gtcgtaatcg ctctacccag tcccaggacg tggcgcgggt ctccagtgct      60
tcagattaca acagcagtga attgaaaaca gcctgcagga agcatgagct gtatgtgagt     120
ttccaagacc tgggatggca ggactggatc attgcaccca agggctatgc tgccaattac     180
tgtgatggag aatgctcctt cccactcaac gcacacatga atgcaaccaa ccacgcgatt     240
gtgcagacct tggttcacct tatgaacccc gagtatgtcc ccaaaccgtg ctgtgcgcca     300
actaagctaa atgccatctc ggttctttac tttgatgaca actccaatgt cattctgaaa     360
aaatacagga atatggttgt aagagcttgt ggatgccac                             399
```

<210> SEQ ID NO 150
<211> LENGTH: 133
<212> TYPE: PRT
<213> ORGANISM: Artificial Sequence
<220> FEATURE:
<223> OTHER INFORMATION: BMP2/BMP6

<400> SEQUENCE: 150

```
Met Gln Gln Ser Arg Asn Arg Ser Thr Gln Ser Gln Asp Val Ala Arg
1               5                   10                  15
Val Ser Ser Ala Ser Asp Tyr Asn Ser Ser Glu Leu Lys Thr Ala Cys
            20                  25                  30
Arg Lys His Glu Leu Tyr Val Ser Phe Gln Asp Leu Gly Trp Gln Asp
        35                  40                  45
Trp Ile Ile Ala Pro Lys Gly Tyr Ala Ala Asn Tyr Cys Asp Gly Glu
    50                  55                  60
Cys Ser Phe Pro Leu Asn Ala His Met Asn Ala Thr Asn His Ala Ile
65                  70                  75                  80
```

-continued

```
Val Gln Thr Leu Val His Leu Met Asn Pro Glu Tyr Val Pro Lys Pro
                85                  90                  95

Cys Cys Ala Pro Thr Lys Leu Asn Ala Ile Ser Val Leu Tyr Phe Asp
            100                 105                 110

Asp Asn Ser Asn Val Ile Leu Lys Lys Tyr Arg Asn Met Val Val Arg
        115                 120                 125

Ala Cys Gly Cys His
    130
```